United States Patent
Tremblay et al.

(10) Patent No.: US 11,084,872 B2
(45) Date of Patent: Aug. 10, 2021

(54) METHOD FOR TREATING BREAST CANCER

(71) Applicant: ADC THERAPEUTICS SA, Epalinges (CH)

(72) Inventors: Gilles Bernard Tremblay, La Prairie (CA); Anna N. Moraitis, Laval (CA); Mario Filion, Longueuil (CA)

(73) Assignee: ADC Therapeutics SA, Epalinges (CH)

( * ) Notice: Subject to any disclaimer, the term of this patent is extended or adjusted under 35 U.S.C. 154(b) by 185 days.

(21) Appl. No.: 16/164,656

(22) Filed: Oct. 18, 2018

(65) Prior Publication Data

US 2019/0119366 A1    Apr. 25, 2019

Related U.S. Application Data

(63) Continuation of application No. 14/364,937, filed as application No. PCT/CA2013/000011 on Jan. 9, 2013, now abandoned.

(60) Provisional application No. 61/584,629, filed on Jan. 9, 2012.

(51) Int. Cl.
| | |
|---|---|
| C07K 16/18 | (2006.01) |
| C07K 16/30 | (2006.01) |
| A61K 39/395 | (2006.01) |
| A61K 47/68 | (2017.01) |
| A61K 45/06 | (2006.01) |
| A61K 39/00 | (2006.01) |

(52) U.S. Cl.
CPC ............ *C07K 16/18* (2013.01); *A61K 39/395* (2013.01); *A61K 39/39558* (2013.01); *A61K 45/06* (2013.01); *A61K 47/6855* (2017.08); *C07K 16/30* (2013.01); *C07K 16/3015* (2013.01); *A61K 2039/505* (2013.01); *C07K 2317/21* (2013.01); *C07K 2317/24* (2013.01); *C07K 2317/52* (2013.01); *C07K 2317/55* (2013.01); *C07K 2317/56* (2013.01); *C07K 2317/565* (2013.01); *C07K 2317/77* (2013.01); *C07K 2317/92* (2013.01); *C07K 2319/00* (2013.01)

(58) Field of Classification Search
CPC .......... C07K 16/3015; A61K 39/39558; A61K 47/6855
See application file for complete search history.

(56) References Cited

U.S. PATENT DOCUMENTS

| | | | |
|---|---|---|---|
| 4,745,076 A | 5/1988 | Muller et al. | |
| 5,075,447 A | 12/1991 | Muller et al. | |
| 5,585,279 A | 12/1996 | Davidson | |
| 5,708,022 A | 1/1998 | Bastos et al. | |
| 5,712,127 A | 1/1998 | Malek et al. | |
| 6,057,098 A | 5/2000 | Buechler et al. | |
| 6,288,221 B1 | 9/2001 | Grinstaff et al. | |
| 6,358,953 B1 | 3/2002 | Moheno | |
| 6,806,089 B1 | 10/2004 | Lakowicz et al. | |
| 6,812,339 B1 | 11/2004 | Venter et al. | |
| 6,962,910 B2 | 11/2005 | Brewer et al. | |
| 7,030,236 B2 | 4/2006 | Jhaveri et al. | |
| 7,202,234 B2 | 4/2007 | Chow et al. | |
| 7,429,567 B2 | 9/2008 | Lee et al. | |
| 7,439,051 B2 | 10/2008 | Sokoloff et al. | |
| 7,494,788 B2 | 2/2009 | Dunker et al. | |
| 7,501,485 B2 | 3/2009 | Cowsar | |
| 7,521,197 B2 | 4/2009 | Savage | |
| 7,531,533 B2 | 5/2009 | Shoda et al. | |
| 7,550,501 B2 | 6/2009 | Chow et al. | |
| 7,557,213 B2 | 7/2009 | Melikian et al. | |
| 7,560,441 B2 | 7/2009 | Wolfman et al. | |
| 7,585,839 B2 | 9/2009 | Larsen et al. | |
| 7,618,636 B1 | 11/2009 | Masignani et al. | |
| 7,628,989 B2 | 12/2009 | Jakobovits et al. | |
| 7,641,905 B2 | 1/2010 | Jakobovits et al. | |
| 8,216,582 B2 | 7/2012 | Sooknanan et al. | |
| 8,937,163 B2 | 1/2015 | Tremblay et al. | |
| 9,393,302 B2 | 7/2016 | Tremblay et al. | |
| 9,828,426 B2 | 11/2017 | Tremblay et al. | |
| 2002/0049190 A1 | 4/2002 | Bridger et al. | |
| 2002/0106678 A1 | 8/2002 | Robishaw et al. | |
| 2002/0177695 A1 | 11/2002 | Grinstaff et al. | |
| 2003/0065157 A1 | 4/2003 | Lasek | |
| 2003/0087250 A1 | 5/2003 | Monahan et al. | |

(Continued)

FOREIGN PATENT DOCUMENTS

| | | |
|---|---|---|
| CA | 2446185 C | 11/2002 |
| CA | 2615858 A1 | 1/2007 |

(Continued)

OTHER PUBLICATIONS

Padlan, Advances in Protein Chemistry, 1996, 49:57-133.*

(Continued)

*Primary Examiner* — Hong Sang

(74) *Attorney, Agent, or Firm* — Foley & Lardner LLP

(57) ABSTRACT

Breast cancer cells lacking ER protein expression, PgR protein expression and/or showing absence of HER2 protein over-expression (i.e., triple-negative breast cancer cells, basal-like) can be efficiently targeted with an anti-KAAG1 antibody and killed upon delivery of a therapeutic moiety. Antibodies and antigen binding fragments that specifically binds to KAAG1 may thus be used for the, detection and therapeutic treatment of breast cancer cells that are negative for at least one of these markers. The use of antibody conjugates in the treatment of triple-negative breast cancer and/or basal-like breast cancer is disclosed herein.

23 Claims, 21 Drawing Sheets

Specification includes a Sequence Listing.

(56) References Cited

U.S. PATENT DOCUMENTS

| | | |
|---|---|---|
| 2003/0099974 A1 | 5/2003 | Lillie et al. |
| 2003/0118592 A1 | 6/2003 | Ledbetter et al. |
| 2003/0124579 A1 | 7/2003 | Mack et al. |
| 2003/0133939 A1 | 7/2003 | Ledbetter et al. |
| 2003/0170273 A1 | 9/2003 | O'Hagan et al. |
| 2003/0180767 A1 | 9/2003 | Brewer et al. |
| 2003/0219760 A1 | 11/2003 | Gordon et al. |
| 2004/0009939 A1 | 1/2004 | Chada et al. |
| 2004/0014081 A1 | 1/2004 | Alsobrook et al. |
| 2004/0053824 A1 | 3/2004 | Tang et al. |
| 2004/0101874 A1 | 5/2004 | Ghosh et al. |
| 2004/0172684 A1 | 9/2004 | Kovalic et al. |
| 2004/0214272 A1 | 10/2004 | La Rosa et al. |
| 2004/0242606 A1 | 12/2004 | Bavetsias et al. |
| 2005/0008649 A1 | 1/2005 | Shin et al. |
| 2005/0009851 A1 | 1/2005 | Bavetsias et al. |
| 2005/0053930 A1 | 3/2005 | Anderson et al. |
| 2005/0059624 A1 | 3/2005 | Hoerr et al. |
| 2005/0064481 A1 | 3/2005 | Korfhage |
| 2005/0095592 A1 | 5/2005 | Jazaeri et al. |
| 2005/0113345 A1 | 5/2005 | Chow et al. |
| 2005/0123501 A1 | 6/2005 | Lewis |
| 2005/0147621 A1 | 7/2005 | Higgins et al. |
| 2005/0153333 A1 | 7/2005 | Sooknanan |
| 2005/0170450 A1 | 8/2005 | Durocher et al. |
| 2005/0196754 A1 | 9/2005 | Drmanac et al. |
| 2005/0214826 A1 | 9/2005 | Mor et al. |
| 2005/0214831 A1 | 9/2005 | Monahan et al. |
| 2006/0014686 A1 | 1/2006 | Wonsey et al. |
| 2006/0078941 A1 | 4/2006 | Santin |
| 2006/0084594 A1 | 4/2006 | Santin et al. |
| 2006/0188490 A1 | 8/2006 | Hoerr et al. |
| 2006/0229433 A1 | 10/2006 | De Rouge et al. |
| 2007/0027075 A1 | 2/2007 | Smithrud |
| 2007/0060590 A1 | 3/2007 | Shoda et al. |
| 2007/0093467 A1 | 4/2007 | Zhang et al. |
| 2007/0167409 A1 | 7/2007 | Chow et al. |
| 2007/0167443 A1 | 7/2007 | Melikian et al. |
| 2007/0298093 A1 | 12/2007 | Konur et al. |
| 2007/0299068 A1 | 12/2007 | Karp et al. |
| 2008/0025944 A1 | 1/2008 | Hoerr et al. |
| 2008/0070232 A1 | 3/2008 | Durocher |
| 2008/0166355 A1 | 7/2008 | Moheno et al. |
| 2008/0176790 A1 | 7/2008 | DeFrees |
| 2008/0200650 A1 | 8/2008 | Emery et al. |
| 2008/0213268 A1 | 9/2008 | Watts et al. |
| 2008/0274131 A1 | 11/2008 | Renner et al. |
| 2008/0280317 A1 | 11/2008 | Wu et al. |
| 2008/0280818 A1 | 11/2008 | DeFrees |
| 2008/0300348 A1 | 12/2008 | Haddleton et al. |
| 2008/0306007 A1 | 12/2008 | McCluskey et al. |
| 2008/0311145 A1 | 12/2008 | Campion et al. |
| 2009/0074658 A1 | 3/2009 | Lupold et al. |
| 2009/0075832 A1 | 3/2009 | Neuman et al. |
| 2009/0093621 A1 | 4/2009 | Ferrari et al. |
| 2009/0110662 A1 | 4/2009 | Breitenkamp et al. |
| 2009/0137003 A1 | 5/2009 | Tolstrup et al. |
| 2009/0169520 A1 | 7/2009 | Soreq et al. |
| 2009/0176664 A1 | 7/2009 | Chu |
| 2009/0186855 A1 | 7/2009 | Chow et al. |
| 2009/0197345 A1 | 8/2009 | Seppala |
| 2009/0203542 A1 | 8/2009 | Reichmann et al. |
| 2009/0208507 A1 | 8/2009 | Rohlff |
| 2009/0209463 A1 | 8/2009 | Nakamura et al. |
| 2009/0214467 A1 | 8/2009 | Shakhov et al. |
| 2009/0214585 A1 | 8/2009 | Ciocca et al. |
| 2009/0221032 A1 | 9/2009 | Dunker et al. |
| 2009/0226448 A1 | 9/2009 | Glucksmann et al. |
| 2009/0226451 A1 | 9/2009 | Glucksmann et al. |
| 2009/0226921 A1 | 9/2009 | Afar et al. |
| 2009/0232766 A1 | 9/2009 | Wang et al. |
| 2009/0239229 A1 | 9/2009 | Weaver |
| 2009/0253156 A1 | 10/2009 | Patton et al. |
| 2009/0275137 A1 | 11/2009 | Kranz et al. |
| 2009/0297401 A1 | 12/2009 | Lundstrom et al. |
| 2009/0305282 A1 | 12/2009 | Yuen et al. |
| 2009/0305962 A1 | 12/2009 | Bakker et al. |
| 2009/0311681 A1 | 12/2009 | Faure |
| 2009/0325869 A1 | 12/2009 | Theil |
| 2010/0003280 A1 | 1/2010 | O'Hagan et al. |
| 2010/0003305 A1 | 1/2010 | Pattanaik |
| 2010/0040606 A1 | 2/2010 | Lantto et al. |
| 2010/0047261 A1 | 2/2010 | Hoerr et al. |
| 2010/0055077 A1 | 3/2010 | Shakhov et al. |
| 2010/0055731 A1 | 3/2010 | Wang et al. |
| 2010/0056459 A1 | 3/2010 | Bonny |
| 2010/0086537 A1 | 4/2010 | Sooknanan et al. |
| 2010/0086541 A1 | 4/2010 | Wu et al. |
| 2010/0105692 A1 | 4/2010 | Moheno et al. |
| 2010/0111993 A1 | 5/2010 | Tureci et al. |
| 2010/0120627 A1 | 5/2010 | Belouchi et al. |
| 2011/0150979 A1 | 6/2011 | Ray et al. |
| 2011/0223107 A1 | 9/2011 | Tremblay et al. |
| 2011/0233107 A1 | 9/2011 | Lockett |
| 2012/0087862 A1 | 4/2012 | Hood et al. |
| 2012/0093819 A1 | 4/2012 | Tremblay et al. |
| 2012/0128661 A1 | 5/2012 | Sooknanan et al. |
| 2012/0288498 A1 | 11/2012 | Sooknanan et al. |
| 2014/0140990 A1 | 5/2014 | Tremblay et al. |
| 2016/0039930 A1 | 2/2016 | Sooknanan et al. |
| 2017/0017475 A1 | 6/2017 | Tremblay et al. |

FOREIGN PATENT DOCUMENTS

| | | |
|---|---|---|
| CA | 2655933 A1 | 12/2007 |
| EP | 0178450 A2 | 4/1986 |
| EP | 0636031 A1 | 2/1995 |
| EP | 0816377 A2 | 1/1998 |
| EP | 1318835 B1 | 6/2003 |
| EP | 1422242 A1 | 5/2004 |
| EP | 1458410 B1 | 9/2004 |
| EP | 1465933 A1 | 10/2004 |
| EP | 1547581 A1 | 6/2005 |
| EP | 1550458 A1 | 7/2005 |
| EP | 1646661 B1 | 4/2006 |
| EP | 1751179 | 2/2007 |
| EP | 1847533 A1 | 10/2007 |
| EP | 1905844 A2 | 4/2008 |
| EP | 1970383 A1 | 9/2008 |
| EP | 1987356 | 11/2008 |
| EP | 2002036 | 12/2008 |
| EP | 2021467 | 2/2009 |
| EP | 2057465 | 5/2009 |
| EP | 2161291 A2 | 3/2010 |
| WO | WO-1987/004523 A1 | 7/1987 |
| WO | WO-1991/009849 A1 | 7/1991 |
| WO | WO-1996/013510 A1 | 5/1996 |
| WO | WO-1998/058079 A1 | 12/1998 |
| WO | WO-1999/031513 A1 | 6/1999 |
| WO | WO-1999/58546 A1 | 11/1999 |
| WO | WO-2000/001702 A1 | 1/2000 |
| WO | WO-2000/014515 A1 | 3/2000 |
| WO | WO-2000/023448 A1 | 4/2000 |
| WO | WO-2000/025788 A1 | 5/2000 |
| WO | WO-2000/056743 A1 | 9/2000 |
| WO | WO-2001/019798 A2 | 3/2001 |
| WO | WO-2001/046209 A1 | 6/2001 |
| WO | WO-2001/70979 A2 | 9/2001 |
| WO | WO-2001/98468 A2 | 12/2001 |
| WO | WO-2002/070539 A2 | 9/2002 |
| WO | WO-2002/086443 A2 | 10/2002 |
| WO | WO-2002/102235 A2 | 12/2002 |
| WO | WO-2003/043987 A2 | 5/2003 |
| WO | WO-2003/047526 A2 | 6/2003 |
| WO | WO-2003/051401 A2 | 6/2003 |
| WO | WO-2003/068054 A2 | 8/2003 |
| WO | WO-2003/075952 A1 | 9/2003 |
| WO | WO-2003/080672 A1 | 10/2003 |
| WO | WO-2003/087768 A2 | 10/2003 |
| WO | WO-03/99205 A2 | 12/2003 |
| WO | WO-2003/099205 A2 | 12/2003 |
| WO | WO-2004/030615 A2 | 4/2004 |
| WO | WO-2004/076622 A2 | 9/2004 |
| WO | WO-2004/087874 A2 | 10/2004 |

(56) References Cited

FOREIGN PATENT DOCUMENTS

| | | |
|---|---|---|
| WO | WO-2004/104197 A1 | 12/2004 |
| WO | WO-2004/113394 A2 | 12/2004 |
| WO | WO-2005/024055 A1 | 3/2005 |
| WO | WO-2005/039504 A1 | 5/2005 |
| WO | WO-2005/063201 A2 | 7/2005 |
| WO | WO-2005/063288 A1 | 7/2005 |
| WO | WO-2005/070456 A2 | 8/2005 |
| WO | WO-2006/003352 A1 | 1/2006 |
| WO | WO-2006/024518 A1 | 3/2006 |
| WO | WO-2006/027202 A1 | 3/2006 |
| WO | WO-2006/029385 A2 | 3/2006 |
| WO | WO-2006/096989 A2 | 9/2006 |
| WO | WO-2006/102097 A2 | 9/2006 |
| WO | WO-2006/138380 A2 | 12/2006 |
| WO | WO-2007/002559 A1 | 1/2007 |
| WO | WO-2007/002563 A1 | 1/2007 |
| WO | WO-2007/005249 A2 | 1/2007 |
| WO | WO-2007/023287 A1 | 3/2007 |
| WO | WO-2007/045876 A1 | 4/2007 |
| WO | WO-2007/059108 A2 | 5/2007 |
| WO | WO-2007/061853 A2 | 5/2007 |
| WO | WO-2007/073432 A2 | 6/2007 |
| WO | WO-2007/084413 A2 | 7/2007 |
| WO | WO-2007/104948 A2 | 9/2007 |
| WO | WO-2007/110755 A1 | 10/2007 |
| WO | WO-2007/147265 A1 | 12/2007 |
| WO | WO-2008/002267 A1 | 1/2008 |
| WO | WO-2008/016356 A2 | 2/2008 |
| WO | WO-2008/021290 A2 | 2/2008 |
| WO | WO-2008/033932 A2 | 3/2008 |
| WO | WO-2008/052770 A2 | 5/2008 |
| WO | WO-2008/054793 A2 | 5/2008 |
| WO | WO-2008/074004 A2 | 6/2008 |
| WO | WO-2008/082887 A2 | 7/2008 |
| WO | WO-2008/083949 A2 | 7/2008 |
| WO | WO-2008/104804 A2 | 9/2008 |
| WO | WO-2009/004329 A1 | 1/2009 |
| WO | WO-2009/009186 A2 | 1/2009 |
| WO | WO-2009/039854 A2 | 4/2009 |
| WO | WO-2009/044162 A1 | 4/2009 |
| WO | WO-2009/059972 A2 | 5/2009 |
| WO | WO-2009/061681 A2 | 5/2009 |
| WO | WO-2009/069862 A1 | 6/2009 |
| WO | WO-2009/077864 A2 | 6/2009 |
| WO | WO-2009/111088 A2 | 9/2009 |
| WO | WO-2009/114942 A1 | 9/2009 |
| WO | WO-2009/134370 A2 | 11/2009 |
| WO | WO-2009/144230 A1 | 12/2009 |
| WO | WO-2010/003127 A2 | 1/2010 |
| WO | WO-2010/014141 A1 | 2/2010 |
| WO | WO-2010/017479 A1 | 2/2010 |
| WO | WO-2010/033207 A1 | 3/2010 |
| WO | WO-2010/033220 A2 | 3/2010 |
| WO | WO-2010/033240 A2 | 3/2010 |
| WO | WO-2010/037408 A2 | 4/2010 |
| WO | WO-2010/037539 A1 | 4/2010 |
| WO | WO-2010/060186 A1 | 6/2010 |
| WO | WO-2010/096434 A2 | 8/2010 |
| WO | WO-2011/004028 A2 | 1/2011 |
| WO | WO-2011/054112 A1 | 5/2011 |
| WO | WO-2011/112953 A2 | 9/2011 |
| WO | WO-2012/129668 A1 | 10/2012 |
| WO | WO-2013/104050 A2 | 7/2013 |

OTHER PUBLICATIONS

Berglund et al, Protein Science, 2008, 17:606-613.*
Tzartos et al., Methods in Molecular Biology, 1996, 66:55-66.*
Abhinandan, K.R. et al, Analysis and improvements to Kabat and structurally correct numbering of antibody variable domains, Molecular Immunology, 45:3832-3839 (2008).
Agrawal, N., et al., RNA Interference: Biology, Mechanism, and Applications, Microbiology and Molecular Biology Reviews, 67(4):657-685 (2003).
An, Z. et al., IgG2m4, an engineered antibody isotype with reduced Fc function, mAbs 1(6):572-579 (2009).
Benoit M.H. et al., Global analysis of chromosome X gene expression in primary cultures of normal ovarian surface epithelial cells and epithelial ovarian cancer cell lines, International Journal of Oncology, 30(1):5-17 (2007).
Berek, J.S. et al., Chapter 115 Ovarian Cancer, in Holland-Frei Cancer Medicine, 5th Edition, Hamilton (ON): B.C. Decker (2000).
Bergers, G. et al., Extrinsic regulators of epithelial tumor progression: metalloproteinases, Current Opinion in Genetics and Development, 10:120-127 (2000).
Bernard, A. et al., A Unique Epitope on the CD2 Molecule Defined by the Monoclonal Antibody 9-1: Epitope-Specific Modulation of the E-Rosette Receptor and Effects on T-Cell Functions, Human Immunology, 17:388-405 (1986).
Bird, R.E. et al., Single-Chain Antigen-Binding Proteins, Science, 242(4877):423-426 (1988).
Bonome, T. et al., Expression Profiling of Serous Low Malignant Potential, Low-Grade, and High-Grade Tumors of the Ovary, Cancer Research, 65(22):10602-10612 (2005).
Bowie, J.U. et al., Deciphering the Message in Protein Sequences: Tolerance to Amino Acid Substitutions, Science, 247(4948):1306-1310 (1990).
Boyer, C.M. et al., Relative Cytotoxic Activity of Immunotoxins Reactive with Different Epitopes on the Extracellular Domain of the c-erbB-2 (HER-2/neu) Gene Product p. 185, International Journal of Cancer, 82:525-531 (1999).
Bristow, R.E., Surgical standards in the management of ovarian cancer, Current Opinion in Oncology, 12:474-480 (2000).
Brown, E. et al., Carcinosarcoma of the Ovary: 19 Years of Prospective Data from a Single Center, Cancer, 100:2148-2153 (2004).
Brummelkamp, T.R. et al., A System for Stable Expression of Short Interfering RNAs in Mammalian Cells, Science, 296(5567):550-553 (2002).
Burger, R.A., Experience With Bevacizumab in the Management of Epithelial Ovarian Cancer, Journal of Clinical Oncology, 25(20): 2902-2908 (2007).
Burgess, W.H. et al., Possible dissociation of the Heparin-binding and Mitogenic Activities of Heparin-binding (Acidic Fibroblast) Growth Factor-1 from Its Receptor-binding Activities by Site-directed Mutagenesis of a Single Lysine Residue, The Journal of Cell Biology, 111:2129-2138 (1990).
Byers, V.S. et al., Therapeutic strategies with monoclonal antibodies and immunoconjugates, Immunology, 65:329-335 (1988).
Cannistra, S.A. et al., Progress in the Management of Gynecologic Cancer, Journal of Clinical Oncology, 25(20):2865-2866 (2007).
Chambers, A.F. et al., Ovarian Cancer Biomarkers in Urine, Clinical Cancer Research, 12(2):323-327 (2006).
Clackson, T. et al., Making antibody fragments using phage display libraries, Nature, 352:624-628 (1991).
Cody, N.A.L. et al., Influence of monolayer, spheroid, and tumor growth conditions on chromosome 3 gene expression in tumorigenic epithelial ovarian cancer cell lines, BMC Medical Genomics, 1:34 (2008).
Cope, N. et al., Strong evidence that KIAA0319 on Chromosome 6p is a Susceptibility Gene for Developmental Dyslexia, The American Journal of Human Genetics, 76:581-591 (2005).
De Plaen, E. et al., Structure, chromosomal localization, and expression of 12 genes of the MAGE family, Immunogenetics 40:360-369 (1994).
Dennis, C. Off by a whisker, Nature, 442:739-741 (2006).
Dermer, B.G., Another Anniversary for the War on Cancer, Bio/Technology, Vo. 12, p. 320, 1994.
Ebel, W. et al., Preclinical evaluation of MORAb-003, a humanized monoclonal antibody antagonizing folate receptor-alpha. Cancer Immunity, 7:6-13 (2007).
Elbashir, S.M. et al., Duplexes of 21-nucleotide RNAs mediate RNA interference in cultured mammalian cells, Nature, 411(6836):494-498 (2001).
Freshney, R.i., Culture of Animal Cells, A Manual of Basic Technique, Alan R. Liss, Inc., 1983, New York, p. 4.

(56) References Cited

OTHER PUBLICATIONS

Futreal, A.P. et al., A census of human cancer genes, Nature Reviews, 4:177-183 (2004).
GenBank Acc. No. AA744939.1, GI: 2783703, 1998.
GenBankAcc. No. AC002060.4, GI:22507090, first referenced 1997, updated 2002.
GenBank Acc. No. AC068288.6, GI:16418276, first referenced 2001, updated 2005.
GenBank Acc. No. AC104837.2, GI:18249998, first referenced 2001, updated 2002.
GenBank Acc. No. AC109350.5, GI:19526559, first referenced 1998, updated 2002.
GenBank Acc. No. AC117457.11, GI:28557825, first referenced 2002, updated 2003.
GenBank Acc. No. A1922121.1, GI:5658085, first referenced 1999, updated 2000.
GenBank Acc. No. AK092857.1, GI:21751554, first referenced 2002, updated 2004.
GenBank Acc. No. AK092936.1, GI:21751648, first referenced 2002, updated 2004.
GenBank Acc. No. AL157931.17, GI:11493240, first referenced 2000, updated 2009.
GenBank Acc. No. AL583809.3, GI:14250883, 2001.
GenBank Acc. No. AY683003.1, GI:56384942, 2004.
GenBank Acc. No. BC009078.1, GI:14290598, first referenced 2001, updated 2008.
GenBank Acc. No. BC037243, Strausberg et al., Sep. 27, 2002.
GenBank Acc. No. BC073793.1, GI:49258111, first referenced 2002, updated 2006.
GenBank Acc. No. BC092518.1, GI:62201665, first referenced 2002, updated 2005.
GenBank Acc. No. BC037243.1, GI:23337025, first referenced 2002, updated 2008.
GenBank Acc. No. BG213598.1, GI:13735285, 2001.
GenBank Acc. No. BU595315.1, GI:23247074, 2002.
GenBank Acc. No. NM_000077.3, GI:47132606, first referenced 1994, updated 2004.
GenBank Acc. No. NM_000096.3, GI:189458860, first referenced 1977, updated 2008.
GenBank Acc. No. NM_000170.2, GI:108773800, first referenced 1989, updated 2006.
GenBank Acc. No. NM_000802.2, GI:12056965, first referenced 1990, updated 2001.
GenBank Acc. No. NM_001001887.1, GI:49574525, first referenced 1983, updated 2006.
GenBank Acc. No. NM_001007027.2, GI:91984777, first referenced 1995, updated 2006.
GenBank Acc. No. NM_001017920.2, GI:217272871, first referenced 2002, updated 2008.
GenBank Acc. No. NM_001039548.1, GI:88196793, 2004.
GenBank Acc. No. NM_001463.2, GI:38455387, first referenced 1996, updated 2003.
GenBank Acc. No. NM_001565.2, GI:149999381, first referenced 1985, updated 2007.
GenBank Acc. No. NM_001719.2, GI:187608319, first referenced 1990, updated 2008.
GenBank Acc. No. NM_001826.2, GI:206725531, first referenced 1990, updated 2008.
GenBank Acc. No. NM_001878.2, GI:6382069, first referenced 1991, updated 1999.
GenBank Acc. No. NM_003543.3, GI:21264599, first referenced 1997, updated 2002.
GenBank Acc. No. NM_005101.3, GI:193083170, first referenced 1987, updated 2008.
GenBank Acc. No. NM_005192.3, GI:195927023, first referenced 1993, updated 2008.
GenBank Acc. No. NM_005698.2, GI:16445418, first referenced 1997, updated 2001.
GenBank Acc. No. NM_005733.2, GI:195539383, first referenced 1998, updated 2008.
GenBank Acc. No. NM_005832.3, GI:31317293, first referenced 1999, updated 2003.
GenBank Acc. No. NM_006115.3, GI:46249365, first referenced 1997, updated 2004.
GenBank Acc. No. NM_006681.2, GI:195539393, first referenced 1995, updated 2008.
GenBank Acc. No. NM_006820.2, GI:166706908, first referenced 1997, updated 2008.
GenBank Acc. No. NM_006898.4, GI:23510372, first referenced 1989, updated 2002.
GenBank Acc. No. NM_007019.2, GI:32967292, first referenced 1997, updated 2003.
GenBank Acc. No. NM_012112.4, GI:40354199, first referenced 1997, updated 2003.
GenBank Acc. No. NM_013277.3, GI:186910298, first referenced 1997, updated 2008.
GenBank Acc. No. NM_018279.3, GI:89145418, first referenced 1997, updated 2006.
GenBank Acc. No. NM_021955.3, GI:74316012, first referenced 1984, updated 2005.
GenBank Acc. No. NM_022357.3, GI:193211607, first referenced 2003, updated 2008.
GenBank Acc. No. NM_024501.1, GI:13375631, 1989.
GenBank Acc. No. NM_024626.2, GI:99028880, first referenced 2003, updated 2006.
GenBank Acc. No. NM_033445.2, GI:28872747, first referenced 1998, updated 2003.
GenBank Acc. No. NM_152864.2, GI:42476063, first referenced 2001, updated 2004.
GenBank Acc. No. NM_178580.1, GI:30581108, 2001.
GenBank Acc. No. NM_181337.3, GI:198278499, first referenced 1999, updated 2008.
GenBank Acc. No. NM_202003.1, GI:42544160, 1994.
Gorelik, E. et al., Multiplexed Immunobead-based Cytokine Profiling for Early Detection of Ovarian Cancer, Cancer Epidemiology, Biomarkers & Prevention, 14(4):981-987 (2005).
Guo, H.H. et al., Protein tolerance to random amino acid change, Proceedings of the National Academy of Sciences, 101(25):9205-9210 (2004).
Gura, T. Systems for Identifying New Drugs are Often Faulty, Science, 278(5340):1041-1042 (1997).
Hancok et al., Synthetic Peptides for Antibody Production pp. 13-25, Methods in Molecular Biology, 295: Immunochemical Protocols, Third Edition, 2005.
Hannon, G.J., RNA interference, Nature, 418(6894):244-251 (2002).
Hara et al., Cancer Sci, vol. 99(7), pp. 1471-1478, 2008.
Henry, M.D. et al., A Prostate-Specific Membrane Antigen-Targeted Monoclonal Antibody-Chemotherapeutic Conjugate Designed for the Treatment of Prostate Cancer, Cancer Research, 64:7995-8001 (2004).
Huston, J.S. et al., Protein engineering of antibody binding sites: Recovery of specific activity in an anti-digoxin single-chain Fv analogue produced in *Escherichia coli*, Proceedings of the National Academy of Sciences, 85:5879-5883 (1988).
Idusogie, E.E. et al., Mapping of the C1q Biding Sire of Rituxan, a Chimeric Antibody with a Human IgG1 Fc, The Journal of Immunology, 164:4178-4184 (2000).
International Search Report for PCT/CA2012/000296, 6 pages (dated Jul. 18, 2012).
Jain, R.K., Barriers to Drug Delivery in Solid Tumors, Sci Am., vol. 271, pp. 58-65, 1994.
Jemal, A. et al., Cancer Statistics, 2005, CA: A Cancer Journal for Clinicians, 55:10-30 (2005).
Jiang, B. et al., A Novel Peptide Isolated from a Phage Display Peptide Library with Trastuzumab Can Mimic Antigen Epitope of HER-2, The Journal of Biological Chemistry, 280(6):4656-4662 (2005).
Jones, P.T. et al., Replacing the complementarity-determining regions in a human antibody with those from a mouse, Nature, 321(29):522-525 (1986).
Kanapathy Pillai, S.K. et al., Triple-negative breast cancer is associated with EGFR, CK5/6 and c-KIT expression in Malaysian women, BMC Clin. Pathol., 12:18 (2012).

(56) References Cited

OTHER PUBLICATIONS

Kelland, L.R., "Of mice and men": values and liabilities of the athymic nude mouse model in anticancer drug development, European Journal of Cancer, 40:827-836 (2004).
Kelly, R. K. et al., An Antibody-cytotoxic Conjugate BIIB015, is a new targeted therapy for Cripto positive tumours, European Journal of Cancer, vol. 47, pp. 1736-1746, 2011.
Kim, K. et al., Both the epitope specificity and isotype are important in the antitumor effect on monoclonal antibodies against HER-2/neu antigen, International Journal of Cancer, 102:428-434 (2002).
Kipps, T.J. et al., Importance of immunoglobulin isotype in human antibody-dependent, cell-mediated cytotoxicity directed by murine monoclonal antibodies, The Journal of Experimental Medicine, 161:1-17 (1985).
Kozak, K.R. et al., Identification of biomarkers for ovarian cancer using strong anion-exchange ProteinChips: Potential use in diagnosis and prognosis, Proceedings of the National Academy of Sciences, 100:12343-12348 (2003).
Larkin, M.A. et al., Clustal W and Clustal X version 2.0, Bioinformatics, 23(21): 2947-2948 (2007).
Lazar, E. et al., Transforming Growth Factor α: Mutation of Aspartic Acid 47 and Leucine 48 Results in Different Biological Activities, Molecular and Cellular Biology, 8(3):1247-1252 (1988).
Leamon, C.P. et al., Folate-mediated targeting: from diagnostics to drug and gene delivery, Drug Discovery Today, 6(1):44-51 (2001).
Lewis, G.D. et al., Differential responses of human tumor cell lines to anti-p185$^{HER2}$ monoclonal antibodies, Cancer Immunology, Immunotherapy, 37:255-263 (1993).
Li, X. et al., Usage of Monoclonal Antibody BG6 in the Diagnosis and Differential Diagnosis of Breast Cancer, Chinese Journal of Clinical Oncology, 9(6):415-417 (1992) (English abstract).
Li, et al., Genbank Acc. No. AY648683; Jun. 15, 2005.
Liang, et al., Genbank Acc. No. AY436928; Mar. 15, 2004.
Luque, L.E. et al., A Highly Conserved Arginine Is Critical for the Functional Folding of Inhibitor of Apoptosis (IAP) BIR Domains, Biochemistry, 41:13663-13671 (2002).
Masui, H. et al., Mechanism of Antitumor Activity in Mice for Anti-Epidermal Growth Factor Receptor Monoclonal Antibodies with Different Isotypes, Cancer Research, 46:5592-5598 (1986).
MacCallum, R.M. et al. Antibody-antigen Interactions: Contact Analysis and Binding Site Topography, J. Mol. Biol. 262, pp. 732-745, 1996.
McDevitt, M.R. et al., An x-Particle Emitting Antibody ([$^{213}$Bi]J591) for Radioimmunotherapy of Prostate Cancer, Cancer Research, 60:6095-6100 (2000).
McIntosh, M.W. et al., Combining CA I25 and SMR serum markers for diagnosis and early detection of ovarian carcinoma, Gynecologic Oncology 95(1):9-15 (2004).
Menon, U. et al., Prospective Study Using the Risk of Ovarian Cancer Algorithm to Screen for Ovarian Cancer, Journal of Clinical Oncology, 23(31):7919-7926 (2005).
Mor, G. et al., Serum protein markers for early detection of ovarian cancer, Proceedings of the National Academy of Sciences, 102(21):7677-7682 (2005).
Mosmann, T., Rapid Colorimetric Assay for Cellular Growth and Survival: Application to Proliferation and Cytotoxicity Assays, Journal of Immunological Methods, 65:55-63 (1983).
Munodzana, D. et al., Conformational Dependence of *Anaplasma marginale* Major Surface Protein 5 Surface-Exposed B-Cell Epitopes, Infection and Immunity, 66(6):2619-2624 (1998).
NCBI Accession No. M32599.1, first referenced 1990.
NCBI Accession No. NM_001238, first referenced 1991.
NCBI Accession No. NM_003376, 1991.
NCBI Accession No. Q9UBP8, 1999.
NCBI Accession No. X00351, first referenced 1984.
Nicodemus, C.F. et al., Monoclonal antibody therapy of ovarian cancer, Expert Review of Anticancer Therapy, 5(1):87-96 (2005).
Oei, A. L. M., et al., The use of monoclonal antibodies for the treatment of epithelial ovarian cancer (Review), International Journal of Oncology, 32(6):1145-1157 (2008).

Panka, D.J. et al., Variable region framework differences result in decreased or increased affinity of variant anti-digoxin antibodies, Proceedings of the National Academy of Sciences USA, 85:3080-3084 (1988).
Paul, Fundamental Immunology, 3$^{rd}$ Edition, pp. 292-295, 1993.
Pettersen, R.D. et al., CD47 Signals T Cell Death, The Journal of Immunology, 162(12):7031-7040 (1999).
Polyak, M.J. et al., Alanine-170 and proline-172 are critical determinants for extracellular CD20 epitopes; heterogeneity in the fine specificity of CD20 monoclonal antibodies is defined by additional requirements imposed by both amino acid sequence and quaternary structure, Blood, 99(9):3256-3262 (2002).
Portolano, S. et al., Lack of Promiscuity in Autoantigen-Specific H and L Chain Combinations as Revealed by Human H and L Chain "Roulette", The Journal of Immunology, 150:880-887 (1993).
Press, O. et al., Ricin A-chain Containing Immunotoxins Directed Against Different Epitopes on the CD2 Molecule Differ in their Ability to Kill Normal and Malignant T Cells, The Journal of Immunology, 141(12):4410-4417 (1988).
Provencher, D.M. et al., Characterization of Four Novel Epithelial Ovarian Cancer Cell Lines, In Vitro Cellular & Developmental Biology—Animal, 36:357-361 (2000).
Reinecke, P. et al., Multidrug Resistance phenotype and paclitaxel (Taxol) sensitivity in human renal carcinoma cell lines of different histologic types, Cancer Invest., 18(7): 614-625, 2000.
Riemer, A.B. et al., Matching of trastuzumab (Herceptin®) epitope mimics onto the surface of Her-2/neu—a new method of epitope definition, Molecular Immunology, 42:1121-1124 (2005).
Rudikoff, S. et al., Single amino acid substitution altering antigen-binding specificity, Proceedings of the National Academy of Sciences USA, 79:1979-1983 (1982).
Rudnick, S.I. et al., Influence of Affinity and Antigen Internalization on the Uptake and Penetration of Anti-HER2 Antibodies in Solid Tumors, Cancer Research, 71(6):2250-2259 (2011).
Saijo, N. What are the reasons for negative phase III trials of molecular-targeted-based drugs? Cancer Science, 95(10):772-776 (2004).
Samouelian, V. et al., Chemosensitivity and radiosensitivity profiles of four new human epithelial ovarian cancer cell lines exhibiting genetic alterations in BRCA2, TGFβ-RII, KRAS2, TP53 and/or CDNK2A, Cancer Chemotherapy and Pharmacology, 54:497-504 (2004).
Schorge, J.O. et al., Osteopontin as an Adjunct to CA125 in Detecting Recurrent Ovarian Cancer, Clinical Cancer Research, 10:3474-3478 (2004).
Schumacher, J. et al., Strong Genetic Evidence of DCDC2 as a Susceptibility Gene for Dyslexia, The American Journal of Human Genetics, 78(1):52-62 (2006).
Scholler and Urban, CA125 in Ovarian Cancer, Biomark Med 2007, 1(4):513-523.
Seidman, J.D. et al., Surface Epithelial Tumors of the Ovary, *Blaustein's Pathology of the Female Genital Tract*, Kurman, R.J. (Ed.), 5th Ed., New York: Springer-Verlag (2002), pp. 791-904.
Seton-Rogers, L., Breast Cancer: On the origins of tumour subtypes, Nature Reviews: Cancer, vol. 7, 1 page (2007).
Shih, I. et al., Molecular Pathogenesis of Ovarian Borderline Tumors: New Insights and Old Challenges, Clinical Cancer Research, 11(20):7273-7279 (2005).
Simon, I. et al., B7-H4 is a Novel Membrane-Bound Protein and a Candidate Serum and Tissue Biomarker for Ovarian Cancer, Cancer Research, 66(3):1570-1575 (2006).
Skolnick, J. et al., From genes to protein structure and function: novel applications of computational approaches in the genomic era, TIBTech 18:37-39 (2000).
Slingluff, C.L. et al., Melanomas with concordant loss of multiple melanocytic differentiation proteins: immune escape that may be overcome by targeting unique or underfined antigens, Cancer Immunology, Immunotherapy, 48:661-672 (2000).
Stancovski, I. et al., Mechanistic aspect of the opposing effects of monoclonal antibodies to the ERBB2 receptor on tumor growth, The Proceedings of the National Academy of Science in the United States of America, 88:8691-8695 (1991).

(56) References Cited

OTHER PUBLICATIONS

Takada, I. et al., Alteration of a Single Amino Acid in Peroxisome Proliferator-Activated Receptor-α (PPARα) Generates a PPARS Phenotype, Molecular Endocrinology 14(5):733-740 (2000).

Tamura, M. et al., Structural Correlates of an Anticarcinoma Antibody: Identification of Specificity-Determining Residues (SDRs) and Development of a Minimally Immunogenic Antibody Variant by Retention of SDRs Only, The Journal of Immunology, 164:1432-1441 (2000).

Tatusova, T. et al., Blast 2 sequences, a new tool for comparing protein and nucleotide sequences, FEMS Microbiology Letters, 174:247-250 (1999).

Vajdos, F.F., et al., Comprehensive Functional Maps of the Antigen Binding Site of an Anti-Erb2 Antibody Obtained with Shotgun Scanning Mutagenesis, J. Mol. Biol. 320, pp. 415-428, 2002.

Van Den Eynde, B.J. et al., A New Antigen Recognized by Cytolytic T Lymphocytes on a Human Kidney Tumor Results from Reverse Strand transcription, The Journal of Experimental Medicine, 190(12):1793-1799 (1999).

Verhoeyen, M. et al., Reshaping Human Antibodies: Grafting an Antilysozyme Activity, Science, 239:(4847):1534-1535 (1988).

Vogelstein, B. et al., Cancer genes and the pathways they control, Nature Medicine, 10(8):789-799 (2004).

Vucic, D. et al., A Mutational Analysis of the Baculovirus Inhibitor of Apoptosis Op-IAP*, The Journal of Biological Chemistry, 273(51):33915-33921 (1998).

Vuist, W.M.J. et al., Two Distinct Mechanisms of Antitumor Activity Mediated by the Combination of Interleukin 2 and Monoclonal Antibodies, Cancer Research, 50:5767-5772 (1990).

Ward, E.S. et al., Binding activities of a repertoire of single immunoglobulin variable domains secreted from *Escherichia coli*, Nature, 341:544-546 (1989).

Woolas, R.P. et al., Elevation of Multiple Serum Markers in Patients with Stage I Ovarian Cancer, Journal of the National Cancer Institute, 85(21):1748-1751 (1993).

Written Opinion for PCT/CA2009/001586, 8 pages (dated Feb. 2, 2010).

Written Opinion for PCT/CA2013/000011, 9 pages (dated Feb. 6, 2015).

Written Opinion for PCT/CA2012/000296, 7 pages (dated Jul. 18, 2012).

Xu, F. et al., Antibody-induced growth inhibition is mediated through immunochemically and functionally distinct epitopes on the extracellular domain of the c-erbB-2 (HER-2/neu) gene product p185, International Journal of Cancer, 53:401-408 (1993).

Subik, K. et al., The Expression Patterns of ER, PR, HER2, CK5/6, EGFR, Ki-67 and AR by Immunohistochemical Analysis in Breast Cancer Cell Lines, Breast Cancer: Basic and Clinical Research, vol. 4, pp. 35-41, 2010.

Allred, C. D. Issues and Updates: Evaluating Estrogen Receptor-α, progesterone receptor, and HER2 in Breast Cancer, Modern Pathology (2010), 23, S52-S59.

Baccala et al., Expression of Prostate-Specific Membrane Antigen in Tumor-Associated Neovasculature of Rnal Neoplasms, Urology (2007), vol. 70, pp. 385-390.

Foulkes, WD. et al., New England J. Medicine, 2010, vol. 363, pp. 1938-1948.

Chang MH; Karageorgos LE; Meikle PJ., "CD107a (LAMP-1) and CD107b (LAMP-2)", J Biol Regul Homeost Agents, (2002), vol. 16, p. 147-151.

Carter et al., Endocrine-Related Cancer, 2004, 11 :659-687.

Colman, Research in Immunology, 145 :33-36, 1994.

Bendig, Methods: A Companion to Methods in Enzymology, 1995, vol. 8, pp. 83-93.

Khantasup et al., Monoclonal Antibodies in Immunodiagnosis and Immunotherapy, 2015, vol. 34(6), pp. 404-417.

Johnson et al., "The Kabat Database and a Bioinformatics Example," Methods in Molecular Biology, vol. 248, Antibody Engineering: Methods and Protocols, 2004, 11-25.

Ramos-Vara, J.A., "Technical Aspects of Immunohistochemistry," Vet. Pathol., 2005, 42:405-426.

* cited by examiner

| | | |
|---|---|---|
| murine | DVVMTQTPLSLAVSLGDQASISCRSSQSLLHSNGNTYLEWYLQKPGQSPKLLIHTVSNRFSGVPDRFSGSGSGTDFTLKISRVEAEDLGVYYCFQGSHVPLTFGAGTRLELK | 11/80 (86.3%) |
| Humanized1 | DIVMTQTPLSLPVTPGEPASISCRSSQSLLHSNGNTYLEWYLQKPGQSPQLLIYTVSNRFSGVPDRFSGSGSGTDFTLKISRVEAEDVGVYYCFQGSHVPLTFGQGTKLEIK | 0/80 (100%) |
| Humanized2 | DVVMTQTPLSLPVTPGEPASISCRSSQSLLHSNGNTYLEWYLQKPGQSPKLLIYTVSNRFSGVPDRFSGSGSGTDFTLKISRVEAEDVGVYYCFQGSHVPLTFGQGTKLEIK | 2/80 (97.5%) |

CDR-L1   CDR-L2   CDR-L3

| | | |
|---|---|---|
| mouse | QIQLVQSGPEMKKPGASVKMSCKASGYTFTDDYMSWVKQSHGKSLEWIGDINPYNGDTNYNQKFKGKAILTVDKSSSTAYMQLNSLTSEDSAVYYCARDPGAMDYWGQGTSVTVSS | 21/82 (74.4%) |
| Humanized1 | QVQLVQSGAEVKKPGASVKVSCKASGYTFTDDYMSWVRQAPGQGLEWMGDINPYNGDTNYNQKFKGRVTITADTSTSTAYMELSSLRSEDTAVYYCARRPGAMDYWGQGTLVTVSS | 0/82 (100%) |
| Humanized2 | QIQLVQSGAEVKKPGASVKVSCKASGYTFTDDYMSWVRQAPGQGLEWMGDINPYNGDTNYNQKFKGRVTITADKSTSTAYMELSSLRSEDTAVYYCARDPGAMDYWGQGTLVTVSS | 2/82 (97.5%) |
| Humanized3 | QIQLVQSGAEVKKPGASVKVSCKASGYTFTDDYMSWVRQAPGQGLEWIGDINPYNGDTNYNQKFKGRATLTVDKSTSTAYMELSSLRSEDTAVYYCARDPGAMDYWGQGTLVTVSS | 6/82 (92.7%) |
| Humanized4 | QIQLVQSGAEVKKPGASVKVSCKASGYTFTDDYMSWVRQAPGQGLEWIGDINPYNGDTNYNQKFKGKATLTVDKSTSTAYMELSSLRSEDTAVYYCARDPGAMDYWGQGTLVTVSS | 8/82 (90.2%) |

CDR-H1   CDR-H2   CDR-H3

Figure 2a

Variable light chain alignment

```
Mouse VL         DVVMTQTPLSLAVSLGDQASISCRSSQSLLHSNGNTYLEWYLQKPGQSPKLLIHTVSNRF 60
SEQ ID NO.189    DIVMTQTPLSLPVTPGEPASISCRSSQSLLHSNGNTYLEWYLQKPGQSPQLLIYTVSNRF 60
                 *:**********.**:.**:*****************************:***:*****

Mouse VL         SGVPDRFSGSGSGTDFTLKISRVEAEDLGVYYCFQGSHVPLTFGAGTRLELK 112
SEQ ID NO.189    SGVPDRFSGSGSGTDFTLKISRVEAEDVGVYYCFQGSHVPLTFGQGTKLEIK 112
                 ***************************:*************** **:**:*
```

Figure 2b

Variable heavy chain alignment

```
Mouse VH         QIQLVQSGPEMVKPGASVKMSCKASGYTFTDDYMSWVKQSHGKSLEWIGDINPYNGDTNY 60
SEQ ID NO.194    QVQLVQSGAEVKKPGASVKVSCKASGYTFTDDYMSWVRQAPGQGLEWMGDINPYNGDTNY 60
                 *:******.**:*******:*****************:*: *:.***:************

Mouse VH         NQKFKGKAILTVDKSSSTAYMQLNSLTSEDSAVYYCARDPGAMDYWGQGTSVTVSS 116
SEQ ID NO.194    NQKFKGRVTITADTSTSTAYMELSSLRSEDTAVYYCARDPGAMDYWGQGTLVTVSS 116
                 ******:.:*.*. *:*****:*.**.***:******************* *****
```

| Antibody | ka (1/Ms) | kd (1/s) | Kd (nM) | Fold diff. |
|---|---|---|---|---|
| LcHc | 7.72 x 10$^6$ | 1.21 x 10$^{-4}$ | 0.016 | - |
| Lh1Hh1 | 6.93 x 10$^6$ | 3.28 x 10$^{-3}$ | 0.474 | 29.6 |
| Lh2Hh1 | 6.97 x 10$^6$ | 2.37 x 10$^{-3}$ | 0.341 | 21.3 |
| Lh1Hh2 | 5.65 x 10$^6$ | 1.19 x 10$^{-3}$ | 0.211 | 13.2 |
| Lh2Hh2 | 7.40 x 10$^6$ | 1.81 x 10$^{-3}$ | 0.245 | 15.3 |
| Lh1Hh3 | 6.46 x 10$^6$ | 9.60 x 10$^{-4}$ | 0.149 | 9.3 |
| Lh2Hh3 | 4.46 x 10$^6$ | 1.02 x 10$^{-3}$ | 0.228 | 14.3 |
| Lh1Hh4 | 5.14 x 10$^6$ | 7.64 x 10$^{-4}$ | 0.149 | 9.3 |
| Lh2Hh4 | 4.57 x 10$^6$ | 4.70 x 10$^{-4}$ | 0.103 | 6.4 |

Figure 6

METHOD FOR TREATING BREAST CANCER

PRIORITY CLAIM

This patent application is a continuation of U.S. patent application Ser. No. 14/364,937 filed on Jun. 12, 2014, which is a national stage filing under 35 U.S.C. 0.371 of international application No. PCT/CA2013/000011 filed on Jan. 9, 2013, which claimed priority to U.S. Provisional Application No. 61/584,629 filed on Jan. 9, 2012. The entire contents of each of these priority applications are incorporated herein by reference.

SEQUENCE LISTING

In accordance with 37 C.F.R. § 1.52(e)(5), a Sequence Listing in the form of a text file (entitled "113029-0400_SL.txt", created on Oct. 29, 2020 and of 246,853 bytes) is incorporated herein by reference in its entirety.

PARTIES TO A JOINT RESEARCH AGREEMENT

The claimed invention was made by, on behalf of, and/or in connection with one or more of the following parties to a joint research agreement: Alethia Biotherapeutics Inc. and National Research Council of Canada.

BACKGROUND

World wide, greater than 1 million women are diagnosed with breast cancer each year. Breast cancer is a very heterogeneous disease made up of dozens of different types that are distinguished using a histological classification system. A large subtype and a majority of cases are histologically identified as luminal A or luminal B which can be grossly characterized as exhibiting estrogen receptor (ER) expression with low grade or higher grade histology, respectively (Santana-Davila and Perez, 2010). Immunohistochemical methods are used to measure the expression of progesterone receptor (PgR) which, when coupled with ER-positive status allows the classification of a tumor as being hormone responsive. Furthermore, the over-expression or amplification of human epidermal growth factor receptor 2 (HER2) can be monitored either with immunohistochemistry or fluorescence in situ hybridization (FISH). Generally, the expression of these three markers in breast tumors is associated with a better clinical outcome because there are several treatment options available for patients that target these proteins (de Ruijter et al., 2011), including tamoxifen, Arimidex™ (anastrozole), Aromasin™ (exemestane), Femara™ (letrozole), Faslodex™ (fulvestrant), Herceptin™ (trastuzumab) or Tykerb™ (lapatinib).

Another histological subtype of breast cancer consists of the basal-like cancers which are associated with, among others, a higher histological grade, increase mitotic index and high Ki67 expression (Santana-Davila and Perez, 2010). The vast majority of basal-like cancers are comprised of triple-negative breast cancer (TNBC) cases, which make up a between 15-20% of all diagnosed breast cancer cases (Ismail-Khan and Bui, 2010). TNBC is defined by the lack of protein expression of ER, PgR and the absence of HER2 protein over-expression. The relationship between basal-like cancer and TNBC is not easily delineated since not all TNBC are basal-like and not all basal-like cancers are TNBC, but approximately 75% of cases in these categories share characteristics of both. TNBC is associated with poor prognosis consisting of low five-year survival rates and high recurrence.

Patients with TNBC develop their disease earlier in life compared with other breast cancer subtypes and are often diagnoses at the pre-menopausal stage (Carey et al., 2006). Triple-negative breast cancer shows an increased propensity of recurrence after treatment and seem to be more aggressive than other breast carcinoma subtypes (Nofech-Mozes et al., 2009), similar to those of the basal-like breast cancer subtype. Consequently, the overall five-year survival of TNBC patients is significantly lower than those diagnosed with other subtypes of breast cancer. There is currently no acceptable specific molecular marker for TNBC. Despite this lack, these tumors do respond to chemotherapy (Kriege et al., 2009). Patients have shown better response to cytotoxic agents in the adjuvant setting as well as in the neoadjuvant setting when administered agents such as 5-fluorouracil, doxorubicin and cyclophosphamide (Rouzier et al. 2005). Other agents that have shown some efficacy include platinum based compounds such as cisplatin and anti-tubulin compounds such as taxanes (Santana-Davila and Perez, 2010).

As mentioned above, there are no specific targets for TNBC but this has not impeded the trial of target agents such as the inhibition of Poly [ADP-ribose] polymerase 1 (PARP1). PARP1 is an enzyme that participates in the repair of DNA single-strand breaks by associating with corrupted DNA strands and mediating the recruitment of enzymes needed to repair single-strand breaks (de Ruijter et al., 2011). Thus the strategy has been to inhibit PARP1 activity as a means of allowing cancer cells to accumulate more DNA single-strand breaks, which ultimately leads to genetic instability, mitotic arrest and apoptosis. Promising clinical results were achieved in patients that showed mutations in BRCA1 and/or BRCA2, important mediators of genetic maintenance and homologous recombination required for proper cell division. Indeed, patients with BRCA1 mutations, which are presumably deficient in these genetic stability pathways, showed greater response to PARP1 inhibitors compared with those who were wild type for BRCA1 (Fong et al., 2009). It is clear that targeting PARP1 in TNBC patients who are carriers of BRCA mutation represents a promising strategy. The combination of ER/PgR/HER2 status with that of the genetic profile of the BRCA1/2 genes might offer the best characterization for deciding the proper treatment options for TNBC patients.

Other strategies also examined the use of EGFR inhibitors, either as monoclonal antibodies or small molecule inhibitors or anti-angiogenic compounds to target VEGF. Several clinical trials have evaluated the efficacy of these compounds but none of them have shown significant response when administered alone. However, mild efficacy was observed in patients treated with these inhibitors in combination with other cytotoxic agents (Santana-Davila and Perez, 2010).

Notwithstanding the recent advances in the understanding and the treatment for breast cancer, the use of chemotherapy is invariably associated with severe adverse reactions, which limit their use. Consequently, the need for more specific strategies such as combining antigen tissue specificity with the selectivity of monoclonal antibodies should permit a significant reduction in off-target-associated side effects. There are no TNBC specific antigens that are currently under investigation as therapeutic targets for monoclonal antibodies. Thus, TNBC patients have little options because of the inability to target a specific marker of protein that is expressed in these tumors. There are urgent needs to identify new proteins expressed in TNBC for applications as new diagnostic markers and novel targeted therapies.

Kidney associated antigen 1 (KAAG1), the protein sequence which is identified herein as SEQ ID NO.:2, was originally cloned from a cDNA library derived from a histocompatibility leukocyte antigen-B7 renal carcinoma cell line as an antigenic peptide presented to cytotoxic T lymphocytes (Van den Eynde et al., 1999; Genebank accession no. Q9UBP8, the cDNA sequence is represented by nucleotides 738-992 of SEQ ID NO.:1). The locus containing KAAG1 was found to encode two genes transcribed in both directions on opposite strands. The sense strand was found to encode a transcript that encodes a protein termed DCDC2. Expression studies by these authors found that the KAAG1 antisense transcript was tumor specific and exhibited very little expression in normal tissues whereas the DCDC2 sense transcript was ubiquitously expressed (Van den Eynde et al., 1999). The expression of the KAAG1 transcript in cancer, and in particular ovarian cancer, renal cancer, lung cancer, colon cancer, breast cancer and melanoma was disclosed in international application No. PCT/CA2007/001134 published on Dec. 27, 2007 under No. WO 2007/147265. Van den Eynde et al., also observed RNA expression in renal carcinomas, colorectal carcinomas, melanomas, sarcomas, leukemias, brain tumors, thyroid tumors, mammary carcinomas, prostatic carcinomas, oesophageal carcinomas, bladder tumor, lung carcinomas and head and neck tumors. Recently, strong genetic evidence obtained through linkage disequilibrium studies found that the VMP/DCDC2/KAAG1 locus was associated with dyslexia (Schumacher et al., 2006; Cope et al., 2005). One of these reports pointed to the DCDC2 marker as the culprit in dyslexic patients since the function of this protein in cortical neuron migration was in accordance with symptoms of these patients who often display abnormal neuronal migration and maturation (Schumacher et al., 2006).

The Applicant has obtained a panel of antibodies and antigen binding fragment that bind to the KAAG1 protein. These antibodies or antigen binding fragments were shown to target three regions of the protein; amino acids 1 to 35, amino acids 36 to 60 amino acids 61 to 84. The Applicant found that antibodies targeting a region between amino acids 30 to 84 were the most advantageous for therapeutic purposes as they recognized KAAG1 located at the surface of tumor cells. The Applicant has shown that some of these antibodies and antigen binding fragments can mediate antibody-dependent cell cytotoxicity and/or are internalized by tumor cells, which makes them good candidates to deliver a payload to tumor cells. The Applicant has also generated chimeric and humanized antibodies based on selected antibody candidates and has shown that these antibodies can inhibit tumor cell formation and invasion (see PCT/CA2009/001586 published on Jun. 3, 2010 under No. WO2010/060186 and PCT/CA2010/001785 published on May 12, 2011 under No. WO2011/054112). Finally, the Applicant found that these antibodies could be used for the treatment and diagnosis of ovarian cancer, skin cancer, renal cancer, colorectal cancer, sarcoma, leukemia, brain tumor, thyroid tumor, breast cancer, prostate cancer, oesophageal tumor, bladder tumor, lung tumor and head and neck tumor and metastatic form of these cancers.

The Applicant has now come to the unexpected discovery that breast cancer cells lacking ER protein expression, PgR protein expression and/or showing absence of HER2 protein over-expression (i.e., triple-negative breast cancer cells, basal-like) can be efficiently targeted with an antibody or antigen binding fragment that specifically binds to KAAG1. Anti-KAAG1 antibodies may thus be used for the, detection and therapeutic treatment of breast cancer cells that are negative for at least one of these markers.

BRIEF DESCRIPTION OF THE DRAWINGS

FIG. 1a is an amino acid sequence alignment of the 3A4 variable domains of the murine (SEQ ID NO:48), humanized light chain 1 (SEQ ID NO:189) and humanized light chain 2 (SEQ ID NO:190). The light chain has two humanized variants (Lh1 an Lh2). The CDRs are shown in bold and indicated by CDRL1, CDRL2 and CDRL3. Back mutations in the human framework regions that are murine amino acids are underlined in the humanized sequences.

FIG. 1b is an amino acid sequence alignment of the 3A4 variable domains of the murine (SEQ ID NO: 46), humanized heavy chain 1 (SEQ ID NO:194), humanized heavy chain 2 (SEQ ID NO:195), humanized heavy chain 3 (SEQ ID NO:196) and humanized heavy chain 4 (SEQ ID NO:197). The heavy chain has four humanized variants (Hh1 to Hh4). The CDRs are shown in bold and indicated by CDRH1, CDRH2 and CDRH3. Back mutations in the human framework regions that are murine amino acids are underlined in the humanized sequences.

FIG. 2a is an alignment of murine 3A4 light chain variable region (SEQ ID NO.: 48 with a light chain variable region variant (SEQ ID NO.:189) using the ClustalW2 program (Larkin M. A., et al., (2007) ClustalW and ClustalX version 2. *Bioinformatics* 2007 23(21): 2947-2948) where an "*" (asterisk) indicates positions which have a single, fully conserved residue, wherein ":" (colon) indicates conservation between groups of strongly similar properties–scoring>0.5 in the Gonnet PAM 250 matrix and where "." (period) indicates conservation between groups of weakly similar properties–scoring=<0.5 in the Gonnet PAM 250 matrix.

FIG. 2b is an alignment of murine 3A4 heavy chain variable region (SEQ ID NO.:) with a heavy chain variable region variant (SEQ ID NO.:194) using the ClustalW2 program (Larkin M. A., et al., (2007) ClustalW and ClustalX version 2. *Bioinformatics* 2007 23(21): 2947-2948) where an "*" (asterisk) indicates positions which have a single, fully conserved residue, wherein ":" (colon) indicates conservation between groups of strongly similar properties–scoring>0.5 in the Gonnet PAM 250 matrix and where "." (period) indicates conservation between groups of weakly similar properties–scoring=<0.5 in the Gonnet PAM 250 matrix.

FIG. 6 is a Table listing the rate and affinity constants for the murine and humanized variants of the 3A4 antibody.

SUMMARY OF THE INVENTION

Figure 3A:
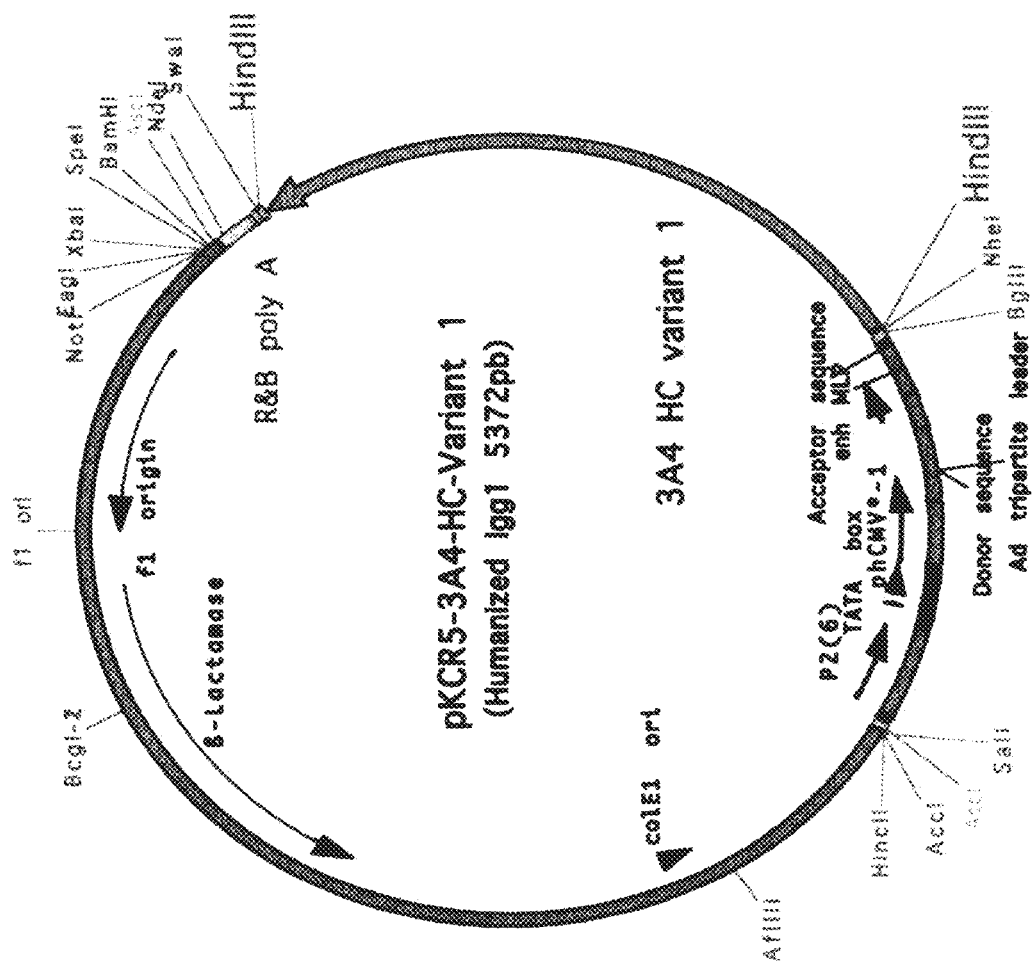
FIG. 3a represents plasmid map of pKCR5-3A4-HC-Variant 1. The heavy chains of the humanized 3A4 variants were cloned in the same manner into the HindIII site of pK-CR5. Consequently the resulting plasmids are identical to pKCR5-3A4-HC variant 1 except for the sequence of the heavy chain immunoglobulin variable domain.

The present invention provides a method of treating or detecting cancer or cancer cells (in vitro or in vivo) in an individual in need.

In accordance with the present invention, methods of treatment or detection may be carried out with an antibody capable of binding to KAAG1 or an antigen binding fragment thereof.

The individual in need may comprise, for example, an individual having or suspected of having cancer. Such individual may have a cancer or cancer cells originating from a breast carcinoma.

The cancer or cancer cells may more particularly originate from a breast carcinoma characterized as being triple-negative or basal-like.

Therefore, the individuals who may benefit from methods of treatment or detection described herein may include those suffering from breast carcinoma.

The breast carcinoma may comprise tumors cells showing a decrease or a lost in the expression of the estrogen receptor.

The breast carcinoma may comprise tumor cells showing a decrease or a lost in the expression of the progesterone receptor.

The breast carcinoma may comprise tumor cells showing a decrease or a lost in the expression of Her2.

The breast carcinoma may comprise tumor cells showing a decrease or a lost in Her2 overexpression.

More particularly, the breast carcinoma may comprise tumor cells showing either 1) a decrease or a loss in expression of the estrogen receptor and the progesterone receptor, 2) a decrease or a loss in expression of the estrogen receptor and a decrease or a loss of Her2 overexpression, 3) a decrease or a loss in expression of the progesterone receptor and a decrease or a loss of Her2 overexpression or 4) a decrease or a loss in expression of the estrogen receptor, a decrease or a loss in expression of the progesterone receptor and a decrease or a loss of Her2 overexpression.

Even more particularly, the breast carcinoma may comprise tumor cells showing either 1) a loss in expression of the estrogen receptor and the progesterone receptor, 2) a loss in expression of the estrogen receptor and a loss of Her2 expression, 3) a loss in expression of the progesterone receptor and a loss of Her2 expression or 4) a loss in expression of the estrogen receptor, a loss in expression of the progesterone receptor and a loss of Her2 expression.

In accordance with the present invention, the individual may carry breast cancer cells that are characterized as being triple-negative or may have a tumor categorized as being a triple-negative breast cancer.

In accordance with the present invention, the individual may carry breast cancer cells that are characterized as basal-like, or may have a tumor categorized as being a basal-like breast cancer.

Other individuals who would benefit from treatment with an anti-AAG1 include those having carcinoma comprising tumors cells exhibiting an epithelial-to-mesenchymal transition (EMT) phenotype.

Commonly used molecular markers of EMT include, for example, a reduced expression of E-cadherin, cytokeratin and β-catenin (in the membrane) and/or an increased expression of Snail, Slug, Twist, ZEB1, ZEB2, N-cadherin, vimentin, α-smooth muscle actin, matrix metalloproteinases etc. (see for example, Kalluri and Weinberg, The Journal of Clinical Investigation, 119(6), p 1420-1428; 2009; Fassina et al., Modern Pathology, 25; p 86-99; 2012; Lee et al., JCB; 172; p 973-981; 2006). An EMT phenotype may also be distinguished by an increased capacity for migration, invasion of by resistance to anoikis/apoptosis. Cells that are are undergoing epithelia-to-mesenchymal transition may thus be detected by a reduction of epithelial markers and apparition of mesenchymal markers or EMT phenotypes.

In accordance with the present invention, the method may thus comprise, for example, administering an antibody or antigen binding fragment which is capable of specific binding to KAAG1 to an individual in need. The individual in need is preferentially selected on the basis of their tumor lacking ER expression, PgR expression and/or by the absence of HER2 protein over-expression. Clinical testing for these markers is usually performed using histopathologic methods (immunohistochemistry, FISH, etc.) and/or by gene expression studies (see for example Dent et al, 2007, Bernstein and Lacey, 2011). The individual in need may thus be an individual who has received a diagnosis of triple-negative breast cancer or basal-like breast cancer. The individual in need may be an individual which is unresponsive to hormonal therapy and/or to transtuzumab therapy (or other anti-Her2 antibodies). Alternatively, the individual in need may be an individual carrying tumor cells that have the ability of undergoing epithelial-to-mesenchymal transition or that have acquired a mesenchymal phenotype.

The present invention thus provides a method of treating triple-negative breast cancer or basal-like breast cancer by administering an inhibitor of KAAG1 activity or expression to an individual in need.

In accordance with the present invention, the KAAG1 inhibitor may thus comprise an antibody described herein or an antigen binding fragment thereof.

Also in accordance with the present invention, the KAAG1 inhibitor may comprise a nucleotide sequence complementary to SEQ ID NO.:1 or to a fragment thereof. More particularly, the KAAG1 inhibitor may comprise a nucleotide sequence complementary to nucleotides 738 to 992 (inclusively) of SEQ ID NO.:1 or to a fragment thereof. For example, the inhibitor may include at least 10 consecutive nucleotides (at least 15, at least 20) which are complementary to SEQ ID NO.:1 or to nucleotides 738 to 992 (inclusively) of SEQ ID NO.:1. More particular type of KAAG1 inhibitor includes a siRNA which inhibit expression of SEQ ID NO.:1.

Suitable antibodies or antigen binding fragments include those that are capable of binding to KAAG1 at the surface of tumor cells. Such antibodies or antigen binding fragments thereof may preferentially bind an epitope included within amino acids 30 to 84 of KAAG1 inclusively.

Alternatively such antibodies or antigen binding fragments thereof may bind an epitope located within amino acids 36 to 60 (inclusively) or within amino acids 61 to 84 (inclusively) of KAAG1.

The epitope may particularly be located or comprised within amino acids 50 to 70, 50 to 65, 51 to 65, 52 to 65, 53 to 65, 54 to 65, 54 to 64, 54 to 63, 54 to 62, 54 to 61, 54 to 60, 50 to 62; 50 to 61, or 50 to 60 (inclusively or exclusively).

In accordance with an embodiment of the invention, the antibody or antigen binding fragment may bind an epitope comprised within amino acids 50 to 70 of KAAG1.

In a further embodiment of the invention, the antibody or antigen binding fragment may bind an epitope comprised within amino acids 50 to 62 of KAAG1.

In yet a further embodiment, the antibody or antigen binding fragment may bind an epitope comprised within amino acids 54 to 65 of KAAG1.

Suitable antibodies for therapeutic treatment include for example, those which mediate antibody-dependent cell cytotoxicity.

Other even more suitable antibodies for therapeutic treatment include those that are conjugated with a therapeutic moiety.

In accordance with the present invention, the antibody may be, for example, a monoclonal antibody, a chimeric antibody, a humanized antibody a human antibody or an antigen binding fragment thereof.

DETAILED DESCRIPTION OF THE INVENTION

Method of Treatment

As indicated herein, the present invention encompass administering an antibody or antigen binding fragment to an individual having a breast cancer characterized as being "triple negative breast cancer" or "basal-like breast cancer".

Classification of breast cancer subtypes as being "triple negative breast cancer" or "basal-like breast cancer" is known in the art (see for example, Foulkes et al, N. Engl. J. Med., 2010; 363:1938-1948) and includes, for example, the following definitions:

"Basal-like breast cancer", may include for example, a subtype of breast cancer comprising a heterogenous group of tumors characterized by the absence of or low levels of expression of estrogen receptors, very low prevalence of Her2 overexpression and expression of genes usually found in the basal or myoepithelial cells of the human breast. Such expression may be determined by microarray analysis.

"Triple-negative breast cancer", may include for example, a tumor characterized by lack of estrogen receptor (ER), progesterone receptor (PR) and Her2 expression. Some investigators accept tumors as being negative for expression of ER or PR only if less than 1% of the cells are positive for ER or PR expression; others consider tumors to be negative for ER or PR expression when up to 10% of cells are positive for expression. Different definitions of HER2-negativity have been used. The two most frequently adopted include tumors with immunohistochemical scores of 0/1+ or 2+ that are lacking HER2 gene amplification after in situ hybridization. Such expression may be especially determined by immunohistochemical staining.

In accordance with the present invention, the method of treatment includes administering a KAAG1 inhibitor to an individual in need. Such KAAG1 inhibitor includes, for example, an antibody or antigen binding fragment thereof which specifically binds to KAAG1.

It is likely that the most potent antibodies or antigen binding fragments may be those having a high affinity for KAAG1. It is also likely that the most potent antibodies or antigen binding fragments may be those that are internalized within a cells compartment such as, for example, a lysosome or an endosome.

As such, the present invention especially encompasses antibodies or antigen binding fragments having a high affinity for KAAG1.

Suitable antibodies or antigen binding fragments include those that are capable of binding to KAAG1 at the surface of tumor cells with a high affinity. Such high affinity antibodies or antigen binding fragments thereof may preferentially bind an epitope included within amino acids 30 to 84 of KAAG1 inclusively.

Alternatively such high affinity antibodies or antigen binding fragments thereof may bind an epitope located within amino acids 36 to 60 (inclusively) or within amino acids 61 to 84 (inclusively) of KAAG1.

The high affinity antibodies or antigen binding fragments may bind, for example, an epitope may particularly be located or comprised within amino acids 50 to 70, 50 to 65, 51 to 65, 52 to 65, 53 to 65, 54 to 65, 54 to 64, 54 to 63, 54 to 62, 54 to 61, 54 to 60, 50 to 62; 50 to 61, or 50 to 60 (inclusively or exclusively).

In accordance with an embodiment of the invention, the high affinity antibody or antigen binding fragment may bind an epitope comprised within amino acids 50 to 70 of KAAG1.

In a further embodiment of the invention, the high affinity antibody or antigen binding fragment may bind an epitope comprised within amino acids 50 to 62 of KAAG1.

In yet a further embodiment, the high affinity antibody or antigen binding fragment may bind an epitope comprised within amino acids 54 to 65 of KAAG1.

Preferred antibodies including high affinity antibodies are those than may be internalized in a cell or cell compartment (e.g., lysosomes or endosomes). The ability of antibodies to be internalized may be determined by method known in the art such as for example and without limitation, by immunofluorescence studies similar to those performed herein.

Antibodies having CDRs identical to those of the 3A4 antibodies are particularly encompassed by the present invention. As such, antibodies having a light chain variable region and/or heavy chain variable region consensus sequences set forth in any of SEQ ID NOs.:186 to 188 and 191 to 193 and specific sequences set forth in SEQ ID No.:46, 48, 189, 190, or 194 to 198 are encompassed by the present invention. Among those, antibodies having a light chain variable region and/or heavy chain variable region consensus sequences set forth in any of SEQ ID NO.: 188 and 196 or specific sequences set forth in SEQ ID NO.:46, 48, 189, 190, or 194 to 198 are particularly contemplated.

The antibodies or antigen binding fragments thereof may preferably be conjugated with a therapeutic moiety.

The antibodies or antigen binding fragments thereof, may have a human constant region. Preferably the antibodies or antigen binding fragments thereof may have a human IgG1 constant region. Alternatively, the antibodies or antigen binding fragments thereof may have an IgG2 constant region.

The method of the present invention may also include administering a KAAG1 inhibitor such as an antibody (e.g., conjugated with a therapeutic moiety) or antigen binding fragment in combination with an anticancer agent such as for example, a small molecule drug, an antibody or antigen binding fragment binding to a target other than KAAG1, a chemotherapeutic or a cytotoxic agent. Example of anticancer agent that could be administered with the KAAG1 inhibitor may include for example, doxorubicin, taxanes, anti-angiogenic agents, platinum salts, PARP inhibitors.

Other methods of treatment encompassed by the present invention include administering other types of KAAG1 inhibitors such as antisense-based therapeutics (siRNA, antisenses, ribozymes, etc.).

Antibodies and Antigen Binding Fragments that Binds to KAAG1

The term "antibody or antigen binding fragment" or similar terms such as "antibodies and antigen binding fragments" encompasses, for example "variant antibody or antigen binding fragment" such as, for example, "humanized antibody or antigen binding fragment".

The term "antibody" refers to intact antibody, monoclonal or polyclonal antibodies. The term "antibody" also encompasses multispecific antibodies such as bispecific antibodies. Human antibodies are usually made of two light chains and two heavy chains each comprising variable regions and constant regions. The light chain variable region comprises 3 CDRs, identified herein as CDRL1, CDRL2 and CDRL3 flanked by framework regions. The heavy chain variable region comprises 3 CDRs, identified herein as CDRH1, CDRH2 and CDRH3 flanked by framework regions.

The term "antigen-binding fragment", as used herein, refers to one or more fragments of an antibody that retain the ability to bind to an antigen (e.g., KAAG1, secreted form of KAAG1 or variants thereof). It has been shown that the antigen-binding function of an antibody can be performed by fragments of an intact antibody. Examples of binding fragments encompassed within the term "antigen-binding fragment" of an antibody include (i) a Fab fragment, a monovalent fragment consisting of the $V_L$, $V_H$, $C_L$ and $C_{H1}$ domains: (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR), e.g., $V_H$ CDR3. Furthermore, although the two domains of the Fv fragment, $V_L$ and $V_H$, are coded for by separate genes, they can be joined, using recombinant methods, by a synthetic linker that enables them to be made as a single polypeptide chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding fragment" of an antibody. Furthermore, the antigen-binding fragments include binding-domain immunoglobulin fusion proteins comprising (i) a binding domain polypeptide (such as a heavy chain variable region, a light chain variable region, or a heavy chain variable region fused to a light chain variable region via a linker peptide) that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The hinge region may be modified by replacing one or more cysteine residues with serine residues so as to prevent dimerization. Such binding-domain immunoglobulin fusion proteins are further disclosed in US 2003/0118592 and US 2003/0133939. These antibody fragments are obtained using conventional techniques known to those with skill in the art, and the fragments are screened for utility in the same manner as are intact antibodies.

A typical antigen binding site is comprised of the variable regions formed by the pairing of a light chain immunoglobulin and a heavy chain immunoglobulin. The structure of the antibody variable regions is very consistent and exhibits very similar structures. These variable regions are typically comprised of relatively homologous framework regions (FR) interspaced with three hypervariable regions termed Complementarity Determining Regions (CDRs). The overall binding activity of the antigen binding fragment is often dictated by the sequence of the CDRs. The FRs often play a role in the proper positioning and alignment in three dimensions of the CDRs for optimal antigen binding.

As used herein the term "high affinity" refers to an affinity of 10 nM or less. The term "high affinity" especially includes antibodies having an affinity of 5 nM or less. The term "high affinity" even more particularly includes antibodies having an affinity of 1 nM or less, or 0.1 nM or less.

Antibodies and/or antigen binding fragments of the present invention may originate, for example, from a mouse, a rat or any other mammal or from other sources such as through recombinant DNA technologies.

An-KAAG1 antibodies were initially isolated from Fab libraries for their specificity towards the antigen of interest. Exemplary methods on how to convert Fab into full immunoglobulins are provided herein.

The variable regions described herein may be fused with constant regions of a desired species thereby allowing recognition of the antibody by effector cells of the desired species. The constant region may originate, for example, from an IgG1, IgG2, IgG3, or IgG4 subtype. Cloning or synthesizing a constant region in frame with a variable region is well within the scope of a person of skill in the art and may be performed, for example, by recombinant DNA technology.

In certain embodiments of the present invention, antibodies that bind to KAAG1 may be of the IgG1, IgG2, IgG3, or IgG4 subtype. More specific embodiments of the invention relates to an antibody of the IgG1 subtype or especially human IgG1 subtype. Other specific embodiments of the invention relates to an antibody of the IgG2 subtype or especially of the human IgG2 subtype.

The antibody may be a humanized antibody of the IgG1 subtype subtype or especially human IgG1 subtype. Alternatively, the antibody may be a humanized antibody of the IgG2 subtype or especially of the human IgG2 subtype.

The antibody may be, for example, biologically active in mediating antibody-dependent cellular cytotoxicity (ADCC), complement-mediated cytotoxicity (CMC), or associated with immune complexes. The typical ADCC involves activation of natural killer (NK) cells and is reliant on the recognition of antibody-coated cells by Fc receptors on the surface of the NK cells. The Fe receptors recognize the Fc domain of antibodies such as present on IgG1, which bind to the surface of a target cell, in particular a cancerous cell that expresses an antigen, such as KAAG1. Once bound to the Fc receptor of IgG the NK cell releases cytokines and cytotoxic granules that enter the target cell and promote cell death by triggering apoptosis.

The present invention described a collection of antibodies that bind to KAAG1 or to a KAAG1 variant. In certain embodiments, the antibodies may be selected from the group consisting of polyclonal antibodies, monoclonal antibodies such as chimeric or humanized antibodies, antibody fragments such as antigen binding fragments, single chain antibodies, domain antibodies, and polypeptides with an antigen binding region.

In an aspect of the invention, the isolated antibody or antigen binding fragment of the present invention may be capable of inducing killing (elimination, destruction, lysis) of KAAG1-expressing tumor cells or KAAG1 variant-expressing tumor cells (e.g., in an ADCC-dependent manner).

In a further aspect of the invention, the isolated antibody or antigen binding fragment of the present invention may especially be characterized by its capacity of reducing spreading of tumor cells expressing KAAG1 or a KAAG1 variant.

In an additional aspect of the invention, the isolated antibody or antigen binding fragment of the present invention may be characterized by its capacity of decreasing or impairing formation of tumors expressing KAAG1 or a KAAG1 variant.

In an exemplary embodiment of the invention, the isolated antibody or antigen binding fragment may comprise amino acids of a constant region, which may originate, for example, from a human antibody.

In another exemplary embodiment of the invention, the isolated antibody or antigen binding fragment may comprise framework amino acids of a human antibody.

Without being limited to the exemplary embodiments presented herein, the Applicant as generated specific antibodies and antigen binding fragments that may be useful for the purposes described herein.

The following is a list of antibodies that were generated and shown to bind in a specific manner to KAAG1; 3D3, 3A4, 3C4, 3G10, 3A2, 3F6, 3E8, 3E10, 3A9, 3B1, 3G5, 3B2, 3B8, 3G8, 3F7, 3E9, 3G12, 3C3, 3E12, 4A2, 3F10, 3F4, 3B11, 3D1, 3C2, 3E6 and 3H3. Sequences of the antibody light chain or heavy chain, variable regions or complementary determining regions (CDRs) are available in international application No. PCT/CA2009/001586 published on Jun. 3, 2010 under No. WO2010/060186A8, in international application No. PCT/CA2010/001795 published on May 12, 2011 under No. WO2011/054112A1 or in international application No. PCT/CA2012/000296 published on Oct. 4, 2012 under No. WO2012/129668A1.

In most instances, the sequence of the CDRs has been provided separately or is shown in bold herein.

Amongst, these antibodies, the 3D3, 3A4, 3G10 and 3C4 were selected for in vitro and/or in vivo biological testing. The 3A4 antibody appeared to have the best characteristics. Based on our experiments, the 3A4 antibody when conjugated with a therapeutic moiety (e.g. a cytotoxic agent) is more effective in killing cancer cells than its non-conjugated version.

In an exemplary embodiment, the antibody or antigen binding fragment may comprise any individual CDR or a combination of CDR1, CDR2 and/or CDR3 of the light chain variable region. The CDR3 may more particularly be selected. Combination may include for example, CDRL1 and CDRL3; CDRL1 and CDRL2; CDRL2 and CDRL3 and; CDRL1, CDRL2 and CDRL3.

In another exemplary embodiment, the antibody or antigen binding fragment may comprise any individual CDR or a combination of CDR1, CDR2 and/or CDR3 of the heavy chain variable region. The CDR3 may more particularly be selected. Combination may include for example, CDRH1 and CDRH3; CDRH1 and CDRH2; CDRH2 and CDRH3 and; CDRH1, CDRH2 and CDRH3.

In accordance with the present invention, the antibody or antigen binding fragment may comprise at least two CDRs of a CDRL1, a CDRL2 or a CDRL3.

Also in accordance with the present invention, the antibody or antigen binding fragment may comprise one CDRL1, one CDRL2 and one CDRL3.

Further in accordance with the present invention, the antibody or antigen binding fragment may comprise:
 a. At least two CDRs of a CDRL1, CDRL2 or CDRL3 and;
 b. At least two CDRs of a CDRH1, one CDRH2 or one CDRH3.

The antibody or antigen binding fragment may more preferably comprise one CDRL1, one CDRL2 and one CDRL3.

The antibody or antigen binding fragment may also more preferably comprise one CDRH1, one CDRH2 and one CDRH3.

When only one of the light chain variable region or the heavy chain variable region is available, an antibody or antigen-binding fragment may be reconstituted by screening a library of complementary variable regions using methods known in the art (Portolano et al. The Journal of Immunology (1993) 150:880-887, Clarkson et al., Nature (1991) 352:624-628).

Exemplary embodiments of the present invention encompass antibodies or antigen binding fragments having the CDRs of the light chain and/or heavy chains of the 3D3, 3A4, 3C4, 3G10, 3A2, 3F6, 3E8, 3E10, 3A9, 381, 3G5, 3B2, 3B8, 3G8, 3F7, 3E9, 3G12, 3C3, 3E12, 4A2, 3F10, 3F4, 3811, 3D1, 3C2, 3E6 or 3H3 antibodies. More particular embodiments of the invention include antibodies or antigen binding fragments having the CDRs of the light chain and/or heavy chains of the 3D3, 3A4, 304 or 3G10 antibodies. Even more particular embodiments of the invention include antibodies or antigen binding fragments having the CDRs of the light chain and/or heavy chains of the 3A4 antibody. The invention thus encompassed any monoclonal, chimeric, human, or humanized antibody comprising one or more CDRs of the 3A4 antibody.

Antibodies or antigen binding fragments that may be used in methods of the present invention, include those having CDRs of the 3A4 antibody and may comprise, for example, a CDRH1 as set forth in SEQ ID NO.:49, a CDRH2 as set forth in SEQ ID NO.:50 or in SEQ ID NO.:212, a CDRH3 as set forth in SEQ ID NO.:51, a CDRL1 as set forth in SEQ ID NO.: 52, a CDRL2 as set forth in SEQ ID NO.:53 and a CDRL3 as set forth in SEQ ID NO.: 54.

The present invention therefore encompass, antibodies and antigen binding fragment which are capable of specific binding to KAAG1 and which may comprise sequences selected from the group consisting of:
 a. the 3CDRs of a light chain variable region defined in SEQ ID NO.:16 and/or the 3CDRs of a heavy chain variable region defined in SEQ ID NO.:18,
 b. the 3CDRs of a light chain variable region defined in SEQ ID NO.:20 and/or the 3CDRs of a heavy chain variable region defined in SEQ ID NO.:22;
 c. the 3CDRs of a light chain variable region defined in SEQ ID NO.:24 and/or the 3CDRs of a heavy chain variable region defined in SEQ ID NO.:26;
 d. the 3CDRs of a light chain variable region defined in SEQ ID NO.:48 and/or the 3CDRs of a heavy chain variable region defined in SEQ ID NO.:46;
 e. the 3CDRs of a light chain variable region defined in SEQ ID NO.:103 and/or the 3CDRs of a heavy chain variable region defined in SEQ ID NO.:126,
 f. the 3CDRs of a light chain variable region defined in SEQ ID NO.:104 and/or the 3CDRs of a heavy chain variable region defined in SEQ ID NO.:127,
 g. the 3CDRs of a light chain variable region defined in SEQ ID NO.:105 and/or the 3CDRs of a heavy chain variable region defined in SEQ ID NO.:128,
 h. the 3CDRs of a light chain variable region defined in SEQ ID NO.:106 and/or the 3CDRs of a heavy chain variable region defined in SEQ ID NO.:145,
 i. the 3CDRs of a light chain variable region defined in SEQ ID NO.:107 and/or the 3CDRs of a heavy chain variable region defined in SEQ ID NO.:129,
 j. the 3CDRs of a light chain variable region defined in SEQ ID NO.:108 and/or the 3CDRs of a heavy chain variable region defined in SEQ ID NO.:130,
 k. the 3CDRs of a light chain variable region defined in SEQ ID NO.:109 and/or the 3CDRs of a heavy chain variable region defined in SEQ ID NO.:141,
 l. the 3CDRs of a light chain variable region defined in SEQ ID NO.:110 and/or the 3CDRs of a heavy chain variable region defined in SEQ ID NO.:131,
 m. the 3CDRs of a light chain variable region defined in SEQ ID NO.: 111 and/or the 3CDRs of a heavy chain variable region defined in SEQ ID NO.:134,
 n. the 3CDRs of a light chain variable region defined in SEQ ID NO.:112 and/or the 3CDRs of a heavy chain variable region defined in SEQ ID NO.:135,
 o. the 3CDRs of a light chain variable region defined in SEQ ID NO.:113 and/or the 3CDRs of a heavy chain variable region defined in SEQ ID NO.:136,
 p. the 3CDRs of a light chain variable region defined in SEQ ID NO.:114 and/or the 3CDRs of a heavy chain variable region defined in SEQ ID NO.:133,
 q. the 3CDRs of a light chain variable region defined in SEQ ID NO.:115 and/or the 3CDRs of a heavy chain variable region defined in SEQ ID NO.:140,
 r. the 3CDRs of a light chain variable region defined in SEQ ID NO.:116 and/or the 3CDRs of a heavy chain variable region defined in SEQ ID NO.:137,
 s. the 3CDRs of a light chain variable region defined in SEQ ID NO.:117 and/or the 3CDRs of a heavy chain variable region defined in SEQ ID NO:144,
 t. the 3CDRs of a light chain variable region defined in SEQ ID NO.:118 and/or the 3CDRs of a heavy chain variable region defined in SEQ ID NO.:139,
 u. the 3CDRs of a light chain variable region defined in SEQ ID NO.:119 and/or the 3CDRs of a heavy chain variable region defined in SEQ ID NO.:132,
 v. the 3CDRs of a light chain variable region defined in SEQ ID NO.:120 and/or the 3CDRs of a heavy chain variable region defined in SEQ ID NO.:142,
 w. the 3CDRs of a light chain variable region defined in SEQ ID NO.:121 and/or the 3CDRs of a heavy chain variable region defined in SEQ ID NO.:138,
 x. the 3CDRs of a light chain variable region defined in SEQ ID NO.:122 and/or the 3CDRs of a heavy chain variable region defined in SEQ ID NO.:146, y. the 3CDRs of a light chain variable region defined in SEQ ID NO.:123 and/or the 3CDRs of a heavy chain variable region defined in SEQ ID NO.:153,
z. the 3CDRs of a light chain variable region defined in SEQ ID NO.:124 and/or the 3CDRs of a heavy chain variable region defined in SEQ ID NO.:143,
aa. the 3CDRs of a light chain variable region defined in SEQ ID NO.:189 and/or the 3CDRs of a heavy chain variable region defined in SEQ ID NO.:194,
bb. the 3CDRs of a light chain variable region defined in SEQ ID NO.:189 and/or the 3CDRs of a heavy chain variable region defined in SEQ ID NO.:195,
cc. the 3CDRs of a light chain variable region defined in SEQ ID NO.:189 and/or the 3CDRs of a heavy chain variable region defined in SEQ ID NO.:196,
dd. the 3CDRs of a light chain variable region defined in SEQ ID NO.:189 and/or the 3CDRs of a heavy chain variable region defined in SEQ ID NO.:197,
ee. the 3CDRs of a light chain variable region defined in SEQ ID NO.:190 and/or the 3CDRs of a heavy chain variable region defined in SEQ ID NO.:194,
ff. the 3CDRs of a light chain variable region defined in SEQ ID NO.:190 and/or the 3CDRs of a heavy chain variable region defined in SEQ ID NO.:195,
gg. the 3CDRs of a light chain variable region defined in SEQ ID NO.:190 and/or the 3CDRs of a heavy chain variable region defined in SEQ ID NO.:196, or
hh. the 3CDRs of a light chain variable region defined in SEQ ID NO.:190 and/or the 3CDRs of a heavy chain variable region defined in SEQ ID NO.:197.

Other exemplary embodiments of the invention encompass antibodies or antigen binding fragments having the light chain and/or heavy chains of the 3D3, 3A4, 3C4, 3G10, 3A2, 3F6, 3E8, 3E10, 3A9, 3B, 3G5, 3B2, 3B8, 3G8, 3F7, 3E9, 3G12, 3C3, 3E12, 4A2, 3F10, 3F4, 3B11, 3D1, 3C2, 3E6 or 3H3 antibodies. More particular embodiments of the invention include antibodies or antigen binding fragments having the light chain and/or heavy chains of the 3D3, 3A4, 3C4 or 3G10 antibodies. Even more particular embodiments of the invention include antibodies or antigen binding fragments having the light chain and/or heavy chains of the 3A4 antibody (humanized and non-humanized).

The present invention therefore encompass, antibodies and antigen binding fragment which are capable of specific binding to KAAG1 and which may comprise sequences selected from the group consisting of:
a. the light chain variable region defined in SEQ ID NO.:16 (encoded by SEQ ID NO.:15) and/or the heavy chain variable region defined in SEQ ID NO.:18 (encoded by SEQ ID NO.:17),
b. the light chain variable region defined in SEQ ID NO.:20 (encoded by SEQ ID NO.:19) and/or the heavy chain variable region defined in SEQ ID NO.:22 (encoded by SEQ ID NO.:21):
c. the light chain variable region defined in SEQ ID NO.:24 (encoded by SEQ ID NO.:23) and/or the heavy chain variable region defined in SEQ ID NO.:26 (encoded by SEQ ID NO.:25);
d. the light chain variable region defined in SEQ ID NO.:48 and/or the heavy chain variable region defined in SEQ ID NO.:46,
e. the light chain variable region defined in SEQ ID NO.:103 and/or the heavy chain variable region defined in SEQ ID NO.:126,
f. the light chain variable region defined in SEQ ID NO.:104 and/or the heavy chain variable region defined in SEQ ID NO.:127,
g. the light chain variable region defined in SEQ ID NO.:105 and/or the heavy chain variable region defined in SEQ ID NO.:128,
h. the light chain variable region defined in SEQ ID NO.:106 and/or the heavy chain variable region defined in SEQ ID NO.:145,
i. the light chain variable region defined in SEQ ID NO.:107 and/or the heavy chain variable region defined in SEQ ID NO.:129,
j. the light chain variable region defined in SEQ ID NO.:108 and/or the heavy chain variable region defined in SEQ ID NO.:130,
k. the light chain variable region defined in SEQ ID NO.:109 and/or the heavy chain variable region defined in SEQ ID NO.:141,
l. the light chain variable region defined in SEQ ID NO.:110 and/or the heavy chain variable region defined in SEQ ID NO.:131,
m. the light chain variable region defined in SEQ ID NO.:111 and/or the heavy chain variable region defined in SEQ ID NO.:134,
n. the light chain variable region defined in SEQ ID NO.:112 and/or the heavy chain variable region defined in SEQ ID NO.:135,
o. the light chain variable region defined in SEQ ID NO.:113 and/or the heavy chain variable region defined in SEQ ID NO.:140,
p. the light chain variable region defined in SEQ ID NO.:114 and/or the heavy chain variable region defined in SEQ ID NO.:133,
q. the light chain variable region defined in SEQ ID NO.:115 and/or the heavy chain variable region defined in SEQ ID NO.:140,
r. the light chain variable region defined in SEQ ID NO.:116 and/or the heavy chain variable region defined in SEQ ID NO.:137,
s. the light chain variable region defined in SEQ ID NO.:117 and/or the heavy chain variable region defined in SEQ ID NO.:144,
t. the light chain variable region defined in SEQ ID NO.:118 and/or the heavy chain variable region defined in SEQ ID NO.:139,
u. the light chain variable region defined in SEQ ID NO.:119 and/or the heavy chain variable region defined in SEQ ID NO.:132,
v. the light chain variable region defined in SEQ ID NO.:120 and/or the heavy chain variable region defined in SEQ ID NO.:142,
w. the light chain variable region defined in SEQ ID NO.:121 and/or the heavy chain variable region defined in SEQ ID NO.:138,
x. the light chain variable region defined in SEQ ID NO.:122 and/or the heavy chain variable region defined in SEQ ID NO.:146,
y. the light chain variable region defined in SEQ ID NO.:123 and/or the heavy chain variable region defined in SEQ ID NO.:147;
z. the light chain variable region defined in SEQ ID NO.:124 and/or the heavy chain variable region defined in SEQ ID NO.:144;
aa. the light chain variable region defined in SEQ ID NO.:189 and/or the heavy chain variable region defined in SEQ ID NO.:194,
bb. the light chain variable region defined in SEQ ID NO.:189 and/or the heavy chain variable region defined in SEQ ID NO.:195, cc. the light chain variable region defined in SEQ ID NO.:190 and/or the heavy chain variable region defined in SEQ ID NO.:194, dd. the light chain variable region defined in SEQ ID NO.:190 and/or the heavy chain variable region defined in SEQ ID NO.:195, ee. the light chain variable region defined in SEQ ID NO.:190 and/or the heavy chain variable region defined in SEQ ID NO.:196, or ff. the light chain variable region defined in SEQ ID NO.:190 and/or the heavy chain variable region defined in SEQ ID NO.:197.

The framework region of the heavy and/or light chains described herein may be derived from one or more of the framework regions illustrated in the antibodies described herein. The antibody or antigen binding fragments may thus comprise one or more of the CDRs described herein (e.g., selected from the specific CDRs or consensus CDRs of SEQ ID NO.:72 to 88 or CDR variants of SEQ ID NO.:89-102) and framework regions originating from those described herein. In SEQ ID Nos. 103-154, the expected CDRs are shown in bold, while the framework regions are not.

Table 1 refers to the complete sequences of light and heavy chain of some of the anti-KAAG1 antibodies which were selected for biological testing.

TABLE 1

| Antibody designation | Chain type | Nucleotide sequence (SEQ ID NO.:) | Amino acid sequence (SEQ ID NO.:) |
|---|---|---|---|
| 3D3 | Light (L) | 3 | 4 |
| 3D3 | Heavy (H) | 5 | 6 |
| 3G10 | Light | 7 | 8 |
| 3G10 | Heavy | 9 | 10 |
| 3C4 | Light | 11 | 12 |
| 3C4 | Heavy | 13 | 14 |
| Humanized 3D3 | Light | | 166 |
| Humanized 3D3 | Heavy | | 167 |
| Humanized 3C4 | Light | | 170 |
| Humanized 3C4 | Heavy | | 171 |
| Humanized 3A4 | Light (Lh1) | | 199 |
| Humanized 3A4 | Light (Lh2) | | 200 |
| Humanized 3A4 | Heavy (Hh1) | | 202 |
| Humanized 3A4 | Heavy (Hh2) | | 203 |
| Humanized 3A4 | Heavy (Hh3) | | 204 |
| Humanized 3A4 | Heavy (Hh4) | | 205 |

Epitope mapping studies revealed that the 3D3 antibody interacts with a KAAG1 epitope spanned by amino acids 36-60, inclusively. The 3G10 and 3A4 antibodies interact with a KAAG1 epitope spanned by amino acids 61-84, inclusively and the 3C4 antibody interacts with a KAAG1 epitope spanned by amino acids 1-35. Although, the 3G10 and 3A4 binds a similar region, the 3G10 antibody does not bind to KAAG1 as efficiently as the 3A4 antibody.

It is to be understood herein, that the light chain variable region of the specific combination provided above may be changed for any other light chain variable region. Similarly, the heavy chain variable region of the specific combination provided above may be changed for any other heavy chain variable region.

Sequences of light and heavy chain variable regions of selected antibodies that bind to KAAG1 are disclosed in Table 2

TABLE 2

| Ab. designation | Variable region type | Nucleotide (SEQ ID NO.:) | Amino acid (SEQ ID NO.:) |
|---|---|---|---|
| 3D3 | Light (VL) | 15 | 16 |
| 3D3 | Heavy (VH) | 17 | 18 |
| 3G10 | Light | 19 | 20 |
| 3G10 | Heavy | 21 | 22 |
| 3C4 | Light | 23 | 24 |
| 3C4 | Heavy | 25 | 26 |
| 3A2 | Light | | 103 |
| 3A2 | Heavy | | 126 |
| 3E10 | Light | | 106 |
| 3E10 | Heavy | | 145 |
| 3G12 | Light | | 121 |
| 3G12 | Heavy | | 138 |
| 3A4 | Light | 47 | 48 |
| 3A4 | Heavy | 45 | 46 |
| Humanized 3D3 | Light | | 168 |
| Humanized 3D3 | Heavy | | 169 |
| Humanized 3C4 | Light | | 172 |
| Humanized 3C4 | Heavy | | 173 |
| Humanized 3A4 | Light (Lvh1) | | 189 |
| Humanized 3A4 | Light (Lvh2) | | 190 |
| Humanized 3A4 | Heavy (Hvh1) | | 194 |
| Humanized 3A4 | Heavy (Hvh2) | | 195 |
| Humanized 3A4 | Heavy (Hvh3) | | 197 |
| Humanized 3A4 | Heavy (Hvh4) | | 198 |

SEQ ID NOs. 103-154 correspond to the light chain and heavy chain variable regions of other antibodies which were shown to bind KAAG1.

CDR sequence of the light and heavy chain variable regions of selected antibodies that bind to KAAG1 are disclosed in Table 3.

TABLE 3

| Ab. designation | Chain type | CDR | SEQ ID NO.: | a.a sequence |
|---|---|---|---|---|
| 3D3 | Light (L) | CDR L1 | 27 | KSSQSLLNSNFQKNFLA |
| 3D3 | Light | CDR L2 | 28 | FASTRES |
| 3D3 | Light | CDR L3 | 29 | QQHYSTPLT |
| 3D3 | Heavy (H) | CDR H1 | 30 | GYIFTDYEIH |
| 3D3 | Heavy | CDR H2 | 31 | VIDPETGNTA |
| 3D3 | Heavy | CDR H3 | 32 | MGYSDY |
| 3G10 | Light | CDR L1 | 33 | RSSQSLLHSNGNTYLE |
| 3G10 | Light | CDR L2 | 34 | KVSNRFS |
| 3G10 | Light | CDR L3 | 35 | FQGSHVPLT |
| 3G10 | Heavy | CDR H1 | 36 | GYTFTDNYMN |
| 3G10 | Heavy | CDR H2 | 37 | DINPYYGTTT |
| 3G10 | Heavy | CDR H3 | 38 | ARDDWFDY |
| 3C4 | Light | CDR L1 | 39 | KASQDIHNFLN |
| 3C4 | Light | CDR L2 | 40 | RANRLVD |
| 3C4 | Light | CDR L3 | 41 | LQYDEIPLT |
| 3C4 | Heavy | CDR H1 | 42 | GFSITSGYGWH |
| 3C4 | Heavy | CDR H2 | 43 | YINYDGHND |
| 3C4 | Heavy | CDR H3 | 44 | ASSYDGLFAY |

TABLE 3-continued

| Ab. designation | Chain type | CDR | SEQ ID NO. | a.a sequence |
|---|---|---|---|---|
| 3A2 | Light | CDR L1 | 148 | KSSQSLLHSDGKTYLN |
| 3A2 | Light | CDR L2 | 149 | LVSKLDS |
| 3A2 | Light | CDR L3 | 150 | WQGTHFPRT |
| 3A2 | Heavy | CDR H1 | 151 | GYTFTD YNMH |
| 3A2 | Heavy | CDR H2 | 152 | YINPYNDVTE |
| 3A2 | Heavy | CDR H3 | 153 | AWFGL RQ |
| 3E10 | Light | CDR L1 | 154 | RSSKSLLHSNGN TYLY |
| 3E10 | Light | CDR L2 | 155 | RMSNLAS |
| 3E10 | Light | CDR L3 | 156 | MQHLEYPYT |
| 3E10 | Heavy | CDR H1 | 157 | GDTFTD YYMN |
| 3E10 | Heavy | CDR H2 | 158 | DINPNYGGIT |
| 3E10 | Heavy | CDR H3 | 159 | QAYYRNS DY |
| 3G12 | Light | CDR L1 | 160 | KASQDVGTAVA |
| 3G12 | Light | CDR L2 | 161 | WTSTRHT |
| 3G12 | Light | CDR L3 | 162 | QQHYSIPLT |
| 3G12 | Heavy | CDR H1 | 163 | GYIFTDYEIH |
| 3G12 | Heavy | CDR H2 | 164 | VIDPETGNTA |
| 3G12 | Heavy | CDR H3 | 165 | MGYSDY |
| 3A4 | Light | CDR L1 | 52 | RSSQSLLHSNGNTYLE |
| 3A4 | Light | CDR L2 | 53 | TVSNRFS |
| 3A4 | Light | CDR L3 | 54 | FQGSHVPLT |
| 3A4 | Heavy | CDR H1 | 49 | GYTFTDDYMS |
| 3A4 | Heavy | CDR H2 | 50 or 212 | DINPYNGDTNYNQKFKG or DINPYNGDTN |
| 3A4 | Heavy | CDR H3 | 51 | DPGAMDY |

Variant Antibody and Antigen Binding Fragments

The present invention also encompasses variants of the antibodies or antigen binding fragments described herein. Variant antibodies or antigen binding fragments included are those having a variation in the amino acid sequence. For example, variant antibodies or antigen binding fragments included are those having at least one variant CDR (two, three, four, five or six variant CDRs, etc. or even twelve variant CDRs), a variant light chain variable region, a variant heavy chain variable region, a variant light chain and/or a variant heavy chain. Variant antibodies or antigen binding fragments included in the present invention are those having, for example, similar or improved binding affinity in comparison with the original antibody or antigen binding fragment.

As used herein the term "variant" applies to any of the sequence described herein and includes for example, a variant CDR (either CDRL1, CDRL2, CDRL3, CDRH1, CDRH2 and/or CDRH3), a variant light chain variable region, a variant heavy chain variable region, a variant light chain, a variant heavy chain, a variant antibody, a variant antigen binding fragment and a KAAG1 variant.

The sites of greatest interest for substitutional mutagenesis include the hypervariable regions (CDRs), but modifications in the framework region or even in the constant region are also contemplated. Exemplary embodiments of CDR variants are provided in SEQ ID NOs.: 72-102.

Conservative substitutions may be made by exchanging an amino acid (of a CDR, variable chain, antibody, etc.) from one of the groups listed below (group 1 to 6) for another amino acid of the same group.

Other exemplary embodiments of conservative substitutions are shown in Table 1A under the heading of "preferred substitutions". If such substitutions result in a undesired property, then more substantial changes, denominated "exemplary substitutions" in Table 1A, or as further described below in reference to amino acid classes, may be introduced and the products screened.

It is known in the art that variants may be generated by substitutional mutagenesis and retain the biological activity of the polypeptides of the present invention. These variants have at least one amino acid residue in the amino acid sequence removed and a different residue inserted in its place. For example, one site of interest for substitutional mutagenesis may include a site in which particular residues obtained from various species are identical. Examples of substitutions identified as "conservative substitutions" are shown in Table 1A. If such substitutions result in a change not desired, then other type of substitutions, denominated "exemplary substitutions" in Table 1A, or as further described herein in reference to amino acid classes, are introduced and the products screened.

Substantial modifications in function or immunological identity are accomplished by selecting substitutions that differ significantly in their effect on maintaining (a) the structure of the polypeptide backbone in the area of the substitution, for example, as a sheet or helical conformation. (b) the charge or hydrophobicity of the molecule at the target site, or (c) the bulk of the side chain. Naturally occurring residues are divided into groups based on common side chain properties:

(group 1) hydrophobic: norleucine, methionine (Met), Alanine (Ala), Valine (Val), Leucine (Leu), Isoleucine (Ile)
(group 2) neutral hydrophilic: Cysteine (Cys), Serine (Ser), Threonine (Thr)
(group 3) acidic: Aspartic acid (Asp), Glutamic acid (Glu)
(group 4) basic: Asparagine (Asn), Glutamine (Gin), Histidine (His), Lysine (Lys), Arginine (Arg)
(group 5) residues that influence chain orientation: Glycine (Gly), Proline (Pro); and
(group 6) aromatic: Tryptophan (Trp), Tyrosine (Tyr), Phenylalanine (Phe)

Non-conservative substitutions will entail exchanging a member of one of these classes for another.

TABLE 1A

Amino acid substitution

| Original residue | Exemplary substitution | Conservative substitution |
|---|---|---|
| Ala (A) | Val, Leu, Ile | Val |
| Arg (R) | Lys, Gln, Asn | Lys |
| Asn (N) | Gln, His, Lys, Arg, Asp | Gln |
| Asp (D) | Glu, Asn | Glu |
| Cys (C) | Ser, Ala | Ser |
| Gln (Q) | Asn; Glu | Asn |
| Glu (E) | Asp, Gln | Asp |
| Gly (G) | Ala | Ala |
| His (H) | Asn, Gln, Lys, Arg, | Arg |

TABLE 1A-continued

Amino acid substitution

| Original residue | Exemplary substitution | Conservative substitution |
|---|---|---|
| Ile (I) | Leu, Val, Met, Ala, Phe, norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala, Tyr | Tyr |
| Pro (P) | Ala | Ala |
| Ser (S) | Thr | Thr |
| Thr (T) | Ser | Ser |
| Trp (W) | Tyr, Phe | Tyr |
| Tyr (Y) | Trp, Phe, Thr, Ser | Phe |
| Val (V) | Ile, Leu, Met, Phe, Ala, Norleucine | Leu |

Variation in the amino acid sequence of the variant antibody or antigen binding fragment may include an amino acid addition, deletion, insertion, substitution etc., one or more modification in the backbone or side-chain of one or more amino acid, or an addition of a group or another molecule to one or more amino acids (side-chains or backbone).

Variant antibody or antigen binding fragment may have substantial sequence similarity and/or sequence identity in its amino acid sequence in comparison with that the original antibody or antigen binding fragment amino acid sequence. The degree of similarity between two sequences is based upon the percentage of identities (identical amino acids) and of conservative substitution.

Generally, the degree of similarity and identity between variable chains has been determined herein using the Blast2 sequence program (Tatiana A. Tatusova, Thomas L. Madden (1999), "Blast 2 sequences—a new tool for comparing protein and nucleotide sequences", FEMS Microbiol Lett. 174:247-250) using default settings, i.e., blastp program, BLOSUM62 matrix (open gap 11 and extension gap penalty 1; gapx dropoff 50, expect 10.0, word size 3) and activated filters.

Percent identity will therefore be indicative of amino acids which are identical in comparison with the original peptide and which may occupy the same or similar position. Percent similarity will be indicative of amino acids that are identical and those that are replaced with conservative amino acid substitution in comparison with the original peptide at the same or similar position.

Variants of the present invention therefore comprise those which may have at least 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity with an original sequence or a portion of an original sequence.

Exemplary embodiments of variants are those having at least 81% sequence identity to a sequence described herein and 81%, 82%, 83%, 84%, 85%, 86%, 87%, 88%, 89%, 90%, 91%, 92%, 93%, 94%, 95%, 96%, 97%, 98%, 99% or 100% sequence similarity with an original sequence or a portion of an original sequence.

Other exemplary embodiments of variants are those having at least 82% sequence identity to a sequence described herein and 82%, 83%, 84%, 85%, 86%, 87%, 88%, 89%, 90%, 91%, 92%, 93%, 94%, 95%, 96%, 97%, 98%, 99% or 100% sequence similarity with an original sequence or a portion of an original sequence.

Further exemplary embodiments of variants are those having at least 85% sequence identity to a sequence described herein and 85%, 86%, 87%, 88%, 89%, 90%, 91%, 92%, 93%, 94%, 95%, 96%, 97%, 98%, 99% or 100% sequence similarity with an original sequence or a portion of an original sequence.

Other exemplary embodiments of variants are those having at least 90% sequence identity to a sequence described herein and 90%, 91%, 92%, 93%, 94%, 95%, 96%, 97%, 98%, 99% or 100% sequence similarity with an original sequence or a portion of an original sequence.

Additional exemplary embodiments of variants are those having at least 95% sequence identity to a sequence described herein and 95%, 96%, 97%, 98%, 99% or 100% sequence similarity with an original sequence or a portion of an original sequence.

Yet additional exemplary embodiments of variants are those having at least 97% sequence identity to a sequence described herein and 97%, 98%, 99% or 100% sequence similarity with an original sequence or a portion of an original sequence.

For a purpose of concision the applicant provides herein a Table 18 illustrating exemplary embodiments of individual variants encompassed by the present invention and comprising the specified % sequence identity and % sequence similarity. Each "X" is to be construed as defining a given variant.

TABLE 1B

| | | Percent (%) sequence identity | | | | | | | | | | | | | | | | | | | |
|---|---|---|---|---|---|---|---|---|---|---|---|---|---|---|---|---|---|---|---|---|---|
| | | 80 | 81 | 82 | 83 | 84 | 85 | 86 | 87 | 88 | 89 | 90 | 91 | 92 | 93 | 94 | 95 | 96 | 97 | 98 | 99 | 100 |
| Percent (%) | 80 | X | | | | | | | | | | | | | | | | | | | | |
| | 81 | X | X | | | | | | | | | | | | | | | | | | | |
| | 82 | X | X | X | | | | | | | | | | | | | | | | | | |
| | 83 | X | X | X | X | | | | | | | | | | | | | | | | | |
| | 84 | X | X | X | X | X | | | | | | | | | | | | | | | | |
| | 85 | X | X | X | X | X | X | | | | | | | | | | | | | | | |
| | 86 | X | X | X | X | X | X | X | | | | | | | | | | | | | | |
| | 87 | X | X | X | X | X | X | X | X | | | | | | | | | | | | | |
| | 88 | X | X | X | X | X | X | X | X | X | | | | | | | | | | | | |
| | 89 | X | X | X | X | X | X | X | X | X | X | | | | | | | | | | | |
| | 90 | X | X | X | X | X | X | X | X | X | X | X | | | | | | | | | | |
| | 91 | X | X | X | X | X | X | X | X | X | X | X | X | | | | | | | | | |
| | 92 | X | X | X | X | X | X | X | X | X | X | X | X | X | | | | | | | | |
| | 93 | X | X | X | X | X | X | X | X | X | X | X | X | X | X | | | | | | | |
| | 94 | X | X | X | X | X | X | X | X | X | X | X | X | X | X | X | | | | | | |
| | 95 | X | X | X | X | X | X | X | X | X | X | X | X | X | X | X | X | | | | | |

TABLE 1B-continued

| | | 80 | 81 | 82 | 83 | 84 | 85 | 86 | 87 | 88 | 89 | Percent (%) sequence identity 90 | 91 | 92 | 93 | 94 | 95 | 96 | 97 | 98 | 99 | 100 |
|---|---|---|---|---|---|---|---|---|---|---|---|---|---|---|---|---|---|---|---|---|---|---|
| | 96 | X | X | X | X | X | X | X | X | X | X | X | X | X | X | X | X | X | | | | |
| | 97 | X | X | X | X | X | X | X | X | X | X | X | X | X | X | X | X | X | X | | | |
| | 98 | X | X | X | X | X | X | X | X | X | X | X | X | X | X | X | X | X | | X | | |
| | 99 | X | X | X | X | X | X | X | X | X | X | X | X | X | X | X | X | X | | | X | |
| | 100 | X | X | X | X | X | X | X | X | X | X | X | X | X | X | X | X | X | X | X | X | X |

The present invention encompasses CDRs, light chain variable regions, heavy chain variable regions, light chains, heavy chains, antibodies and/or antigen binding fragments which comprise at least 70% identity or at least 80% identity with the sequence described herein.

The present invention therefore encompass, antibodies and antigen binding fragment which are capable of specific binding to KAAG1 and which may comprise sequences selected from the group consisting of:

a. a light chain variable region having at least 70% sequence identity with SEQ ID NO.:16 and a heavy chain variable region having at least 70% sequence identity with SEQ ID NO.:18,
b. a light chain variable region having at least 70% sequence identity with SEQ ID NO.:20 and a heavy chain variable region having at least 70% sequence identity with SEQ ID NO.:22;
c. a light chain variable region having at least 70% sequence identity with SEQ ID NO.:24 and a heavy chain variable region having at least 70% sequence identity with SEQ ID NO.:26;
d. a light chain variable region having at least 70% sequence identity with SEQ ID NO.:48 and a heavy chain variable region having at least 70% sequence identity with SEQ ID NO.:46;
e. a light chain variable region having at least 70% sequence identity with SEQ ID NO.:103 and a heavy chain variable region having at least 70% sequence identity with SEQ ID NO.:126,
f. a light chain variable region having at least 70% sequence identity with SEQ ID NO.:104 and a heavy chain variable region having at least 70% sequence identity with SEQ ID NO.:127,
g. a light chain variable region having at least 70% sequence identity with SEQ ID NO.:105 and a heavy chain variable region having at least 70% sequence identity with SEQ ID NO.:128,
h. a light chain variable region having at least 70% sequence identity with SEQ ID NO.:106 and a heavy chain variable region having at least 70% sequence identity with SEQ ID NO.:145,
i. a light chain variable region having at least 70% sequence identity with SEQ ID NO.:107 and a heavy chain variable region having at least 70% sequence identity with SEQ ID NO.:128,
j. a light chain variable region having at least 70% sequence identity with SEQ ID NO.:108 and a heavy chain variable region having at least 70% sequence identity with SEQ ID NO.:130,
k. a light chain variable region having at least 70% sequence identity with SEQ ID NO.:109 and a heavy chain variable region having at least 70% sequence identity with SEQ ID NO.:141,
l. a light chain variable region having at least 70% sequence identity with SEQ ID NO.:110 and a heavy chain variable region having at least 70% sequence identity with SEQ ID NO.:131,
m. a light chain variable region having at least 70% sequence identity with SEQ ID NO.:111 and a heavy chain variable region having at least 70% sequence identity with SEQ ID NO.:134,
n. a light chain variable region having at least 70% sequence identity with SEQ ID NO.:112 and a heavy chain variable region having at least 70% sequence identity with SEQ ID NO.:135,
o. a light chain variable region having at least 70% sequence identity with SEQ ID NO.:113 and a heavy chain variable region having at least 70% sequence identity with SEQ ID NO.:136,
p. a light chain variable region having at least 70% sequence identity with SEQ ID NO.:114 and a heavy chain variable region having at least 70% sequence identity with SEQ ID NO.:133,
q. a light chain variable region having at least 70% sequence identity with SEQ ID NO.:115 and a heavy chain variable region having at least 70% sequence identity with SEQ ID NO.:140,
r. a light chain variable region having at least 70% sequence identity with SEQ ID NO.:116 and a heavy chain variable region having at least 70% sequence identity with SEQ ID NO.:137,
s. a light chain variable region having at least 70% sequence identity with SEQ ID NO.:117 and a heavy chain variable region having at least 70% sequence identity with SEQ ID NO.:144,
t. a light chain variable region having at least 70% sequence identity with SEQ ID NO.:118 and a heavy chain variable region having at least 70% sequence identity with SEQ ID NO.:139,
u. a light chain variable region having at least 70% sequence identity with SEQ ID NO.:119 and a heavy chain variable region having at least 70% sequence identity with SEQ ID NO.:132,
v. a light chain variable region having at least 70% sequence identity with SEQ ID NO.:120 and a heavy chain variable region having at least 70% sequence identity with SEQ ID NO.:142,
w. a light chain variable region having at least 70% sequence identity with SEQ ID NO.:121 and a heavy chain variable region having at least 70% sequence identity with SEQ ID NO.:138,
x. the light chain variable region having at least 70% sequence identity with SEQ ID NO.:122 and a heavy chain variable region having at least 70% sequence identity with SEQ ID NO.:146,
y. a light chain variable region having at least 70% sequence identity with SEQ ID NO.:123 and a heavy chain variable region having at least 70% sequence identity with SEQ ID NO.:147, or;

z. a light chain variable region having at least 70% sequence identity with SEQ ID NO.:124 and a heavy chain variable region having at least 70% sequence identity with SEQ ID NO.:143.

In accordance with the present invention, the variant antibodies or antigen binding fragments may comprise CDRs that are identical to those of the corresponding light chain and/or heavy chain variable region. In other instance the variant antibodies or antigen binding fragments may comprise variant CDR(s).

Therefore, exemplary embodiments of a variant antibody or antigen binding fragment of the present invention are those comprising a light chain variable region comprising a sequence which is at least 70%, 75%, 80% identical to SEQ ID NOs.:16, 20, 24, 103, 106 or 121. The CDRs of such variant may be identical to those of the corresponding non-variant (wild type sequence) antibody or antigen binding fragment or may vary by 1-3 amino acids.

Another exemplary embodiment of a variant antibody light chain variable region encompasses a light chain variable region having CDR amino acid sequences that are 100% identical to the CDR amino acid sequence of SEQ ID NO.:16 and having for example from 1 to 22 amino acid modifications (e.g., conservative or non-conservative amino acid substitutions) in its framework region in comparison with the framework region of SEQ ID NO.:16. A SEQ ID NO.:16 variant is provided in SEQ ID NO:168.

An exemplary embodiment of a variant antibody light chain variable region encompasses a light chain variable region having CDR amino acid sequences that are 100% identical to the CDR amino acid sequence of SEQ ID NO.:20 and having for example from 1 to 22 amino acid modifications (e.g., conservative or non-conservative amino acid substitutions) in its framework region in comparison with the framework region of SEQ ID NO.:20.

An exemplary embodiment of a variant antibody light chain variable region encompasses a light chain variable region having CDR amino acid sequences that are 100% identical to the CDR amino acid sequence of SEQ ID NO.:24 and having for example from 1 to 21 amino acid modifications (e.g., conservative or non-conservative amino acid substitutions) in its framework region in comparison with the framework region of SEQ ID NO.:24. A SEQ ID NO.:24 variant is provided in SEQ ID NO.:172.

An exemplary embodiment of a variant antibody light chain variable region encompasses a light chain variable region having CDR amino acid sequences that are 100% identical to the CDR amino acid sequence of SEQ ID NO.:103 and having for example from 1 to 22 amino acid modifications (e.g., conservative or non-conservative amino acid substitutions) in its framework region in comparison with the framework region of SEQ ID NO.:103.

An exemplary embodiment of a variant antibody light chain variable region encompasses a light chain variable region having CDR amino acid sequences that are 100% identical to the CDR amino acid sequence of SEQ ID NO.:106 and having for example from 1 to 22 amino acid modifications (e.g., conservative or non-conservative amino acid substitutions) in its framework region in comparison with the framework region of SEQ ID NO.:106.

An exemplary embodiment of a variant antibody light chain variable region encompasses a light chain variable region having CDR amino acid sequences that are 100% identical to the CDR amino acid sequence of SEQ ID NO.:121 and having for example from 1 to 21 amino acid modifications (e.g., conservative or non-conservative amino acid substitutions) in its framework region in comparison with the framework region of SEQ ID NO.:121.

In some instances, the variant antibody light chain variable region may comprise amino acid deletions or additions (in combination or not with amino acid substitutions). Often 1, 2, 3, 4 or 5 amino acid deletions or additions may be tolerated.

Other exemplary embodiments of a variant antibody or antigen binding fragment of the present invention are those comprising a heavy chain variable region comprising a sequence which is at least 70%, 75%, 80% identical to 18, 22, 26, 126, 138 or 145. The CDRs of such variant may be identical to those of the corresponding non-variant (wild type sequence) antibody or antigen binding fragment or may vary by 1-3 amino acids.

An exemplary embodiment of a variant antibody heavy chain variable region encompasses a heavy chain variable region having CDR amino acid sequences that are 100% identical to the CDR amino acid sequence of SEQ ID NO.:18 and having, for example, from 1 to 22 amino acid modifications (e.g., conservative or non-conservative amino acid substitutions) in its framework region in comparison with the framework region of SEQ ID NO.:18. A SEQ ID NO.:18 variant is provided in SEQ ID NO.:169.

An exemplary embodiment of a variant antibody heavy chain variable region encompasses a heavy chain variable region having CDR amino acid sequences that are 100% identical to the CDR amino acid sequence of SEQ ID NO.:22 and having, for example, from 1 to 23 amino acid modifications (e.g., conservative or non-conservative amino acid substitutions) in its framework region in comparison with the framework region of SEQ ID NO.:22.

An exemplary embodiment of a variant antibody heavy chain variable region encompasses a heavy chain variable region having CDR amino acid sequences that are 100% identical to the CDR amino acid sequence of SEQ ID NO.:26 and having, for example, from 1 to 23 amino acid modifications (e.g., conservative or non-conservative amino acid substitutions) in its framework region in comparison with the framework region of SEQ ID NO.:26. A SEQ ID NO.:26 variant is provided in SEQ ID NO.:173.

An exemplary embodiment of a variant antibody heavy chain variable region encompasses a heavy chain variable region having CDR amino acid sequences that are 100% identical to the CDR amino acid sequence of SEQ ID NO.:126 and having, for example, from 1 to 23 amino acid modifications (e.g., conservative or non-conservative amino acid substitutions) in its framework region in comparison with the framework region of SEQ ID NO.:126.

An exemplary embodiment of a variant antibody heavy chain variable region encompasses a heavy chain variable region having CDR amino acid sequences that are 100% identical to the CDR amino acid sequence of SEQ ID NO.:145 and having, for example, from 1 to 23 amino acid modifications (e.g., conservative or non-conservative amino acid substitutions) in its framework region in comparison with the framework region of SEQ ID NO.:145.

An exemplary embodiment of a variant antibody heavy chain variable region encompasses a heavy chain variable region having CDR amino acid sequences that are 100% identical to the CDR amino acid sequence of SEQ ID NO.:138 and having, for example, from 1 to 22 amino acid modifications (e.g., conservative or non-conservative amino acid substitutions) in its framework region in comparison with the framework region of SEQ ID NO.:138.

In some instances, the variant antibody heavy chain variable region may comprise amino acid deletions or additions (in combination or not with amino acid substitutions). Often 1, 2, 3, 4 or 5 amino acid deletions or additions may be tolerated.

Variant CDRS

Also encompassed by the present invention are polypeptides, antibodies or antigen binding fragments comprising variable chains having at least one conservative amino acid substitution in at least one of the CDRs described herein (in comparison with the original CDR).

The present invention also encompasses are polypeptides, antibodies or antigen binding fragments comprising variable chains having at least one conservative amino acid substitution in at least two of the CDRs (in comparison with the original CDRs).

The present invention also encompasses are polypeptides, antibodies or antigen binding fragments comprising variable chains having at least one conservative amino acid substitution in the 3 CDRs (in comparison with the original CDRs).

The present invention also encompasses are polypeptides, antibodies or antigen binding fragments comprising variable chains having at least two conservative amino acid substitutions in at least one of the CDRs (in comparison with the original CDRs).

The present invention also encompasses are polypeptides, antibodies or antigen binding fragments comprising variable chains having at least two conservative amino acid substitutions in at least two of the CDRs (in comparison with the original CDRs).

The present invention also encompasses are polypeptides, antibodies or antigen binding fragments comprising variable chains having at least two conservative amino acid substitutions in the 3 CDRs (in comparison with the original CDRs).

Comparison of the amino acid sequences of the light chain variable regions or the heavy chain variable regions of antibodies showing the greatest characteristics allowed us to derive consensus sequences within the CDRs and within the variable regions. The consensus for CDRs are provided in SEQ ID Nos: 72 to 88.

The present invention therefore provides in an exemplary embodiment, an isolated antibody or antigen binding fragment comprising a light chain variable region having;
a. a CDRL1 sequence selected from the group consisting of SEQ ID NO.:72 and SEQ ID NO.:73;
b. a CDRL2 sequence selected from the group consisting of SEQ ID NO.:74, SEQ ID NO.: 75 and SEQ ID NO.:76, or;
c. a CDRL3 sequence selected from the group consisting of SEQ ID NO.:77, SEQ ID NO.:78 and SEQ ID NO.:79.

The present invention therefore provides in an exemplary embodiment, an isolated antibody or antigen binding fragment comprising a heavy chain variable region having;
a. a CDRH1 sequence comprising SEQ ID NO.:80;
b. a CDRH2 sequence selected from the group consisting of SEQ ID NO.:81, SEQ ID NO.:82, SEQ ID NO.:83, SEQ ID NO.:84 and SEQ ID NO.:85, or,
c. a CDRH3 sequence selected from the group consisting of SEQ ID NO.:86, SEQ ID NO.:87 and SEQ ID NO.:88.

In accordance with the present invention, the antibody may comprise a CDRL1 sequence comprising or consisting of formula:

$$X_{1a}SSX_{2a}SLLX_{3a}X_{4a}X_{5a}X_{6a}X_{7a}X_{8a}X_{9a}X_{10a}LX_{11a}$$ (SEQ ID NO.: 72)

wherein $X_{1a}$ may be a basic amino acid;
wherein $X_{2a}$ may be a basic amino acid;
wherein $X_{3a}$ may be H, Y or N;
wherein $X_{4a}$ may be S, T, N or R;
wherein $X_{5a}$ may be absent, S or N;
wherein $X_{6a}$ may be D, F or N;
wherein $X_{7a}$ may be G or Q;
wherein $X_{8a}$ may be K, L or N;
wherein $X_{9a}$ may be T or N;
wherein $X_{10a}$ may be an aromatic amino acid, and;
wherein $X_{11a}$ may be A, N, E or Y.

In an exemplary embodiment of the invention $X_{1a}$ may be K or R.

In a further embodiment of the invention $X_{2a}$ may be Q or K.

In yet a further embodiment of the invention $X_{3a}$ may be N or H.

In an additional embodiment of the invention $X_{10a}$ may be Y or F.

More specific embodiments of the invention include CDRL1 of SEQ ID NO.:72 where: $X_{1a}$ is K; $X_{2a}$ is Q; $X_{3a}$ is N; $X_{3a}$ is H; $X_{4a}$ is S; $X_{4a}$ is T; $X_{5a}$ is S; $X_{5a}$ is absent; $X_{6a}$ is N; $X_{7a}$ is Q; $X_{7a}$ is G; $X_{8a}$ is K; $X_{9a}$ is N; $X_{9a}$ is T; $X_{10a}$ is Y; or $X_{11a}$ is A.

In accordance with the present invention, the antibody may comprise a CDRL1 sequence comprising or consisting of formula:

$$KASQDX_{1b}X_{2b}X_{3b}X_{4b}X_{5b}X_{6b}$$ (SEQ ID NO.: 73)

wherein $X_{1b}$ may be an hydrophobic amino acid;
wherein $X_{2b}$ may be G or H;
wherein $X_{3b}$ may be T, N or R;
wherein $X_{4b}$ may be F, Y or A;
wherein $X_{5b}$ may be an hydrophobic amino acid, and;
wherein $X_{6b}$ may be N or A.

In an exemplary embodiment of the invention $X_{1b}$ may be V or I.

In another exemplary embodiment of the invention $X_{5b}$ may be V or L.

More specific embodiments of the invention include CDRL1 of SEQ ID NO.:73 where $X_{1b}$ is I; $X_{2b}$ is H; $X_{3d}$ is T; $X_{3b}$ is N; $X_{4b}$ is Y; $X_{4b}$ is F; $X_{5b}$ is L or $X_{6b}$ is N.

Other exemplary embodiments of CDRL1 are provided in SEQ ID NOs. 89 and 90.

In accordance with the present invention, the antibody may comprise a CDRL2 sequence comprising or consisting of formula:

$$FX_{1c}STX_{2c}X_{3c}S$$ (SEQ ID NO.: 74)

Wherein $X_{1c}$ is A or G;
Wherein $X_{2c}$ is R or T, and;
Wherein $X_{3c}$ is E, K or A.

In an exemplary embodiment of the invention $X_{1c}$ may be A and $X_{2c}$ may be T.

In another exemplary embodiment of the invention $X_{1c}$ may be A and $X_{2c}$ may be R.

Other specific embodiments of the invention include CDRL2 of SEQ ID NO.:74 where $X_{1c}$ is A; $X_{2c}$ is R or $X_{3c}$ is E.

In accordance with the present invention, the antibody may comprise a CDRL2 sequence comprising or consisting of formula:

$$X_{1d}VSX_{2d}X_{3d}X_{4d}S$$ (SEQ ID NO.: 75)

Wherein $X_{1d}$ may be L or K;
Wherein $X_{2d}$ may be a basic amino acid;
Wherein $X_{3d}$ may be L or R and;
Wherein $X_{4d}$ may be D or F.
In an exemplary embodiment of the invention $X_{2d}$ may be K or N.
Other specific embodiments of the invention include CDRL2 of SEQ ID NO.:75 where $X_{1d}$ is L; $X_{2d}$ is K; $X_{3d}$ is L or $X_{4d}$ is D.

In accordance with the present invention, the antibody may comprise a CDRL2 sequence comprising or consisting of formula:

$$X_{1e}ANRLVX_{2e}$$ (SEQ ID NO.: 76)

Wherein $X_{1e}$ may be a basic amino acid, and;
Wherein $X_{2e}$ may be D or A.
In an exemplary embodiment of the invention $X_{1e}$ may be R or H.
Other specific embodiments of the invention include CDRL2 of SEQ ID NO.:76 where $X_{1e}$ is R or $X_{2e}$ is D.
Other exemplary embodiments of CDRL2 are provided in SEQ ID NOs.: 91-93.

In accordance with the present invention, the antibody may comprise a CDRL3 sequence comprising or consisting of formula:

$$X_{1f}QX_{2f}X_{3f}X_{4f}X_{5f}PLT$$ (SEQ ID NO.: 77)

Wherein $X_{1f}$ may be Q or L;
Wherein $X_{2f}$ may be an aromatic amino acid;
Wherein $X_{3f}$ may be D, F or Y;
Wherein $X_{4f}$ may be E, A, N or S, and;
Wherein $X_{5s}$ may be I, F or T.
In an exemplary embodiment of the invention $X_2$ may be Y or H.
In another exemplary embodiment of the invention $X_{3f}$ may be Y or D.
In yet another exemplary embodiment of the invention $X_{5f}$ may be I or T.
Other specific embodiments of the invention include CDRL3 of SEQ ID NO.:77 where $X_{1f}$ is Q; $X_{2f}$ is H; $X_{3f}$ is D; $X_{3f}$ is Y; $X_{4f}$ is S; $X_{4f}$ is E; $X_{4f}$ is A; $X_{5f}$ is T, or $X_{5f}$ is I.

In accordance with the present invention, the antibody may comprise a CDRL3 sequence comprising or consisting of formula:

$$QQHX_{1g}X_{2g}X_{3g}PLT$$ (SEQ ID NO.: 78)

Wherein $X_{1g}$ may be an aromatic amino acid;
Wherein $X_{2g}$ may be N or S, and;
Wherein $X_{3g}$ may be I or T.
In an exemplary embodiment of the invention $X_{1g}$ may be F or Y
Other specific embodiments of the invention include CDRL3 of SEQ ID NO.:78 where $X_{2g}$ is S or $X_{3g}$ is T.

In accordance with the present invention, the antibody may comprise a CDRL3 sequence comprising or consisting of formula:

$$X_{1h}QGX_{2h}HX_{3h}PX_{4h}T$$ (SEQ ID NO.: 79)

Wherein $X_{1h}$ may be an aromatic amino acid;
Wherein $X_{2h}$ may be a neutral hydrophilic amino acid;
Wherein $X_{3h}$ may be F or V, and;
Wherein $X_{4h}$ may be R or L.
In an exemplary embodiment of the invention $X_{1h}$ may be W or F.
In another exemplary embodiment of the invention $X_{2h}$ may be S or T.
Other specific embodiments of the invention include CDRL3 of SEQ ID NO.:79 where $X_{1h}$ is W; $X_{2h}$ is T; $X_{3h}$ is F, or $X_{4h}$ is R.
Other exemplary embodiments of CDRL3 are provided in SEQ ID NOs. 94 and 95.

In accordance with the present invention, the antibody may comprise a CDRH1 sequence comprising or consisting of formula:

$$GYX_{1i}FX_{2i}X_{3i}YX_{4i}X_{5i}H$$ (SEQ ID NO.: 80)

Wherein $X_{1i}$ may be T, I or K;
Wherein $X_{2i}$ may be a neutral hydrophilic amino acid;
Wherein $X_{3i}$ may be an acidic amino acid;
Wherein $X_{4i}$ may be E, N or D, and;
Wherein $X_{5i}$ may be hydrophobic amino acid.
In an exemplary embodiment of the invention $X_{2i}$ may be T or S.
In another exemplary embodiment of the invention $X_{3i}$ may be D or E.
In yet another exemplary embodiment of the invention $X_{4i}$ may be N or E.
In a further exemplary embodiment of the invention $X_{5i}$ may be M, I or v.
Other specific embodiments of the invention include CDRH1 of SEQ ID NO.:80 where $X_{2i}$ is T; $X_{3i}$ is D; $X_{4i}$ is E; $X_{5i}$ is I or $X_{5i}$ is M.
Other exemplary embodiments of CDRH1 are provided in SEQ ID NOs.: 96 and 97.

In accordance with the present invention, the antibody may comprise a CDRH2 sequence comprising or consisting of formula:

$$X_{1j}X_{2j}DPX_{3j}TGX_{4j}TX_{5j}$$ (SEQ ID NO.: 81)

Wherein $X_{1j}$ may be V or G
Wherein $X_{2j}$ may be a hydrophobic amino acid;
Wherein $X_{3j}$ may be A, G or E;
Wherein $X_{4j}$ may be R, G, D, A, S, N or V, and;
Wherein $X_{5j}$ may be a hydrophobic amino acid.
In an exemplary embodiment of the invention $X_{2j}$ may be I or L.
In another exemplary embodiment of the invention $X_{5j}$ may be A or V.
Other specific embodiments of the invention include CDRH2 of SEQ ID NO.:81 where $X_{1j}$ is V; $X_{2j}$ is I; $X_{3j}$ is E; $X_{4j}$ is D or $X_{5j}$ is A.

In accordance with the present invention, the antibody may comprise a CDRH2 sequence comprising or consisting of formula:

$$VX_{1k}DPX_{2k}TGX_{3k}TA \quad \text{(SEQ ID NO.: 82)}$$

Wherein $X_{1k}$ may be an hydrophobic amino acid;
Wherein $X_{2k}$ may be A, E or G;
Wherein $X_{3k}$ may be R, G, A, S, N V or D.
In an exemplary embodiment of the invention $X_{1k}$ may be L or I.

Other specific embodiments of the invention include CDRH2 of SEQ ID NO.:82 where $X_{1k}$ is I; $X_{2k}$ is E, or $X_{3k}$ is D.

In accordance with the present invention, the antibody may comprise a CDRH2 sequence comprising or consisting of formula:

$$YIX_{1l}X_{2l}X_{3l}GX_{4l}X_{5l}X_{6l} \quad \text{(SEQ ID NO.: 83)}$$

Wherein $X1_l$ may be S or N;
Wherein $X_{2l}$ may be an aromatic amino acid
Wherein $X_{3l}$ may be D, E or N;
Wherein $X4_l$ may be a D or H;
Wherein $X_{5l}$ may be Y, S or N;
Wherein $X_{6l}$ may be D, E or N.
In an exemplary embodiment of the invention $X_{3l}$ may be D or N.
In another exemplary embodiment of the invention $X_{6l}$ may be D or N.

Other specific embodiments of the invention include CDRH2 of SEQ ID NO.:83 where $X_{2l}$ is F or Y, $X_{3l}$ is N, $X_{4l}$ is D or $X_{6l}$ is N.

In accordance with the present invention, the antibody may comprise a CDRH2 sequence comprising or consisting of formula:

$$X_{1m}INPYNX_{2m}VTE \quad \text{(SEQ ID NO.: 84)}$$

wherein $X_{1m}$ may be N or Y, and;
wherein $X_{2m}$ may be E, D or N.
In an exemplary embodiment of the invention $X_{2m}$ may be D or N.

Other specific embodiments of the invention include CDRH2 of SEQ ID NO.:84 where $X_{1m}$ is N or $X_{2m}$ is D.

In accordance with the present invention, the antibody may comprise a CDRH2 sequence comprising or consisting of formula:

$$DINPX_{1n}YGX_{2n}X_{3n}T \quad \text{(SEQ ID NO.: 85)}$$

Wherein $X_{1n}$ may be N or Y,
Wherein $X_{2n}$ may be G or T and;
wherein $X_{3n}$ may be I or T.
Other exemplary embodiments of CDRH2 are provided in SEQ ID NOs. 98 and 99.

In accordance with the present invention, the antibody may comprise a CDRH3 sequence comprising or consisting of formula:

$$MX_{1o}X_{2o}X_{3o}DY \quad \text{(SEQ ID NO.: 86)}$$

Wherein $X_{1o}$ may be G or S;
Wherein $X_{2o}$ may be Y or H, and;
wherein $X_{3o}$ may be A or S.
Other specific embodiments of the invention include CDRH3 of SEQ ID NO.:86 where $X_{1o}$ is G; $X_{2o}$ is Y or $X_{3o}$ is S.

In accordance with the present invention, the antibody may comprise a CDRH3 sequence comprising or consisting of formula:

$$IX_{1p}YAX_{2p}DY \quad \text{(SEQ ID NO.: 87)}$$

Wherein $X_{1p}$ may be G or S and;
Wherein $X_{2p}$ may be absent or M.
Other specific embodiments of the invention include CDRH3 of SEQ ID NO.:87 where $X_{1p}$ is S or $X_{2p}$ is M.

In accordance with the present invention, the antibody may comprise a CDRH3 sequence comprising or consisting of formula:

$$AX_{1q}X_{2q}GLRX_{3q} \quad \text{(SEQ ID NO.: 88)}$$

Wherein $X_{1q}$ may be R or W;
Wherein $X_{2q}$ may be an aromatic amino acid and;
wherein $X_{3q}$ may be a basic amino acid.
In an exemplary embodiment of the invention $X_{2q}$ may be W or F.
In another exemplary embodiment of the invention $X_{3q}$ may be Q or N.

Other specific embodiments of the invention include CDRH3 of SEQ ID NO.:88 where $X_{1q}$ is R; $X_{2q}$ is W or $X_{3q}$ is N.

Variant antibodies or antigen binding fragments encompassed by the present invention include those that may comprise an insertion, a deletion or an amino acid substitution (conservative or non-conservative). These variants may have at least one amino acid residue in its amino acid sequence removed and a different residue inserted in its place.

Humanized Antibodies

Exemplary embodiments of variant antibodies and antigen binding fragments of the present invention are a group of antibodies and antigen binding fragments capable of binding to KAAG1 and characterized herein as being humanized.

The humanized antibodies and antigen binding fragments of the present invention includes more particularly, humanized 3D3, 3A4 or 3C4 antibodies and antigen binding fragments. The humanized 3D3, 3A4 or 3C4 antibodies have at least one amino acid difference in a framework region in comparison with the monoclonal 3D3, 3A4 or 3C4 antibody.

Humanized 3A4 antibodies having CDRs identical to those of the monoclonal 3A4 antibody (VL: SEQ ID NO.: 48, VH: SEQ ID NO.:46) were generated and tested. These humanized antibodies comprise up to 11 amino acid substitutions (from one to eleven) in the variable light chain framework region and up to 23 amino acid substitutions (from one to twenty-three) in the variable heavy chain framework region in comparison with the monoclonal 3A4 antibody. The applicant has shown that these humanized 3A4 antibodies bind to KAAG1 as efficiently as the monoclonal 3A4 antibody.

Exemplary embodiments of variant antibody or antigen binding fragments include those having a light chain variable region as set forth in SEQ ID NO.:186:

SEQ ID NO.: 186
DXVMTQTPLSLXVXXGXXASISCRSSQSLLHSNGNTYLEWYLQKPGQSPX

LLIHTVSNRFSGVPDRFSGSGSGTDFTLKISRVEAEDXGVYYCFQGSHVP

LTFGXGTXLEXK, wherein at least one of the amino acids identified by X is an amino acid substitution (conservative or non-conservative) in comparison with a corresponding amino acid in the polypeptide set forth in SEQ ID NO.:48. The amino acid substitution may be, for example, an amino acid found at a corresponding position of a natural human antibody or a human antibody consensus. The amino acid substitution may be, for example conservative.

Another exemplary embodiment of a variant antibody or antigen binding fragment include those having a light chain variable region as set forth in SEQ ID NO.:187:

SEQ ID NO.: 187
DX$_{e1}$VMTQTPLSLX$_{e2}$VX$_{e3}$X$_{e4}$GX$_{e5}$X$_{e6}$ASISCRSSQSLLHSNGNTYL

EWYLQKPGQSPX$_{e7}$LLIHTVSNRFSGVPDRFSGSGSGTDFTLKISRVEAE

DX$_{e8}$GVYYCFQGSHVPLTFGX$_{e9}$GTX$_{e10}$LEX$_{e11}$K,

Wherein X$_{e1}$ may be a hydrophobic amino acid;
Wherein X$_{e2}$ may be A or P;
Wherein X$_{e3}$ may be neutral hydrophilic amino acid;
Wherein X$_{e4}$ may be L or P;
Wherein X$_{e5}$ may be an acidic amino acid;
Wherein X$_{e6}$ may be Q or P;
Wherein X$_{e7}$ may be a basic amino acid;
Wherein X$_{e8}$ may be a hydrophobic amino acid;
Wherein X$_{e9}$ may be A or Q;
Wherein X$_{e10}$ may be a basic amino acid; or
Wherein X$_{e11}$ may be a hydrophobic amino acid,
wherein at least one of the amino acid identified by X is an amino acid substitution (conservative or non-conservative) in comparison with a corresponding amino acid in the polypeptide set forth in SEQ ID NO:48.

An additional exemplary embodiment of a variant antibody or antigen binding fragment include those having a light chain variable region as set forth in SEQ ID NO.:188:

SEQ ID NO.: 188
DX$_{E1}$VMTQTPLSLX$_{E2}$VX$_{E3}$X$_{E4}$GX$_{E5}$X$_{E6}$ASISCRSSQSLLHSNGNTYL

EWYLQKPGQSPX$_{E7}$LLIHTVSNRFSGVPDRFSGSGSGTDFTLKISRVEAE

DX$_{E8}$GVYYCFQGSHVPLTFGX$_{E9}$GTX$_{E10}$LEX$_{E11}$K

Wherein X$_{E1}$ may be V or I
Wherein X$_{E2}$ may be A or P
Wherein X$_{E3}$ may be S or T
Wherein X$_{E4}$ may be L or P
Wherein X$_{E5}$ may be D or E
Wherein X$_{E6}$ may be Q or P
Wherein X$_{E7}$ may be K or Q
Wherein X$_{E8}$ may be L or V
Wherein X$_{E9}$ may be A or Q
Wherein X$_{E10}$ may be R or K or
Wherein X$_{E11}$ may be L or I, wherein at least one of the amino acid identified by X is an amino acid substitution (conservative or non-conservative) in comparison with a corresponding amino acid in the polypeptide set forth in SEQ ID NO.:48.

In accordance with an embodiment, the light chain variable domain variant may have a sequence as set forth in SEQ ID NO.:189 or 190:

SEQ ID NO.: 189
DIVMTQTPLSLPVTPGEPASISCRSSQSLLHSNGNTYLEWYLQKPGQSPQ

LLIYTVSNRFSGVPDRFSGSGSGTDFTLKISRVEAEDVGVYYCFQGSHVP

LTFGQGTKLEIK.

SEQ ID NO.: 190
DVVMTQTPLSLPVTPGEPASISCRSSQSLLHSNGNTYLEWYLQKPGQSPK

LLIYTVSNRFSGVPDRFSGSGSGTDFTLKISRVEAEDVGVYYCFQGSHVP

LTFGQGTKLEIK.

Exemplary embodiments of variant antibody or antigen binding fragments include those having a heavy chain variable region as set forth in SEQ ID NO.:191.

SEQ ID NO.: 191
QXQLVQSGXEXXKPGASVKXSCKASGYTFTDDYMSWVXQXXGXXLEWXGD

INPYNGDTNYNQKFKGXXXXTXDXSXSTAYMXLXSLXSEDXAVYYCARDP

GAMDYWGQGTXVTVSS, wherein at least one of the amino acid identified by X is an amino acid substitution (conservative or non-conservative) in comparison with a corresponding amino acid in the polypeptide set forth in SEQ ID NO.:46. The amino acid substitution may be, for example, an amino acid found at a corresponding position of a natural human antibody or a human antibody consensus. The amino acid substitution may be, for example conservative.

Another exemplary embodiment of a variant antibody or antigen binding fragment include those having a heavy chain variable region as set forth in SEQ ID NO.:192:

SEQ ID NO.: 192
QX$_{f1}$QLVQSGX$_{f2}$EX$_{f3}$X$_{bf4}$KPGASVKX$_{f5}$SCKASGYTFTDDYMSWV

X$_{f6}$QX$_{f7}$X$_{f8}$GX$_{f9}$X$_{f10}$LEWX$_{f11}$GDINPYNCDTNYNQKFKGX$_{f12}$

X$_{f13}$X$_{b14}$X$_{f15}$TX$_{f16}$DX$_{f17}$SX$_{f18}$STAYMX$_{f19}$LX$_{f20}$SLX$_{f21}$S

EDX$_{f22}$AVYYCARDPGAMDYWGQGTX$_{f23}$VTVSS,

Wherein X$_{f1}$ may be a hydrophobic amino acid;
Wherein X$_{bf2}$ may be P or A;
Wherein X$_{f3}$ may be a hydrophobic amino acid;
Wherein X$_{f4}$ may be V or K;
Wherein X$_{f5}$ may be a hydrophobic amino acid;
Wherein X$_{f6}$ may be a basic amino acid;
Wherein X$_{f7}$ may be S or A;
Wherein X$_{f8}$ may be H or P;
Wherein X$_{f9}$ may be a basic amino acid;
Wherein X$_{f10}$ may be S or G:
Wherein X$_{f11}$ may be a hydrophobic amino acid;
Wherein X$_{f12}$ may be a basic amino acid;
Wherein X$_{f13}$ may be a hydrophobic amino acid;
Wherein X$_{f14}$ may be I or T;
Wherein X$_{f15}$ may be a hydrophobic amino acid;
Wherein X$_{f16}$ may be a hydrophobic amino acid;

Wherein $X_{f17}$ may be K or T;
Wherein $X_{f18}$ may be a neutral hydrophilic amino acid;
Wherein $X_{f19}$ may be Q or E;
Wherein $X_{f20}$ may be N or S;
Wherein $X_{f21}$ may be T or R;
Wherein $X_{f22}$ may be a neutral hydrophilic amino acid; or
Wherein $X_{f23}$ may be S or L,
wherein at least one of the amino acid identified by X is an amino acid substitution (conservative or non-conservative) in comparison with a corresponding amino acid in the polypeptide set forth in SEQ ID NO.:46.

An additional exemplary embodiment of a variant antibody or antigen binding fragment include those having a heavy chain variable region as set forth in SEQ ID NO.:193:

```
                                         SEQ ID NO.: 193
QXF1QLVQSGXF2EXF3XF4KPGASVKXF5SCKASGYTFTDDYNASWV

XF6QXF7XF8GXF9XF10LEWXF11GDINPYNGDTNYNQKFKGXF12

XF13XF14XF15TXF16DXF17SXF18STAYMXF19LXF20SLXF21S

EDXF22AVYYCARDPGAMDYWGQGTXF23VTVSS
```

Wherein $X_{F1}$ may be I or V;
Wherein $X_{F2}$ may be P or A;
Wherein $X_{F3}$ may be M or V;
Wherein $X_{F4}$ may be V or K;
Wherein $X_{F5}$ may be M or V;
Wherein $X_{F6}$ may be K or R;
Wherein $X_{F7}$ may be S or A;
Wherein $X_{F8}$ may be H or P;
Wherein $X_{F9}$ may be K or Q;
Wherein $X_{F10}$ may be S or G;
Wherein $X_{F11}$ may be I or M;
Wherein $X_{F12}$ may be K or R;
Wherein $X_{F13}$ may be A or V;
Wherein $X_{F14}$ may be I or T;
Wherein $X_{F15}$ may be L or I;
Wherein $X_{F16}$ may be V or A;
Wherein $X_{F17}$ may be K or T;
Wherein $X_{F18}$ may be S or T;
Wherein $X_{F19}$ may be Q or E;
Wherein $X_{F20}$ may be N or S;
Wherein $X_{F21}$ may be T or R;
Wherein $X_{F22}$ may be S or T; or
Wherein $X_{F23}$ is S or L,
wherein at least one of the amino acid identified by X is an amino acid substitution (conservative or non-conservative) in comparison with a corresponding amino acid in the polypeptide set forth in SEQ ID NO.:46.

In accordance with an embodiment, the heavy chain variable domain variant may have a sequence as set forth in any one of SEQ ID NO.194 to 197:

```
                                         SEQ ID NO.: 194
QVQLVQSGAEVKKPGASVKVSCKASGYTFTDDYMSWVRQAPGQGLEWMGD

INPYNGDTNYNQKFKGRVTITADTSTSTAYMELSSLRSEDTAVYYCARDP

GAMDYWGQGTLVTVSS.

SEQ ID NO.: 195
QIQLVQSGAEVKKPGASVKVSCKASGYTFTDDYMSWVRQAPGQGLEWMGD

INPYNGDTNYNQKFKGRVTITADKSTSTAYMELSSLRSEDTAVYYCARDP

GAMDYWGQGTLVTVSS.

SEQ ID NO.: 196
QIQLVQSGAEVKKPGASVKVSCKASGYTFTDDYMSWVRQAPGQGLEWIGD

INPYNGDTNYNQKFKGRATLTVDKSTSTAYMELSSLRSEDTAVYYCARDP

GAMDYWGQGTLVTVSS.

SEQ ID NO.: 197
QIQLVQSGAEVKKPGASVKVSCKASGYTFTDDYMSVWKQAPGQGLEWIGD

INPYNGDTNYNQKFKGKATLTVDKSTSTAYMELSSLRSEDTAVYYCARDP

GAMDYWGQGTLVTVSS.
```

In accordance with an embodiment of the invention, the humanized 3D3 antibody may have a light chain variable region of formula:

```
                                         (SEQ ID NO.: 174)
DIVMTQSPXSLAVSXGXXXTXNCKSSQSLLNSNFQKNFLAWYQQKPGQXP

KLLIYFASTRESSXPDRFXGSGSGTDFTLTISSXQAEDXAXYXCQQHYST

PLTFGXGTKLEXK;
``` wherein at least one of the amino acid identified by X is an amino acid substitution (conservative or non-conservative) in comparison with a corresponding amino acid in the polypeptide set forth in SEQ ID NO.:16. The amino acid substitution may be, for example conservative.

In accordance with a more specific embodiment, the humanized 3D3 antibody may have a light chain variable region of formula:

```
                                         (SEQ ID NO.: 175)
DIVMTQSPXA1SLAVSXA2GXA3XA4XA5TXA6NCKSSQSLLNSNFQKNF

LAWYQQKPGQXA7PKLLIYFASTRESSXA8PDRFXA9GSGSGTDFTLTIS

SXA10QAEDXA11AXA12YXA13CQQHYSTPLTFGXA14GTKLEXA15K;
```

Wherein $X_{A1}$ may be, for example, D or S;
Wherein $X_{A2}$ may be, for example, a hydrophobic amino acid or more particularly L or I;
Wherein $X_{A3}$ may be, for example, E or Q;
Wherein $X_{A4}$ may be, for example, a basic amino acid or more particularly R or K;
Wherein $X_{A5}$ may be, for example, a hydrophobic amino acid or more particularly A or V;
Wherein $X_{A6}$ may be, for example, a hydrophobic amino acid or more particularly I or M;
Wherein $X_{A7}$ may be, for example, P or S;
Wherein $X_{A8}$ may be, for example, a hydrophobic amino acid or more particularly V or I;
Wherein $X_{A9}$ may be, for example, S or I;
Wherein $X_{A10}$ may be, for example, a hydrophobic amino acid or more particularly L or V;
Wherein $X_{A11}$ may be, for example, a hydrophobic amino acid or more particularly V or L;
Wherein $X_{A12}$ may be, for example, V or D;
Wherein $X_{A13}$ may be, for example, an aromatic amino acid or more particularly Y or F;
Wherein $X_{A14}$ may be, for example, Q or A and;
Wherein $X_{A15}$ may be, for example, a hydrophobic amino acid or more particularly I or L.

In accordance with an even more specific embodiment, the humanized 3D3 antibody may have a light chain variable region of formula:

(SEQ ID NO.: 176)
DIVMTQSPX$_{a1}$SLAVSX$_{a2}$GX$_{a3}$X$_{a4}$X$_{a5}$TX$_{a6}$NCKSSQSLLNSNFQKNF

LAWYQQKPGQX$_{a7}$PKLLIYFASTRESSX$_{a8}$PDRFX$_{a9}$GSGSGTDFTLTIS

SX$_{a10}$QAEDX$_{a11}$AX$_{a12}$YX$_{a13}$CQQHYSTPLTFGX$_{a14}$GTKLEX$_{a15}$K;

Wherein X$_{a1}$ may be, for example, D or S;
Wherein X$_{a2}$ may be, for example, L or I;
Wherein X$_{a3}$ may be, for example, E or Q;
Wherein X$_{a4}$ may be, for example, R or K;
Wherein X$_{a5}$ may be, for example, A or V;
Wherein X$_{a6}$ may be, for example, I or M;
Wherein X$_{a7}$ may be, for example, P or S;
Wherein X$_{a8}$ may be, for example, V or i;
Wherein X$_{a9}$ may be, for example, S or I;
Wherein X$_{a10}$ may be, for example, L or V;
Wherein X$_{a11}$ may be, for example, V or L,
Wherein X$_{a12}$ may be, for example, V or D;
Wherein X$_{a13}$ may be, for example, Y or F;
Wherein X$_{a14}$ may be, for example, Q or A and;
Wherein X$_{a15}$ is for example, I or L.

In accordance with an embodiment of the present invention, the humanized 3D3 antibody may have a heavy chain variable region of formula:
EVQLXQSXAEXXXPGASVXXSCK-ASGYIFTDYEIHWVXQXPXXGLEWXGVIDPE TGN-TAFNQKFKGXXTXTADXSXSTAYMELSSLT-SEDXAVYYCMGYSDYWGQGTXXTV SS (SEQ ID NO.:177); wherein at least one of the amino acid identified by X is an amino acid substitution (conservative or non-conservative) in comparison with a corresponding amino acid in the polypeptide set forth in SEQ ID NO.:18. The amino acid substitution may be, for example conservative.

In accordance with a more specific embodiment, the humanized 3D3 antibody may have a heavy chain variable region of formula:

(SEQ ID NO.: 178)
EVQLX$_{B1}$QSX$_{B2}$AEX$_{B3}$X$_{B4}$X$_{B5}$PGASVX$_{B6}$X$_{B7}$SCKASGYIFTDYEIHW

VX$_{B8}$QX$_{B9}$PX$_{B10}$X$_{B11}$GLEWX$_{B12}$GVIDPETGNTAFNQKFKGX$_{B13}$

X$_{B14}$TX$_{B15}$TADX$_{B16}$SX$_{B17}$STAYMELSSLTSEDX$_{B18}$AVYYCMGYSDY

WGQGTX$_{B19}$X$_{B20}$TVSS,

Wherein X$_{B1}$ may be, for example, V or Q;
Wherein X$_{B2}$ may be, for example, G or V;
Wherein X$_{B3}$ may be, for example, a hydrophobic amino acid or more particularly V or L;
Wherein X$_{B4}$ may be, for example, K or V;
Wherein X$_{B5}$ may be, for example, a basic amino acid or more particularly K or R;
Wherein X$_{B6}$ may be, for example, K or T;
Wherein X$_{B7}$ may be, for example, a hydrophobic amino acid or more particularly V or L;
Wherein X$_{B8}$ may be, for example, a basic amino acid or more particularly R or K;
Wherein X$_{B9}$ may be, for example, A or T;
Wherein X$_{B10}$ may be, for example, G or V;
Wherein X$_{B11}$ may be, for example, Q or H;
Wherein X$_{B12}$ may be, for example, a hydrophobic amino acid or more particularly M or I;
Wherein X$_{B13}$ may be, for example, a basic amino acid or more particularly R or K;
Wherein X$_{B14}$ may be, for example, a hydrophobic amino acid or more particularly V or A;
Wherein X$_{B15}$ may be, for example, a hydrophobic amino acid or more particularly I or L;
Wherein X$_{B16}$ may be, for example, T or I;
Wherein X$_{B17}$ may be, for example, a neutral hydrophilic amino acid or more particularly T or S;
Wherein X$_{B18}$ may be, for example, a neutral hydrophilic amino acid or more particularly T or S;
Wherein X$_{B19}$, may be, for example, L or T and;
Wherein X$_{B20}$ may be, for example, a hydrophobic amino acid or more particularly V or L.

In accordance with a more specific embodiment, the humanized 3D3 antibody may have a heavy chain variable region of formula:

(SEQ ID NO.: 179)
EVQLX$_{b1}$QSX$_{b2}$AEX$_{b3}$X$_{b4}$X$_{b5}$PGASVX$_{b6}$X$_{b7}$SCKASGYIFTDYEIHW

VX$_{b8}$QX$_{b9}$PX$_{b10}$X$_{b11}$GLEWX$_{b12}$GVIDPETGNTAFNQKFKGX$_{b13}$

X$_{b14}$TX$_{b15}$TADX$_{b16}$SX$_{b17}$STAYMELSSLTSEDX$_{b18}$AVYYCMGYSDY

WGQGTX$_{b19}$X$_{b20}$TVSS;

Wherein X$_{b1}$ may be, for example, V or Q;
Wherein X$_{b2}$ may be, for example, G or V;
Wherein X$_{b3}$ may be, for example, V or L;
Wherein X$_{b4}$ may be, for example, K or V;
Wherein X$_{b5}$ may be, for example, K or R;
Wherein X$_{b6}$ may be, for example, K or T;
Wherein X$_{b7}$ may be, for example, V or L;
Wherein X$_{b8}$ may be, for example, R or K;
Wherein X$_{b9}$ may be, for example, A or T;
Wherein X$_{b10}$ may be, for example, G or V;
Wherein X$_{b11}$ may be, for example, Q or H;
Wherein X$_{b12}$ may be, for example, M or I;
Wherein X$_{b13}$ may be, for example, R or K;
Wherein X$_{b14}$ may be, for example, V or A;
Wherein X$_{b15}$ may be, for example, I or L;
Wherein X$_{b16}$ may be, for example, T or I;
Wherein X$_{b17}$ may be, for example, T or S;
Wherein X$_{b18}$ may be, for example, T or S;
Wherein X$_{b19}$ may be, for example, L or T;
Wherein X$_{b20}$ may be, for example, V or L.

In accordance with an embodiment of the present invention, the humanized 3C4 antibody may have a light chain variable region of formula:
DIVMXQSPSSXXASXGXRVTITCKASQDIHN-FLNWFQQKPGKXPKTLIFRANRL VDGVPSRFSGSGSGXDYXLTISSLXXEDXXXY-SCLQYDEIPLTFGXGTKLEXX (SEQ ID NO.:180); wherein at least one of the amino acid identified by X is an amino acid substitution (conservative or non-conservative) in comparison with a corresponding amino acid in the polypeptide set forth in SEQ ID NO.:24. The amino acid substitution may be, for example conservative.

In accordance with a more specific embodiment, the humanized 3C4 antibody may have a light chain variable region of formula:

(SEQ ID NO.: 181)
DIVMX$_{C1}$QSPSSX$_{C2}$X$_{C3}$ASX$_{C4}$GX$_{C5}$RVTITCKASQDIHNFLNWFQQKP

GKX$_{C6}$PKTLIFRANRLVDGVPSRFSGSGSGX$_{C7}$DYX$_{C8}$LTISSLX$_{C9}$

X$_{C10}$EDX$_{C11}$X$_{C12}$X$_{C13}$YSCLQYDEIPLTFGX$_{C14}$GTKLEX$_{C15}$X$_{C16}$;

Wherein X$_{C1}$ may be, for example, a neutral hydrophilic amino acid or more particularly T or S;

Wherein $X_{C2}$ may be, for example, a hydrophobic amino acid or more particularly L or M;
Wherein $X_{C3}$ may be, for example, S or Y;
Wherein $X_{C4}$ may be, for example, a hydrophobic amino acid or more particularly V or L;
Wherein $X_{C5}$ may be, for example, an acidic amino acid or more particularly D or E;
Wherein $X_{C6}$ may be, for example, A or S;
Wherein $X_{C7}$ may be, for example, T or Q;
Wherein $X_{C8}$ may be, for example, a neutral hydrophilic amino acid or more particularly T or S;
Wherein $X_{C9}$ may be, for example, Q or E;
Wherein $X_{C10}$ may be, for example, P or F;
Wherein $X_{C11}$ may be, for example, F or L;
Wherein $X_{C12}$ may be, for example, A or G;
Wherein $X_{C13}$ may be, for example, T or I;
Wherein $X_{C14}$ may be, for example, Q or A;
Wherein $X_{C15}$ may be, for example, a hydrophobic amino acid or more particularly I or L, and; wherein $X_{C16}$ may be, for example, a basic amino acid or more particularly K or R.

In accordance with a more specific embodiment, the humanized 3C4 antibody may have a light chain variable region of formula:

(SEQ ID NO.: 182)
DIVMX$_{c1}$QSPSSX$_{c2}$X$_{c3}$ASX$_{c4}$GX$_{c5}$RVTITCKASQDIHNFLNWF

QQKPGKX$_{c6}$PKTLI FRANRLVDGVPSRFSGSGSGX$_{c7}$DYX$_{c8}$LTISSL

X$_{c9}$X$_{c10}$EDX$_{c11}$X$_{c12}$X$_{c13}$YSCLQYDEIPLTFGX$_{c14}$GTKLE

X$_{c15}$X$_{c16}$;

Wherein $X_{c1}$ may be, for example, T or S;
Wherein $X_{c2}$ may be, for example, L or M;
Wherein $X_{c3}$ may be, for example, S or Y;
Wherein $X_{c4}$ may be, for example, V or L;
Wherein $X_{c5}$ may be, for example, D or E;
Wherein $X_{c6}$ may be, for example, A or S;
Wherein $X_{c7}$ may be, for example, T or Q;
Wherein $X_{c8}$ may be, for example, T or S;
Wherein $X_{c9}$ may be, for example, Q or E;
Wherein $X_{c10}$ may be, for example, P or F;
Wherein $X_{c11}$ may be, for example, F or L;
Wherein $X_{c2}$ may be, for example, A or G;
Wherein $X_{c13}$ may be, for example, T or I;
Wherein $X_{c14}$ may be, for example, Q or A;
Wherein $X_{c15}$ may be, for example, I or L and;
wherein $X_{c16}$ may be, for example, K or R.

In accordance with an embodiment of the present invention, the humanized 3C4 antibody may have a heavy chain variable region of formula:
EVQLQESGPXLVKPSQXLSLTCTVXGFSITSGYGWHWIRQXPGXXLEWXGYIN YDGHNDYNPSLKSRXXIXQDTSKNQFXLXLXSVTXXDTAXYYCASSYDGLFAYWGQG TLVTVSX (SEQ ID NO.:183); wherein at least one of the amino acid identified by X is an amino acid substitution (conservative or non-conservative) in comparison with a corresponding amino acid in the polypeptide set forth in SEQ ID NO.:26. The amino acid substitution may be, for example conservative.

In accordance with a more specific embodiment, the humanized 3C4 antibody may have a heavy chain variable region of formula:

(SEQ ID NO.: 184)
EVQLQESGPX$_{D1}$LVKPSQX$_{D2}$LSLTCTVX$_{D3}$GFSITSGYGWHWIRQ

X$_{D4}$PGX$_{D5}$X$_{D6}$LEWX$_{D7}$GYINYDGHNDYNPSLKSRX$_{D8}$X$_{D9}$IX$_{D10}$QDTS

KNQFX$_{D11}$LX$_{D12}$LX$_{D13}$SVTX$_{D14}$X$_{D15}$DTAX$_{D16}$YYCASSYDGLFAYW

GQGTLVTVSX$_{D17}$;

Wherein $X_{D1}$ may be, for example, G or D;
Wherein $X_{D2}$ may be, for example, a neutral hydrophilic amino acid or more particularly T or S;
Wherein $X_{D3}$ may be, for example, a neutral hydrophilic amino acid or more particularly S or T;
Wherein $X_{D4}$ may be, for example, H or F;
Wherein $X_{D5}$ may be, for example, K or N;
Wherein $X_{D6}$ may be, for example, G or K;
Wherein $X_{D7}$ may be, for example, a hydrophobic amino acid or more particularly I or M;
Wherein $X_{D8}$ may be, for example, a hydrophobic amino acid or more particularly V or I;
Wherein $X_{D9}$ may be, for example, a neutral hydrophilic amino acid or more particularly T or S;
Wherein $X_{D10}$ may be, for example, a neutral hydrophilic amino acid or more particularly S or T;
Wherein $X_{D11}$ may be, for example, a neutral hydrophilic amino acid or more particularly S or F;
Wherein $X_{D12}$ may be, for example, a basic amino acid or more particularly K or Q;
Wherein $X_{D13}$ may be, for example, S or N;
Wherein $X_{D14}$ may be, for example, A or T;
Wherein $X_{D15}$ may be, for example, A or E;
Wherein $X_{D16}$ may be, for example, V or T and;
Wherein $X_{D17}$ may be any amino acid, A or absent.

In accordance with a more specific embodiment, the humanized 3C4 antibody may have a heavy chain variable region of formula:

(SEQ ID NO.: 185)
EVQLQESGPX$_{d1}$LVKPSQX$_{d2}$LSLTCTVX$_{d3}$GFSITSGYGWHWIRQ

X$_{d4}$PGX$_{d5}$X$_{d6}$LEWX$_{d7}$GYINYDGHNDYNPSLKSRX$_{d8}$X$_{d9}$IX$_{d10}$QDTS

KNQFX$_{d11}$LX$_{d12}$X$_{d13}$SVTX$_{d14}$X$_{d15}$DTAX$_{d16}$YYCASSYDGLFAYW

GQGTLVTVSX$_{d17}$;

Wherein $X_{d1}$ may be, for example, G or D;
Wherein $X_{d2}$ may be, for example, T or S;
Wherein $X_{d3}$ may be, for example, S or T;
Wherein $X_{d4}$ may be, for example, H or F;
Wherein $X_{d5}$ may be, for example, K or N;
Wherein $X_{d6}$ may be, for example, G or K;
Wherein $X_{d7}$ may be, for example, I or M;
Wherein $X_{d8}$ may be, for example, V or I;
Wherein $X_{d9}$ may be, for example, T or S;
Wherein $X_{10}$ may be, for example, S or T;
Wherein $X_{d11}$ may be, for example, S or F;
Wherein $X_{d12}$ may be, for example, K or Q;
Wherein $X_{d13}$ may be, for example, S or N;
Wherein $X_{d14}$ may be, for example, A or T;
Wherein $X_{d15}$ may be, for example, A or E;
Wherein $X_{d16}$ may be, for example, V or T and;
Wherein $X_{d17}$, A or absent.

Accordingly, the present invention provides in one aspect, an antibody or antigen binding fragment thereof capable of specific binding to Kidney associated antigen 1 (KAAG1) which may have a light chain variable region at least 70% identical to SEQ ID NO.:16 and/or a heavy chain variable region at least 70% identical to SEQ ID NO.:18 The antibody or antigen binding fragment thereof may also comprise at least one amino acid substitution in comparison with SEQ ID NO.:16 or SEQ ID NO.:18.

The present invention also provides in another aspect, an antibody or antigen binding fragment thereof which may have a light chain variable region at least 70% identical to SEQ ID NO.:24 and/or a heavy chain variable region at least 70% identical to SEQ ID NO.:26. The antibody or antigen binding fragment thereof may also comprise at least one amino acid substitution in comparison with SEQ ID NO.:24 or SEQ ID NO.:26.

The present invention also provides in another aspect, an antibody or antigen binding fragment thereof which may have a light chain variable region at least 70% identical to SEQ ID NO.:48 and/or a heavy chain variable region at least 70% identical to SEQ ID NO.:46. The antibody or antigen binding fragment thereof may also comprise at least one amino acid substitution in comparison with SEQ ID NO.:48 or SEQ ID NO.:46.

In accordance with an embodiment of the invention, the amino acid substitution may be outside of a complementarity determining region (CDR). An antibody or antigen binding fragment having such an amino acid sequence encompasses, for example, a humanized antibody or antigen binding fragment.

As used herein the term "from one to twenty-five" includes every individual values and ranges such as for example, 1, 2, 3, and up to 25; 1 to 25; 1 to 24, 1 to 23, 1 to 22, 1 to 21, 1 to 20, 1 to 19; 1 to 18; 1 to 17; 1 to 16; 1 to 15 and so on; 2 to 25, 2 to 24, 2 to 23, 2 to 22, 2 to 21, 2 to 20; 2 to 19; 2 to 18; 2 to 17 and so on; 3 to 25, 3 to 24, 3 to 23, 3 to 22, 3 to 21, 3 to 20; 3 to 19; 3 to 18 and so on; 4 to 25, 4 to 24, 4 to 23, 4 to 22, 4 to 21, 4 to 20; 4 to 19; 4 to 18; 4 to 17; 4 to 16 and so on; 5 to 25, 5 to 24, 5 to 23, 5 to 22, 5 to 21, 5 to 20; 5 to 19; 5 to 18; 5 to 17 and so on, etc.

As used herein the term "from one to twenty-three" includes every individual values and ranges such as for example, 1, 2, 3, and up to 23; 1 to 23, 1 to 22, 1 to 21, 1 to 20, 1 to 19; 1 to 18; 1 to 17; 1 to 16; 1 to 15 and so on; 2 to 23, 2 to 22, 2 to 21, 2 to 20; 2 to 19; 2 to 18; 2 to 17 and so on; 3 to 23, 3 to 22, 3 to 21, 3 to 20; 3 to 19; 3 to 18 and so on; 4 to 23, 4 to 22, 4 to 21, 4 to 20; 4 to 19; 4 to 18; 4 to 17; 4 to 16 and so on; 5 to 25, 5 to 24, 5 to 23, 5 to 22, 5 to 21, 5 to 20; 5 to 19; 5 to 18; 5 to 17 and so on, etc.

As used herein the term "from one to twenty" includes every individual values and ranges such as for example, 1, 2, 3, and up to 20; 1 to 20; 1 to 19; 1 to 18; 1 to 17; 1 to 16; 1 to 15 and so on; 2 to 20; 2 to 19; 2 to 18; 2 to 17 and so on; 3 to 20; 3 to 19; 3 to 18 and so on; 4 to 20; 4 to 19; 4 to 18; 4 to 17; 4 to 16 and so on; 5 to 20; 5 to 19; 5 to 18; 5 to 17 and so on, etc.

Likewise, the term "from one to fifteen" includes every individual values and ranges such as for example, 1, 2, 3, and up to 15; 1 to 15; 1 to 14; 1 to 13; 1 to 12; 1 to 11; 1 to 10 and so on; 2 to 15; 2 to 14; 2 to 13; 2 to 12 and so on; 3 to 15; 3 to 14; 3 to 13 and so on; 4 to 15; 4 to 14; 4 to 13; 4 to 12; 4 to 11 and so on; 5 to 15; 5 to 14; 5 to 13; 5 to 12 and so on, etc.

Likewise, the term "from one to eleven" includes every individual values and ranges such as for example, 1, 2, 3, and up to 11; 1 to 11; 1 to 10, 1 to 9, 1 to 8, 1 to 7, and so on; 2 to 11; 2 to 10; 2 to 9; 2 to 8 and so on; 3 to 11; 3 to 10; 3 to 9 and so on; 4 to 11; 4 to 10; 4 to 9; 4 to 8; 4 to 7 and so on; 5 to 11; 5 to 10; 5 to 9; 5 to 8 and so on, etc.

In a more specific embodiment of the invention, the number of amino acid substitutions that may be accommodated in a humanized light chain variable region derived from SEQ ID NO.:16 may be for example, from 1 to 15 amino acid substitutions.

In yet a more specific embodiment of the invention, the number of amino acid substitutions that may be accommodated in a humanized heavy chain variable region derived from SEQ ID NO.:18 may be for example, from 1 to 20 amino acid substitutions. In some instances, when considering a humanized version of SEQ ID NO.:18, it may be useful to have at least three amino acid substitutions.

In a further more specific embodiment of the invention, the number of amino acid substitutions that may be accommodated in a humanized light chain variable region derived from SEQ ID NO.:24 may be for example, from 1 to 16 amino acid substitutions.

In yet a further more specific embodiment of the invention, the number of amino acid substitutions that may be accommodated in a humanized heavy chain variable region of SEQ ID NO.:26 may be for example, from 1 to 17 amino acid substitutions.

In a further more specific embodiment of the invention, the number of amino acid substitutions that may be accommodated in a humanized light chain variable region derived from SEQ ID NO.:48 may be for example, from 1 to 11 amino acid substitutions.

In yet a further more specific embodiment of the invention, the number of amino acid substitutions that may be accommodated in a humanized heavy chain variable region of SEQ ID NO.:46 may be for example, from 1 to 23 amino acid substitutions.

In accordance with an embodiment of the invention, the one to twenty amino acid substitutions may be for example, in the light chain variable region.

In accordance with an embodiment of the invention, the one to twenty amino acid substitutions may be for example, in the heavy chain variable region.

A humanized antibody or antigen binding fragment may therefore have a light chain variable region having up to twenty amino acid substitutions in comparison with SEQ ID NO.:16 or SEQ ID NO.:24 and may have a heavy chain variable region having up to twenty amino acid substitutions in comparison with SEQ ID NO.:18 or SEQ ID NO.:26. A humanized antibody or antigen binding fragment may therefore have a light chain variable region having up to twenty-five amino acid substitutions in comparison with SEQ ID NO.:48 and may have a heavy chain variable region having up to twenty-five amino acid substitutions in comparison with SEQ ID NO.:46.

It is to be understood herein that when the humanized antibody or antigen binding fragment has two light chain variable regions and two heavy chain variable regions, each one of the light chain variable regions may independently have up to twenty-five, twenty-four, twenty-three, twenty-two, twenty-one, twenty, nineteen, eighteen, seventeen, sixteen, fifteen, fourteen, thirteen, twelve, eleven, ten, nine, eight, seven, six, five, four, three, two, one amino acid substitutions and each one of the heavy chain variable regions may have up to twenty-five, twenty-four, twenty-three, twenty-two, twenty-one, twenty, nineteen, eighteen, seventeen, sixteen, fifteen, fourteen, thirteen, twelve, eleven, ten, nine, eight, seven, six, five, four, three, two, one amino acid substitutions.

As discussed herein the amino acid substitutions may be conservative or non-conservative. In an exemplary embodiment the amino acid substitutions may be conservative.

It is to be understood herein that the humanized antibody or antigen binding fragment of the invention may also have a light chain variable region and/or heavy chain variable region showing a deletion in comparison with SEQ ID NO.:16, SEQ ID NO.:18, SEQ ID NO.:189, SEQ ID NO.: 190, SEQ ID NO.:194, SEQ ID NO.:195, SEQ ID NO.:196, SEQ ID NO.:197, SEQ ID NO.:24 and/or SEQ ID NO.:26. Such deletion may be found, for example, at an amino- or carboxy-terminus of the light chain variable region and/or heavy chain variable region.

Another exemplary embodiment of the humanized antibody or antigen binding fragment of the present invention includes for example, an antibody or antigen binding fragment having a light chain variable region which may comprise at least 90 consecutive amino acids of any of SEQ ID NO.:186, SEQ ID NO.:187, SEQ ID NO.:188, SEQ ID NO.:189 or SEQ ID NO.:190.

As used herein the term "at least 90 consecutive amino acids of SEQ ID NO.:186" also includes the terms "at least 91, 92, 93, 94, 95, 96, 97, 98, 99, 100, 101, 102, 103, 104, 105, 106, 107, 108, 109, 110, 111, or at least 112 consecutive amino acids". The term "at least 90 consecutive amino acids of SEQ ID NO.: 186" encompasses any possible sequence of at least 90 consecutive amino acids found in SEQ ID NO.:186 and especially those sequences which include the 3 CDRs of SEQ ID NO.:186, such as, for example a sequence comprising amino acids 6 to 108, 5 to 109, 13 to 103, 14 to 111 of SEQ ID NO.:186 and so on.

As used herein the term "at least 90 consecutive amino acids of SEQ ID NO.:187" also includes the terms "at least 91, 92, 93, 94, 95, 96, 97, 98, 99, 100, 101, 102, 103, 104, 105, 106, 107, 108, 109, 110, 111, or at least 112 consecutive amino acids". The term "at least 90 consecutive amino acids of SEQ ID NO.:187" encompasses any possible sequence of at least 90 consecutive amino acids found in SEQ ID NO.:187 and especially those sequences which include the 3 CDRs of SEQ ID NO.:187, such as, for example a sequence comprising amino acids 7 to 109, 12 to 104, 22 to 113, 18 to 112 of SEQ ID NO.:187 and so on.

The terms "at least 90 consecutive amino acids of SEQ ID NO.:188", "at least 90 consecutive amino acids of SEQ ID NO.:189" or "at least 90 consecutive amino acids of SEQ ID NO.:190" has a similar meaning.

In accordance with the present invention, the antibody or antigen binding fragment of the present invention may have, for example, a light chain variable region as set forth in SEQ ID NO.:189 or 190.

The humanized antibody or antigen binding fragment of the invention includes (or further includes) for example, a heavy chain variable region which may comprise at least 90 consecutive amino acids of any of SEQ ID NOs.:191, 192, 193, 194, 195, 196 or 197.

As used herein the term "at least 90 consecutive amino acids of SEQ ID NO.:191" also includes the terms "at least 91, 92, 93, 94, 95, 96, 97, 98, 99, 100, 101, 102, 103, 104, 105, 106, 107, 108, 109, 110, 111, 112, 113, 114, 115 or at least 116 consecutive amino acids". The term "at least 90 consecutive amino acids of SEQ ID NO.:191" encompasses any possible sequence of at least 90 consecutive amino acids found in SEQ ID NO.:191 and especially those sequences which include the 3 CDRs of SEQ ID NO.:191, such as, for example a sequence comprising amino acids 1 to 106, 2 to 112, 11 to 113, 7 to 102 of SEQ ID NO.:191 and so on.

As used herein the term "at least 90 consecutive amino acids of SEQ ID NO.:192" also includes the terms "at least 91, 92, 93, 94, 95, 96, 97, 98, 99, 100, 101, 102, 103, 104, 105, 106, 107, 108, 109, 110, 111, 112, 113, 114, 115 or at least 116 consecutive amino acids". The term "at least 90 consecutive amino acids of SEQ ID NO.:192" encompasses any possible sequence of at least 90 consecutive amino acids found in SEQ ID NO.:192 and especially those sequences which include the 3 CDRs of SEQ ID NO.:192, for example a sequence comprising amino acids 6 to 109, 8 to 113, 1 to 102, 2 to 105 of SEQ ID NO.:192 and so on.

The terms "at least 90 consecutive amino acids of SEQ ID NO.:193", "at least 90 consecutive amino acids of SEQ ID NO.:194", "at least 90 consecutive amino acids of SEQ ID NO.:195", "at least 90 consecutive amino acids of SEQ ID NO.:196" or "at least 90 consecutive amino acids of SEQ ID NO.:197" has a similar meaning.

In accordance with the present invention, the antibody or antigen binding fragment of the present invention may have, for example, a heavy chain variable region as set forth in SEQ ID NO.:194, 195, 196 or 197.

In accordance with the present invention the antibody or antigen binding fragment may comprise, for example, a) a light chain variable region which may comprise at least 90 consecutive amino acids of SEQ ID NO.:186 and a heavy chain variable region which may comprise at least 90 consecutive amino acids of any of SEQ ID NO.:191, SEQ ID NO.:192, SEQ ID NO.:193, SEQ ID NO.:194, SEQ ID NO.:195, SEQ ID NO.:196 or SEQ ID NO.:197;

b) a light chain variable region which may comprise at least 90 consecutive amino acids of SEQ ID NO.:187 and a heavy chain variable region which may comprise at least 90 consecutive amino acids of any of SEQ ID NO.:191, SEQ ID NO.:192, SEQ ID NO.:193, SEQ ID NO.:194, SEQ ID NO.:195, SEQ ID NO.:196 or SEQ ID NO.:197;

c) a light chain variable region which may comprise amino acids at least 90 consecutive amino acids of SEQ ID NO.:188 and a heavy chain variable region which may comprise at least 90 consecutive amino acids of any of SEQ ID NO.:191, SEQ ID NO.:192, SEQ ID NO.:193, SEQ ID NO.:194, SEQ ID NO.:195, SEQ ID NO.:196 or SEQ ID NO.:197;

d) a light chain variable region which may comprise at least 90 consecutive amino acids of SEQ ID NO.:189 and a heavy chain variable region which may comprise at least 90 consecutive amino acids of any of SEQ ID NO.:191, SEQ ID NO.:92, SEQ ID NO.:193, SEQ NO.193, SEQ ID NO.:194, SEQ ID NO.:195, SEQ ID NO.:196 or SEQ ID NO.:197 or e) a light chain variable region which may comprise at least 90 consecutive amino acids of SEQ ID NO.:190 and a heavy chain variable region which may comprise at least 90 consecutive amino acids of any of SEQ ID NO.:191, SEQ ID NO.:192, SEQ ID NO.:193, SEQ ID NO.:194, SEQ ID NO.:195, SEQ ID NO.:196 or SEQ ID NO.:197.

In accordance with a more specific embodiment of the invention, the light chain variable region may comprise at least 90 consecutive amino acids of SEQ ID NO.:189 or 190 and the heavy chain variable region may comprise at least 90 consecutive amino acids of SEQ ID NO.:194, 195, 196 or 197.

In accordance with an even more specific embodiment of the invention, the light chain variable region may be as set forth in SEQ ID NO.:189 and the heavy chain variable region may be as set forth in SEQ ID NO.:194.

In accordance with an even more specific embodiment of the invention, the light chain variable region may be as set forth in SEQ ID NO.:189 and the heavy chain variable region may be as set forth in SEQ ID NO.:195.

In accordance with an even more specific embodiment of the invention, the light chain variable region may be as set forth in SEQ ID NO.:189 and the heavy chain variable region may be as set forth in SEQ ID NO.:196.

In accordance with an even more specific embodiment of the invention, the light chain variable region may be as set forth in SEQ ID NO.:189 and the heavy chain variable region may be as set forth in SEQ ID NO.:197.

In accordance with an even more specific embodiment of the invention, the light chain variable region may be as set forth in SEQ ID NO.:190 and the heavy chain variable region may be as set forth in SEQ ID NO.:194.

In accordance with an even more specific embodiment of the invention, the light chain variable region may be as set forth in SEQ ID NO.:190 and the heavy chain variable region may be as set forth in SEQ ID NO.:195.

In accordance with an even more specific embodiment of the invention, the light chain variable region may be as set forth in SEQ ID NO.:190 and the heavy chain variable region may be as set forth in SEQ ID NO.:196.

In accordance with an even more specific embodiment of the invention, the light chain variable region may be as set forth in SEQ ID NO.:190 and the heavy chain variable region may be as set forth in SEQ ID NO.:197.

Another exemplary embodiment of the humanized antibody or antigen binding fragment of the present invention includes for example, an antibody or antigen binding fragment having a light chain variable region which may comprise at least 90 consecutive amino acids of any of SEQ ID NO.:174, SEQ ID NO.:175, SEQ ID NO.:176 or SEQ ID NO.:168.

As used herein the term "at least 90 consecutive amino acids of SEQ ID NO.:174" also includes the terms "at least 91, 92, 93, 94, 95, 96, 97, 98, 99, 100, 101, 102, 103, 104, 105, 106, 107, 108, 109, 110, 111, 112 or at least 113 consecutive amino acids". The term "at least 90 consecutive amino acids of SEQ ID NO.:174" encompasses any possible sequence of at least 90 consecutive amino acids found in SEQ ID NO.:174 and especially those sequences which include the 3 CDRs of SEQ ID NO.:174, such as, for example a sequence comprising amino acids 6 to 108, 5 to 109, 13 to 103, 14 to 111 of SEQ ID NO.:174 and so on.

As used herein the term "at least 90 consecutive amino acids of SEQ ID NO.:175" also includes the terms "at least 91, 92, 93, 94, 95, 96, 97, 98, 99, 100, 101, 102, 103, 104, 105, 106, 107, 108, 109, 110, 111, 112 or at least 113 consecutive amino acids". The term "at least 90 consecutive amino acids of SEQ ID NO.:175" encompasses any possible sequence of at least 90 consecutive amino acids found in SEQ ID NO.:175 and especially those sequences which include the 3 CDRs of SEQ ID NO.:175, such as, for example a sequence comprising amino acids 7 to 109, 12 to 104, 22 to 113, 18 to 112 of SEQ ID NO.:175 and so on.

The terms "at least 90 consecutive amino acids of SEQ ID NO.:176" or "at least 90 consecutive amino acids of SEQ ID NO.:168" has a similar meaning.

In accordance with the present invention, the antibody or antigen binding fragment of the present invention may have, for example, a light chain variable region as set forth in SEQ ID NO.:168.

The humanized antibody or antigen binding fragment of the invention includes (or further includes) for example, a heavy chain variable region which may comprise at least 90 consecutive amino acids of any of SEQ ID NOs.:177, 178, 179 or 169.

As used herein the term "at least 90 consecutive amino acids of SEQ ID NO.:177" also includes the terms "at least 91, 92, 93, 94, 95, 96, 97, 98, 99, 100, 101, 102, 103, 104, 105, 106, 107, 108, 109, 110, 111, 112 or at least 113 consecutive amino acids". The term "at least 90 consecutive amino acids of SEQ ID NO.:177" encompasses any possible sequence of at least 90 consecutive amino acids found in SEQ ID NO.:177 and especially those sequences which include the 3 CDRs of SEQ ID NO.:177, such as, for example a sequence comprising amino acids 1 to 106, 2 to 112, 11 to 113, 7 to 102 of SEQ ID NO.:177 and so on.

As used herein the term "at least 90 consecutive amino acids of SEQ ID NO.:178" also includes the terms "at least 91, 92, 93, 94, 95, 96, 97, 98, 99, 100, 101, 102, 103, 104, 105, 106, 107, 108, 109, 110, 111, 112 or at least 113 consecutive amino acids". The term "at least 90 consecutive amino acids of SEQ ID NO.:178" encompasses any possible sequence of at least 90 consecutive amino acids found in SEQ ID NO.:178 and especially those sequences which include the 3 CDRs of SEQ ID NO.:178, for example a sequence comprising amino acids 6 to 109, 8 to 113, 1 to 102, 2 to 105 of SEQ ID NO.:178 and so on.

The terms "at least 90 consecutive amino acids of SEQ ID NO.:179" or "at least 90 consecutive amino acids of SEQ ID NO.:169" has a similar meaning.

In accordance with the present invention, the antibody or antigen binding fragment of the present invention may have, for example, a heavy chain variable region as set forth in SEQ ID NO.:169.

In accordance with the present invention the antibody or antigen binding fragment may comprise, for example,
  f) a light chain variable region which may comprise at least 90 consecutive amino acids of SEQ ID NO.:174 and a heavy chain variable region which may comprise at least 90 consecutive amino acids of any of SEQ ID NO.:177, SEQ ID NO.:178, SEQ ID NO.:179 or SEQ ID NO.:169;
  g) a light chain variable region which may comprise at least 90 consecutive amino acids of SEQ ID NO.:175 and a heavy chain variable region which may comprise at least 90 consecutive amino acids of any of SEQ ID NO.:177, SEQ ID NO.:178, SEQ ID NO.:179 or SEQ ID NO.:169;
  h) a light chain variable region which may comprise amino acids at least 90 consecutive amino acids of SEQ ID NO.:176 and a heavy chain variable region which may comprise at least 90 consecutive amino acids of any of SEQ ID NO.:177, SEQ ID NO.:178, SEQ ID NO.:179 or SEQ ID NO.:169 or;
  i) a light chain variable region which may comprise at least 90 consecutive amino acids of SEQ ID NO.:168 and a heavy chain variable region which may comprise at least 90 consecutive amino acids of any of SEQ ID NO.:177, SEQ ID NO.:178, SEQ ID NO.:179 or SEQ ID NO.:169.

In accordance with a more specific embodiment of the invention, the light chain variable region may comprise at least 90 consecutive amino acids of SEQ ID NO.:168 and the heavy chain variable region may comprise at least 90 consecutive amino acids of SEQ ID NO.:169.

In accordance with an even more specific embodiment of the invention, the light chain variable region may be as set forth in SEQ ID NO.:168 and the heavy chain variable region may be as set forth in SEQ ID NO.:169.

Other exemplary embodiments of the humanized antibodies or antigen binding fragments of the invention are those which may comprise a light chain variable region which may comprise at least 90 consecutive amino acids of any of SEQ ID Nos. 180, 181, 182 or 172.

As used herein the term "at least 90 consecutive amino acids of SEQ ID NO.:180" also includes the terms "at least 91, 92, 93, 94, 95, 96, 97, 98, 99, 100, 101, 102, 103, 104, 105, 106 or at least 107, consecutive amino acids". The term "at least 90 consecutive amino acids of SEQ ID NO.:180" encompasses any possible sequence of at least 90 consecutive amino acids found in SEQ ID NO.:180 and especially those sequences which include the 3 CDRs of SEQ ID NO.:180, for example a sequence comprising amino acids 6 to 102, 11 to 106, 1 to 106, 3 to 95, 5 to 95 of SEQ ID NO.:180 and so on.

As used herein the term "at least 90 consecutive amino acids of SEQ ID NO.:181" also includes the terms "at least 91, 92, 93, 94, 95, 96, 97, 98, 99, 100, 101, 102, 103, 104, 105, 106 or at least 107, consecutive amino acids". The term "at least 90 consecutive amino acids of SEQ ID NO.:181" encompasses any possible sequence of at least 90 consecutive amino acids found in SEQ ID NO.:181 and especially those sequences which include the 3 CDRs of SEQ ID NO:181, for example a sequence comprising amino acids 9 to 106, 10 to 101, 1 to 98, 3 to 99, 7 to 107 of SEQ ID NO.:181 and so on.

The terms "at least 90 consecutive amino acids of SEQ ID NO.:182" or "at least 90 consecutive amino acids of SEQ ID NO.:172" has a similar meaning.

In accordance with the present invention, the antibody or antigen binding fragment of the present invention may have, for example, a light chain variable region as set forth in SEQ ID NO.:172.

The humanized antibody or antigen binding fragment of the invention includes (or further includes) for example, a heavy chain variable region which may comprise at least 90 consecutive amino acids of any of SEQ ID NOs.:183, 184, 185 or 173.

As used herein the term "at least 90 consecutive amino acids of SEQ ID NO.:183" also includes the terms "at least 91, 92, 93, 94, 95, 96, 97, 98, 99, 100, 101, 102, 103, 104, 105, 106, 107, 108, 109, 110, 111, 112, 113, 114, 115 or at least 116 consecutive amino acids". The term "at least 90 consecutive amino acids of SEQ ID NO.:183" encompasses any possible sequence of at least 90 consecutive amino acids found in SEQ ID NO.:183 and especially those sequences which include the 3 CDRs of SEQ ID NO.:183, such as, for example a sequence comprising amino acids 6 to 111, 1 to 106, 2 to 104, 5 to 106, 10 to 107 of SEQ ID NO.:183 and so on.

As used herein the term "at least 90 consecutive amino acids of SEQ ID NO.:185" also includes the terms "at least 91, 92, 93, 94, 95, 96, 97, 98, 99, 100, 101, 102, 103, 104, 105, 106, 107, 108, 109, 110, 111, 112, 113, 114, 115 or at least 116 consecutive amino acids". The term "at least 90 consecutive amino acids of SEQ ID NO.:185" encompasses any possible sequence of at least 90 consecutive amino acids found in SEQ ID NO.:185 and especially those sequences which include the 3 CDRs of SEQ ID NO.:185, such as, for example a sequence comprising amino acids 3 to 107, 1 to 115, 1 to 110, 22 to 116, 20 to 115 of SEQ ID NO.:185 and so on.

The terms "at least 90 consecutive amino acids of SEQ ID NO.:184" or "at least 90 consecutive amino acids of SEQ ID NO.:173" has a similar meaning.

In accordance with the present invention, the antibody or antigen binding fragment of the present invention may have, for example, a heavy chain variable region as set forth in SEQ ID NO.:173.

In accordance with the present invention the antibody or antigen binding fragment may comprise, for example, a) a light chain variable region which may comprise at least 90 consecutive amino acids of SEQ ID NO.:180 and a heavy chain variable region which may comprise at least 90 consecutive amino acids of any of SEQ ID NO.:183, SEQ ID NO.:184, SEQ ID NO.:185 or SEQ ID NO.:173;

b) a light chain variable region which may comprise at least 90 consecutive amino acids of SEQ ID NO.:181 and a heavy chain variable region which may comprise at least 90 consecutive amino acids of any of SEQ ID NO.:183, SEQ ID NO.:184, SEQ ID NO.:185 or SEQ ID NO.:173;

c) a light chain variable region which may comprise amino acids at least 90 consecutive amino acids of SEQ ID NO.:182 and a heavy chain variable region which may comprise at least 90 consecutive amino acids of any of SEQ ID NO.:183, SEQ ID NO.:184, SEQ ID NO.:185 or SEQ ID NO.:173 or;

d) a light chain variable region which may comprise at least 90 consecutive amino acids of SEQ ID NO.:172 and a heavy chain variable region which may comprise at least 90 consecutive amino acids of any of SEQ ID NO.:183, SEQ ID NO.:184, SEQ ID NO.:185 or SEQ ID NO.:173.

In accordance with a more specific embodiment of the invention, the light chain variable region may have at least 90 consecutive amino acids of SEQ ID NO.:172 and the heavy chain variable region may have at least 90 consecutive amino acids of SEQ ID NO.:173.

In accordance with an even more specific embodiment of the invention, the light chain variable region may be as set forth in SEQ ID NO.:172 and the heavy chain variable region may be as set forth in SEQ ID NO.:173.

The antibody or antigen binding fragment of the present invention may have a light chain variable region and/or heavy chain variable region as described above and may further comprise amino acids of a constant region, such as, for example, amino acids of a constant region of a human antibody.

In an exemplary embodiment, the antibody or antigen binding fragment of the present invention may comprise, for example, a human IgG1 constant region.

In accordance with another exemplary embodiment of the invention, the antigen binding fragment may be, for example, a scFv, a Fab, a Fab' or a (Fab')$_2$.

Production of the Antibodies in Cells

The anti-KAAG1 antibodies that are disclosed herein can be made by a variety of methods familiar to those skilled in the art, such as hybridoma methodology or by recombinant DNA methods.

In an exemplary embodiment of the invention, the anti-KAAG1 antibodies may be produced by the conventional hybridoma technology, where a mouse is immunized with an antigen, spleen cells isolated and fused with myeloma cells lacking HGPRT expression and hybrid cells selected by hypoxanthine, aminopterin and thymine (HAT) containing media.

In an additional exemplary embodiment of the invention, the anti-KAAG1 antibodies may be produced by recombinant DNA methods.

In order to express the anti-KAAG1 antibodies, nucleotide sequences able to encode any one of a light and heavy immunoglobulin chains described herein or any other may be inserted into an expression vector, i.e., a vector that contains the elements for transcriptional and translational control of the inserted coding sequence in a particular host. These elements may include regulatory sequences, such as enhancers, constitutive and inducible promoters, and 5' and 3' un-translated regions. Methods that are well known to those skilled in the art may be used to construct such expression vectors. These methods include in vitro recombinant DNA techniques, synthetic techniques, and in vivo genetic recombination.

A variety of expression vector/host cell systems known to those of skill in the art may be utilized to express a polypeptide or RNA derived from nucleotide sequences able to encode any one of a light and heavy immunoglobulin chains described herein. These include, but are not limited to, microorganisms such as bacteria transformed with recombinant bacteriophage, plasmid, or cosmid DNA expression vectors; yeast transformed with yeast expression vectors; insect cell systems infected with baculovirus vectors; plant cell systems transformed with viral or bacterial expression vectors; or animal cell systems. For long-term production of recombinant proteins in mammalian systems, stable expression in cell lines may be effected. For example, nucleotide sequences able to encode any one of a light and heavy immunoglobulin chains described herein may be transformed into cell lines using expression vectors that may contain viral origins of replication and/or endogenous expression elements and a selectable or visible marker gene on the same or on a separate vector. The invention is not to be limited by the vector or host cell employed. In certain embodiments of the present invention, the nucleotide sequences able to encode any one of a light and heavy immunoglobulin chains described herein may each be ligated into a separate expression vector and each chain expressed separately. In another embodiment, both the light and heavy chains able to encode any one of a light and heavy immunoglobulin chains described herein may be ligated into a single expression vector and expressed simultaneously.

Alternatively, RNA and/or polypeptide may be expressed from a vector comprising nucleotide sequences able to encode any one of a light and heavy immunoglobulin chains described herein using an in vitro transcription system or a coupled in vitro transcription/translation system respectively.

In general, host cells that contain nucleotide sequences able to encode any one of a light and heavy immunoglobulin chains described herein and/or that express a polypeptide encoded by the nucleotide sequences able to encode any one of a light and heavy immunoglobulin chains described herein, or a portion thereof, may be identified by a variety of procedures known to those of skill in the art. These procedures include, but are not limited to, DNA/DNA or DNA/RNA hybridizations, PCR amplification, and protein bioassay or immunoassay techniques that include membrane, solution, or chip based technologies for the detection and/or quantification of nucleic acid or amino acid sequences. Immunological methods for detecting and measuring the expression of polypeptides using either specific polyclonal or monoclonal antibodies are known in the art. Examples of such techniques include enzyme-linked immunosorbent assays (ELISAs), radioimmunoassays (RIAs), and fluorescence activated cell sorting (FACS). Those of skill in the art may readily adapt these methodologies to the present invention.

Host cells comprising nucleotide sequences able to encode any one of a light and heavy immunoglobulin chains described herein may thus be cultured under conditions for the transcription of the corresponding RNA (mRNA, siRNA, shRNA etc.) and/or the expression of the polypeptide from cell culture. The polypeptide produced by a cell may be secreted or may be retained intracellularly depending on the sequence and/or the vector used. In an exemplary embodiment, expression vectors containing nucleotide sequences able to encode any one of a light and heavy immunoglobulin chains described herein may be designed to contain signal sequences that direct secretion of the polypeptide through a prokaryotic or eukaryotic cell membrane.

Due to the inherent degeneracy of the genetic code, other DNA sequences that encode the same, substantially the same or a functionally equivalent amino acid sequence may be produced and used, for example, to express a polypeptide encoded by nucleotide sequences able to encode any one of a light and heavy immunoglobulin chains described herein. The nucleotide sequences of the present invention may be engineered using methods generally known in the art in order to alter the nucleotide sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In addition, a host cell strain may be chosen for its ability to modulate expression of the inserted sequences or to process the expressed polypeptide in the desired fashion. Such modifications of the polypeptide include, but are not limited to, acetylation, carboxylation, glycosylation, phosphorylation, lipidation, and acylation. In an exemplary embodiment, anti-KAAG1 antibodies that contain particular glycosylation structures or patterns may be desired. Post-translational processing, which cleaves a "prepro" form of the polypeptide, may also be used to specify protein targeting, folding, and/or activity. Different host cells that have specific cellular machinery and characteristic mechanisms for post-translational activities (e.g., CHO, HeLa, MDCK, HEK293, and W138) are available commercially and from the American Type Culture Collection (ATCC) and may be chosen to ensure the correct modification and processing of the expressed polypeptide.

Those of skill in the art will readily appreciate that natural, modified, or recombinant nucleic acid sequences may be ligated to a heterologous sequence resulting in translation of a fusion polypeptide containing heterologous polypeptide moieties in any of the aforementioned host systems. Such heterologous polypeptide moieties may facilitate purification of fusion polypeptides using commercially available affinity matrices. Such moieties include, but are not limited to, glutathione S-transferase (GST), maltose binding protein, thioredoxin, calmodulin binding peptide, 6-His (His) (SEQ ID NO: 217), FLAG, c-myc, hemaglutinin (HA), and antibody epitopes such as monoclonal antibody epitopes.

In yet a further aspect, the present invention relates to a polynucleotide which may comprise a nucleotide sequence encoding a fusion protein. The fusion protein may comprise a fusion partner (e.g., HA, Fc, etc.) fused to the polypeptide (e.g., complete light chain, complete heavy chain, variable regions, CDRs etc.) described herein.

Those of skill in the art will also readily recognize that the nucleic acid and polypeptide sequences may be synthesized, in whole or in part, using chemical or enzymatic methods well known in the art. For example, peptide synthesis may be performed using various solid-phase techniques and machines such as the ABI 431A Peptide synthesizer (PE Biosystems) may be used to automate synthesis. If desired, the amino acid sequence may be altered during synthesis and/or combined with sequences from other proteins to produce a variant protein.

Antibody Conjugates

The antibody or antigen binding fragment of the present invention may be conjugated with a detectable moiety (i.e., for detection or diagnostic purposes) or with a therapeutic moiety (for therapeutic purposes)

A "detectable moiety" is a moiety detectable by spectroscopic, photochemical, biochemical, immunochemical, chemical and/or other physical means. A detectable moiety may be coupled either directly and/or indirectly (for example via a linkage, such as, without limitation, a DOTA or NHS linkage) to antibodies and antigen binding fragments thereof of the present invention using methods well known in the art. A wide variety of detectable moieties may be used, with the choice depending on the sensitivity required, ease of conjugation, stability requirements and available instrumentation. A suitable detectable moiety include, but is not limited to, a fluorescent label, a radioactive label (for example, without limitation, $^{125}I$, $In^{111}$, $Tc^{99}$, $I^{131}$ and including positron emitting isotopes for PET scanner etc), a nuclear magnetic resonance active label, a luminescent label, a chemiluminescent label, a chromophore label, an enzyme label (for example and without limitation horseradish peroxidase, alkaline phosphatase, etc.), quantum dots and/or a nanoparticle. Detectable moiety may cause and/or produce a detectable signal thereby allowing for a signal from the detectable moiety to be detected.

In another exemplary embodiment of the invention, the antibody or antigen binding fragment thereof may be coupled (modified) with a therapeutic moiety (e.g., drug, cytotoxic moiety).

In an exemplary embodiment, the anti-KAAG1 antibodies and antigen binding fragments may comprise an inhibitor, a chemotherapeutic or cytotoxic agent. For example, the antibody and antigen binding fragments may be conjugated to the chemotherapeutic or cytotoxic agent. Such chemotherapeutic or cytotoxic agents include, but are not limited to, Yttrium-90, Scandium-47, Rhenium-186, Iodine-131, Iodine-125, and many others recognized by those skilled in the art (e.g., lutetium (e.g., $Lu^{177}$), bismuth (e.g., $Bi^{213}$), copper (e.g., $Cu^{67}$)). In other instances, the chemotherapeutic or cytotoxic agent may comprise, without limitation, 5-fluorouracil, adriamycin, irinotecan, platinum-based compounds such as cisplatin and anti-tubulin or anti-mitotic compounds such as, taxanes, doxorubicin and cyclophosphamide, pseudomonas endotoxin, ricin and other toxins. Suitable antibody drug conjugates are selected amongst those having an $IC_{50}$ in the range of 0.001 nM to 150 nM, 0.001 nM to 100 nM, 0.001 nM to 50 nM, 0.001 nM to 20 nM or 0.001 nM to 10 nM (inclusively). The cytotoxic drug used for conjugation is thus selected on the basis of these criteria.

Alternatively, in order to carry out the methods of the present invention and as known in the art, the antibody or antigen binding fragment of the present invention (conjugated or not) may be used in combination with a second molecule (e.g., a secondary antibody, etc.) which is able to specifically bind to the antibody or antigen binding fragment of the present invention and which may carry a desirable detectable, diagnostic or therapeutic moiety.

Pharmaceutical Compositions of the Antibodies and their Use

Pharmaceutical compositions of the anti-KAAG1 antibodies or antigen binding fragments (conjugated or not) are also encompassed by the present invention. The pharmaceutical composition may comprise an anti-KAAG1 antibody or an antigen binding fragment and may also contain a pharmaceutically acceptable carrier.

Other aspects of the invention relate to a composition which may comprise the antibody or antigen binding fragment described herein and a carrier.

The present invention also relates to a pharmaceutical composition which may comprise the antibody or antigen binding fragment described herein and a pharmaceutically acceptable carrier.

In addition to the active ingredients, a pharmaceutical composition may contain pharmaceutically acceptable carriers comprising water, PBS, salt solutions, gelatins, oils, alcohols, and other excipients and auxiliaries that facilitate processing of the active compounds into preparations that may be used pharmaceutically. In other instances, such preparations may be sterilized.

As used herein, "pharmaceutical composition" means therapeutically effective amounts of the agent together with pharmaceutically acceptable diluents, preservatives, solubilizers, emulsifiers, adjuvant and/or carriers. A "therapeutically effective amount" as used herein refers to that amount which provides a therapeutic effect for a given condition and administration regimen. Such compositions are liquids or lyophilized or otherwise dried formulations and include diluents of various buffer content (e.g., Tris-HCl, acetate, phosphate), pH and ionic strength, additives such as albumin or gelatin to prevent absorption to surfaces, detergents (e.g., Tween 20, Tween 80, Pluronic F68, bile acid salts). Solubilizing agents (e.g., glycerol, polyethylene glycerol), antioxidants (e.g., ascorbic acid, sodium metabisulfite), preservatives (e.g., thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils). Also comprehended by the invention are particulate compositions coated with polymers (e.g., poloxamers or poloxamines). Other embodiments of the compositions of the invention incorporate particulate forms protective coatings, protease inhibitors or permeation enhancers for various routes of administration, including parenteral, pulmonary, nasal, oral, vaginal, rectal routes. In one embodiment the pharmaceutical composition is administered parenterally, paracancerally, transmucosally, transdermally, intramuscularly, intravenously, intradermally, subcutaneously, intraperitonealy, intraventricularly, intracranially and intratumorally.

Further, as used herein "pharmaceutically acceptable carrier" or "pharmaceutical carrier" are known in the art and include, but are not limited to, 0.01-0.1 M or 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's orfixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

For any compound, the therapeutically effective dose may be estimated initially either in cell culture assays or in animal models such as mice, rats, rabbits, dogs, or pigs. An animal model may also be used to determine the concentration range and route of administration. Such information may then be used to determine useful doses and routes for administration in humans. These techniques are well known to one skilled in the art and a therapeutically effective dose refers to that amount of active ingredient that ameliorates the symptoms or condition. Therapeutic efficacy and toxicity may be determined by standard pharmaceutical procedures in cell cultures or with experimental animals, such as by calculating and contrasting the $ED_{50}$ (the dose therapeutically effective in 50% of the population) and $LD_{50}$ (the dose lethal to 50% of the population) statistics. Any of the therapeutic compositions described above may be applied to any subject in need of such therapy, including, but not limited to, mammals such as dogs, cats, cows, horses, rabbits, monkeys, and humans.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

Methods of Use

The term "treatment" for purposes of this disclosure refers to both therapeutic treatment and prophylactic or preventative measures, wherein the object is to prevent or slow down (lessen) the targeted pathologic condition or disorder. Those in need of treatment include those already having the disorder as well as those prone to have the disorder or those in whom the disorder is to be prevented.

The present invention provides in one aspect thereof, a method of treating an individual having or suspected of having breast cancer with an antibody or antigen binding fragment which is capable of specific binding to KAAG1.

In accordance with the present invention, the individual may have a breast cancer that is negative for the estrogen receptor expression, the progesterone receptor expression and/or Her2 expression (or overexpression).

Also in accordance with the present invention, the individual may have a breast cancer that has low expression for at least one of estrogen receptor, progesterone receptor and/or Her2.

For example, the tumor may be negative for (or have low expression of) both estrogen receptor expression and progesterone receptor expression.

In accordance with the present invention, the individual may have a breast cancer that is characterized as being triple-negative or basal-like.

Yet other aspects of the invention relate to the use of the isolated antibody or antigen binding fragment described herein in the treatment or diagnosis of breast cancer characterized by a lack of estrogen receptor expression, progesterone receptor expression and/or Her2 overexpression or by low expression of at least one of these three markers.

In accordance with the present invention, the method may comprise, for example, administering an antibody or antigen binding fragment which is capable of specific binding to KAAG1 to an individual in need. The individual in need is preferentially selected on the basis of a lack of ER expression, PgR expression and/or by the absence of HER2 protein over-expression. Clinical testing for these markers is usually performed using histopathologic methods (immunohistochemistry, FISH, etc.) and/or by gene expression studies (see for example Dent et al, 2007, Bernstein and Lacey, 2011). The individual in need may thus be an individual who has received a diagnosis of triple-negative breast cancer or basal-like breast cancer.

The present invention thus particularly relates to the therapeutic treatment of individual having triple-negative breast cancer or basal-like cancer with an anti-KAAG1 antibody.

Suitable antibodies or antigen binding fragments include those that are capable of specific binding to KAAG1 at the surface of tumor cells. Such antibodies may preferentially bind an epitope included within amino acids 30 to 84 of KAAG1 inclusively (e.g., within amino acids 36 to 60 (inclusively) or within amino acids 61 to 84 (inclusively) of KAAG1).

Suitable antibodies may be those which mediate antibody-dependent cell cytotoxicity and those that are conjugated with a therapeutic moiety.

In accordance with the present invention, the antibody may be, for example, a monoclonal antibody, a chimeric antibody or a humanized antibody or an antigen binding fragment thereof.

The method of the present invention may include administering the antibody or antigen binding fragment in combination with an inhibitor, a chemotherapeutic or a cytotoxic agent.

Other methods of treatment encompassed by the present invention include administering other types of KAAG1 inhibitors such as antisense-based therapeutics (siRNA, antisenses, ribozymes, etc.).

The present invention thus provides a method of treating triple-negative breast cancer or basal-like breast cancer by administering an inhibitor of KAAG1 activity or expression to an individual in need.

The inhibitor may comprise a nucleotide sequence complementary to SEQ ID NO.:1 or to a fragment thereof. More particularly, the inhibitor may comprise a nucleotide sequence complementary to nucleotides 738 to 992 (inclusively) of SEQ ID NO.:1 or to a fragment thereof. For example, the inhibitor may include at least 10 consecutive nucleotides (at least 15, at least 20) which are complementary to SEQ ID NO.:1 or to nucleotides 738 to 992 (inclusively) of SEQ ID NO.:1.

In certain instances, the anti-KAAG1 antibodies and fragments may interact with cancer cells that express KAAG1 and induce an immunological reaction by mediating ADCC. In other instances, the anti-KAAG1 antibodies and fragments may block the interaction of KAAG1 with its protein partners.

In certain instances, the anti-KAAG1 antibodies and antigen binding fragments thereof may be administered concurrently with other treatments given for the same condition (inhibitors, chemotherapeutics or cytotoxic agents). As such, the antibodies may be administered with a PARP1 inhibitor, a EGFR inhibitor, anti-mitotics (e.g., taxanes), platinum-based agents (e.g., cisplatin), DNA damaging agents (e.g. Doxorubicin) and other anti-cancer therapies that are known to those skilled in the art. In other instances, the anti-KAAG1 antibodies and antigen binding fragments thereof may be administered with other therapeutic antibodies. These include, but are not limited to, antibodies that target EGFR, CD-20, and Her2.

The present invention relates in a further aspect thereof to a method for inhibiting the growth of KAAG1-expressing cell that are estrogen receptor-negative (ER–), progesterone receptor negative (PgR–) and/or that lacks Her2 overexpression (Her2–), the method may comprise contacting the cell with an effective amount of the antibody or antigen binding fragment described herein.

The present invention also encompasses method of treating cancer or inhibiting the growth of a KAAG1 expressing cells that are estrogen receptor-negative (ER–), progesterone receptor negative (PgR–) and/or that lacks Her2 overexpression (Her2–), in a mammal, the method may comprise administering the antibody or antigen binding fragment described herein to a mammal in need.

In further aspects, the present invention provides method of treatment, diagnostic methods and method of detection using the antibody or antigen binding fragment of the present invention and the use of these antibodies or antigen binding fragment in the manufacture of a pharmaceutical composition or drug for such purposes.

Method of treatment encompassed by the present invention includes administering an antibody or antigen binding fragment described herein to a mammal in need, and especially to a patient having or susceptible of having a cancer characterized as being estrogen receptor-negative (ER–), progesterone receptor negative (PgR–) and/or that lacks Her2 overexpression (Her2–), The invention also provides in further aspects, methods for reducing tumor spread, tumor invasion, tumor formation or for inducing tumor lysis, which may comprise administering an isolated antibody or antigen binding fragment to a mammal in need.

The invention therefore relates to the use of the isolated antibody or antigen binding fragment described herein in the (manufacture of a pharmaceutical composition for) treatment of cancer, reduction of tumor spread, tumor invasion, tumor formation or for inducing tumor lysis of KAAG1-expressing tumor cells that are estrogen receptor-negative (ER–), progesterone receptor negative (PgR–) and/or that lacks Her2 overexpression (Her2–).

The antibody or antigen binding fragment may more particularly be applicable for malignant tumor including, for example, a malignant tumor having the ability to metastasize and/or tumor cells characterized by anchorage-independent growth. The antibody or antigen binding fragment of the present invention may also be used in the diagnosis of cancer. The diagnosis of cancer may be performed in vivo by administering the antibody or antigen binding fragment of the present invention to a mammal having or suspected of having a cancer. The diagnosis may also be performed ex vivo by contacting a sample obtained from the mammal with the antibody or antigen binding fragment and determining the presence or absence of cells (tumor cells) expressing KAAG1 or a KAAG1 variant.

The present invention also encompasses method of detecting cancer or detecting a KAAG1 expressing cells that are estrogen receptor-negative (ER–), progesterone receptor negative (PgR–) and/or that lacks Her2 overexpression (Her2–), in a mammal, the method may comprise administering the antibody or antigen binding fragment described herein to a mammal in need.

The present invention relates in another aspect thereof to a method for detecting a cell expressing KAAG1 or a KAAG1 variant, the method may comprise contacting the cell with an antibody or antigen binding fragment described herein and detecting a complex formed by the antibody and the KAAG1– or KAAG1 variant-expressing cell. Exemplary embodiments of antibodies or antigen binding fragments used in detection methods are those which are capable of binding to the extracellular region of KAAG1.

Other exemplary embodiments of antibodies or antigen binding fragments used in detection methods are those which bind to KAAG1 or KAAG1 variant expressed at the surface of tumor cells that are estrogen receptor-negative (ER–), progesterone receptor negative (PgR–) and/or that lacks Her2 overexpression (Her2–).

Another aspect of the invention relates a method for detecting KAAG1 (SEQ ID NO.:2), a KAAG1 variant having at least 80% sequence identity with SEQ ID NO.:2 or a secreted form of circulating form of KAAG1 or KAAG1 variant, the method may comprise contacting a cell expressing KAAG1 or the KAAG1 variant or a sample (biopsy, serum, plasma, urine etc.) comprising or suspected of comprising KAAG1 or the KAAG1 variant with the antibody or antigen binding fragments described herein and measuring binding. The sample may originate from a mammal (e.g., a human) which may have cancer (e.g., breast cancer that is characterized as being estrogen receptor-negative (ER–), progesterone receptor negative (PgR–) and/or that lacks Her2 overexpression (Her2–), such as basal-like breast cancer or triple-negative breast cancer) or may be suspected of having cancer. The sample may be a tissue sample obtained from the mammal or a cell culture supernatant.

In accordance with the invention the sample may be a serum sample, a plasma sample, a blood sample or ascitic fluid obtained from the mammal. The antibody or antigen binding fragment described herein may advantageously detect a secreted or circulating form (circulating in blood) of KAAG1.

The method may comprise quantifying the complex formed by the antibody or antigen binding fragment bound to KAAG1 or to the KAAG1 variant.

The binding of an antibody to an antigen will cause an increase in the expected molecular weight of the antigen. A physical change therefore occurs upon specific binding of the antibody or antigen binding fragment and the antigen.

Such changes may be detected using, for example, electrophoresis followed by Western blot and coloration of the gel or blot, mass spectrometry, HPLC coupled with a computer or else. Apparatus capable of computing a shift in molecular weight are known in the art and include for example, Phosphorimager™.

When the antibody comprises for example a detectable label, the antigen-antibody complex may be detected by the fluorescence emitted by the label, radiation emission of the label, enzymatic activity of a label provided with its substrate or else.

Detection and/or measurement of binding between an antibody or antigen binding fragment and an antigen may be performed by various methods known in the art. Binding between an antibody or antigen binding fragment and an antigen may be monitored with an apparatus capable of detecting the signal emitted by the detectable label (radiation emission, fluorescence, color change etc.). Such apparatus provides data which indicates that binding as occurred and may also provide indication as to the amount of antibody bound to the antigen. The apparatus (usually coupled with a computer) may also be capable of calculating the difference between a background signal (e.g., signal obtained in the absence of antigen-antibody binding) or background noise and the signal obtained upon specific antibody-antigen binding. Such apparatuses may thus provide the user with indications and conclusions as to whether the antigen has been detected or not.

Additional aspects of the invention relate to kits which may include one or more container containing one or more antibodies or antigen binding fragments described herein.

Nucleic Acids, Vectors and Cells

Antibodies are usually made in cells allowing expression of the light chain and heavy chain expressed from a vector(s) comprising a nucleic acid sequence encoding the light chain and/or heavy chain.

The present therefore encompasses nucleic acids capable of encoding any of the CDRs, light chain variable regions, heavy chain variable regions, light chains, heavy chains described herein.

The present invention therefore relates in a further aspect to a nucleic acid encoding a light chain variable region and/or a heavy chain variable region of an antibody which is capable of specific binding to KAAG1.

Exemplary embodiments of nucleic acids encompassed by the present invention includes a nucleic acid selected from the group consisting of a nucleic acid having at least 70% sequence identity (i.e., at least 75%, at least 80% sequence identity) with any one of SEQ ID NOs.:3, 5, 7, 9, 11, 13, 15, 17, 19, 21, 23, 25, 45 and 47, fragments (e.g., of at least 10, at least 15, at least 20 consecutive nucleotides) and complement thereof.

In accordance with an embodiment of the invention, the nucleic acid may especially encode a light chain variable region and/or heavy chain variable region of an antibody which may be capable of inducing killing (elimination, destruction, lysis) of KAAG1- or KAAG1 variant-expressing tumor cells.

In accordance with another embodiment of the invention, the nucleic acid may especially encode a light chain variable region and/or heavy chain variable region of an antibody which may be capable of reducing spreading of KAAG1- or KAAG1 variant-expressing tumor cells.

In accordance with yet another embodiment of the invention, the nucleic acid may particularly encode a light chain variable region and/or heavy chain variable region of an antibody which may be capable of decreasing or impairing formation of KAAG1- or KAAG1 variant-expressing tumors.

Exemplary embodiments of nucleic acids of the present invention include nucleic acids encoding a light chain variable region comprising:
  a. a CDRL1 sequence selected from the group consisting of SEQ ID NO.:72 and SEQ ID NO.:73;
  b. a CDRL2 sequence selected from the group consisting of SEQ ID NO.:74, SEQ ID NO.: 75 and SEQ ID NO.:76, or;
  c. a CDRL3 sequence selected from the group consisting of SEQ ID NO.:77, SEQ ID NO.:78 and SEQ ID NO.:79.

In accordance with the present invention, the nucleic acid may encode a light chain variable region which may comprise at least two CDRs of a CDRL1, a CDRL2 or a CDRL3.

Also in accordance with the present invention, the nucleic acid may encode a light chain variable region which may comprise one CDRL1, one CDRL2 and one CDRL3.

The present invention also relates to a nucleic acid encoding a heavy chain variable region comprising:
  a. a CDRH1 sequence comprising SEQ ID NO.:80;
  b. a CDRH2 sequence selected from the group consisting of SEQ ID NO.:81, SEQ ID NO.:82, SEQ ID NO.:83, SEQ ID NO.:84 and SEQ ID NO.:85, or;
  c. a CDRH3 sequence selected from the group consisting of SEQ ID NO.:86, SEQ ID NO.:87 and SEQ ID NO.:88.

In accordance with the present invention, the nucleic acid may encode a heavy chain variable region which may comprise at least two CDRs of a CDRH1, a CDRH2 or a CDRH3.

In accordance with the present invention, the nucleic acid may encode a heavy chain variable region which may comprise one CDRH1, one CDRH2 and one CDRH3.

Also encompassed by the present invention are nucleic acids encoding antibody variants having at least one conservative amino acid substitution.

In accordance with the present invention, the nucleic acid may encode a CDR comprising at least one conservative amino acid substitution.

In accordance with the present invention, the nucleic acid may encode a CDR comprising at least one conservative amino acid substitution in at least two of the CDRs.

In accordance with the present invention, the nucleic acid may encode a CDR comprising at least one conservative amino acid substitution in the 3 CDRs.

In accordance with the present invention, the nucleic acid may encode a CDR comprising at least two conservative amino acid substitutions in at least one of the CDRs.

In accordance with the present invention, the nucleic acid may encode a CDR comprising at least two conservative amino acid substitutions in at least two of the CDRs.

In accordance with the present invention, the nucleic acid may encode a CDR comprising at least two conservative amino acid substitutions in the 3 CDRs.

Other aspects of the invention relate to a nucleic acid encoding a light chain variable region having at least 70%, 75%, 80% sequence identity with a sequence selected from the group consisting of SEQ ID NO.:16, SEQ ID NO.:20, SEQ ID NO.:24, SEQ ID NO.:103, SEQ ID NO.:104, SEQ ID NO.:105, SEQ ID NO.:106, SEQ ID NO.:107, SEQ ID NO.:108, SEQ ID NO.:109, SEQ ID NO.:110, SEQ ID NO.:111. SEQ ID NO.:112, SEQ ID NO.:113, SEQ ID NO.:114, SEQ ID NO.:115, SEQ ID NO.:116, SEQ ID NO.:117, SEQ ID NO.:118, SEQ ID NO.:119, SEQ ID NO.:120, SEQ ID NO.:121, SEQ ID NO.:122, SEQ ID NO.:123, SEQ ID NO.:124 and SEQ ID NO.:125.

Yet other aspects of the invention relate to a nucleic acid encoding a heavy chain variable region having at least 70%, 75%, 80% sequence identity to a sequence selected from the group consisting of SEQ ID NO.:18, SEQ ID NO.:22, SEQ ID NO.:26, SEQ ID NO.:126, SEQ ID NO.:127, SEQ ID NO.:128, SEQ ID NO.:129, SEQ ID NO.:130, SEQ ID NO.:131, SEQ ID NO.:132, SEQ ID NO.:133, SEQ ID NO.:134, SEQ ID NO.:135, SEQ ID NO.:136, SEQ ID NO.:137, SEQ ID NO.:138, SEQ ID NO.:139, SEQ ID NO.:140, SEQ ID NO.:141, SEQ ID NO.:142, SEQ ID NO.:143, SEQ ID NO.:144, SEQ ID NO.:145, SEQ ID NO.:146 and SEQ ID NO.:147.

In yet another aspect, the present invention relates to a vector comprising the nucleic acids described herein.

In accordance with the present invention, the vector may be an expression vector.

Vector that contains the elements for transcriptional and translational control of the inserted coding sequence in a particular host are known in the art. These elements may include regulatory sequences, such as enhancers, constitutive and inducible promoters, and 5' and 3' un-translated regions. Methods that are well known to those skilled in the art may be used to construct such expression vectors. These methods include in vitro recombinant DNA techniques, synthetic techniques, and in vivo genetic recombination.

In another aspect the present invention relates to an isolated cell that may comprise the nucleic acid described herein.

The isolated cell may comprise a nucleic acid encoding a light chain variable region and a nucleic acid encoding a heavy chain variable region either on separate vectors or on the same vector. The isolated cell may also comprise a nucleic acid encoding a light chain and a nucleic acid encoding a heavy chain either on separate vectors or on the same vector.

In accordance with the present invention, the cell may be capable of expressing, assembling and/or secreting an antibody or antigen binding fragment thereof.

In another aspect, the present invention provides a cell which may comprise and/or may express the antibody described herein.

In accordance with the invention, the cell may comprise a nucleic acid encoding a light chain variable region and a nucleic acid encoding a heavy chain variable region.

The cell may be capable of expressing, assembling and/or secreting an antibody or antigen binding fragment thereof.

The examples below are presented to further outline details of the present invention.

EXAMPLES

Example 1

This example discloses the methods used to convert the Fabs into full IgG1 chimeric monoclonal antibodies.

Aside from the possibility of conducting interaction studies between the Fab monoclonals and the KAAG1 protein, the use of Fabs may be limited with respect to conducting meaningful in vitro and in vivo studies to validate the biological function of the antigen. Thus, it was necessary to transfer the light and heavy chain variable regions contained in the Fabs to full antibody scaffolds, to generate mouse-human chimeric IgG1s. The expression vectors for both the light and heavy immunoglobulin chains were constructed such that i) the original bacterial signal peptide sequences upstream of the Fab expression vectors were replaced by mammalian signal peptides and ii) the light and heavy chain constant regions in the mouse antibodies were replaced with human constant regions. The methods to accomplish this transfer utilized standard molecular biology techniques that are familiar to those skilled in the art.

Light chain expression vector—an existing mammalian expression plasmid, called pTTVH8G (Durocher et al., 2002), designed to be used in the 293E transient transfection system was modified to accommodate the mouse light chain variable region. The resulting mouse-human chimeric light chain contained a mouse variable region followed by the human kappa constant domain. The cDNA sequence encoding the human kappa constant domain was amplified by PCR with primers OGS1773 and OGS1774 (SEQ ID NOS:55 and 56, respectively). The nucleotide sequence and the corresponding amino acid sequence for the human kappa constant region are shown in SEQ ID NOS: 57 and 58, respectively. The resulting 321 base pair PCR product was ligated into pTTVH8G immediately downstream of the signal peptide sequence of human VEGF A (NM_003376). This cloning step also positioned unique restriction endonuclease sites that permitted the precise positioning of the cDNAs encoding the mouse light chain variable regions. The sequence of the final expression plasmid, called pTTVK1, is shown in SEQ ID NO.:59. Based on the sequences disclosed in Table 2, PCR primers specific for the light chain variable regions of antibodies 3D3, 3G10, 3C4 and 3A4 (SEQ ID NOS:15, 19, 23 and 47, respectively) were designed that incorporated, at their 5'-end, a sequence identical to the last 20 base pairs of the VEGF A signal peptide. The sequences of these primers are shown in SEQ ID NOS:60, 61, 62 and 213. The same reverse primer was used to amplify all three light chain variable regions of 3D3, 3G10 and 3C4 since the extreme 3'-ends were identical. This primer (SEQ ID NO.:63) incorporated, at its 3'-end, a sequence identical to the first 20 base pairs of the human kappa constant domain. Primer SE ID NO.:214 was used to amplify the 3A4 light chain variable region. Both the PCR fragments and the digested pTTVK1 were treated with the 3'-5' exonuclease activity of T4 DNA polymerase resulting in complimentary ends that were joined by annealing. The annealing reactions were transformed into competent E. coli and the expression plasmids were verified by sequencing to ensure that the mouse light chain variable regions were properly inserted into the pTTVK1 expression vector. Those skilled in the art will readily recognize that the method used for construction of the light chain expression plasmids applies to all anti-KAAG1 antibodies contained in the original Fab library.

Heavy chain expression vector—the expression vector that produced the heavy chain immunoglobulins was designed in a similar manner to the pTTVK1 described above for production of the light chain immunoglobulins. Plasmid pYD11 (Durocher et al., 2002), which contains the human IgGK signal peptide sequence as well as the CH2 and CH3 regions of the human Fc domain of IgG1, was modified by ligating the cDNA sequence encoding the human constant CH1 region. PCR primers OGS1769 and OGS1770 (SEQ ID NOS:64 and 65), designed to contain unique restriction endonuclease sites, were used to amplify the human IgG1 CH1 region containing the nucleotide sequence and corresponding amino acid sequence shown in SEQ ID NOS:66 and 67. Following ligation of the 309 base pair fragment of human CH1 immediately downstream of the IgGK signal peptide sequence, the modified plasmid (SEQ ID NO.:68) was designated pYD15. When a selected heavy chain variable region is ligated into this vector, the resulting plasmid encodes a full IgG1 heavy chain immunoglobulin with human constant regions. Based on the sequences disclosed in Table 2, PCR primers specific for the heavy chain variable regions of antibodies 3D3, 3G10, 3C4 and 3A4 (SEQ ID NOS:17, 21, 25 and 45, respectively) were designed that incorporated, at their 5'-end, a sequence identical to the last 20 base pairs of the IgGK signal peptide. The sequences of these primers are shown in SEQ ID NOS:69 (3D3 and 3G10 have the same 5'-end sequence), SEQ ID NO.: 70 or SEQ ID NO.:215 for 3A4. The same reverse primer was used to amplify all three heavy chain variable regions of 3D3, 3C4 and 3G10 since the extreme 3'-ends were identical. This primer (SEQ ID NO.:71) incorporated, at its 3'-end, a sequence identical to the first 20 base pairs of the human CH1 constant domain. For the 3A4 heavy chain variable region, SEQ ID NO.:216 was used. Both the PCR fragments and the digested pYD15 were treated with the 3'-5' exonuclease activity of T4 DNA polymerase resulting in complimentary ends that were joined by annealing. The annealing reactions were transformed into competent E. coli and the expression plasmids were verified by sequencing to ensure that the mouse heavy chain variable regions were properly inserted into the pYD15 expression vector. Those skilled in the art will readily recognize that the method used for construction of the heavy chain expression plasmids applies to all anti-KAAG1 antibodies contained in the original Fab library.

Expression of human IgG1s in 293E cells—The expression vectors prepared above that encoded the light and heavy chain immunoglobulins were expressed in 293E cells using the transient transfection system (Durocher et al., 2002). Other methods of transient or stable expression may be used. The ratio of light to heavy chain was optimized in order to achieve the most yield of antibody in the tissue culture medium and it was found to be 9:1 (L:H). The ability of the anti-KAAG1 antibodies (monoclonal, chimeric or humanized) to bind to recombinant Fc-KAAG1 was measured by ELISA and compared with the original mouse Fabs.

The scheme used to convert other Fabs into a complete IgG (including the 3A4) and for expression of the antibodies is described in more details in international application No. PCT/CA2012/000296, the entire content of which is incorporated herein by reference.

Example 2

Humanization of the 3A4 Mouse Monoclonal Antibody

International patents No. PCT/CA2009/001586, PCT/CA2010/001795 and No. PCT/CA2012/000296, described exemplary methodology used to generate the humanized light chain and heavy chain variable regions.

Humanization of the 3A4 antibody light chain variable region involved 11 mutations to its proposed humanized framework for 100% framework humanization. Humanization of the 3A4 antibody heavy chain variable region involved 23 mutations to its proposed humanized framework for 100% framework humanization. These 100% humanized variable region sequences are labelled Lvh1 and Hvh1, respectively (SEQ ID NOs:189 and 194). Additional humanized sequences were also designed in which several residues from the 3A4 mouse sequences were retained based on careful structural and comparative sequence analyses that indicate a high probability of altering antigen-binding affinity if mutations are to be introduced at these positions. These sequences of the variable regions are labelled Lvh2, Hvh2, Hvh3 and Hvh4 (SEQ ID NOs: 190, 195, 196 and 197).

The two humanized light chain variants (including the constant region) are identified herein as Lh1 (SEQ ID NO.: 199) and Lh2 (SEQ ID NO.:200). The four humanized heavy chain variants (including the constant region are identified herein as Hh1 (SEQ ID NO.:202), Hh2 (SEQ ID NO.:203), Hh3 (SEQ ID NO.:204) and Hh4 (SEQ ID NO.:205). The two humanized light chain and 4 humanized heavy chain can be assembled into 8 humanized antibodies (Lh1Hh1, Lh1Hh2, Lh1Hh3, Lh1Hh4, Lh2Hh1, Lh2Hh2, Lh2Hh3, and Lh2Hh4).

In the case of 3A4 light-chain humanized sequence Lvh2 (SEQ ID NO:190), framework residues Val-L2 and Lys-L45 were retained from the mouse sequence since residue L2 is semi-buried, contacts both CDR-L1 and CDR-L3, and has antigen-contacting propensity, while residue L45 approaches the heavy-chain. We note that both these murine residues may occur in human frameworks. In the case of 3A4 heavy-chain humanized sequence Hvh2 (SEQ ID NO:195), framework residues Ile-H2 and Lys-L73 were retained from the mouse sequence since residue H2 is semi-buried, contacts both CDR-H1 and CDR-H3, and has antigen-contacting propensity, while residue H73 belongs to the Vernier zone supporting CDR-H2, and both these murine residues may occur in human frameworks. In the case of 3A4 heavy-chain humanized sequence Hvh3 (SEQ ID NO:196), Ile-H2 and Lys-L73 back-mutations were retained and in addition to these, framework residues Ile-H48, Ala-H67, Leu-H69 and Val-H71 were retained from the mouse sequence since all these additional murine residues are buried residues and belong to the Vernier zone supporting CDR-H2, and also murine residue H71 may occur in human frameworks. In the case of 3A4 heavy-chain humanized sequence Hvh4 (SEQ ID NO:197), all 6 back-mutations of the Hvh3 humanized variant were included plus additional two mouse framework residues Lys-H38 and Lys-H66 since they represent semi-buried residues close to CDR-H2. The resulting amino acid sequences of the murine and humanized chains are listed in Table 1. The alignment of the murine and humanized light chain variable regions is shown in FIG. 1a and the alignment of the murine and humanized heavy chain variable regions is shown in FIG. 1b.

FIGS. 2a and 2b is an alignment of the murine light chain variable region with the 100% humanized light chain variable region and the murine heavy chain variable region with the 100% humanized heavy chain variable region respectively. This figure illustrates the amino acids that are preserved and those that have been chosen for substitution.

Example 3

Assembly and Expression of 3A4 Humanized Variant Antibodies

The purpose of these investigations is to determine the kinetics parameters of anti-clusterin antibodies. In particular, to determine whether the humanization of the 3A4 anti-KAAG1 monoclonal antibody affects the kinetics parameters of its binding to human KAAG1. To this end, a kinetic analysis method was developed using the ProteOn XPR36 instrument from BioRad. Human KAAG1 was immobilized on a sensor chip. Full length antibodies or Fab fragments were injected and allowed to interact with the immobilized KAAG1.

Construction of Plasmid Encoding the Chimeric (Murine) Heavy and Light Chains of 3A4

The heavy and light chains of the chimeric antibody were amplified by PCR from the original murine immunoglobulin chains using the following oligonucleotide primer pairs: heavy chain, 5'-oligo encoded by SEQ ID NO: 206 and 3'-oligo encoded by SEQ ID NO:207; light chain, 5'-oligo encoded by SEQ ID NO: 208 and 3'-oligo encoded by SEQ ID NO:209. The resulting PCR products were digested by Hind III and cloned into pK-CR5 (SEQ ID NO:210) previously digested with Hind III.

Construction of Plasmids Encoding the Humanized Heavy Chain 3A4 Variants 1, 2, 3 and 4

The fragments coding for the humanized heavy chain region of the antibody 3A4 (Hh1, Hh2, Hh3 and Hh4) were ordered from GenScript (Piscataway, USA). The DNA fragments including the kozak and stop codon sequences were digested with HindIII and cloned into the HindIII site of plasmid pK-CR5 previously dephosphorylated with calf intestinal phosphatase (NEB) to prevent recircularization. FIG. 3a shows the map of the plasmid pK-CR5-3A4-HC-variant1. All heavy chain variants of the humanized 3A4 were constructed in a similar manner.

Construction of Plasmids Encoding the Humanized Light Chain 3A4 Variants 1 and 2

Figure 3B:
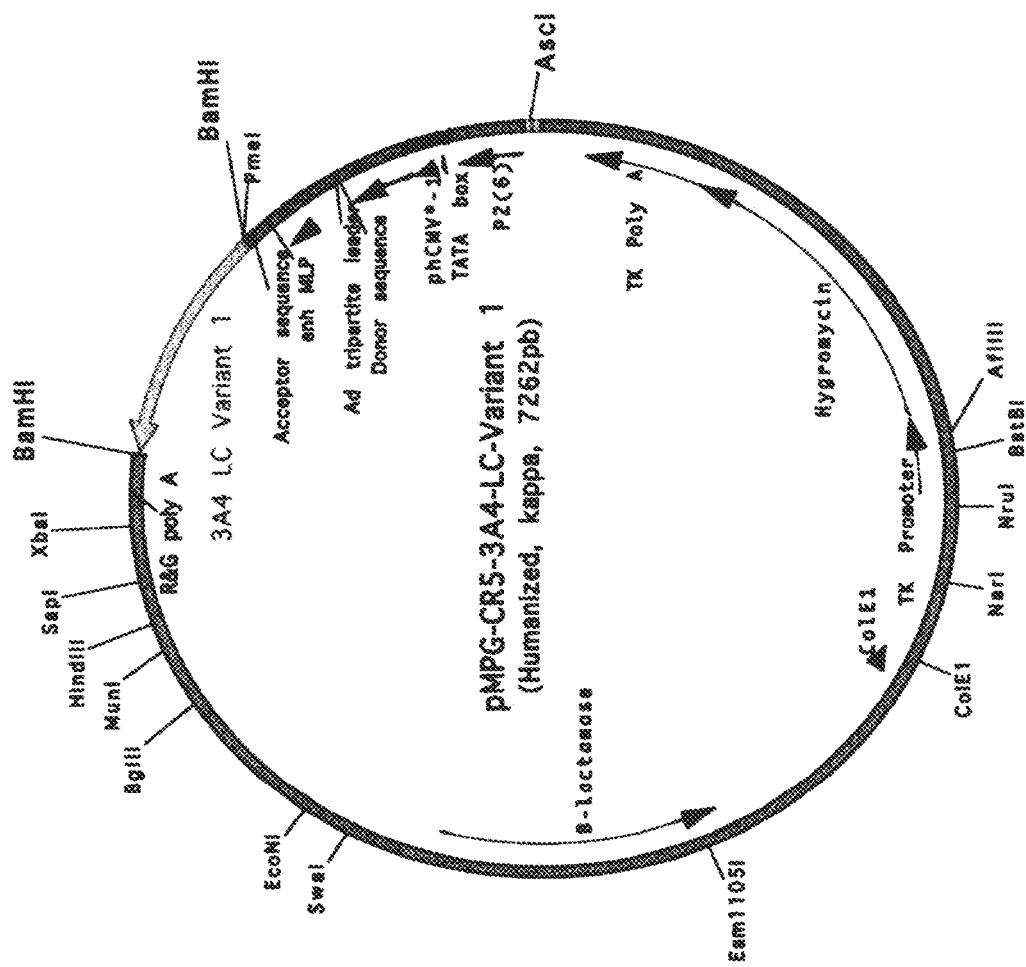
FIG. 3b represents plasmid map of pMPG-CR5-3A4-LC-Variant 1. The light chains of the humanized variants 1 and 2 of 3A4 antibody were cloned in the same manner into the BamHI site of pMPG-CR5. Consequently, the resulting plasmid is identical to pMPG-CR5-3A4-LC-Variant 1, except for the sequence of the light chain immunoglobulin variable domain.

The fragments coding for the human light chain regions of the antibody 3A4 (Lh1 and Lh2) were ordered from GenScript. The DNA fragments including the kozak and stop codon sequences was digested with BamHI and cloned into the BamHI site of plasmid pMPG-CR5 (SEQ ID NO:211) previously dephosphorylated with calf intestinal phosphatase (NEB) to prevent recircularization. FIG. 3b shows the map of the plasmid pMPG-CR5-3A4-LC-variant1. All light chain variants of the humanized 3A4 were constructed in a similar manner.

Transient Transfection Study

Plasmid DNA was isolated from small cultures of E. coli using the Mini-Prep kit (Qiagen Inc, Mississauga, ON) according to the manufacturer's recommendation. Briefly, 2 ml of LB medium containing 100 µg/ml of ampicillin were inoculated with a single colony picked after ligation and transformation. The cultures were incubated at 37° C. overnight with vigorous shaking (250 RPM). The plasmid was then isolated from 1.5 ml of culture using the protocols, buffers, and columns provided by the kit. The DNA was eluted using 50 µl of sterile water. Plasmid DNA was isolated from large culture of E. coli using the Plasmid Plus Maxi kit (Qiagen Inc, Mississauga, ON) according to the manufacturer's recommendation, 200 mL of LB medium containing 100 µg/mL ampicillin were inoculated with a single fresh colony of E. coli and incubated overnight at 37° C. with vigorous shaking (250 RPM). The bacteria (130 mL of culture for the heavy chain and 180 mL of culture for the light chain) were pelleted by centrifugation at 6000×g, for 15 min, at 4° C. and the plasmid was isolated using the protocols, buffers and columns provided by the kit. The pure plasmids was resuspended in sterile 50 mM Tris, pH8 and quantified by measuring the optical density at 260 nm. Before transfection the purified plasmid were sterilized by extraction with phenol/chloroform followed by ethanol precipitation. The plasmid were resuspended in sterile 50 mM Tris, pH 8 and quantified by optical density at 260 nm.

Before transfection, the cells (CHO-cTA) were washed with PBS and resuspended at a concentration of $4.0 \times 10^6$ cell/ml in growth medium (CD-CHO, Invitrogen) without dextran sulfate for 3 h in suspension culture. For each plasmid combination, 45 ml of cells were transfected by adding slowly 5 ml of CDCHO medium supplemented with 10 µg/ml of each plasmid and 50 µg/ml of polyethylenimine (PEI Max; Polysciences). The final concentration was 1 µg/ml of each plasmid and 5 µg/ml of PEI. After 2 h, the cells were transferred at 30° C. The next days, 50 µg/mL of dextran sulfate and 3.75 ml of each supplement (Efficient Feed A and B Invitrogen) were added to the cells and they were incubated at 30° C. for 13 days, 2.5 ml of Feed A and 2.5 ml of Feed B were added at day 4, 6, 8 and 11. On day 13, the supernatant was clarified by centrifugation and filtered through a 0.22 µM filter.

CHO cells (CHOcTA) were transfected with plasmids encoding the different variants of humanized heavy and light chains of the 3A4 antibody regulated by the CR5 promoter. Transfection with different combinations of light and heavy chains was performed. As control, cells were also transfected with plasmids encoding the chimeric/murine antibody.

Figure 4:
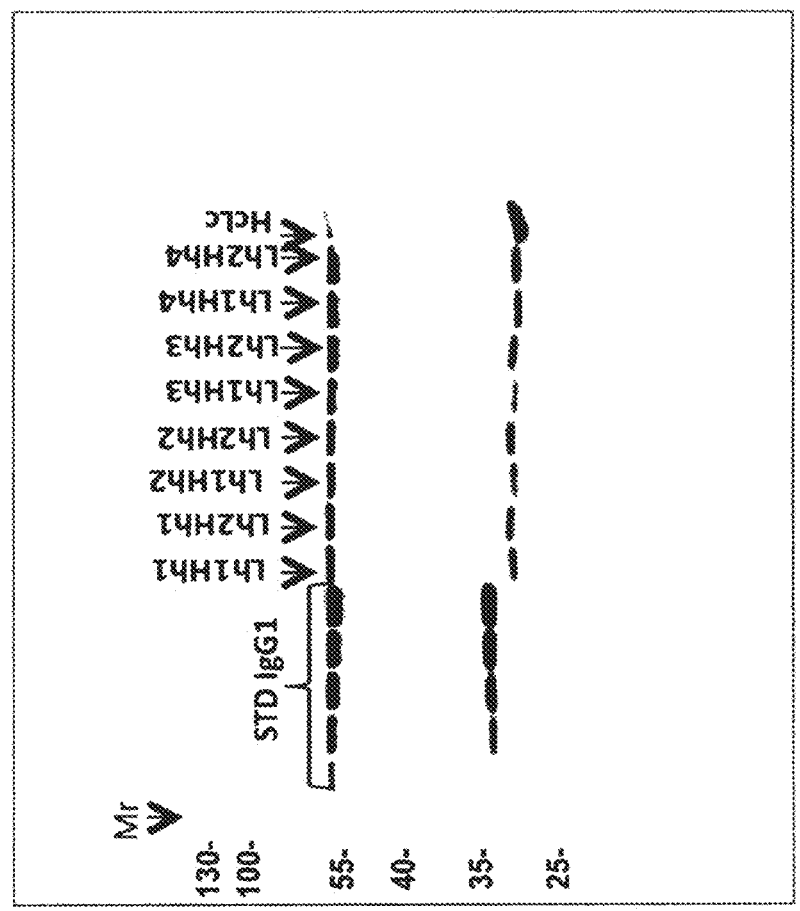
FIG. 4 represents an analysis of antibody production after transient transfection in CHO cells. Supernatant (13 days post-transfection) of CHOcTA cells transfected with the different combinations of light and heavy chains of humanized 3A4 antibody were analyzed by western blot. Quantification of antibody produced in the supernatants was determined after scanning the bands of the western blot against dilution of a known standard (human purified IgG antibody). Mr molecular weight marker (kDa).

Purification of Antibody 15 ml of supernatant from the CHO cell transfections were concentrated by centrifugation using the Amicon Ultra (Ultacell-50k) cassette at 1500 rpm. The concentrated antibody (550 µl) was purified using the Nab spin kit Protein A Plus (Thermo Scientific) according to the manufacture's recommendations. The purified antibodies were then desalted using PBS and the concentrating Amicon Ultra (Ultracel-10K) cassette at 2500 rpm to a final volume of 250 µl. The purified antibody was quantified by reading the $OD_{280}$ using the Nanodrop spectrophotometer and kept frozen at −20° C. An aliquote of the purified antibody was resuspended into an equal volume of Laemmli 2× and heated at 95° C. for 5 min and chilled on ice. A standard curve was made using known amount of purified human IgG1 kappa from Human Myeloma plasma (Athens Research). The samples were separated on a polyacrylamide Novex 10% Tris-Glycine gel (Invitrogen Canada Inc., Burlington, ON) and transferred onto a Hybond-N nitrocellulose membrane (Amersham Bioscience Corp., Baie d'Urfée, QC) for 1 h at 275 mA. The membrane was blocked for 1 h in 0.15% Tween 20, 5% skimmed milk in PBS and incubated for 1 hr with an Goat anti-Human IgG (H+L) conjugated to Cy5 (Jackson, Cat #109-176-099). The signal was revealed and quantified by scanning with the Typhoon Trio+ scanner (GE Healtcare). As shown in FIG. 4, all combinations of the 3A4 humanized antibody variants were expressed in CHO cells.

Example 4

Kinetic Analysis of Murine and Humanized 3A4 Antibody Supplies

GLM sensorchips, the Biorad ProteOn amine coupling kit (EDC, sNHS and ethanolamine), and 10 mM sodium acetate buffers were purchased from Bio-Rad Laboratories (Mississauga, ON). HEPES buffer, EDTA, and NaCl were purchased from from Sigma-Aldrich (Oakville, ON). Ten percent Tween 20 solution was purchased from Teknova (Hollister, Calif.). The goat anti-human IgG Fc fragment specific antibody was purchased from Jackson ImmunoResearch. The gel filtration column Superdex 75 10/300 GL was purchased from GE Healthcare.

Gel Filtration

Figure 5:
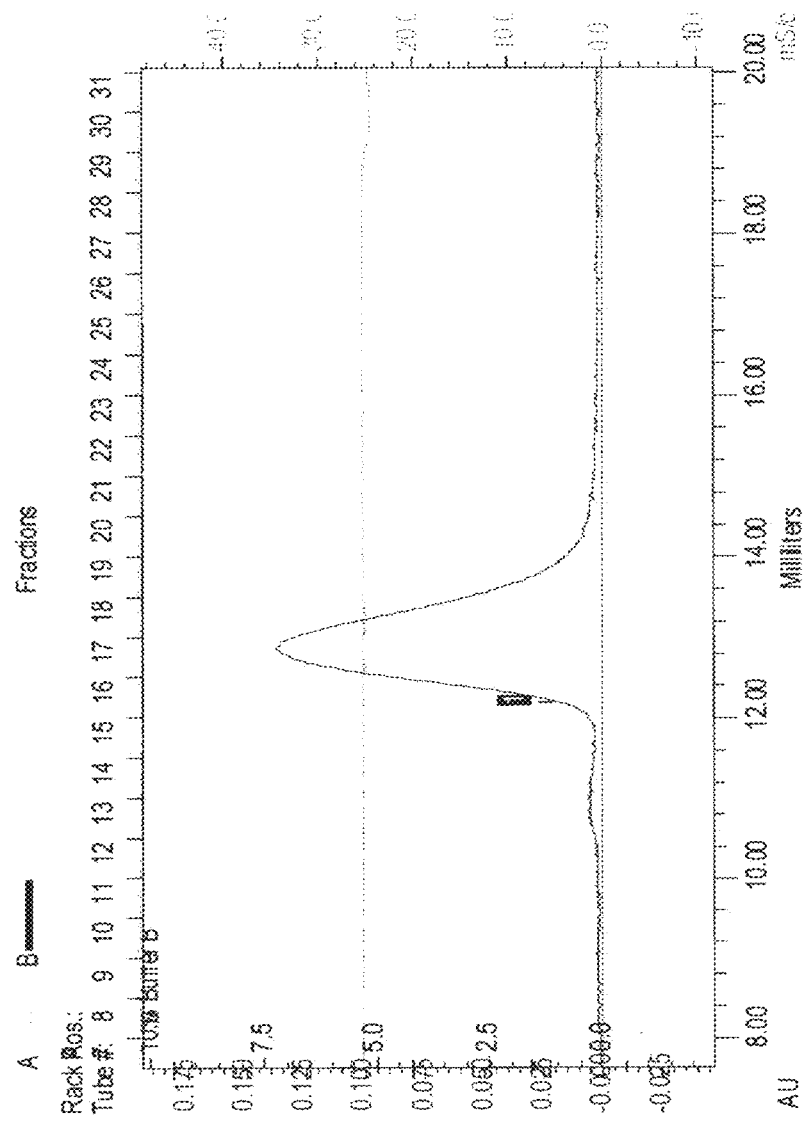
FIG. 5 is a graph of a Superdex G75 gel filtration of recombinant KAAG1 sample. KAAG1 was injected over the gel filtration and separated at 0.4 ml/min. The largest peak between fractions 15-19.

The KAAG1 protein at a concentration of 3.114 mg/ml and a volume of 220 µL was injected onto the Superdex G75 column, The separation was done at 0.4 ml/min in HBST running buffer (see below) without Tween 20. The volume of the fractions collected was 500 µL. Concentration of KAAG1 in each fraction was determined by $OD_{280}$ using an extension coefficient of 5500 and a MW of 8969. FIG. 5 represents the profile of the gel filtration of KAAG1. A small peak of potential aggregate is eluting at around 11 mil. The protein eluting at 13 ml was used as analyte for the SPR assay (fractions 15-19).

SPR Biosensor Assays

All surface plasmon resonance assays were carried out using a BioRad ProteOn XPR36 instrument (Bio-Rad Laboratories Ltd. (Mississauga, ON) with HBST running buffer (10 mM HEPES, 150 mM NaCl, 3.4 mM EDTA, and 0.05% Tween 20 pH 7.4) at a temperature of 25'C. The anti-mouse Fc capture surface was generated using a GLM sensorchip activated by a 1:5 dilution of the standard BioRad sNHS/EDC solutions injected for 300 s at 30 µL/min in the analyte (horizontal) direction. Immediately after the activation, a 13 µg/mL solution of anti-human IgG Fc fragment specific in 10 mM NaOAc pH 4.5 was injected in the analyte direction at a flow rate of 25 µL/min until approximately 8000 resonance units (RUs) were immobilized. Remaining active groups were quenched by a 300 s injection of 1M ethanolamine at 30 µL/min in the analyte direction, and this also ensures mock-activated interspots are created for blank referencing. The screening of the 3A4 variants for binding to KAAG1 occurred in two steps: an indirect capture of 3A4 variants from cell supernatant onto the anti-human IgG Fc fragment specific surface in the ligand direction(vertical) followed by a KAAG1 injection in the analyte direction. Firstly, one buffer injection for 30 s at 100 uL/min in the ligand direction was used to stabilize the baseline. For each 3A4 capture, unpurified 3A4 variants in cell-culture media were diluted to 4% in HBST, or approximately 1.25 μg/mL of purified 3A4 in HBST was used. Four to five 3A4 variants along with wild-type 3A4 were simultaneously injected in individual ligand channels for 240 s at flow 25 μL/min. This resulted in a saturating 3A4 capture of approximately 400-700 RUs onto the anti-human IgG Fc fragment specific surface. The first ligand channel was left empty to use as a blank control if required. This 3A4 capture step was immediately followed by two buffer injections in the analyte direction to stabilize the baseline, and then the gel filtration purified KAAG1 was injected. For a typical screen, five KAAG1 concentrations (8, 2.66, 0.89, 0.29, and 0.098 nM) and buffer control were simultaneously injected in individual analyte channels at 50 μL/min for 120 s with a 600s dissociation phase, resulting in a set of binding sensorgrams with a buffer reference for each of the captured 3A4 variants. The anti-human IgG Fc fragment specific—3A4 complexes were regenerated by a 18 s pulse of 0.85% phosphoric acid for 18 s at 100 μL/min to prepare the anti-human IgG Fc fragment specific surface for the next injection cycle. Sensorgrams were aligned and double-referenced using the buffer blank injection and interspots, and the resulting sensorgrams were analyzed using ProteOn Manager software v3.0. The kinetic and affinity values were determined by fitting the referenced sensorgrams to the 1:1 Langmuir binding model using local $R_{max}$, and affinity constants ($K_D$ M) were derived from the resulting rate constants ($k_d$ $s^{-1}$/$k_a$ $M^{-1}s^{-1}$).

Determination of Rate and Affinity Constants

Figure 7A:
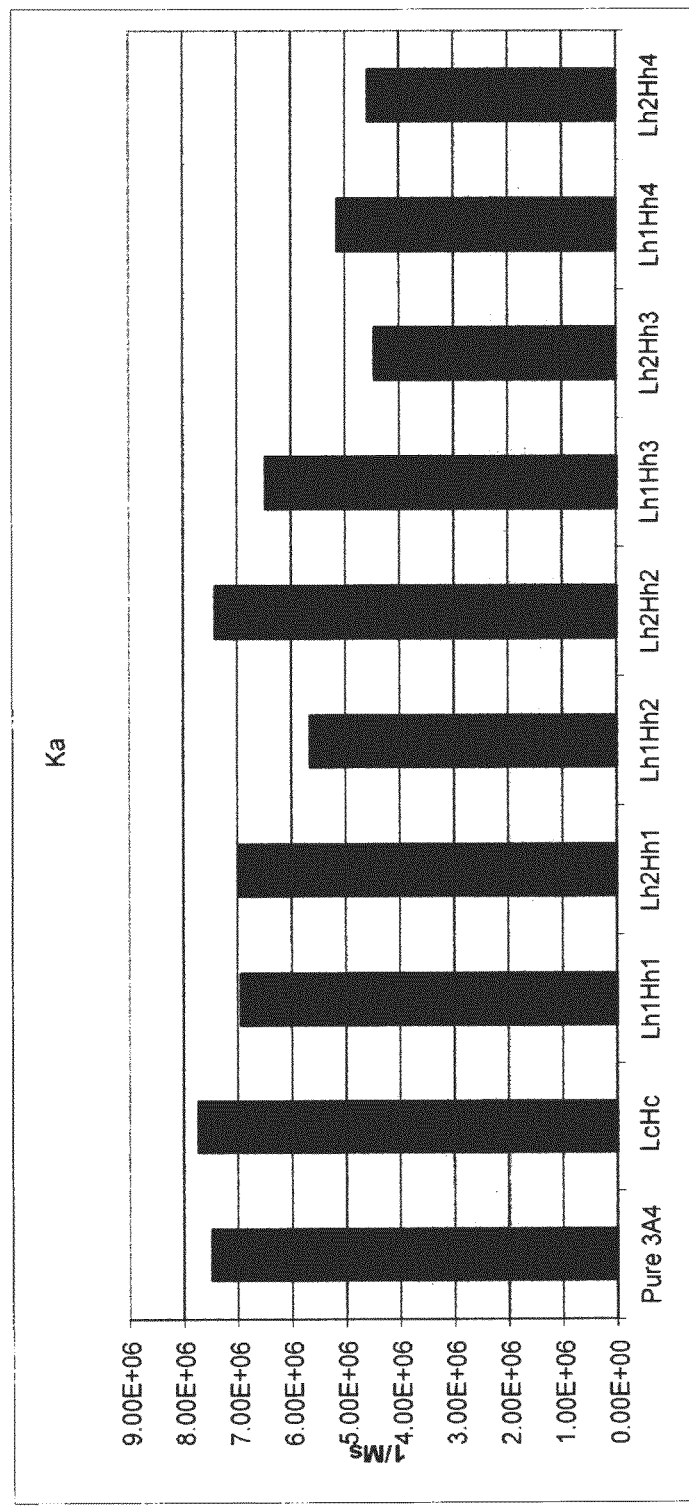
FIG. 7a is an histogram illustrating the association rates ($K_a$) of the humanized antibodies.
Figure 7B:
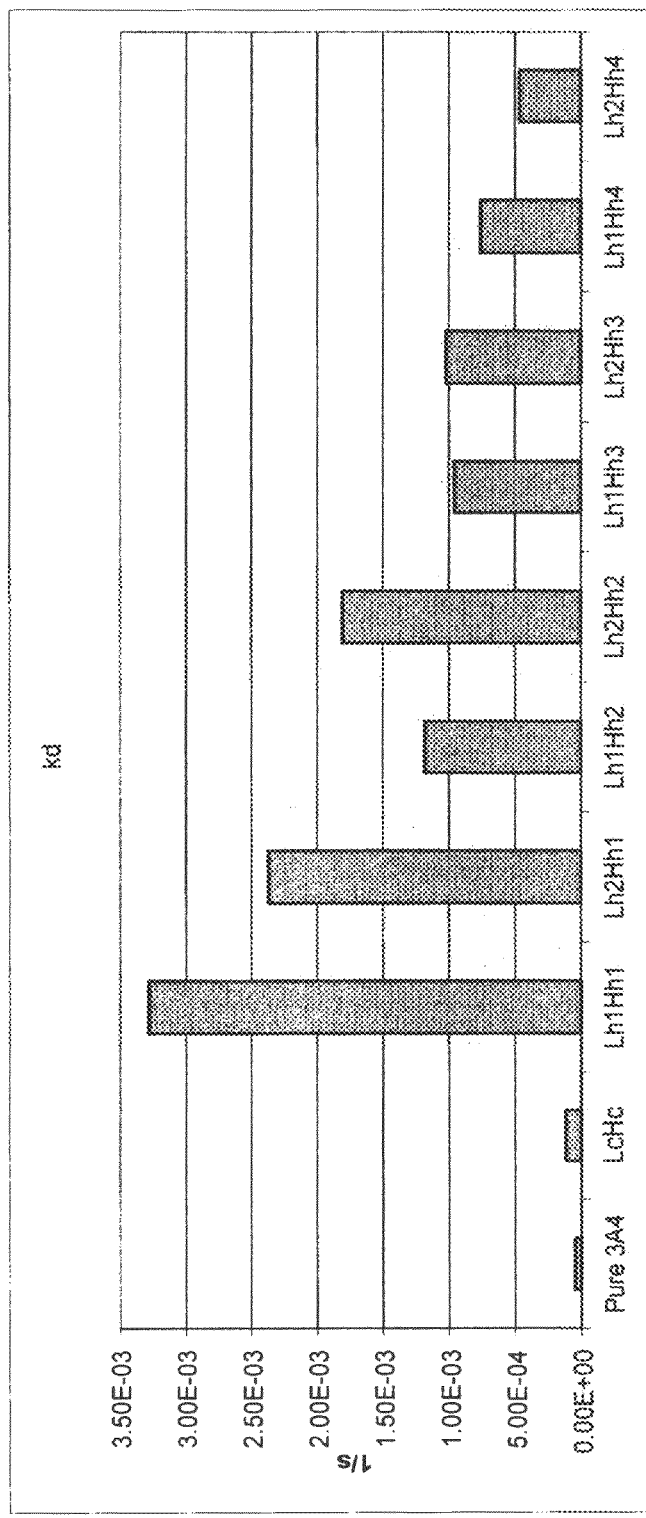
FIG. 7b is an histogram illustrating the dissociation rates ($K_d$) of the humanized antibodies.
Figure 7C:
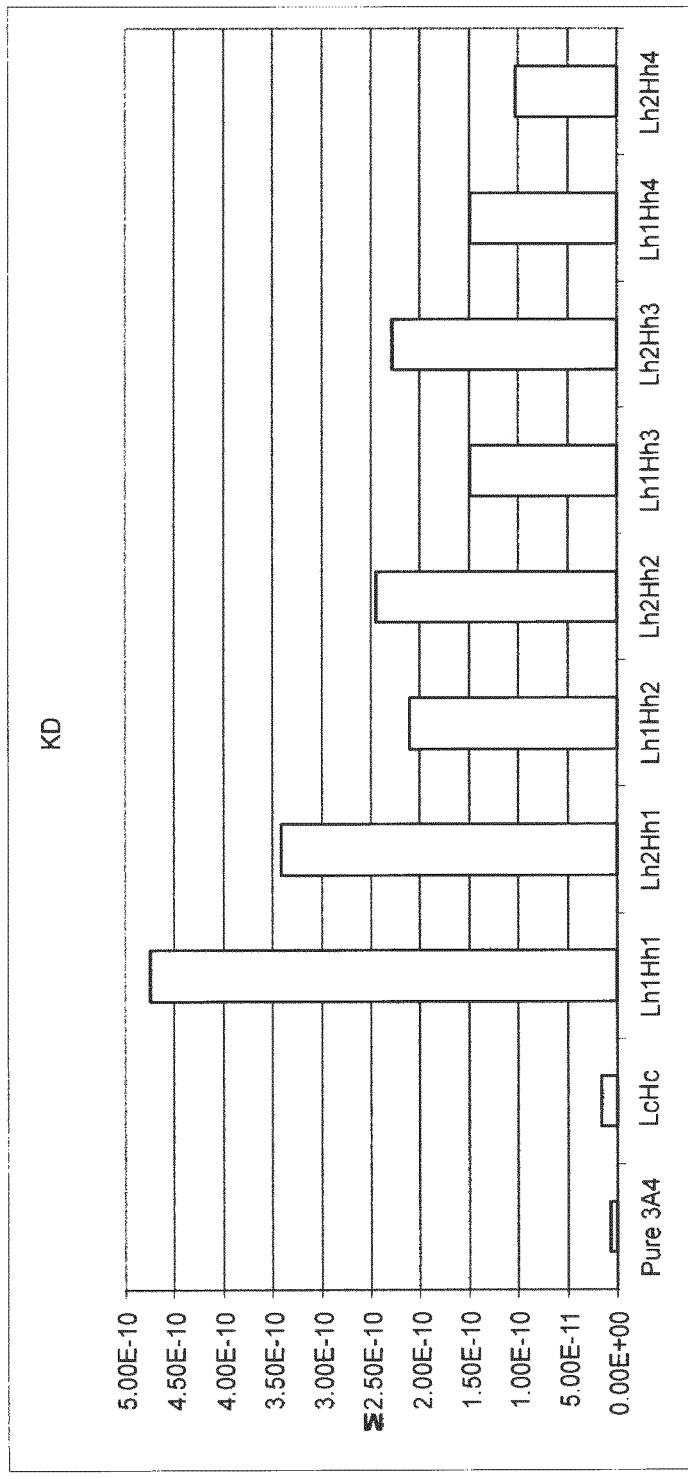
FIG. 7c is an histogram illustrating the affinity constants ($K_D$) of the humanized antibodies.

FIG. 6 summarizes the association ($k_a$, 1/Ms) and dissociation ($k_d$, 1/s) rate constants as well as affinity ($K_D$, M) constants for the interaction of KAAG1 with purified murine 3A4, murine 3A4 transiently expressed as a chimeric and transiently expressed humanized variants. These constants are graphically represented in FIG. 7a-c. The association rate constant is very similar for the pure parental, chimeric and humanized 3A4 variants (FIG. 7a). The dissociation rate constants is similar for the transiently express chimeric as compared to the pure parental 3A4 with suggest that the transfection procedure did not alter the parameters of the interaction of KAAG1 with the antibody (FIG. 7b). However, all humanized variants seem to have a slightly altered off rate, i.e. quicker dissociation rate (FIG. 7b). This is reflected in the affinity constants (FIG. 7c). In summary, there is a linear correlation between the binding affinity (log $K_D$) of the humanized variant and the number of back-mutations made in the parent antibody (LcHc) with a decrease in the binding affinity as the number of mutations is increasing. However, the difference in binding affinity is only 4 fold different between the worse variant (H1 L1, 0.47 nM) which has no mouse residue retained and the best variant which has 10 mouse residues retained (H4L2, 0.1 nM). Finally, the binding affinity of all variants for KAAG1 was found to be sub-nanomolar and the best variant (H4L2, 0.1 nM) exhibited an affinity about 6-fold weaker than the murine (LcHc, 0.057 nM). Overall, these results indicate that humanization was successful as all of the variants displayed high affinity for KAAG1.

Example 5

Binding of 3A4 Humanized Variants to KAAG1 in an ELSA

Figure 8A:
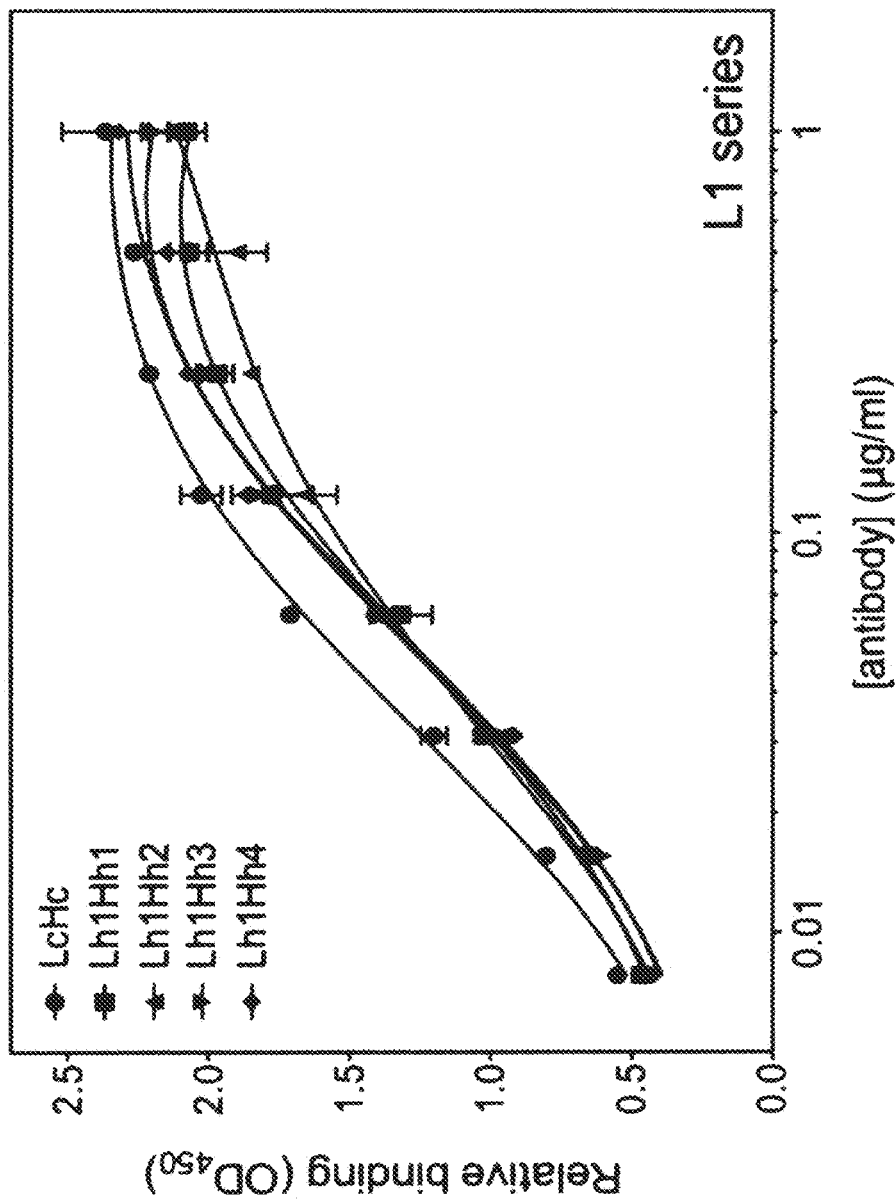
FIG. 8a illustrates humanized 3A4 variants binding to KAAG1 in an ELISA. This figure shows the comparative binding of 3A4 humanized antibody variants and the murine 3A4. Concentration-dependent binding profiles of the humanized heavy chains (Hh1, Hh2, Hh3 and Hh4) assembled with the Lh1 light chain variant.
Figure 8B:
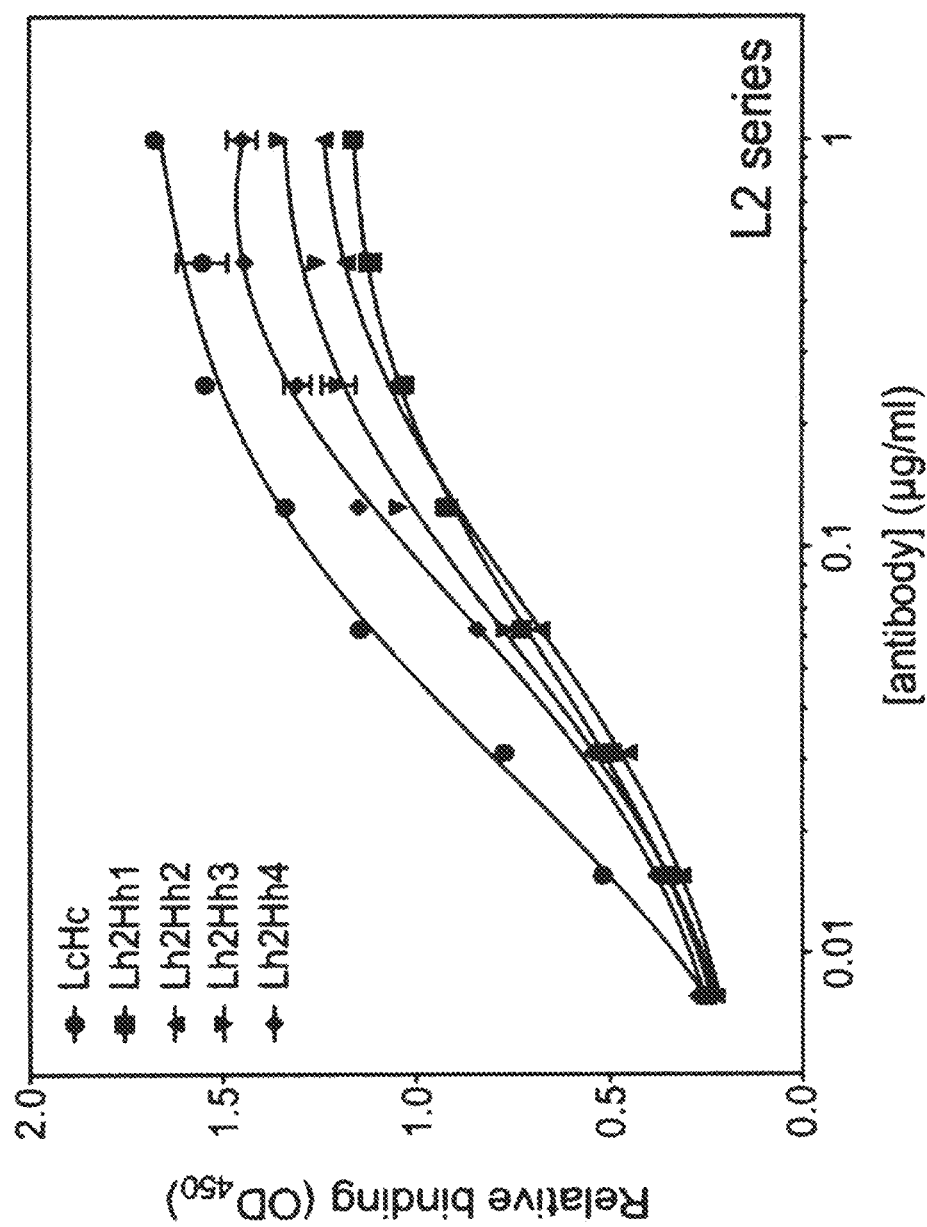
FIG. 8b illustrates humanized 3A4 variants binding to KAAG1 in an ELISA. This figure shows the comparative binding of 3A4 humanized antibody variants and the murine 3A4. Concentration-dependent binding profiles of the humanized heavy chains (Hh1, Hh2, Hh3 and Hh4) assembled with the Lh2 light chain variant.

ELISA methods were also used to compare the binding activity of the humanized 3A4 variants to the murine 3A4 antibody. Recombinant human KAAG1 was coated in 96-well plates O/N, washed and incubated for 1 h at RT with increasing quantities of murine or humanized 3A4 variants. Following another round of washing steps, an anti-human antibody conjugated to HRP was added to the wells and the bound 3A4 antibody was measured calorimetrically at $Abs_{450}$. As shown in FIG. 8a, the humanized variants (Lh1Hh1, Lh1Hh2, Lh1Hh3 and Lh1Hh4) displayed very similar binding to KAAG1 when compared to the murine 3A4 (LcHc), which has a high affinity of 0.016 nM. This result indicated that all four humanized heavy chain variants were comparable to the original h3A4 heavy chain when assembled with the L1 variant of the humanized light chain. FIG. 8a shows the results when the heavy chain variants were assembled with Lh2 variant of the 3A4 humanized light chain. In this instance, there was a difference in the binding of the variants. For example, Lh2hh4 was the variant with the closest profile compared to the murine 3A4. This was in agreement with the SPR data, which showed that the variant 4 of the heavy chain had the highest affinity for KAAG1. Taken together, these binding results show that the humanized variants all interact with human KAAG1 in this assay. Although there were some subtle differences, the binding in ELISA was in concordance with the SPR results.

Example 6

Binding of 3A4 Humanized Variants on the Surface of Cancer Cells

Figure 9:
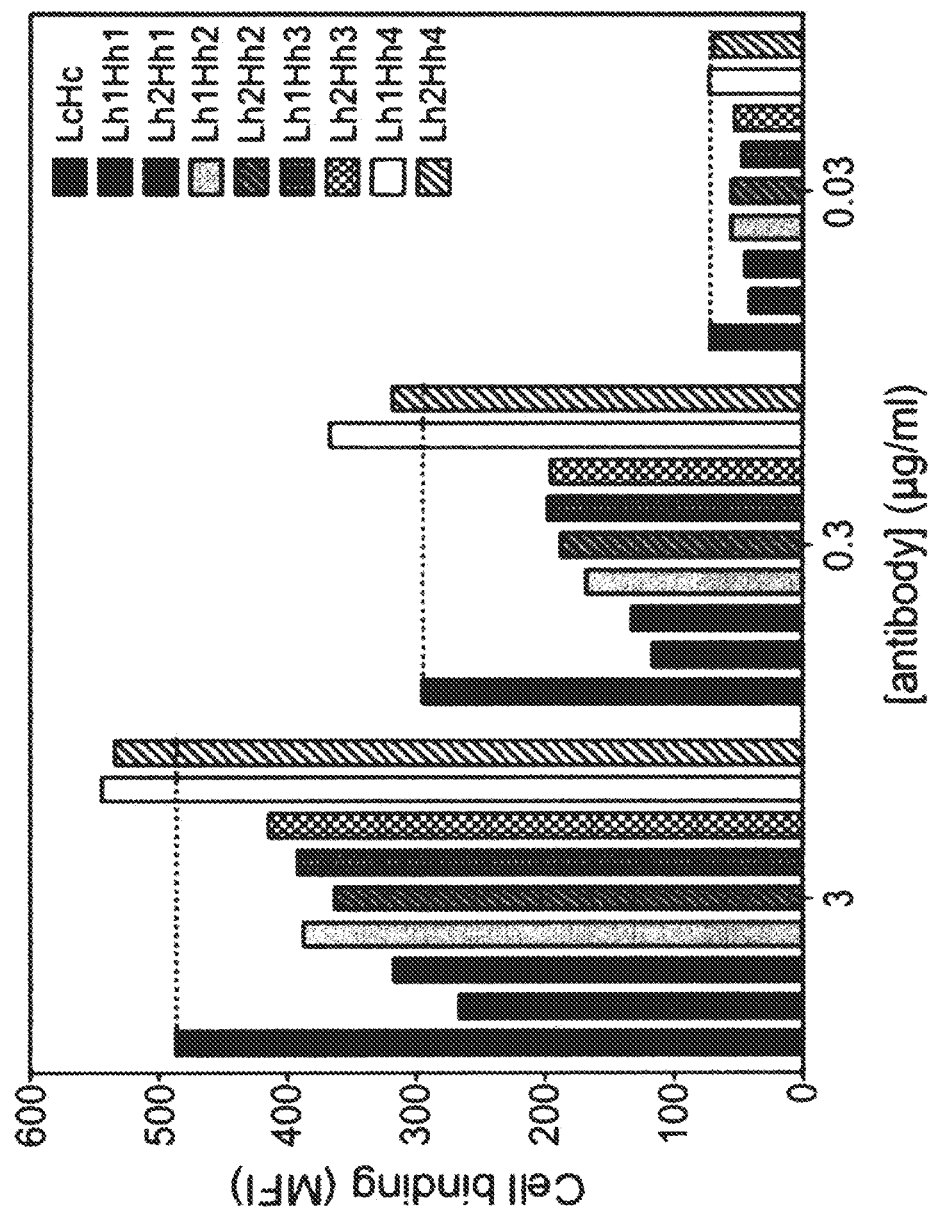
FIG. 9 illustrates humanized 3A4 variants binding to KAAG1 on the surface of cancer cells. This illustration shows the comparative binding activity of the humanized and the murine 3A4 antibodies on the unpermeabilized SKOV-3 ovarian cancer cells.

Flow cytometry was used to evaluate the capacity of the humanized 3A4 variants to interact with KAAG1 expressed on the surface of cancer cells. To this end, SKOV-3 ovarian cancer cells, which we had previously showed were efficiently bound by 3A4 by flow cytometry, were incubated with the eight humanized variants and the original murine antibody. Briefly, SKOV-3 cells were detached from the plate with EDTA and incubated on ice with either 3.0 mg/ml, 0.3 mg/ml or 0.3 mg/ml of the antibodies for 1h. After three washing steps, the cells were incubated with the secondary antibody, anti-human IgG-conjugated to FITC for 1 h on ice. Cell surface fluorescence was measured in a flow cytometer and the values ae shown in the histogram of FIG. 9. As depicted, all variants could detect KAAG1 on the surface on unpermeabilized and the strongest signals were obtained at the highest concentration of 3A4 antibodies (3 mg/ml) and decreased as the concentration of the antibody was decreased. Among the different variants, the ones with the most murine back-mutations (FIG. 9, see Lh1Hh4 and Lh2Hh4) interacted with KAAG1 on the surface of cells with the highest activity. In fact, Lh1Hh4 and Lh2hh4 appeared to be slight improved cell surface binding to KAAG1 compared to the murine 3A4 antibody (LcHc).

Example 7

This example describes the use of anti-KAAG1 antibodies for detecting the expression of KAAG1 in TNBC.

Figure 10:
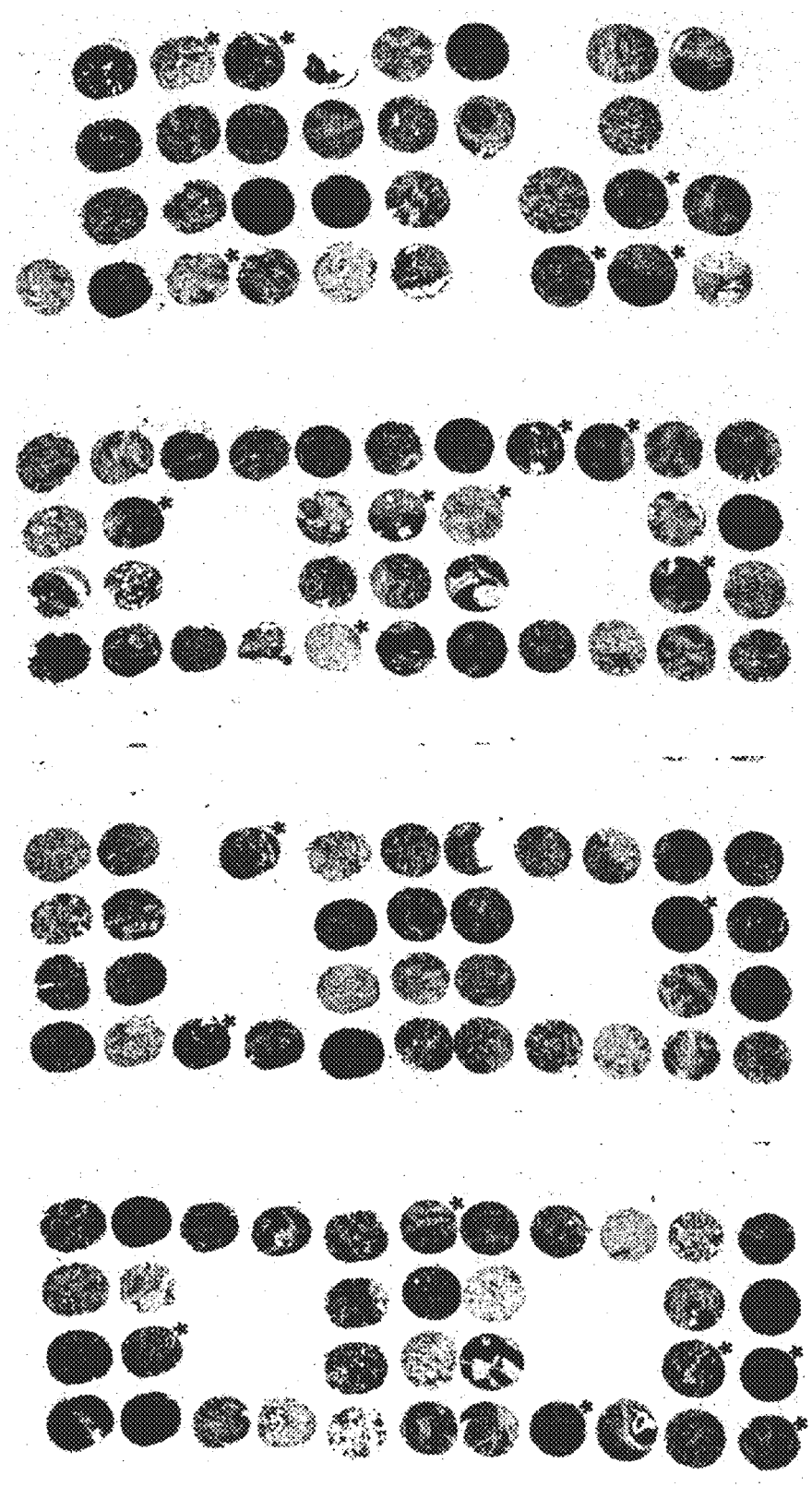
FIG. 10 shows a scan of a tissue microarray containing 139 biopsy samples obtained from breast cancer patients. The samples were blotted with the 3A4 anti-KAAG1 antibody and showed that the vast majority of the breast tumors expressed very high level of KAAG1 antigen. The confirmed TNBC samples are marked with an asterisk.

As a means of determining if the KAAG1 antigen was present in TNBC samples, immunohistochemistry was conducted. Tissue microarrays were obtained that contained 139 breast tumor samples generated from patient biopsies. Paraffin-embedded epithelial breast tumor samples were placed on glass slides and fixed for 15 min at 50° C. Deparaffinization was conducted by treating 2× with xylene followed by dehydration in successive 5 min washes in 100%, 80%, and 70% ethanol. The slides were washed 3× in PBS for 5 min and treated with antigen retrieval solution (1 mM EDTA, pH 8.0) to unmask the antigen. Endogenous peroxide reactive species were removed by incubating slides with H$_2$O$_2$ in methanol and blocking was performed by incubating the slides with serum-free blocking solution (Santa Cruz Biotech) for 5 min at room temperature. The primary antibody (anti-KAAG1 3A4) was added for 1 h at room temperature. KAAG1-reactive antigen was detected by incubating with biotin-conjugated mouse anti-kappa followed by streptavidin-HRP tertiary antibody. Positive staining was revealed by treating the slides with DAB-hydrogen peroxide substrate for less than 5 min and subsequently counterstained with hematoxylin. The KAAG1 protein was found to be expressed at very high levels in the vast majority of breast tumor samples. A representative array containing 139 tumors is depicted in FIG. 10. In particular, 15/20 biopsy samples confirmed to be TNBC (FIG. 10, samples identified by an asterisk) were stained strongly for KAAG1 expression with the 3A4 antibody. Taken together, these immunohistochemical studies illustrate the utility of detecting KAAG1 in breast cancer, in particular TNBC, with the monoclonal antibodies.

Example 8

This example describes the use of anti-KAAG1 antibodies for detecting the expression of KAAG1 in TNBC cell lines.

Figure 11:
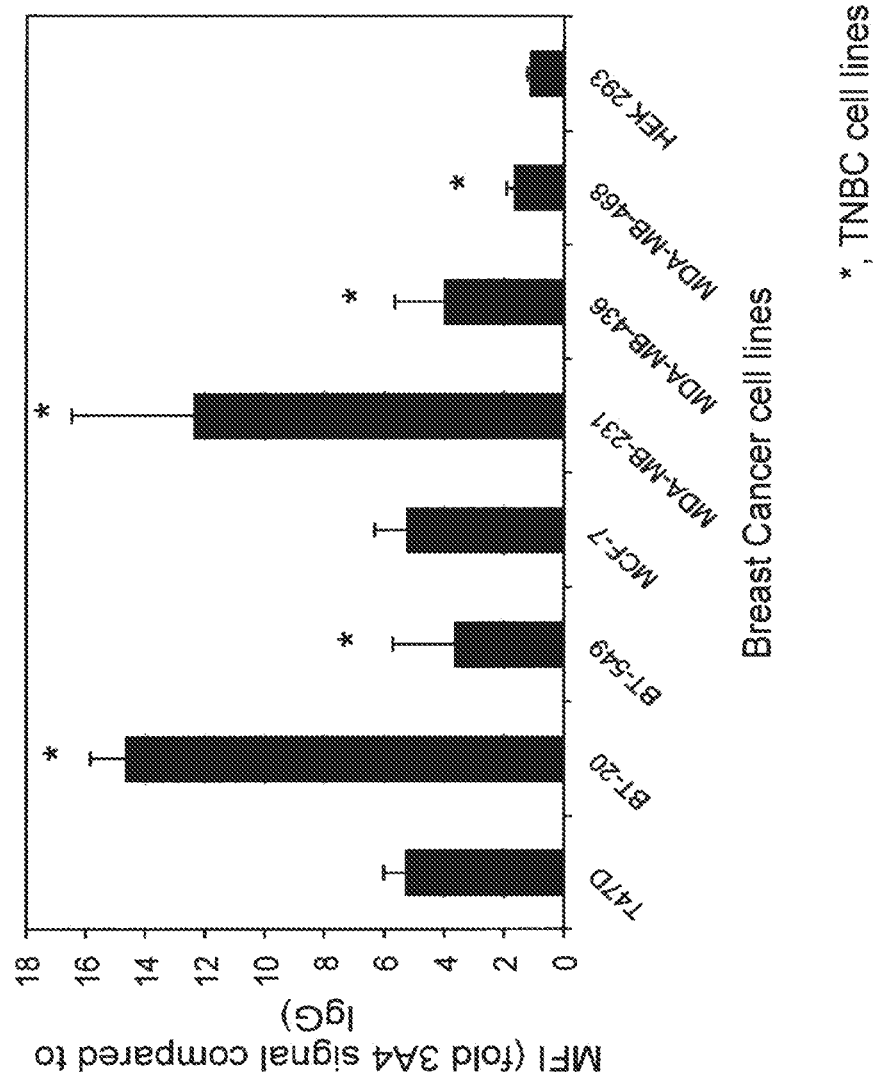
FIG. 11 shows the results of flow cytometry performed using MDA-MB-231, MDA-MB-436, MDA-MB-468, BT-20, BT-549, T47D, MCF-7 and 293-6E cell lines incubated with the 3A4 anti-KAAG1 antibody (blue bars of the histogram) compared with a control IgG (red bars). This is a representative results from an experiment that was performed in triplicate. The TNBC cell lines are marked with an asterisk.

Combined results from the bioinformatics analysis of the primary structure of the cDNA encoding KAAG1, biochemical studies, and immunohistochemical detection of the protein in epithelial cells suggested that the KAAG1 antigen was located at the cell surface. However, more direct evidence was required to demonstrate that KAAG1 is indeed expressed on the surface of TNBC cells. To conduct this analysis, breast cancer cell lines were obtained from a commercial vendor (ATCC, Manassas, Va.) and used in flow cytometry experiments. RT-PCR expression analyses using KAAG1 mRNA specific primers previously showed that certain breast cancer cell lines expressed KAAG1 mRNA (see PCT/CA2007/001134). Therefore some of these cell lines were selected to determine the presence of the KAAG1 antigen at their surface. To verify this, the triple-negative MDA-MB-231, MDA-MB-436, MDA-MB-468, BT-20 and BT-549 cell lines were tested for surface expression of KAAG1 using the 3A4 anti-KAAG1 antibody. In addition, breast cancer cell lines, which are not triple-negative, namely T47D and MCF-7, were also included in the analysis. Finally, a control cell line, 293-6E, that exhibits undetectable level of KAAG1 antigen expression was included as a negative control for the flow cytometry experiment (FCM). For the purpose of FCM analysis, the cells were harvested using 5 mM EDTA, counted with a hemocytometer, and resuspended in FCM buffer (0.5% BSA, 0.01% goat serum in 1×PBS) at a cell density of 2×10$^6$ cells/ml. Chimeric 3A4 anti-KAAG1 antibody or a control IgG were added to 100 µl of cells at a final concentration of 0.5 µg/ml and incubated on ice for 1 h. The cells were washed in cold FCM buffer to remove unbound antibodies, resuspended in 100 µl FCM buffer containing anti-human IgG conjugated to FITC secondary antibody (diluted 1:200) and incubated on ice for 45 min. Following another washing step in cold FCM buffer, the cells were resuspended in 300 µl FCM buffer and analyzed with a flow cytometer. 10 µg/ml propidium iodide was added to each sample to allow for gating of dead cells. The results from three independent experiments are shown in FIG. 11, where the mean fluorescence intensity (MFI) fold Induction represents the geometric mean value of the signal obtained when the cells were incubated with 3A4 antibody over that of the negative human IgG control, which was arbitrarily set to 1. Incubation of the antibodies with the control 293-6EHEK-293 cells resulted in fluorescence signals that were similar to the signal obtained when the cells were incubated in the absence of the primary antibody. Furthermore, there was no significant difference between the signal obtained with 3A4 compared to the control IgG. Moreover, when the control IgG was incubated with the breast cancer cell lines, the signals were very similar to those obtained with the control 293-6E cells. By contrast, detectable fluorescence signal was observed when the 3A4 antibody was incubated with all breast cancer cells lines. Although variable amount of fluorescence was observed, the highest amount of KAAG1 was detected on the surface of MDA-MB-231 and BT-20 cell lines, two TNBC cell lines (see FIG. 11, TNBC cell lines are indicated with an asterisk). In fact all five TNBC cell lines were positive for KAAG1 expression under these conditions. T47 D and MCF-7 cells also expressed KAAG1. Taken together, this flow cytometry analysis shows that TNBC cell line express high level of KAAG1 on their cell surface.

Example 9

Methods for Use of the 3A4 Anti-KAAG1 Antibody as an Antibody Conjugate

Figure 12:
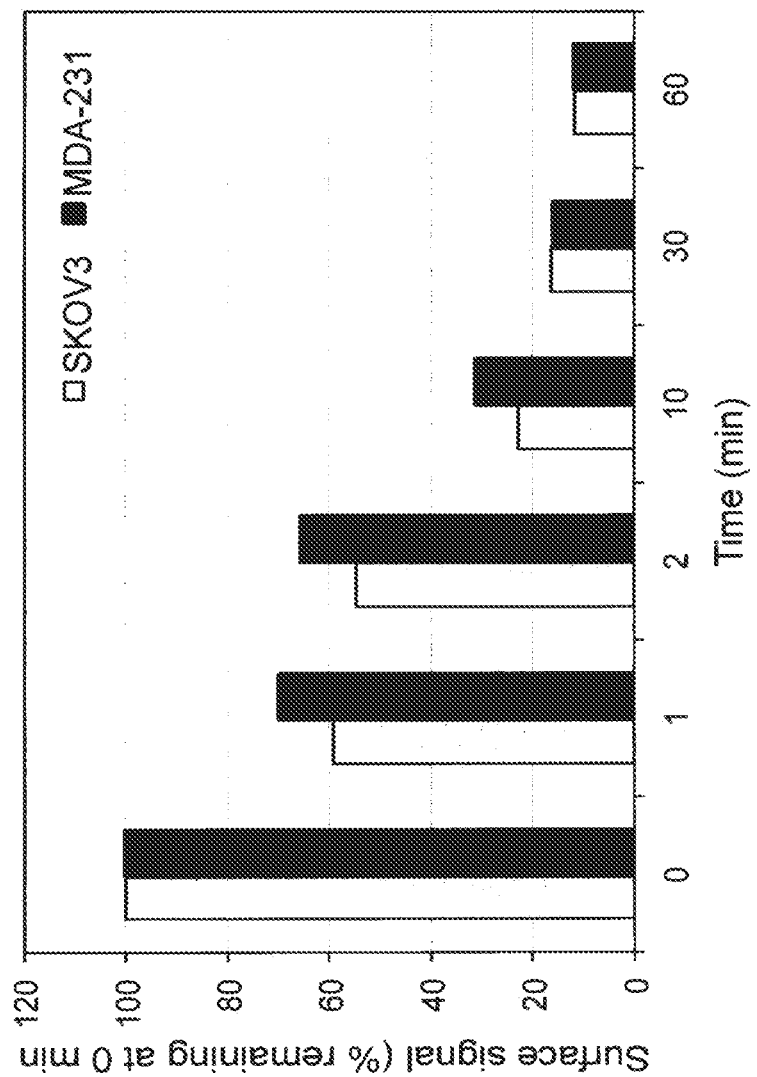
FIG. 12 represents the detection of the KAAG1 antigen on the surface of MDA-MB-231 cells by flow cytometry with the 3A4 anti-KAAG1 antibody. The fluorescence signal decreases with time when the cells were incubated at 37° C., which suggests that the KAAG1/antibody complex was internalized during the incubation when the cells were incubated with 3A4.

As demonstrated above, the KAAG1 antigen was detected by 3A4 on the surface of cancer cells using flow cytometry. There are several different molecular events that can occur upon binding of an antibody to its target on the surface of cells. These include i) blocking accessibility to another cell-surface antigen/receptor or a ligand, ii) formation of a relatively stable antibody-antigen complex to allow cells to be targeted via ADCC or CDC, iii) signalling events can occur as exemplified by agonistic antibodies, iv) the complex can be internalized, or v) the complex can be shed from the cell surface. To address this question we examined the behavior of the 3A4 antibody-KAAG1 complex on the surface of the cells. The ovarian cancer cell line, SKOV3, was used as a positive control in this experiment since it was successfully used in previous internalization experiments (see PCT/CA20091001586). MDA-MB-231 TNBC cells were plated, washed, and incubated with 0.5 µg/ml chimeric 3A4 antibody as described in Example 3. After washing, complete medium was added and the cells placed at 37° C. for up to 60 minutes. The cells were removed at the indicated times (see FIG. 12), rapidly cooled, prepared for flow cytometry with FITC-conjugated anti-human IgG and the results were expressed as the percentage of mean fluorescence intensity remaining on the cell surface compared with the signal at time 0 minutes (see FIG. 12, Surface signal (% remaining at 0 min) As illustrated in FIG. 12, the fluorescence signal decreased rapidly when 3A4 was incubated with MDA-MB-231 cells (FIG. 12, black bars, indicated by MDA-231 in the figure) and seemed to achieve a maximum loss of signal by 30-45 minutes. The loss of signal was comparable to that observed when 3A4 was incubated with the SKOV3 cells (FIG. 12, grey bars). This result indicates that the 3A4/KAAG1 complex disappeared from the cells which indicated that an internalization of the complex likely occurred. Preliminary studies to elucidate the mechanism responsible for this decrease in cell-surface fluorescence have revealed that the complex appears to be internalized. Similar results are expected with humanized 3A4 antibodies.

Figure 13:
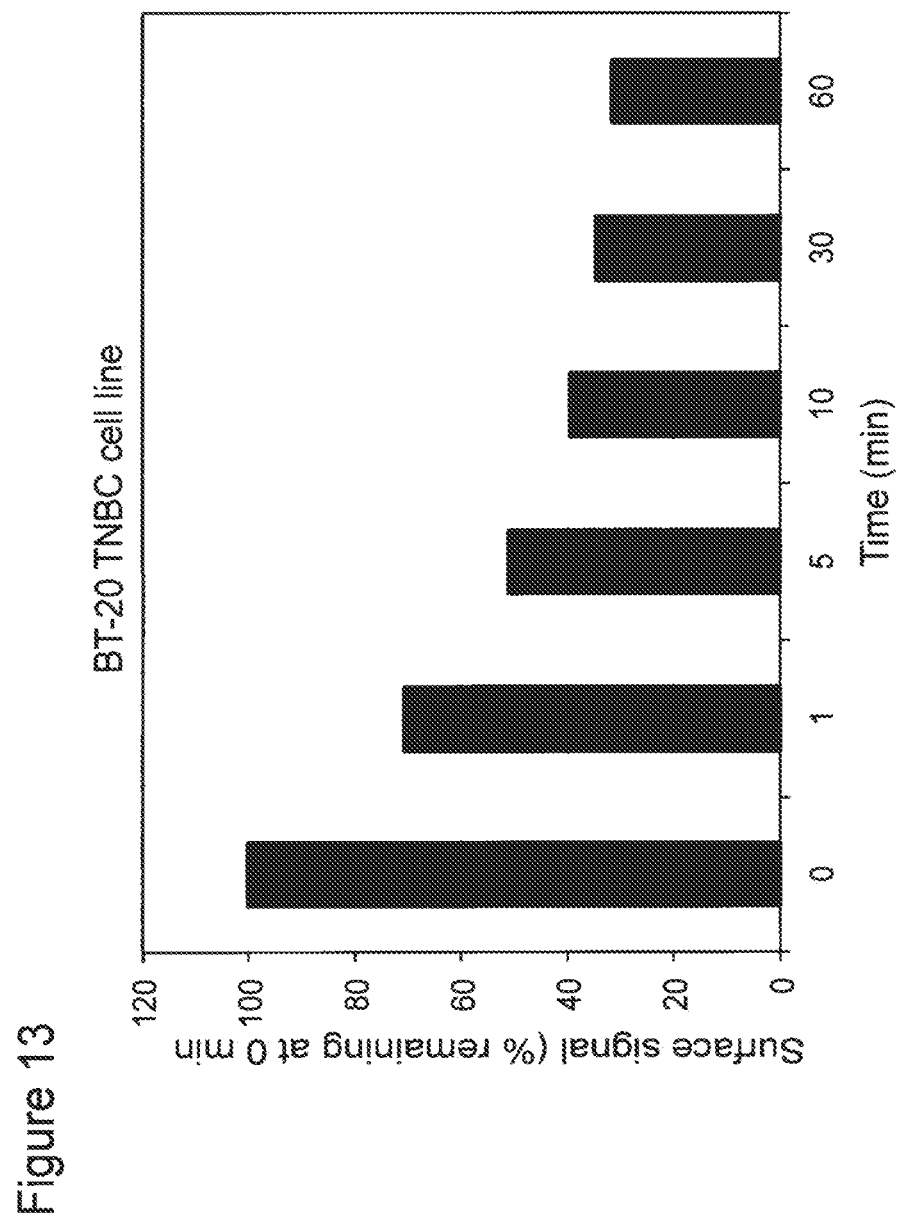
FIG. 13 represents the detection of the KAAG1 antigen on the surface of MDA-MB-436 cells by flow cytometry with the 3A4 anti-KAAG1 antibody. The fluorescence signal decreases with time when the cells were incubated at 37° C., which suggests that the KAAG1/antibody complex was internalized during the incubation when the cells were incubated with 3A4.
Figure 14:
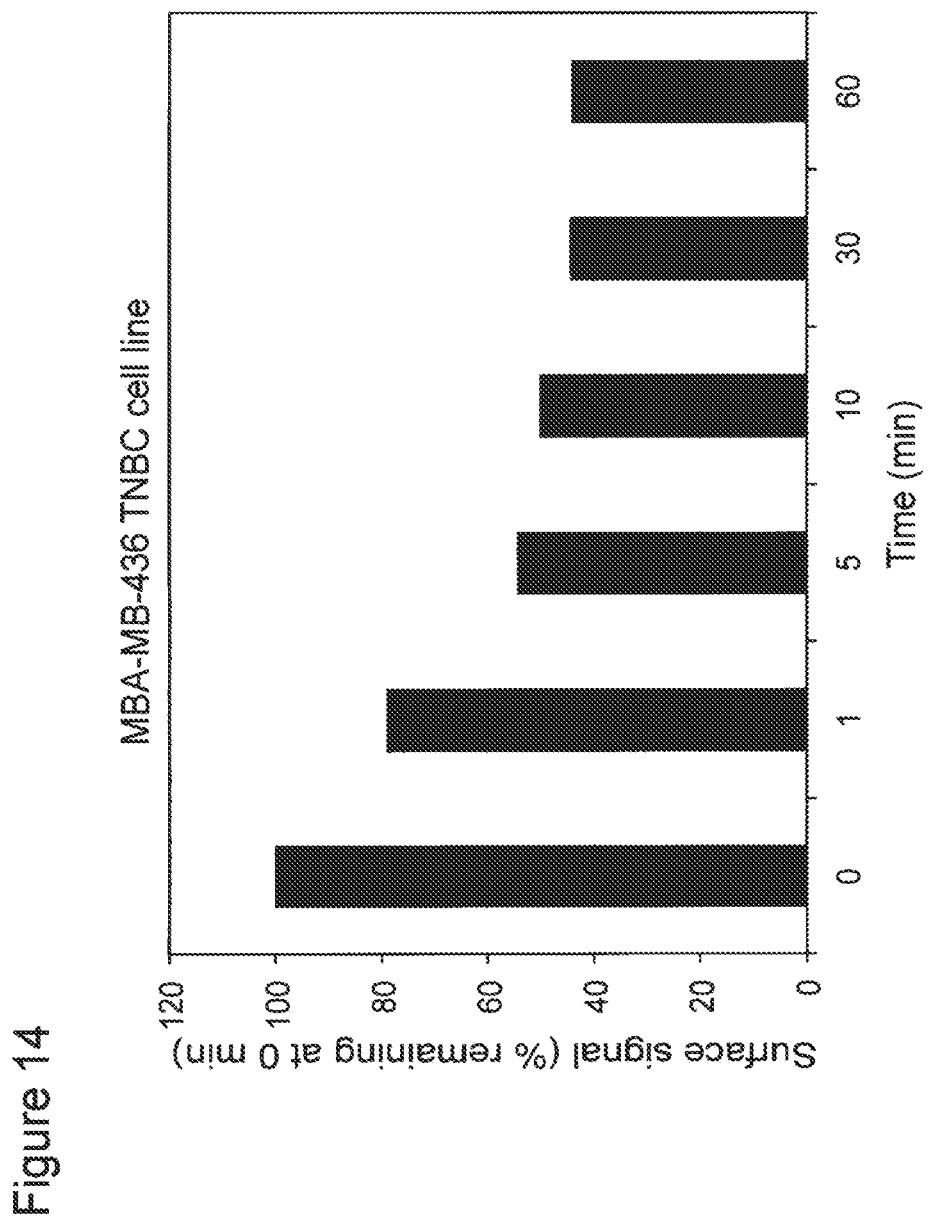
FIG. 14 represents the detection of the KAAG1 antigen on the surface of BT-20 cells by flow cytometry with the 3A4 anti-KAAG1 antibody. The fluorescence signal decreases with time when the cells were incubated at 37° C., which suggests that the KAAG1/antibody complex was internalized during the incubation when the cells were incubated with 3A4.
Figure 15:
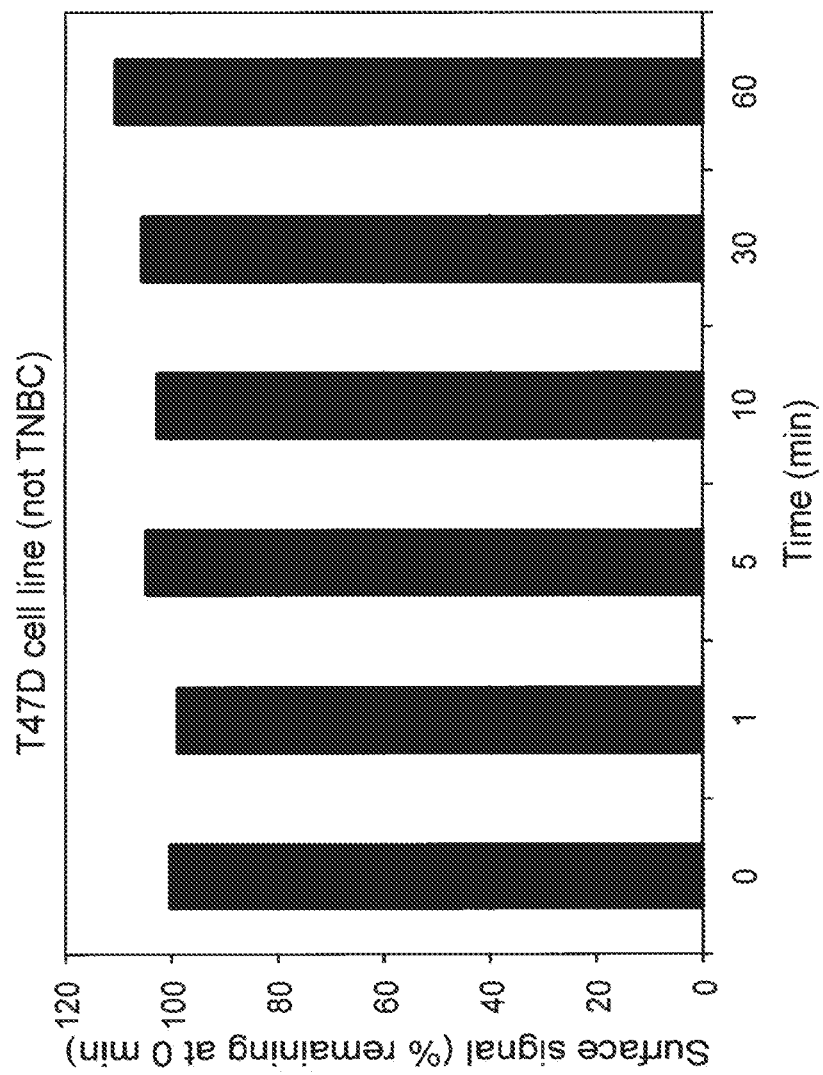
FIG. 15 represents the detection of the KAAG1 antigen on the surface of T47D cells by flow cytometry with the 3A4 anti-KAAG1 antibody. The fluorescence signal decreases with time when the cells were incubated at 37° C., which suggests that the KAAG1/antibody complex was internalized during the incubation when the cells were incubated with 3A4.

Similar results were observed in two additional TNBC cell lines, namely MDA-MB-436 (FIG. 13) and BT-20 (FIG. 14) confirming that the internalization of the 3A4/KAAG1 complex on the surface of multiple TNBC cell lines. By contrast, despite similar MFI levels of 3A4 binding on the surface of MDA-MB-436 and T47D (FIG. 11), the loss of signal at the cell surface was not observed when 3A4 was incubated with the T47D cell line. This finding suggests the possibility that internalization of the 3A4/KAAG1 complex might occur to a higher degree in TNBC cells (FIG. 15) compared with cells that are not triple-negative.

Figure 16:
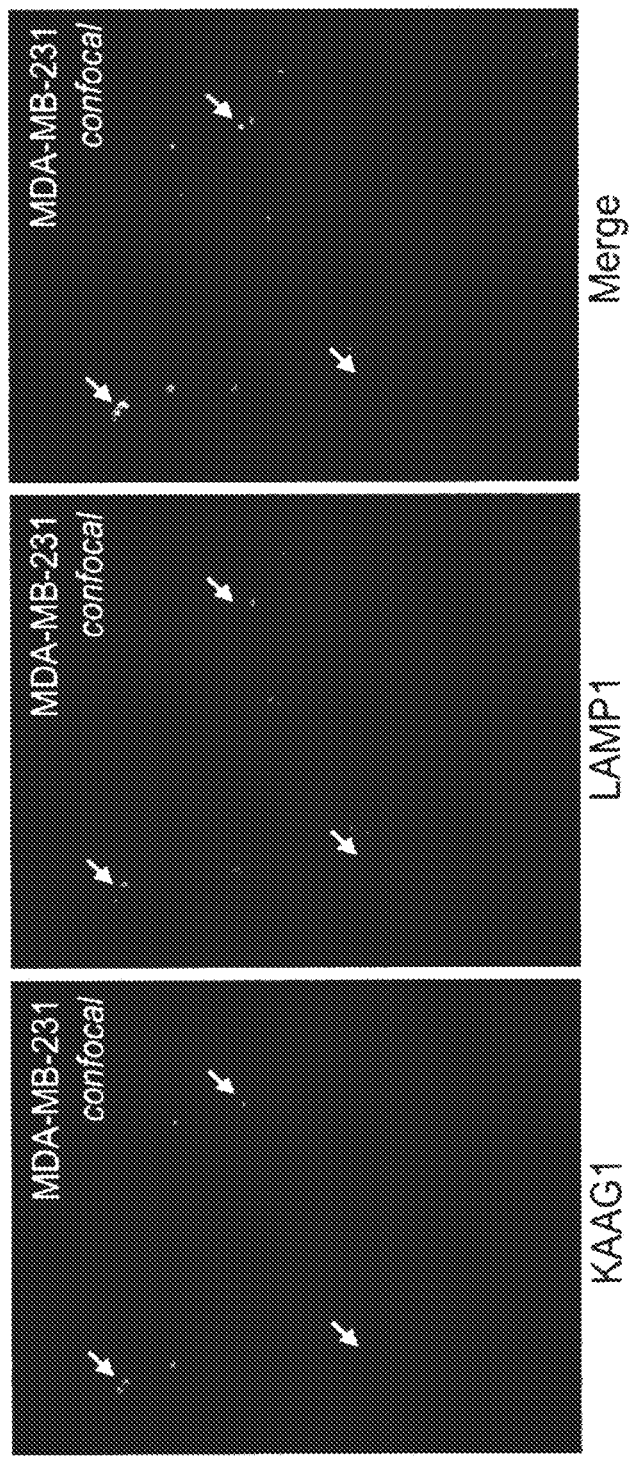
FIG. 16 represents immunofluorescence data performed on live MDA-MB-231 cells with the 3A4 anti-KAAG1 antibody and the anti-LAMP1 antibody. The immunofluorescence signal associated with the anti-KAAG1 antibody is shown in the left panel, the immunofluorescence signal associated LAMP1 is shown in the middle panel and the merging of both images is shown in the right panel. These data illustrates the co-localization of KAAG1 and LAMP1 near the peri-nuclear area.
Figure 17:
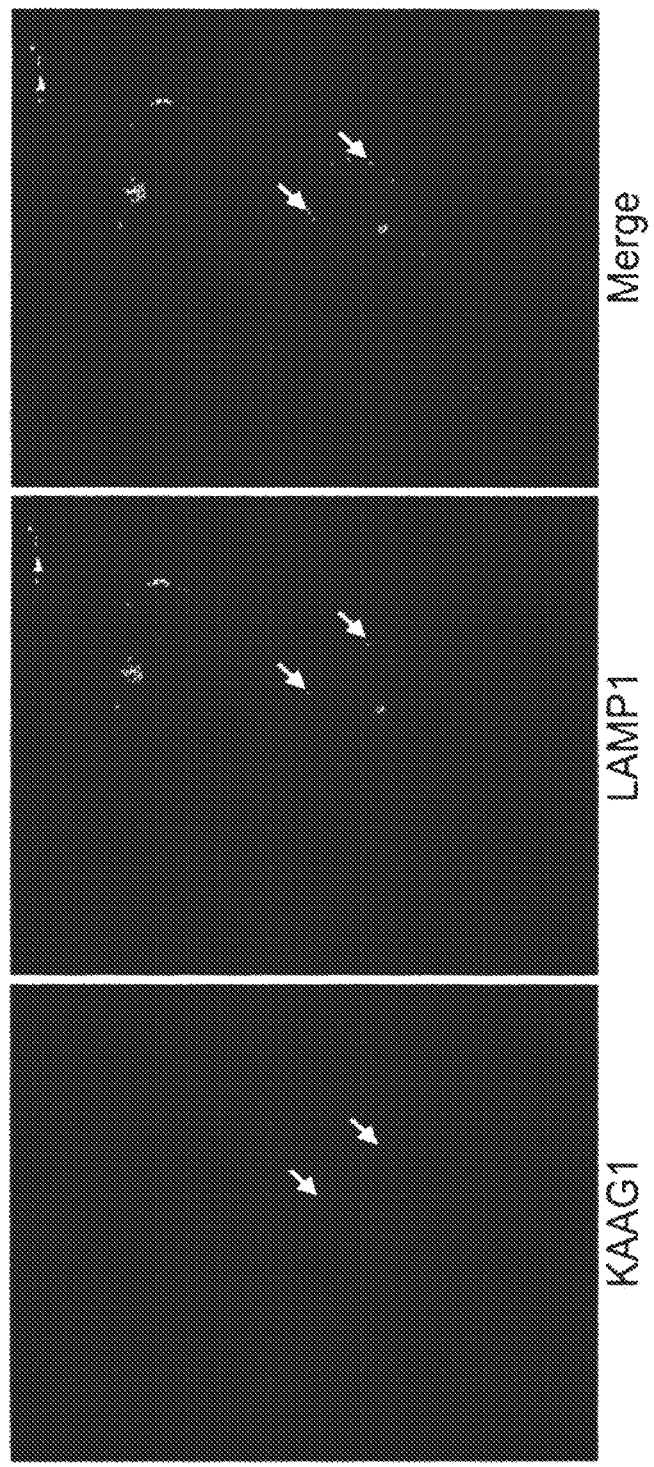
FIG. 17 represents immunofluorescence data performed on live MDA-MB-231 cells with the 3A4 anti-KAAG1 antibody and the anti-LAMP1 antibody. The immunofluorescence signal associated with the anti-KAAG1 antibody is shown in the left panel, the immunofluorescence signal associated LAMP1 is shown in the middle panel and the merging of both images is shown in the right panel. These data illustrates the localization of KAAG1 with LAMP1 a marker of late endosomes/lysosomes.

These findings were further confirmed by conducting immunofluorescence on live cells to see if this internalization could be microscopically observed. MDA-MB-231 cells were seeded on cover slips and once the cells were properly adhered, fresh medium was added containing the 3A4 anti-KAAG1 chimeric antibody at 10 ug/ml and incubating at 37 C for 4 h. The cells were washed in PBS then fixed in 4% paraformaldehyde (in PBS) for 20 min. After washing, the cells were permeabilized with 0.1% Triton X-100 in PBS for 5 min. Blocking was performed with 1.5% dry milk in PBS for 1h. Lysosomal-associated membrane protein 1 (LAMP1, Chang et al., 2002) was detected by incubating with anti-LAMP1 (Santa Cruz, sc-18821, diluted 1:100) in 1.5% milk in PBS for 2h. After washing in PBS, the secondary antibodies were added together in 1.5% milk and incubated for 1 h. For the anti-KAAG1 chimeric antibody the secondary antibody was a Rhodamine Red-X conjugated donkey anti-human IgG (H+L) diluted 1:300. For the anti-LAMP1 antibody the secondary antibody was a DyLight488-conjugated goat anti-mouse IgG (H+L) diluted 1:300. Both secondary antibodies were from Jackson ImmunoResearch. The coverslips were washed in PBS and mounted in ProLong Gold antifade reagent with DAPI. As seen in FIG. 7, after 4 hours of incubation at 37 C in the presence of MDA-MB-231 cancer cells, the 3A4 antibody was able to be detected in complexes predominantly near the peri-nuclear area (arrows, see red staining in the left panel in FIG. 16), which is typical of endosomal-lysosomal-based internalization pathways. This observation was further confirmed when a lysosomal marker, LAMP1 was visualized and was found to be also expressed in these areas (arrows, see green staining in the middle panel in FIG. 16). Importantly, the merging of the two images resulted in the appearance of yellow-orange structures indicating that the 3A4 and the anti-LAMP1 antibodies were present in the same structures (arrows, see yellow staining in the right panel in FIG. 16). The co-localization of 3A4, which binds to KAAG1 on the surface of cancer cells, with LAMP1, a marker of late endosomes/lysosomes, shows that the antibody/antigen complex was internalized and that it follows a pathway that is amenable for the release of a payload that would be conjugated to the 3A4 antibody. Identical results were observed in another TNBC cell line, BT-20 (see FIG. 17).

Taken together, these studies demonstrated that antibodies specific for KAAG1 such as 3A4 might have uses as an antibody conjugate, in particular, as an antibody-drug conjugate (ADO). Thus, the high level of TNBC specificity of KAAG1 coupled with the capacity of this target to be internalized in cells support the development of applications as an ADC.

Example 10

In order to demonstrate that anti-KAAG1 antibodies can efficiently target and kill cells lacking ER protein expression, PgR protein expression and/or showing absence of HER2 protein over-expression, we generated two antibody drug conjugates (ADCs); 3A4-ADC1 and 3A4-ADC2.

To that effect, we used the chimeric 3A4 antibody and conjugated a cytotoxic drug via a highly stable peptide linker that is selectively cleaved by lysosomal enzymes after internalization (3A4-ADC1), or conjugated with another anti-mitotic drug via a non-cleavable linker (3A4-ADC2). The cytotoxic drug may become active once internalized in the cells.

The ability of the 3A4 ADCs to detect KAAG1 on the surface of TNBC cells was determined using flow cytometry using the methods described herein. Briefly, unconjugated 3A4, 3A4-ADC1, 3A4-ADC2 and a control IgG were incubated in the presence of MDA-231 TNBC cells, which are KAAG1 positive. Results indicated that the conjugation of 3A4 with either drug did not affect its binding to triple negative breast cancer cells such as MDA-231 (data not shown).

Having confirmed that the 3A4 ADCs could bind to KAAG1 expressed on the surface of TNBC cells, their cytotoxicity against these cells was evaluated in cell proliferation assays. MDA-231 or TOV-112D cells were cultured as described above in previous examples. The cells were seeded at 3000 cells/well in 96-well plates in 200 Pal of media per well overnight at 37° C., in 5% $CO_2$. The next day, media was replaced with fresh media containing antibodies, at concentrations ranging from 0.122 nM to 500 nM, and incubated at 37° C. for 72 h. All conditions were performed in triplicate wells. The number of surviving cells was determined by performing a cellular proliferation assay, using CellTiter 96 Aqueous One Solution (Promega, Madison, Wis.), following manufacturer's protocol. Following the collection of the raw data, the results were expressed as the percentage survival compared to the number of cells in the wells treated with PBS, which was set to 100%. Results indicated that the unconjugated 3A4 did not affect the proliferation of MDA-231 cells at all concentrations tested. In contrast, the 3A4 ADCs tested showed significant cytotoxicity.

These results indicate that 3A4 antibody conjugates may be used as an alternative treatment for patients having triple negative breast cancer or basal-like breast cancer. Similar results are expected for conjugates based on humanized 3A4 antibodies.

The present description refers to a number of documents, the content of which is incorporated herein by reference in their entirety.

```
SEQ ID NO.: 1
GAGGGGCATCAATCACACCGAGAAGTCACAGCCCCTCAACCACTGAGGTGTGGGGGGTAGGGAT

CTGCATTTCTTCATATCAACCCCACACTATAGGGCACCTAAATGGGTGGGCGGTGGGGGAGACCG

ACTCACTTGAGTTTCTTGAAGGCTTCCTGGCCTCCAGCCACGTAATTGCCCCCGCTCTGGATCTG

GTCTAGCTTCCGGATTCGGTGGCCAGTCCGCGGGGTGTAGATGTTCCTGACGGCCCCAAAGGGTG

CCTGAACGCCGCCGGTCACCTCCTTCAGGAAGACTTCGAAGCTGGACACCTTCTTCTCATGGATG

ACGACGCGGCGCCCCGCGTAGAAGGGGTCCCCGTTGCGGTACACAAGCACGCTCTTCACGACGGG
```

CTGAGACAGGTGGCTGGACCTGGCGCTGCTGCCGCTCATCTTCCCCGCTGGCCGCCGCCTCAGCT

CGCTGCTTCGCGTCGGGAGGCACCTCCGCTGTCCCAGCGGCCTCACCGCACCCAGGGCGCGGGAT

CGCCTCCTGAAACGAACGAGAAACTGACGAATCCACAGGTGAAAGAGAAGTAACGGCCGTGCGCC

TAGGCGTCCACCCAGAGGAGACACTAGGAGCTTGCAGGACTCGGAGTAGACGCTCAAGTTTTTCA

CCGTGGCGTGCACAGCCAATCAGGACCCGCAGTGCGCGCACCACACCAGGTTCACCTGCTACGGG

CAGAATCAAGGTGGACAGCTTCTGAGCAGGAGCCGGAAACGCGCGGGGCCTTCAAACAGGCACGC

CTAGTGAGGGCAGGAGAGAGGAGGACGCACACACACACACACACACAAATATGGTGAAACCCAAT

TTCTTACATCATATCTGTGCTACCCTTTCCAAACAGCCTA

SEQ ID NO.: 2
MDDDAAPRVEGVPVAVHKHALHDGLRQVAGPGAAAAHLPRWPPPQLAASRREAPPLSQRPHRTQG

AGSPPETNEKLTNPQVKEK

SEQ ID NO.: 3
GACATTGTGATGACCCAGTCTCCATCCTCCCTGGCTGTGTCAATAGGACAGAAGGTCACTATGAA

CTGCAAGTCCAGTCAGAGCCTTTTAAATAGTAACTTTCAAAAGAACTTTTTGGCCTGGTACCAGC

AGAAACCAGGCCAGTCTCCTAAACTTCTGATATACTTTGCATCCACTCGGGAATCTAGTATCCCT

GATCGCTTCATAGGCAGTGGATCTGGGACAGATTTCACTCTTACCATCAGCAGTGTGCAGGCTGA

AGACCTGGCAGATTACTTCTGTCAGCAACATTATAGCACTCCGCTCACGTTCGGTGCTGGGACCA

AGCTGGAGCTGAAAGCTGTGGCTGCACCATCTGTCTTCATCTTCCCGCCATCTGATGAGCAGTTG

AAATCTGGAACTGCCTCTGTTGTGTGCCTGCTGAATAACTTCTATCCCAGAGAGGCCAAAGTACA

GTGGAAGGTGGATAACGCCCTCCAATCGGGTAACTCCCAGGAGAGTGTCACAGAGCAGGACAGCA

AGGACAGCACCTACAGCCTCAGCAGCACCCTGACGCTGAGCAAAGCAGACTACGAGAAACACAAA

GTCTACGCCTGCGAAGTCACCCATCAGGGCCTGAGCTCGCCCGTCACAAAGAGCTTCAACAGGGG

AGAGTGT

SEQ ID NO.: 4
DIVMTQSPSSLAVSIGQKVTMNCKSSQSLLNSNFQKNFLAWYQQKPGQSPKLLIYFASTRESSIP

DRFIGSGSGTDFTLTISSVQAEDLADYFCQQHYSTPLTFGAGTKLELKAVAAPSVFIFPPSDEQL

KSGTASVVCLLNNFYPREAKVQWKVDNALQSGNSQESVTEQDSKDSTYSLSSTLTLSKADYEKHK

VYACEVTHQGLSSPVTKSFNRGEC

SEQ ID NO.: 5
GAGGTTCAGCTGCAGCAGTCTGTAGCTGAGCTGGTGAGGCCTGGGGCTTCAGTGACGCTGTCCTG

CAAGGCTTCGGGCTACATATTTACTGACTATGAGATACACTGGGTGAAGCAGACTCCTGTGCATG

GCCTGGAATGGATTGGGGTTATTGATCCTGAAACTGGTAATACTGCCTTCAATCAGAAGTTCAAG

GGCAAGGCCACACTGACTGCAGACATATCCTCCAGCACAGCCTACATGGAACTCAGCAGTTTGAC

ATCTGAGGACTCTGCCGTCTATTACTGTATGGGTTATTCTGATTATTGGGCCAAGGCACCACTC

TCACAGTCTCCTCAGCCTCAACGAAGGGCCCATCTGTCTTTCCCCTGGCCCCCTCCTCCAAGAGC

ACCTCTGGGGGCACAGCGGCCCTGGGCTGCCTGGTCAAGGACTACTTCCCCGAACCGGTGACGGT

GTCGTGGAACTCAGGCGCCCTGACCAGCGGCGTGCACACCTTCCCGGCTGTCCTACAGTCCTCAG

GACTCTACTCCCTCAGCAGCGTGGTGACCGTGCCCTCCAGCAGCTTGGGCACCCAGACCTACATC

TGCAACGTGAATCACAAGCCCAGCAACACCAAGGTGGACAAGAAAGTTGAGCCCAAATCTTGTGA

ATTCACTCACACATGCCCACCGTGCCCAGCACCTGAACTCCTGGGGGGACCGTCAGTCTTCCTCT

TCCCCCCAAAACCCAAGGACACCCTCATGATCTCCCGGACCCCTGAGGTCACATGCGTGGTGGTG

GACGTGAGCCACGAAGACCCTGAGGTCAAGTTCAACTGGTACGTGGACGGCGTGGAGGTGCATAA

-continued

```
TGCCAAGACAAAGCCGCGGGAGGAGCAGTACAACAGCACGTACCGTGTGGTCAGCGTCCTCACCG

TCCTGCACCAGGACTGGCTGAATGGCAAGGAGTACAAGTGCAAGGTCTCCAACAAAGCCCTCCCA

GCCCCCATCGAGAAAACCATCTCCAAAGCCAAAGGGCAGCCCCGAGAACCACAGGTGTACACCCT

GCCCCCATCCCGGGATGAGCTGACCAAGAACCAGGTCAGCCTGACCTGCCTGGTCAAAGGCTTCT

ATCCCAGCGACATCGCCGTGGAGTGGGAGAGCAATGGGCAGCCGGAGAACAACTACAAGACCACG

CCTCCCGTGCTGGACTCCGACGGCTCCTTCTTCCTCTACAGCAAGCTCACCGTGGACAAGAGCAG

GTGGCAGCAGGGGAACGTCTTCTCATGCTCCGTGATGCATGAGGCTCTGCACAACCACTACACGC

AGAAGAGCCTCTCCCTGTCTCCCGGGAAA
```

SEQ ID NO.: 6
EVQLQQSVAELVRPGASVTLSCKASGYIFTDYEIHWVKQTPVHGLEWIGVIDPETGNTAFNQKFK

GKATLTADISSSTAYMELSSLTSEDSAVYYCMGYSDYWGQTTLTVSSASTKGPSVFPLAPSSKS

TSGGTAALGCLVKDYFPEPVTVSWNSGALTSGVHTFPAVLQSSGLYSLSSVVTVPSSSLGTQTYI

CNVNHKPSNTKVDKKVEPKSCEFTHTCPPCPAPELLGGPSVFLFPPKPKDTLMISRTPEVTCVVV

DVSHEDPEVKFNWYVDGVEVHNAKTKPREEQYNSTYRVVSVLTVLHQDWLNGKEYKCKVSNKALP

APIEKTISKAKGQPREPQVYTLPPSRDELTKNQVSLTCLVKGFYPSDIAVEWESNGQPENNYKTT

PPVLDSDGSFFLYSKLTVDKSRWQQGNVFSCSVMHEALHNHYTQKSLSLSPGK

SEQ ID NO.: 7
```
GATGTTTTGATGACCCAAACTCCACGCTCCCTGTCTGTCAGTCTTGGAGATCAAGCCTCCATCTC

TTGTAGATCGAGTCAGAGCCTTTTACATAGTAATGGAAACACCTATTTAGAATGGTATTTGCAGA

AACCAGGCCAGCCTCCAAAGGTCCTGATCTACAAAGTTTCCAACCGATTTTCTGGGGTCCCAGAC

AGGTTCAGTGGCAGTGGATCAGGGACAGATTTCACACTCAAGATCAGCGGAGTGGAGGCTGAGGA

TCTGGGAGTTTATTACTGCTTTCAAGGTTCACATGTTCCTCTCACGTTCGGTGCTGGGACCAAGC

TGGAGCTGAAAGCTGTGGCTGCACCATCTGTCTTCATCTTCCCGCCATCTGATGAGCAGTTGAAA

TCTGGAACTGCCTCTGTTGTGTGCCTGCTGAATAACTTCTATCCCAGAGAGGCCAAAGTACAGTG

GAAGGTGGATAACGCCCTCCAATCGGGTAACTCCCAGGAGAGTGTCACAGAGCAGGACAGCAAGG

ACAGCACCTACAGCCTCAGCAGCACCCTGACGCTGAGCAAAGCAGACTACGAGAAACACAAAGTC

TACGCCTGCGAAGTCACCCATCAGGGCCTGAGCTCGCCCGTCACAAAGAGCTTCAACAGGGGAGA

GTGT
```

SEQ ID NO.: 8
DVLMTQTPRSLSVSLGDQASISCRSSQSLLHSNGNTYLEWYLQKPGQPPKVLIYKVSNRFSGVPD

RFSGSGSGTDFTLKISGVEAEDLGVYYCFQGSHVPLTFGAGTKLELKAVAAPSVFIFPPSDEQLK

SGTASVVCLLNNFYPREAKVQWKVDNALQSGNSQESVTEQDSKDSTYSLSSTLTLSKADYEKHKV

YACEVTHQGLSSPVTKSFNRGEC

SEQ ID NO.: 9
```
GAGATCCAGCTGCAGCAGTCTGGACCTGAGTTGGTGAAGCCTGGGGCTTCAGTGAAGATATCCTG

TAAGGCTTCTGGATACACCTTCACTGACAACTACATGAACTGGGTGAAGCAGAGCCATGGAAAGA

GCCTTGAGTGGATTGGAGATATTAATCCTTACTATGGTACTACTACCTACAACCAGAAGTTCAAG

GGCAAGGCCACATTGACTGTAGACAAGTCCTCCCGCACAGCCTACATGGAGCTCCGCGGCCTGAC

ATCTGAGGACTCTGCAGTCTATTACTGTGCAAGAGATGACTGGTTTGATTATTGGGCCAAGGGA

CTCTGGTCACTGTCTCTGCAGCCTCAACGAAGGGCCCATCTGTCTTTCCCCTGGCCCCTCCTCC

AAGAGCACCTCTGGGGGCACAGCGGCCCTGGGCTGCCTGGTCAAGGACTACTTCCCCGAACCGGT

GACGGTGTCGTGGAACTCAGGCGCCCTGACCAGCGGCGTGCACACCTTCCCGGCTGTCCTACAGT

CCTCAGGACTCTACTCCCTCAGCAGCGTGGTGACCGTGCCCTCCAGCAGCTTGGGCACCCAGACC
```

-continued

TACATCTGCAACGTGAATCACAAGCCCAGCAACACCAAGGTGGACAAGAAAGTTGAGCCCAAATC

TTGTGAATTCACTCACACATGCCCACCGTGCCCAGCACCTGAACTCCTGGGGGGACCGTCAGTCT

TCCTCTTCCCCCCAAAACCCAAGGACACCCTCATGATCTCCCGGACCCCTGAGGTCACATGCGTG

GTGGTGGACGTGAGCCACGAAGACCCTGAGGTCAAGTTCAACTGGTACGTGGACGGCGTGGAGGT

GCATAATGCCAAGACAAAGCCGCGGGAGGAGCAGTACAACAGCACGTACCGTGTGGTCAGCGTCC

TCACCGTCCTGCACCAGGACTGGCTGAATGGCAAGGAGTACAAGTGCAAGGTCTCCAACAAAGCC

CTCCCAGCCCCCATCGAGAAAACCATCTCCAAAGCCAAAGGGCAGCCCCGAGAACCACAGGTGTA

CACCCTGCCCCCATCCCGGGATGAGCTGACCAAGAACCAGGTCAGCCTGACCTGCCTGGTCAAAG

GCTTCTATCCCAGCGACATCGCCGTGGAGTGGGAGAGCAATGGGCAGCCGGAGAACAACTACAAG

ACCACGCCTCCCGTGCTGGACTCCGACGGCTCCTTCTTCCTCTACAGCAAGCTCACCGTGGACAA

GAGCAGGTGGCAGCAGGGGAACGTCTTCTCATGCTCCGTGATGCATGAGGCTCTGCACAACCACT

ACACGCAGAAGAGCCTCTCCCTGTCTCCCGGGAAA

SEQ ID NO.: 10
EIQLQQSGPELVKPGASVKISCKASGYTFTDNYMNWVKQSHGKSLEWIGDINPYYGTTTYNQKFK

GKATLTVDKSSRTAYMELRGLTSEDSAVYYCARDDWFDYWGQGTLVTVSAASTKGPSVFPLAPSS

KSTSGGTAALGCLVKDYFPEPVTVSWNSGALTSGVHTFPAVLQSSGLYSLSSVVTVPSSSLGTQT

YICNVNHKPSNTKVDKKVEPKSCEFTHTCPPCPAPELLGGPSVFLFPPKPKDTLMISRTPEVTCV

VVDVSHEDPEVKFNWYVDGVEVHNAKTKPREEQYNSTYRVVSVLTVLHQDWLNGKEYKCKVSNKA

LPAPIEKTISKAKGQPREPQVYTLPPSRDELTKNQVSLTCLVKGFYPSDIAVEWESNQPPENNYK

TTPPVLDSDGSFFLYSKLTVDKSRWQQGNVFSCSVMHEALHNHYTQKSLSLSPGK

SEQ ID NO.: 11
GACATCGTTATGTCTCAGTCTCCATCTTCCATGTATGCATCTCTAGGAGAGAGAGTCACTATCAC

TTGCAAGGCGAGTCAGGACATTCATAACTTTTTAAACTGGTTCCAGCAGAAACCAGGAAAATCTC

CAAAGACCCTGATCTTTCGTGCAAACAGATTGGTAGATGGGGTCCCATCAAGGTTCAGTGGCAGT

GGATCTGGGCAAGATTATTCTCTCACCATCAGCAGCCTGGAGTTTGAAGATTTGGGAATTTATTC

TTGTCTACAGTATGATGAGATTCCGCTCACGTTCGGTGCTGGGACCAAGCTGGAGCTGAGAGCTG

TGGCTGCACCATCTGTCTTCATCTTCCCGCCATCTGATGAGCAGTTGAAATCTGGAACTGCCTCT

GTTGTGTGCCTGCTGAATAACTTCTATCCCAGAGAGGCCAAAGTACAGTGGAAGGTGGATAACGC

CCTCCAATCGGGTAACTCCCAGGAGAGTGTCACAGAGCAGGACAGCAAGGACAGCACCTACAGCC

TCAGCAGCACCCTGACGCTGAGCAAAGCAGACTACGAGAAACACAAAGTCTACGCCTGCGAAGTC

ACCCATCAGGGCCTGAGCTCGCCCGTCACAAAGAGCTTCAACAGGGGAGAGTGT

SEQ ID NO.: 12
DIVMSQSPSSMYASLGERVTITCKASQDIHNFLNWFQQKPGKSPKTLIFRANRLVDGVPSRFSGS

GSGQDYSLTISSLEFEDLGIYSCLQYDEIPLTFGAGTKLELRAVAAPSVFIFPPSDEQLKSGTAS

VVCLLNNFYPREAKVQWKVDNALQSGNSQESVTEQDSKDSTYSLSSTLTLSKADYEKHKVYACEV

THQGLSSPVTKSFNRGEC

SEQ ID NO.: 13
GAGGTGCAGCTTCAGGAGTCAGGACCTGACCTGGTGAAACCTTCTCAGTCACTTTCACTCACCTG

CACTGTCACTGGCTTCTCCATCACCAGTGGTTATGGCTGGCACTGGATCCGGCAGTTTCCAGGAA

ACAAACTGGAGTGGATGGGCTACATAAACTACGATGGTCACAATGACTACAACCCATCTCTCAAA

AGTCGAATCTCTATCACTCAAGACACATCCAAGAACCAGTTCTTCCTGCAGTTGAATTCTGTGAC

TACTGAGGACACAGCCACATATTACTGTGCAAGCAGTTACGACGGCTTATTTGCTTACTGGGGCC

-continued
```
AAGGGACTCTGGTCACTGTCTCTGCAGCCTCAACGAAGGGCCCATCTGTCTTTCCCCTGGCCCCC

TCCTCCAAGAGCACCTCTGGGGGCACAGCGGCCCTGGGCTGCCTGGTCAAGGACTACTTCCCCGA

ACCGGTGACGGTGTCGTGGAACTCAGGCGCCCTGACCAGCGGCGTGCACACCTTCCCGGCTGTCC

TACAGTCCTCAGGACTCTACTCCCTCAGCAGCGTGGTGACCGTGCCCTCCAGCAGCTTGGGCACC

CAGACCTACATCTGCAACGTGAATCACAAGCCCAGCAACACCAAGGTGGACAAGAAAGTTGAGCC

CAAATCTTGTGAATTCACTCACACATGCCCACCGTGCCCAGCACCTGAACTCCTGGGGGGACCGT

CAGTCTTCCTCTTCCCCCCAAAACCCAAGGACACCCTCATGATCTCCCGGACCCCTGAGGTCACA

TGCGTGGTGGTGGACGTGAGCCACGAAGACCCTGAGGTCAAGTTCAACTGGTACGTGGACGGCGT

GGAGGTGCATAATGCCAAGACAAAGCCGCGGGAGGAGCAGTACAACAGCACGTACCGTGTGGTCA

GCGTCCTCACCGTCCTGCACCAGGACTGGCTGAATGGCAAGGAGTACAAGTGCAAGGTCTCCAAC

AAAGCCCTCCCAGCCCCCATCGAGAAAACCATCTCCAAAGCCAAAGGGCAGCCCCGAGAACCACA

GGTGTACACCCTGCCCCCATCCCGGGATGAGCTGACCAAGAACCAGGTCAGCCTGACCTGCCTGG

TCAAAGGCTTCTATCCCAGCGACATCGCCGTGGAGTGGGAGAGCAATGGGCAGCCGGAGAACAAC

TACAAGACCACGCCTCCCGTGCTGGACTCCGACGGCTCCTTCTTCCTCTACAGCAAGCTCACCGT

GGACAAGAGCAGGTGGCAGCAGGGGAACGTCTTCTCATGCTCCGTGATGCATGAGGCTCTGCACA

ACCACTACACGCAGAAGAGCCTCTCCCTGTCTCCCGGGAAA

SEQ ID NO.: 14
EVQLQESGPDLVKPSQSLSLTCTVTGFSITSGYGWHWIRQFPGNKLEWMGYINYDGHNDYNPSLK

SRISITQDTSKNQFFLQLNSVTTEDTATYYCASSYDGLFAYWGQGTLVTVSAASTKGPSVFPLAP

SSKSTSGGTAALGCLVKDYFPEPVTVSWNSGALTSGVHTFPAVLQSSGLYSLSSVVTVPSSSLGT

QTYICNVNHKPSNTKVDKKVEPKSCEFTHTCPPCPAPELLGGPSVFLFPPKPKDTLMISRTPEVT

CVVVDVSHEDPEVKFNWYVDGVEVHNAKTKPREEQYNSTYRVVSVLTVLHQDWLNGKEYKCKVSN

KALPAPIEKTISKAKGQPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQKSLSLSPGK

SEQ ID NO.: 15
GACATTGTGATGACCCAGTCTCCATCCTCCCTGGCTGTGTCAATAGGACAGAAGGTCACTATGAA

CTGCAAGTCCAGTCAGAGCCTTTTAAATAGTAACTTTCAAAAGAACTTTTTGGCCTGGTACCAGC

AGAAACCAGGCCAGTCTCCTAAACTTCTGATATACTTTGCATCCACTCGGGAATCTAGTATCCCT

GATCGCTTCATAGGCAGTGGATCTGGGACAGATTTCACTCTTACCATCAGCAGTGTGCAGGCTGA

AGACCTGGCAGATTACTTCTGTCAGCAACATTATAGCACTCCGCTCACGTTCGGTGCTGGGACCA

AGCTGGAGCTGAAA

SEQ ID NO.: 16
DIVMTQSPSSLAVSIGQKVTMKCKSSQSLLNSNFQKNFLAWYQQKPGQSPKLLIYFASTRESSIP

DRFIGSGSGTDFTLTISSVQAEDLADYFCQQHYSTPLTFGAGTKLELK

SEQ ID NO.: 17
GAGGTTCAGCTGCAGCAGTCTGTAGCTGAGCTGGTGAGGCCTGGGGCTTCAGTGACGCTGTCCTG

CAAGGCTTCGGGCTACATATTTACTGACTATGAGATACACTGGGTGAAGCAGACTCCTGTGCATG

GCCTGGAATGGATTGGGGTTATTGATCCTGAAACTGGTAATACTGCCTTCAATCAGAAGTTCAAG

GGCAAGGCCACACTGACTGCAGACATATCCTCCAGCACAGCCTACATGGAACTCAGCAGTTTGAC

ATCTGAGGACTCTGCCGTCTATTACTGTATGGGTTATTCTGATTATTGGGGCCAAGGCACCACTC

TCACAGTCTCCTCA
```

-continued

SEQ ID NO.: 18
EVQLQQSVAELVRPGASVTLSCKASGYIFTDYEIHWVKQTPVHGLEWIGVIDPETGNTAFNQKFK
GKATLTADISSSTAYMELSSLTSEDSAVYYCMGYSDYWGQGTTLTVSS

SEQ ID NO.: 19
GATGTTTTGATGACCCAAACTCCACGCTCCCTGTCTGTCAGTCTTGGAGATCAAGCCTCCATCTC
TTGTAGATCGAGTCAGAGCCTTTTACATAGTAATGGAAACACCTATTTAGAATGGTATTTGCAGA
AACCAGGCCAGCCTCCAAAGGTCCTGATCTACAAAGTTTCCAACCGATTTTCTGGGGTCCCAGAC
AGGTTCAGTGGCAGTGGATCAGGGACAGATTTCACACTCAAGATCAGCGGAGTGGAGGCTGAGGA
TCTGGGAGTTTATTACTGCTTTCAAGGTTCACATGTTCCTCTCACGTTCGGTGCTGGGACCAAGC
TGGAGCTGAAA

SEQ ID NO.: 20
DVLMTQTPRSLSVSLGDQASISCRSSQSLLHSNGNTYLEWYLQKPGQPPKVLIYKVSNRFSGVPD
RFSGSGSGTDFTLKISGVEAEDLGVYYCFQGSHVPLTFGAGTKLELK

SEQ ID NO.: 21
GAGATCCAGCTGCAGCAGTCTGGACCTGAGTTGGTGAAGCCTGGGGCTTCAGTGAAGATATCCTG
TAAGGCTTCTGGATACACCTTCACTGACAACTACATGAACTGGGTGAAGCAGAGCCATGGAAAGA
GCCTTGAGTGGATTGGAGATATTAATCCTTACTATGGTACTACTACCTACAACCAGAAGTTCAAG
GGCAAGGCCACATTGACTGTAGACAAGTCCTCCCGCACAGCCTACATGGAGCTCCGCGGCCTGAC
ATCTGAGGACTCTGCAGTCTATTACTGTGCAAGAGATGACTGGTTTGATTATTGGGGCCAAGGGA
CTCTGGTCACTGTCTCTGCA

SEQ ID NO.: 22
EIQLQQSGPELVKPGASVKISCKASGYTFTDNYMNWVKQSHGKSLEWIGDINPYYGTTTTNQKFK
GKATLTVDKSSRTAYMELRGLTSEDSAVYYCARDDWFDYWGQGTLVTVSA

SEQ ID NO.: 23
GACATCGTTATGTCTCAGTCTCCATCTTCCATGTATGCATCTCTAGGAGAGAGAGTCACTATCAC
TTGCAAGGCGAGTCAGGACATTCATAACTTTTTAAACTGGTTCCAGCAGAAACCAGGAAAATCTC
CAAAGACCCTGATCTTTCGTGCAAACAGATTGGTAGATGGGGTCCCATCAAGGTTCAGTGGCAGT
GGATCTGGGCAAGATTATTCTCTCACCATCAGCAGCCTGGAGTTTGAAGATTTGGGAATTTATTC
TTGTCTACAGTATGATGAGATTCCGCTCACGTTCGGTGCTGGGACCAAGCTGGAGCTGAGA

SEQ ID NO.: 24
DIVMSQSPSSMYASLGERVTITCKASQDIHNFLNWFQQKPGKSPKTLIFRANRLVDGVPSRFSGS
GSGQDYSLTISSLEFEDLGIYSCLQYDEIPLTFGAGTKLELR

SEQ ID NO.: 25
GAGGTGCAGCTTCAGGAGTCAGGACCTGACCTGGTGAAACCTTCTCAGTCACTTTCACTCACCTG
CACTGTCACTGGCTTCTCCATCACCAGTGGTTATGGCTGGCACTGGATCCGGCAGTTTCCAGGAA
ACAAACTGGAGTGGATGGGCTACATAAACTACGATGGTCACAATGACTACAACCCATCTCTCAAA
AGTCGAATCTCTATCACTCAAGACACATCCAAGAACCAGTTCTTCCTGCAGTTGAATTCTGTGAC
TACTGAGGACACAGCCACATATTACTGTGCAAGCAGTTACGACGGCTTATTTGCTTACTGGGGCC
AAGGGACTCTGGTCACTGTCTCTGCA

SEQ ID NO.: 26
EVQLQESGPDLVKPSQSLSLTCTVTGFSITSGYGWHWIRQFPGNKLEWMGYINYDGHNDYNPSLK
SRISITQDTSKNQFFLQLNSVTTEDTATYYCASSYDGLFAYWGQGTLVTVSA

SEQ ID NO.: 27
KSSQSLLNSNFQKNFLA

SEQ ID NO.: 28
FASTRES

-continued

SEQ ID NO.: 29
QQHYSTPLT

SEQ ID NO.: 30
GYIFTDYEIH

SEQ ID NO.: 31
VIDPETGNTA

SEQ ID NO.: 32
MGYSDY

SEQ ID NO.: 33
RSSQSLLHSNGNTYLE

SEQ ID NO.: 34
KVSNRFS

SEQ ID NO.: 35
FQGSHVPLT

SEQ ID NO.: 36
GYTFTDNYMN

SEQ ID NO.: 37
DINPYYGTTT

SEQ ID NO.: 38
ARDDWFDY

SEQ ID NO.: 39
KASQDIHNFLN

SEQ ID NO.: 40
RANRLVD

SEQ ID NO.: 41
LQYDEIPLT

SEQ ID NO.: 42
GFSITSGYGWH

SEQ ID NO.: 43
YINYDGHND

SEQ ID NO.: 44
ASSYDGLFAY

SEQ ID NO.: 45 - 3A4 heavy chain variable region nucleotide
sequence
CAGATCCAGTTGGTGCAATCTGGACCTGAGATGGTGAAGCCTGGGGCTTCAGTGAAGATGTCCTG

TAAGGCTTCTGGATACACATTCACTGACGACTACATGAGCTGGGTGAAACAGAGCCATGGAAAGA

GCCTTGAGTGGATTGGAGATATTAATCCTTACAACGGTGATACTAACTACAACCAGAAGTTCAAG

GGCAAGGCCATATTGACTGTAGACAAATCCTCCAGCACAGCCTACATGCAGCTCAACAGCCTGAC

ATCGGAAGACTCAGCAGTCTATTACTGTGCAAGAGACCCGGGGGCTATGGACTACTGGGGTCAAG

GAACCTCAGTCACCGTCTCCTCA

SEQ ID NO.: 46 - 3A4 heavy chain variable region polypeptide
sequence
QIQLVQSGPEMVKPGASVKMSCKASGYTFTDDYMSWVKQSHGKSLEWIGDINPYNGDTNYNQKFK

GKAILTVDKSSSTAYMQLNSLTSEDSAVYYCARDPGAMDYWGQGTSVTVSS

SEQ ID NO.: 47 - 3A4 light chain variable region nucleotide
sequence
GATGTTGTGATGACCCAAACTCCACTCTCCCTGGCTGTCAGTCTTGGAGATCAAGCCTCCATCTC

TTGCAGATCTAGTCAGAGCCTTCTACATAGTAATGGAAACACCTATTTAGAATGGTACCTTCAGA

AACCAGGCCAGTCTCCAAAGCTCCTGATCCACACAGTTTCCAACCGATTTTCTGGGGTCCCAGAC

AGATTCAGTGGCAGTGGATCAGGGACAGATTTCACACTCAAGATCAGCAGAGTGGAGGCTGAGGA

TCTGGGAGTTTATTACTGCTTTCAAGGTTCACATGTTCCGCTCACGTTCGGTGCTGGGACCAGGC

TGGAGCTGAAA

SEQ ID NO.: 48 - 3A4 light chain variable region polypeptide sequence
DVVMTQTPLSLAVSLGDQASISCRSSQSLLHSNGNTYLEWYLQKPGQSPKLLIHTVSNRFSGVPD

RFSGSGSGTDFTLKISRVEAEDLGVYYCFQGSHVPLTFGAGTRLELK

SEQ ID NO.: 49 - 3A4 heavy chain CDR1 polypeptide sequence
GYTFTDDYMS

SEQ ID NO.: 50 - 3A4 heavy chain CDR2 polypeptide sequence
DINPYNGDTNYNQKFKG

SEQ ID NO.: 51 - 3A4 heavy chain CDR3 polypeptide sequence
DPGAMDY

SEQ ID NO.: 52 - 3A4 light chain CDR1 polypeptide sequence
RSSQSLLHSNGNTYLE

SEQ ID NO.: 53 - 3A4 light chain CDR2 polypeptide sequence
TVSNRFS

SEQ ID NO.: 54 - 3A4 light chain CDR3 polypeptide sequence
FQGSHVPLT

SEQ ID NO.: 55
GTAAGCAGCGCTGTGGCTGCACCATCTGTCTTC

SEQ ID NO.: 56
GTAAGCGCTAGCCTAACACTCTCCCTGTTGAAGC

SEQ ID NO.: 57
GCTGTGGCTGCACCATCTGTCTTCATCTTCCCGCCATCTGATGAGCAGTTGAAATCTGGAACTGC

CTCTGTTGTGTGCCTGCTGAATAACTTCTATCCCAGAGAGGCCAAAGTACAGTGGAAGGTGGATA

ACGCCCTCCAATCGGGTAACTCCCAGGAGAGTGTCACAGAGCAGGACAGCAAGGACAGCACCTAC

AGCCTCAGCAGCACCCTGACGCTGAGCAAAGCAGACTACGAGAAACACAAAGTCTACGCCTGCGA

AGTCACCCATCAGGGCCTGAGCTCGCCCGTCACAAAGAGCTTCAACAGGGGAGAGTGTTAG

SEQ ID NO.: 58
AVAAPSVFIFPPSDEQLKSGTASVVCLLNNFYPREAKVQWKVDNALQSGNSQESVTEQDSKDSTY

SLSSTLTLSKADYEKHKVYACEVTHQGLSSPVTKSFNRGEC

SEQ ID NO.: 59
CTTGAGCCGGCGGATGGTCGAGGTGAGGTGTGGCAGGCTTGAGATCCAGCTGTTGGGGTGAGTAC

TCCCTCTCAAAAGCGGGCATTACTTCTGCGCTAAGATTGTCAGTTTCCAAAAACGAGGAGGATTT

GATATTCACCTGGCCCGATCTGGCCATACACTTGAGTGACAATGACATCCACTTTGCCTTTCTCT

CCACAGGTGTCCACTCCCAGGTCCAAGTTTAAACGGATCTCTAGCGAATTCATGAACTTTCTGCT

GTCTTGGGTGCATTGGAGCCTTGCCTTGCTGCTCTACCTCCACCATGCCAAGTGGTCCCAGGCTT

GAGACGGAGCTTACAGCGCTGTGGCTGCACCATCTGTCTTCATCTTCCCGCCATCTGATGAGCAG

TTGAAATCTGGAACTGCCTCTGTTGTGTGCCTGCTGAATAACTTCTATCCCAGAGAGGCCAAAGT

ACAGTGGAAGGTGGATAACGCCCTCCAATCGGGTAACTCCCAGGAGAGTGTCACAGAGCAGGACA

GCAAGGACAGCACCTACAGCCTCAGCAGCACCCTGACGCTGAGCAAAGCAGACTACGAGAAACAC

AAAGTCTACGCCTGCGAAGTCACCCATCAGGGCCTGAGCTCGCCCGTCACAAAGAGCTTCAACAG

GGGAGAGTGTTAGGGTACCGCGGCCGCTTCGAATGAGATCCCCCGACCTCGACCTCTGGCTAATA

AAGGAAATTTATTTTCATTGCAATAGTGTGTTGGAATTTTTTGTGTCTCTCACTCGGAAGGACAT

ATGGGAGGGCAAATCATTTGGTCGAGATCCCTCGGAGATCTCTAGCTAGAGCCCGCCGCCGGAC

GAACTAAACCTGACTACGGCATCTCTGCCCCTTCTTCGCGGGCAGTGCATGTAATCCCTTCAGT

TGGTTGGTACAACTTGCCAACTGGGCCCTGTTCCACATGTGACACGGGGGGGACCAAACACAAA

GGGGTTCTCTGACTGTAGTTGACATCCTTATAAATGGATGTGCACATTTGCCAACACTGAGTGGC

TTTCATCCTGGAGCAGACTTTGCAGTCTGTGGACTGCAACACAACATTGCCTTTATGTGTAACTC

-continued

```
TTGGCTGAAGCTCTTACACCAATGCTGGGGGACATGTACCTCCCAGGGGCCCAGGAAGACTACGG

GAGGCTACACCAACGTCAATCAGAGGGGCCTGTGTAGCTACCGATAAGCGGACCCTCAAGAGGGC

ATTAGCAATAGTGTTTATAAGGCCCCCTTGTTAACCCTAAACGGGTAGCATATGCTTCCCGGGTA

GTAGTATATACTATCCAGACTAACCCTAATTCAATAGCATATGTTACCCAACGGGAAGCATATGC

TATCGAATTAGGGTTAGTAAAAGGGTCCTAAGGAACAGCGATATCTCCCACCCCATGAGCTGTCA

CGGTTTTATTTACATGGGGTCAGGATTCCACGAGGGTAGTGAACCATTTTAGTCACAAGGGCAGT

GGCTGAAGATCAAGGAGCGGGCAGTGAACTCTCCTGAATCTTCGCCTGCTTCTTCATTCTCCTTC

GTTTAGCTAATAGAATAACTGCTGAGTTGTGAACAGTAAGGTGTATGTGAGGTGCTCGAAAACAA

GGTTTCAGGTGACGCCCCCAGAATAAAATTTGGACGGGGGGTTCAGTGGTGGCATTGTGCTATGA

CACCAATATAACCCTCACAAACCCCTTGGGCAATAAATACTAGTGTAGGAATGAAACATTCTGAA

TATCTTTAACAATAGAAATCCATGGGGTGGGACAAGCCGTAAAGACTGGATGTCCATCTCACAC

GAATTTATGGCTATGGGCAACACATAATCCTAGTGCAATATGATACTGGGGTTATTAAGATGTGT

CCCAGGCAGGGACCAAGACAGGTGAACCATGTTGTTACACTCTATTTGTAACAAGGGGAAAGAGA

GTGGACGCCGACAGCAGCGGACTCCACTGGTTGTCTCTAACACCCCCGAAAATTAAACGGGGCTC

CACGCCAATGGGGCCCATAAACAAAGACAAGTGGCCACTCTTTTTTTTGAAATTGTGGAGTGGGG

GCACGCGTCAGCCCCCACACGCCGCCCTGCGGTTTTGGACTGTAAAATAAGGGTGTAATAACTTG

GCTGATTGTAACCCCGCTAACCACTGCGGTCAAACCACTTGCCCACAAAACCACTAATGGCACCC

CGGGGAATACCTGCATAAGTAGGTGGGCGGGCCAAGATAGGGGCGCGATTGCTGCGATCTGGAGG

ACAAATTACACACACTTGCGCCTGAGCGCCAAGCACAGGGTTGTTGGTCCTCATATTCACGAGGT

CGCTGAGAGCACGGTGGGCTAATGTTGCCATGGGTAGCATATACTACCCAAATATCTGGATAGCA

TATGCTATCCTAATCTATATCTGGGTAGCATAGGCTATCCTAATCTATATCTGGGTAGCATATGC

TATCCTAATCTATATCTGGGTAGTATATGCTATCCTAATTTATATCTGGGTAGCATAGGCTATCC

TAATCTATATCTGGGTAGCATATGCTATCCTAATCTATATCTGGGTAGTATATGCTATCCTAATC

TGTATCCGGGTAGCATATGCTATCCTAATAGAGATTAGGGTAGTATATGCTATCCTAATTTATAT

CTGGGTAGCATATACTACCCAAATATCTGGATAGCATATGCTATCCTAATCTATATCTGGGTAGC

ATATGCTATCCTAATCTATATCTGGGTAGCATAGGCTATCCTAATCTATATCTGGGTAGCATATG

CTATCCTAATCTATATCTGGGTAGTATATGCTATCCTAATTTATATCTGGGTAGCATAGGCTATC

CTAATCTATATCTGGGTAGCATATGCTATCCTAATCTATATCTGGGTAGTATATGCTATCCTAAT

CTGTATCCGGGTAGCATATGCTATCCTCACGATGATAAGCTGTCAAACATGAGAATTAATTCTTG

AAGACGAAAGGGCCTCGTGATACGCCTATTTTTATAGGTTAATGTCATGATAATAATGGTTTCTT

AGACGTCAGGTGGCACTTTTCGGGGAAATGTGCGCGGAACCCCTATTTGTTTATTTTTCTAAATA

CATTCAAATATGTATCCGCTCATGAGACAATAACCCTGATAAATGCTTCAATAATATTGAAAAAG

GAAGAGTATGAGTATTCAACATTTCCGTGTCGCCCTTATTCCCTTTTTTGCGGCATTTTGCCTTC

CTGTTTTTGCTCACCCAGAAACGCTGGTGAAAGTAAAAGATGCTGAAGATCAGTTGGGTGCACGA

GTGGGTTACATCGAACTGGATCTCAACAGCGGTAAGATCCTTGAGAGTTTTCGCCCCGAAGAACG

TTTTCCAATGATGAGCACTTTTAAAGTTCTGCTATGTGGCGCGGTATTATCCCGTGTTGACGCCG

GGCAAGAGCAACTCGGTCGCCGCATACACTATTCTCAGAATGACTTGGTTGAGTACTCACCAGTC

ACAGAAAAGCATCTTACGGATGGCATGACAGTAAGAGAATTATGCAGTGCTGCCATAACCATGAG

TGATAACACTGCGGCCAACTTACTTCTGACAACGATCGGAGGACCGAAGGAGCTAACCGCTTTTT

TGCACAACATGGGGGATCATGTAACTCGCCTTGATCGTTGGGAACCGGAGCTGAATGAAGCCATA
```

-continued

```
CCAAACGACGAGCGTGACACCACGATGCCTGCAGCAATGGCAACAACGTTGCGCAAACTATTAAC
TGGCGAACTACTTACTCTAGCTTCCCGGCAACAATTAATAGACTGGATGGAGGCGGATAAAGTTG
CAGGACCACTTCTGCGCTCGGCCCTTCCGGCTGGCTGGTTTATTGCTGATAAATCTGGAGCCGGT
GAGCGTGGGTCTCGCGGTATCATTGCAGCACTGGGGCCAGATGGTAAGCCCTCCCGTATCGTAGT
TATCTACACGACGGGGAGTCAGGCAACTATGGATGAACGAAATAGACAGATCGCTGAGATAGGTG
CCTCACTGATTAAGCATTGGTAACTGTCAGACCAAGTTTACTCATATATACTTTAGATTGATTTA
AAACTTCATTTTTAATTTAAAAGGATCTAGGTGAAGATCCTTTTTGATAATCTCATGACCAAAAT
CCCTTAACGTGAGTTTTCGTTCCACTGAGCGTCAGACCCCGTAGAAAAGATCAAAGGATCTTCTT
GAGATCCTTTTTTTCTGCGCGTAATCTGCTGCTTGCAAACAAAAAAACCACCGCTACCAGCGGTG
GTTTGTTTGCCGGATCAAGAGCTACCAACTCTTTTTCCGAAGGTAACTGGCTTCAGGAGAGCGCA
GATACCAAATACTGTCCTTCTAGTGTAGCCGTAGTTAGGCCACCACTTCAAGAACTCTGTAGCAC
CGCGTACATACCTCGCTCTGCTAATCCTGTTACCAGTGGGTGCTGCCAGTGGCGATAAGTCGTGT
CTTACCGGGTTGGACTCAAGACGATAGTTACCGGATAAGGCGCAGCGGTCGGGCTGAACGGGGGG
TTCGTGCACACAGCCCAGCTTGGAGCGAACGACCTACACCGAACTGAGATACCTACAGCGTGAGC
ATTGAGAAAGCGCCACGCTTCCCGAAGGGAGAAAGGCGGACAGGTATCCGGTAAGCGGCAGGGTC
GGAACAGGAGAGCGCACGAGGGAGCTTCCAGGGGGAAACGCCTGGTATCTTTATAGTCCTGTCGG
GTTTCGCCACCTCTGACTTGAGCGTCGATTTTTGTGATGCTCGTCAGGGGGCGGAGCCTATGGA
AAAACGCCAGCAACGCGGCCTTTTTACGGTTCCTGGCCTTTTGCTGGCCTTTTGCTCACATGTTC
TTTCCTGCGTTATCCCTGATTCTGTGGATAACCGTATTACCGCCTTTGAGTGAGCTGATACCGC
TCGCCGCAGCCGAACGACCGAGCGCAGCGAGTCAGTGAGCGAGGAAGCGGAAGAGCGCCCAATAC
GCAAACCGCCTCTCCCCGCGCGTTGGCCGATTCATTAATGCAGCTGGCACGACAGGTTTCCCGAC
TGGAAAGCGGGCAGTGAGCGCAACGCAATTAATGTGAGTTAGCTCACTCATTAGGCACCCCAGGC
TTTACACTTTATGCTTCCGGCTCGTATGTTGTGTGGAATTGTGAGCGGATAACAATTTCACACAG
GAAACAGCTATGAGCATGATTACGCCAAGCTCTAGCTAGAGGTCGACCAATTCTCATGTTTGACA
GCTTATCATCGCAGATCCGGGCAACGTTGTTGCATTGCTGCAGGCGCAGAACTGGTAGGTATGGC
AGATCTATACATTGAATCAATATTGGCAATTAGCCATATTAGTCATTGGTTATATAGCATAAATC
AATATTGGCTATTGGCCATTGCATACGTTGTATCTATATCATAATATGTACATTTATATTGGCTC
ATGTCCAATATGACCGCCATGTTGACATTGATTATTGACTAGTTATTAATAGTAATCAATTACGG
GGTCATTAGTTCATAGCCCATATATGGAGTTCCGCGTTACATAACTTACGGTAAATGGCCCGCCT
GGCTGACCGCCCAACGACCCCCGCCCATTGACGTCAATAATGACGTATGTTCCCATAGTAACGCC
AATAGGGACTTTCCATTGACGTCAATGGGTGGAGTATTTACGGTAAACTGCCCACTTGGCAGTAC
ATCAAGTGTATCATATGCCAAGTCCGCCCCCTATTGACGTCAATGACGGTAAATGGCCCGCCTGG
CATTATGCCCAGTACATGACCTTACGGGACTTTCCTACTTGGCAGTACATCTACGTATTAGTCAT
CGCTATTACCATGGTGATGCGGTTTTGGCAGTACACCAATGGGCGTGGATAGCGGTTTGACTCAC
GGGGATTTCCAAGTCTCCACCCCATTGACGTCAATGGGAGTTTGTTTTGGCACCAAAATCAACGG
GACTTTCCAAAATGTCGTAATAACCCCGCCCCGTTGACGCAAATGGGCGGTAGGCGTGTACGGTG
GGAGGTCTATATAAGCAGAGCTCGTTTAGTGAACCGTCAGATCCTCACTCTCTTCCGCATCGCTG
TCTGCGAGGGCCAGCTGTTGGGCTCGCGGTTGAGGACAAACTCTTCGCGGTCTTTCCAGTACTCT
TGGATCGGAAACCCGTCGGCCTCCGAACGGTACTCCGCCACCGAGGGACCTGAGCGAGTCCGCAT
CGACCGGATCGGAAAACCTCTCGAGAAAGGCGTCTAACCAGTCACAGTCGCAAGGTAGGCTGAGC
ACCGTGGCGGGCGGCAGCGGGTGGCGGTCGGGGTTGTTTCTGGCGGAGGTGCTGCTGATGATGTA
```

ATTAAAGTAGGCGGT

SEQ DI NO.: 60
ATGCCAAGTGGTCCCAGGCTGACATTGTGATGACCCAGTCTCC

SEQ ID NO.: 61
ATGCCAAGTGGTCCCAGGCTGATGTTTTGATGACCCAAACTCC

SEQ ID NO.: 62
ATGCCAAGTGGTCCCAGGCTGACATCGTTATGTCTCAGTCTCC

SEQ ID NO.: 63
GGGAAGATGAAGACAGATGGTGCAGCCACAGC

SEQ ID NO.: 64
GTAAGCGCTAGCGCCTCAACGAAGGGCCCATCTGTCTTTCCCCTGGCCCC

SEQ ID NO.: 65
GTAAGCGAATTCACAAGATTTGGGCTCAACTTTCTTG

SEQ ID NO.: 66
GCCTCCACCAAGGGCCCATCGGTCTTCCCCCTGGCACCCTCCTCCAAGAGCACCTCTGGGGGCAC

AGCAGCCCTGGGCTGCCTGGTCAAGGACTACTTCCCCGAACCGGTGACGGTGTCGTGGAACTCAG

GCGCCCTGACCAGCGGCGTGCACACCTTCCCGGCTGTCCTACAGTCCTCAGGACTCTACTCCCTC

AGCAGCGTGGTGACCGTGCCCTCCAGCAGCTTGGGCACCCAGACCTACATCTGCAACGTGAATCA

CAAGCCCAGCAACACCAAGGTGGACAAGAAAGTTGAGCCCAAATCTTGT

SEQ ID NO.: 67
ASTKGPSVFPLAPSSKSTSGGTAALGCLVKDYFPEPVTVSWNSGALTSGVHTFPAVLQSSGLYSL

SSVVTVPSSSLGTQTYICNVNHKPSNTKVDKKVEPKSC

SEQ ID NO.: 68
CTTGAGCCGGCGGATGGTCGAGGTGAGGTGTGGCAGGCTTGAGATCCAGCTGTTGGGGTGAGTAC

TCCCTCTCAAAAGCGGGCATTACTTCTGCGCTAAGATTGTCAGTTTCCAAAAACGAGGAGGATTT

GATATTCACCTGGCCCGATCTGGCCATACACTTGAGTGACAATGACATCCACTTTGCCTTTCTCT

CCACAGGTGTCCACTCCCAGGTCCAAGTTTGCCGCCACCATGGAGACAGACACACTCCTGCTATG

GGTACTGCTGCTCTGGGTTCCAGGTTCCACTGGCGGAGACGGAGCTTACGGGCCCATCTGTCTTT

CCCCTGGCCCCCTCCTCCAAGAGCACCTCTGGGGGCACAGCGGCCCTGGGCTGCCTGGTCAAGGA

CTACTTCCCCGAACCGGTGACGGTGTCGTGGAACTCAGGCGCCCTGACCAGCGGCGTGCACACCT

TCCCGGCTGTCCTACAGTCCTCAGGACTCTACTCCCTCAGCAGCGTGGTGACCGTGCCCTCCAGC

AGCTTGGGCACCCAGACCTACATCTGCAACGTGAATCACAAGCCCAGCAACACCAAGGTGGACAA

GAAAGTTGAGCCCAAATCTTGTGAATTCACTCACACATGCCCACCGTGCCCAGCACCTGAACTCC

TGGGGGGACCGTCAGTCTTCCTCTTCCCCCCAAAACCCAAGGACACCCTCATGATCTCCCGGACC

CCTGAGGTCACATGCGTGGTGGTGGACGTGAGCCACGAAGACCCTGAGGTCAAGTTCAACTGGTA

CGTGGACGGCGTGGAGGTGCATAATGCCAAGACAAAGCCGCGGGAGGAGCAGTACAACAGCACGT

ACCGTGTGGTCAGCGTCCTCACCGTCCTGCACCAGGACTGGCTGAATGGCAAGGAGTACAAGTGC

AAGGTCTCCAACAAAGCCCTCCCAGCCCCCATCGAGAAAACCATCTCCAAAGCCAAAGGGCAGCC

CCGAGAACCACAGGTGTACACCCTGCCCCCATCCCGGGATGAGCTGACCAAGAACCAGGTCAGCC

TGACCTGCCTGGTCAAAGGCTTCTATCCCAGCGACATCGCCGTGGAGTGGGAGAGCAATGGGCAG

CCGGAGAACAACTACAAGACCACGCCTCCCGTGCTGGACTCCGACGGCTCCTTCTTCCTCTACAG

CAAGCTCACCGTGGACAAGAGCAGGTGGCAGCAGGGGAACGTCTTCTCATGCTCCGTGATGCATG

AGGCTCTGCACAACCACTACACGCAGAAGAGCCTCTCCCTGTCTCCCGGGAAATGATCCCCCGAC

CTCGACCTCTGGCTAATAAAGGAAATTTATTTTCATTGCAATAGTGTGTTGGAATTTTTTGTGTC

TCTCACTCGGAAGGACATATGGGAGGGCAAATCATTTGGTCGAGATCCCTCGGAGATCTCTAGCT

-continued

```
AGAGCCCCGCCGCCGGACGAACTAAACCTGACTACGGCATCTCTGCCCCTTCTTCGCGGGGCAGT
GCATGTAATCCCTTCAGTTGGTTGGTACAACTTGCCAACTGAACCCTAAACGGGTAGCATATGCT
TCCCGGGTAGTAGTATATACTATCCAGACTAACCCTAATTCAATAGCATATGTTACCCAACGGGA
AGCATATGCTATCGAATTAGGGTTAGTAAAAGGGTCCTAAGGAACAGCGATGTAGGTGGGCGGGC
CAAGATAGGGGCGCGATTGCTGCGATCTGGAGGACAAATTACACACACTTGCGCCTGAGCGCCAA
GCACAGGGTTGTTGGTCCTCATATTCACGAGGTCGCTGAGAGCACGGTGGGCTAATGTTGCCATG
GGTAGCATATACTACCCAAATATCTGGATAGCATATGCTATCCTAATCTATATCTGGGTAGCATA
GGCTATCCTAATCTATATCTGGGTAGCATATGCTATCCTAATCTATATCTGGGTAGTATATGCTA
TCCTAATTTATATCTGGGTAGCATAGGCTATCCTAATCTATATCTGGGTAGCATATGCTATCCTA
ATCTATATCTGGGTAGTATATGCTATCCTAATCTGTATCCGGGTAGCATATGCTATCCTAATAGA
GATTAGGGTAGTATATGCTATCCTAATTTATATCTGGGTAGCATATACTACCCAAATATCTGGAT
AGCATATGCTATCCTAATCTATATCTGGGTAGCATATGCTATCCTAATCTATATCTGGGTAGCAT
AGGCTATCCTAATCTATATCTGGGTAGCATATGCTATCCTAATCTATATCTGGGTAGTATATGCT
ATCCTAATTTATATCTGGGTAGCATAGGCTATCCTAATCTATATCTGGGTAGCATATGCTATCCT
AATCTATATCTGGGTAGTATATGCTATCCTAATCTGTATCCGGGTAGCATATGCTATCCTCACGA
TGATAAGCTGTCAAACATGAGAATTAATTCTTGAAGACGAAAGGGCCTCGTGATACGCCTATTTT
TATAGGTTAATGTCATGATAATAATGGTTTCTTAGACGTCAGGTGGCACTTTTCGGGGAAATGTG
CGCGGAACCCCTATTTGTTTATTTTTCTAAATACATTCAAATATGTATCCGCTCATGAGACAATA
ACCCTGATAAATGCTTCAATAATATTGAAAAAGGAAGAGTATGAGTATTCAACATTTCCGTGTCG
CCCTTATTCCCTTTTTTGCGGCATTTTGCCTTCCTGTTTTTGCTCACCCAGAAACGCTGGTGAAA
GTAAAAGATGCTGAAGATCAGTTGGGTGCACGAGTGGGTTACATCGAACTGGATCTCAACAGCGG
TAAGATCCTTGAGAGTTTTCGCCCCGAAGAACGTTTTCCAATGATGAGCACTTTTAAAGTTCTGC
TATGTGGCGCGGTATTATCCCGTGTTGACGCCGGGCAAGAGCAACTCGGTCGCCGCATACACTAT
TCTCAGAATGACTTGGTTGAGTACTCACCAGTCACAGAAAAGCATCTTACGGATGGCATGACAGT
AAGAGAATTATGCAGTGCTGCCATAACCATGAGTGATAACACTGCGGCCAACTTACTTCTGACAA
CGATCGGAGGACCGAAGGAGCTAACCGCTTTTTTGCACAACATGGGGGATCATGTAACTCGCCTT
GATCGTTGGGAACCGGAGCTGAATGAAGCCATACCAAACGACGAGCGTGACACCACGATGCCTGC
AGCAATGGCAACAACGTTGCGCAAACTATTAACTGGCGAACTACTTACTCTAGCTTCCCGGCAAC
AATTAATAGACTGGATGGAGGCGGATAAAGTTGCAGGACCACTTCTGCGCTCGGCCCTTCCGGCT
GGCTGGTTTATTGCTGATAAATCTGGAGCCGGTGAGCGTGGGTCTCGCGGTATCATTGCAGCACT
GGGGCCAGATGGTAAGCCCTCCCGTATCGTAGTTATCTACACGACGGGGAGTCAGGCAACTATGG
ATGAACGAAATAGACAGATCGCTGAGATAGGTGCCTCACTGATTAAGCATTGGTAACTGTCAGAC
CAAGTTTACTCATATATACTTTAGATTGATTTAAAACTTCATTTTTAATTTAAAAGGATCTAGGT
GAAGATCCTTTTTGATAATCTCATGACCAAAATCCCTTAACGTGAGTTTTCGTTCCACTGAGCGT
CAGACCCCGTAGAAAAGATCAAAGGATCTTCTTGAGATCCTTTTTTTCTGCGCGTAATCTGCTGC
TTGCAAACAAAAAAACCACCGCTACCAGCGGTGGTTTGTTTGCCGGATCAAGAGCTACCAACTCT
TTTTCCGAAGGTAACTGGCTTCAGCAGAGCGCAGATACCAAATACTGTCCTTCTAGTGTAGCCGT
AGTTAGGCCACCACTTCAAGAACTCTGTAGCACCGCCTACATACCTCGCTCTGCTAATCCTGTTA
CCAGTGGCTGCTGCCAGTGGCGATAAGTCGTGTCTTACCGGGTTGGACTCAAGACGATAGTTACC
GGATAAGGCGCAGCGGTCGGGCTGAACGGGGGGTTCGTGCACACAGCCCAGCTTGGAGCGAACGA
```

-continued

CCTACACCGAACTGAGATACCTACAGCGTGAGCATTGAGAAAGCGCCACGCTTCCCGAAGGGAGA

AAGGCGGACAGGTATCCGGTAAGCGGCAGGGTCGGAACAGGAGAGCGCACGAGGGAGCTTCCAGG

GGGAAACGCCTGGTATCTTTATAGTCCTGTCGGGTTTCGCCACCTCTGACTTGAGCGTCGATTTT

TGTGATGCTCGTCAGGGGGCGGAGCCTATGGAAAAACGCCAGCAACGCGGCCTTTTTACGGTTC

CTGGCCTTTTGCTGGCCTTTTGCTCACATGTTCTTTCCTGCGTTATCCCCTGATTCTGTGGATAA

CCGTATTACCGCCTTTGAGTGAGCTGATACCGCTCGCCGCAGCCGAACGACCGAGCGCAGCGAGT

CAGTGAGCGAGGAAGCGTACATTTATATTGGCTCATGTCCAATATGACCGCCATGTTGACATTGA

TTATTGACTAGTTATTAATAGTAATCAATTACGGGGTCATTAGTTCATAGCCCATATATGGAGTT

CCGCGTTACATAACTTACGGTAAATGGCCCGCCTGGCTGACCGCCCAACGACCCCCGCCCATTGA

CGTCAATAATGACGTATGTTCCCATAGTAACGCCAATAGGGACTTTCCATTGACGTCAATGGGTG

GAGTATTTACGGTAAACTGCCCACTTGGCAGTACATCAAGTGTATCATATGCCAAGTCCGCCCCC

TATTGACGTCAATGACGGTAAATGGCCCGCCTGGCATTATGCCCAGTACATGACCTTACGGGACT

TTCCTACTTGGCAGTACATCTACGTATTAGTCATCGCTATTACCATGGTGATGCGGTTTTGGCAG

TACACCAATGGGCGTGGATAGCGGTTTGACTCACGGGGATTTCCAAGTCTCCACCCCATTGACGT

CAATGGGAGTTTGTTTTGGCACCAAAATCAACGGGACTTTCCAAAATGTCGTAATAACCCCGCCC

CGTTGACGCAAATGGGCGGTAGGCGTGTACGGTGGGAGGTCTATATAAGCAGAGCTCGTTTAGTG

AACCGTCAGATCCTCACTCTCTTCCGCATCGCTGTCTGCGAGGGCCAGCTGTTGGGCTCGCGGTT

GAGGACAAACTCTTCGCGGTCTTTCCAGTACTCTTGGATCGGAAACCCGTCGGCCTCCGAACGGT

ACTCCGCCACCGAGGGACCTGAGCGAGTCCGCATCGACCGGATCGGAAAACCTCTCGAGAAAGGC

GTCTAACCAGTCACAGTCGCAAGGTAGGCTGAGCACCGTGGCGGGCGGCAGCGGGTGGCGGTCGG

GGTTGTTTCTGGCGGAGGTGCTGCTGATGATGTAATTAAAGTAGGCGGT

SEQ ID NO.: 69
GGGTTCCAGGTTCCACTGGCGAGGTTCAGCTGCAGCAGTCTGT

SEQ ID NO.: 70
GGGTTCCAGGTTCCACTGGCGAGGTGCAGCTTCAGGAGTCAGG

SEQ ID NO.: 71
GGGGCCAGGGGAAAGACAGATGGGCCCTTCGTTGAGGC

SEQ ID NO.: 89: Exemplary embodiment of CDRL1
K-S-S-Q-S-L-L-N/H-S/T-S/N/D-N/G-Q/N-K-K/L-N-Y-L-A SEQ ID NO.: 90: Exemplary embodiment of CDRL1
K-A-S-Q-D-I-H-N/T-Y/F-L-N SEQ ID NO.: 91: Exemplary embodiment of CDRL2
F-A-S-T-R-E-S SEQ ID NO.: 92: Exemplary embodiment of CDRL2
L-V-S-K-L-D-S SEQ ID NO.: 93: Exemplary embodiment of CDRL2
R-A-N-R-L-V-D SEQ ID NO.: 94: Exemplary embodiment of CDRL3
Q-Q-H-Y-S-T-P-L-T SEQ ID NO.: 95: Exemplary embodiment of CDRL3
W/L-Q-Y/G-D/T-A/E/H-F-P-R-T SEQ ID NO.: 96: Exemplary embodiment of CDRH1 1
G-Y-T/I-F-T-D/E-Y-E/N-M/I/V-H SEQ ID NO.: 97: Exemplary embodiment of CDRH1
G-F-T/S-I-T-S-G-Y-G-W-H SEQ ID NO.: 98: Exemplary embodiment of CDRH2
V/N/G-I/L-D-P-E/A/G-T/Y-G-X-T-A

```
SEQ ID NO.: 99: Exemplary embodiment of CDRH2
Y-I-N/S-F/Y-N/D-G

SEQ ID NO.: 100: Exemplary embodiment of CDRH3
M-G-Y-S/A-D-Y

SEQ ID NO.: 101: Exemplary embodiment of CDRH3
A-S-S-Y-D-G-F-L-A-Y

SEQ ID NO.: 102: Exemplary embodiment of CDRH3 3
A-R/W-W/F-G-L-R-Q/N

SEQ ID NO. 103 - 3A2 light chain variable region
DAVMTQIPLTLSVTTGQPASLSCKSSQSLLHSDGKTYLNWLLQRPGQSPKRLISLVSKLDSGVPD

RFTGSGSGTDFTLKISRVEAEDLGLYYCWQGTHFPRTFAGGTNLEIK

SEQ ID NO. 104 - 3F6 light chain variable region
SIVMTQTPLTLSVTIGQPASITCKSSQSLLYSDGKTYLNWLLQRPGQSPKRLISLVSKLDSGVPD

GFTGSGSGTDFTLKISRVEAEDLGVYYCWQGTHFPRTFGGGTKLEIK

SEQ ID NO. 105 - 3E8 light chain variable region
DAVMTQIPLTLSVTIGQPASISCKSSQSLLHSDGKTYLNWLLQRPGQSPKRLIYLVSKLDSGVPD

RFTGSGSGTDFTLKISRVEAEDLGVYYCWQGTHFPRTFGGGTKLEIK

SEQ ID NO. 106 - 3E10 light chain variable region
DIVMTQAAPSVPVTPGESVSISCRSSKSLLHSNGNTYLYWFLQRPGQSPQLLIYRMSNLASGVPD

RFSGSGSGTAFTLRISRVEAEDVGVYYCMQHLEYPYTFGGGTKLEIK

SEQ ID NO. 107 - 3A9 light chain variable region
DIVMTQSPSSLAMSLGQKVTMSCKSSQSLLNSNNQLNYLAWYQQKPGQSPKLLVYFASTRKSGVP

DRFIGSGSGTDFTLTITSVQAEDLADYFCQQHFNTPLTFGAGTKLELK

SEQ ID NO. 108 - 3B1 light chain variable region
DIVMTQSPSSLAISVGQKVTMSCKSSQSLLNSSNQKNYLAWYQQKPGQSPKLLVFFASTRESGVP

DRFIGSGSGTDFTLTISSVQAEDLADYFCQQHYSIPLTFGAGTKLELK

SEQ ID NO. 109 - 3G5 light chain variable region
DIVMTQSPSSLAMSVGQKVTMSCKSSQSLLNSSNQKNYLAWYQQKPGQSPKLLVFFASTRESGVP

DRFIGSGSGTDFTLTITSVQAEDLADYFCQQHYSIPLTFGSGTKLELK

SEQ ID NO. 110 - 3B2 light chain variable region
DIVMTQSPSSLAMSVGQKVTMSCKSSQSLLNSSNQKNYLAWYQQKPGQSPKLLVYFASTRESGVP

DRFIGSGSGTDFTLTISSVQAEDLADYFCQQHYSIPLTFGAGTKLELK

SEQ ID NO. 111 - 3B8 light chain variable region
DIVMTQSPSSLAMSVGQKVTMSCKSSQSLLNSSNQKNYLAWYQQKPGQSPKLLVYFASTRESGVP

DRFIGSGSGTDFTLTISSVQAEDLADYFCQQHYSTPLTFGAGTKLELK

SEQ ID NO. 112 - 3G8 light chain variable region
DIVMTQSPSSLAMSVGQKVTMSCKSSQSLLNSSNQKNYLAWYQQKPGQSPKLLVYFASTRESGVP

DRFIGSGSGTDFTLTISSVQAEDLADYFCQQHYSTPLTFGAGTKLELK

SEQ ID NO. 113 - 3F7 light chain variable region
DIVMTQSPSSLAMSVGQKVTMSCKSSQSLLNSSNQKNYLAWYQQKPGQSPKLLIYFASTRESGVP

DRFIGSGSGTDFTLTISSVQAEDLADYFCQQHYSTPLTFGAGTKLELK

SEQ ID NO. 114 - 3E9 light chain variable region
DIVMTQSPSSLAMSVGQKVTMSCKSSQSLLNSSNQKNYLAWYQQKPGQSPKLLVYFASTRESGVP

DRFIGSGSGTEFTLTITSVQAEDLADYFCQQHYSTPLTFGAGTKLELK

SEQ ID NO. 115 - 3C3 light chain variable region
DIVMTQSPSSLAMSVGQKVTMSCKSSQSLLNSSNQKNYLAWYQQKPGQSPKLLVYFGSTRESGVP

DRFIGSGSGTDFTLTISGVQAEDLADYFCQQHYSTPLTFGAGTKLELK

SEQ ID NO. 116 - 3E12 light chain variable region
DIVMTQSPSSLAMSVGQKVTMNCKSSQSLLNRSNQKNYLAWYQQKPGQSPKLLVYFASTRESGVP

DRFIGSGSGTDFTLTISSVQAEDLADYFCQQHYSIPLTFGAGTKLELK
```

-continued

SEQ ID NO. 117 - 4A2 light chain variable region
DIVMTQSPSSLAMSVGQKVTMNCKSSQSLLNNSNQKNYLAWYQQKPGQSPKLLLYFASTRESGVP

DRFIGSGSGTYFTLTISSVQAEDLADYFCQQHYSTPLTFGAGTKLDLK

SEQ ID NO. 118 - 3F10 light chain variable region
DIVMTQSPSSLTMSVGQKVTMSCKSSQSLLNTSNQLNYLAWYQQKPGQSPKLLVYFASTTESGVP

DRFIGSGSGTDFTLTISSVQAEDLADYFCQQHYSTPLTFGAGTKLELK

SEQ ID NO. 119 - 3F4 light chain variable region
DIVMTQSPSSLTVTAGEKVTMSCKSSQSLLNTSNQKNYLAWYQQKPGQSPKLLVYFASTRASGVP

DRFIGSGSGTDFTLTISSVQAEDLADYFCQQHYSTPLTFGAGTKLELK

SEQ ID NO. 120 - 3B11 light chain variable region
DIVMTQSPSSLAMSVGQKVTMSCKSSQSLLNSSNQKNYLAWYQQKPGQSPKLLVYFASTRESGVP

DRFIGSGSGTDFTLTISSVQAEDLADYFCQQHYSTPLTFGAGTKLELK

SEQ ID NO. 121 - 3G12 light chain variable region
DIVMTQSPKFMSTSVGDRVSITCKASQDVGTAVAWYQQKPGQSPELLIYWTSTRHTGVPDRFSGS

GSGTDFTLTISSVQAEDLADYFCQQHYSIPLTFGAGTKLELR

SEQ ID NO. 122 - 3D1 light chain variable region
DIKMTQSPSSMYASLGERVTITCKASQDIHTYLNWFQQKPGKSPETLIYRANRLVDGVPSRFSGS

GSGQDYSLTISSLEYEDMGIYYCLQYDEFPLTFGAGTKLELK

SEQ ID NO. 123 - 3C2 light chain variable region
DIQMTQSPSSMYASLGERVTLTCKASQDIHNYLNWFQQKPGKSPKTLIHRANRLVAGVPSRFSGS

GSGQDYSLTISSLEYEDLGIYYCLQYDAFPLTFGAGTKLELK

SEQ ID NO. 124 - 3E6 light chain variable region
DIQMTQSPSSMYASLGERVTLTCKASQDIHNYLNWFQQKPGKSPKTLIHRANRLVAGVPSRFSGS

GSGQDYSLTISSLEYEDLGTYYCLQYDAFPLTFGAGTKLELK

SEQ ID NO. 125 - 3H3 light chain variable region
DIVMSQSPSSMYASLGERVTITCKASQDIHRFLNWFQQKPGKSPKTLIFHANRLVDGVPSRFSGS

GSGLDYSLTISSLEYEDMGIYFCLQYDAFPLTFGAGTKLELK

SEQ ID NO. 126 - 3A2 heavy chain variable region
HEIQLQQSGPELVKPGASVKMSCKTSGYTFTDYNMHWVKQKPGQGLEWIGYINPYNDVTEYNEKF

KGRATLTSDKSSTAYMDLSSLTSDDSAVYFCAWFGLRQWGQGTLVTVST

SEQ ID NO. 127 - 3F6 heavy chain variable region
HEVQLQQSGPELVKPGASVKMSCKASGYIFTEYNIHWVKQKPGQGPEWIGNINPYNDVTEYNEKF

KGKATLTSDKASSTAYMDLSSLTSEDSAVYYCARWGLRNWGQGTLVTVSA

SEQ ID NO. 128 - 3E8 heavy chain variable region
HEVQLQQSVPELVKPGASVKMSCKTSGYTFTEYNMHWVKQKPGQGPEWIGNINPYNNVTEYNEKF

KGKATLTSDKSSSTAYLDLSSLTSEDSAVYYCARWGLRNWGQGTLVTVSA

SEQ ID NO. 129 - 3A9 heavy chain variable region
HQVQVQQPGAELVRPGASVTLSCKASGYIFTDYEVHWVRQRPVHGLEWIGVIDPETGDTAYNQKF

KGKATLTADKSSSTAYMELSSLTAEDSAVYYCIGYADYWGQGTTLTVSS

SEQ ID NO. 130 - 3B1 heavy chain variable region
HQVQLQQPGAELVRPGASVTLSCKASGYTFTDYEIHWVKQTPVHGLEWIGVIDPETGGTAYNQKF

KGKATLTTDKSSSTAYMELRSLTSEDSAVYYCMGYSDYWGQGTTLTVSS

SEQ ID NO. 131 - 3B2 heavy chain variable region
HEVQLQQSGAELVRPGASVTLSCKASGYSFTDTEIHWVKQTPVHGLEWIGVIDPETGATAYNQKF

KGKATLTADKSSSTAYMELSSLTSEDSAVYYCMGYSDYWGQGTTLTVSS

SEQ ID NO. 132 - 3F4 heavy chain variable region
HEVQLQQSGAELVRPGASVTLSCKASGYTFTDYEIHWVKQTPVHGLEWIGVIDPETGSTAYNQKF

KGKATLTADKASSTAYMELSSLTSEDSAVYYCMGYSDYWGQGTTLTVSS

-continued

SEQ ID NO. 133 - 3E9 heavy chain variable region
HEVQLQQSGAELVRPGASATLSCKASGYTFTDYEMHWVKQTPVHGLEWIGVIDPETGSTAYNQKF

KGKATLTADKSSSTAYMELSSLTSEDSAVYYCMGYADYWGQGTTLTVSS

SEQ ID NO. 134 - 3B8 heavy chain variable region
HEVQLQQSGAELVRPGASVTLSCKASGYTFTDYEIHWVKQTPVHGLEWIGVIDPETGDTAYNQNF

TGKATLTADKSSSTAYMELSSLTSEDSAVYYCMGYADYWGQGTTLTVSS

SEQ ID NO. 135 - 3G8 heavy chain variable region
HQVQLKQSGAELVRPGASVTLSCKASGYTFTDYEVHWVKQTPVHGLEWIGVIDPATGDTAYNQKF

KGKATLTADKSSSTAYMEVSSLTSEDSAVYYCMGYSDYWGQGTTLTVSS

SEQ ID NO. 136 - 3F7 heavy chain variable region
HQAYLQQSGAELVRPGASVTLSCKASGYTFTDYEIHWVKQTPVHGLEWIGVIDPETGDTAYNQKF

KDKATLTADKASSTAYMELSSLTSEDSAVYYCMGYSDYWGQGTTLTVSS

SEQ ID NO. 137 - 3E12 heavy chain variable region
HQVQLQQSEAELVKPGASVKLSCKASGYTFTDYEIHWVKQTPVHGLEWIGVIDPETGDTAYNQKF

KGKATLTADKSSSTAYMELSRLTSEDSAVYYCMGHSDYWGQGTTLTVSS

SEQ ID NO. 138 - 3G12 heavy chain variable region
HEVQLQQSVAELVRPGASVTVSCKASGYIFTDYEIHWVKQTPAHGLEWIGVIDPETGNTAFNQKF

KGKATLTADISSSTAYMELSSLTSEDSAVYYCMGYSDYWGQGTTLTVSS

SEQ ID NO. 139 - 3F10 heavy chain variable region
HEVQLQQSVAELVRPGAPVTLSCKASGYTFTDYEVHWVKQTPVHGLEWIGVIDPETGATAYNQKF

KGKATLTADKSSSAAYMELSRLTSEDSAVYYCMSYSDYWGQGTTLTVSS

SEQ ID NO. 140 - 3C3 heavy chain variable region
HEVQLQQSVAEVVRPGASVTLSCKASGYTFTDYEIHWVKQTPVHGLEWIGVIDPETGVTAYNQRF

RDKATLTTDKSSSTAYMELSSLTSEDSAVYFCMGYSDYWGQGTTLTVSS

SEQ ID NO. 141 - 3G5 heavy chain variable region
HQVQLQQPGAELVRPGASVTLSCKASVGYTFTDYEIHWVKQTPVHGLEWIG**VLDPGTGR-
TA**YNQKF

KDKATLSADKSSSTAYMELSSLTSEDSAVYYCMSYSDYWGPGTTLTVSS

SEQ ID NO. 142 - 3B11 heavy chain variable region
HEVQLQQSVAELVRPGASVTLSCKASGYTFTDYEMHWVKQTPVRGLEWIGVIDPATGDTAYNQKF

KGKATLTADKSSSAAFMELSSLTSEDSAVYYCMGYSDYWGQGTTLTVSS

SEQ ID NO. 143 - 3E6 heavy chain variable region
HQVQLQQSGAELVRPGASVTLSCKASGYTFSDYEMHWVKQTPVHGLEWIGGIDPETGDTVYNQKF

KGKATLTADKSSSTAYMELSSLTSEDSAVYYCISYAMDYWGQGTSVTVSS

SEQ ID NO. 144 - 4A2 heavy chain variable region
HQVKLQQSGTELVRPGASVTLSCKASGYKFTDYEMHWVKQTPVHGLEWIGGIDPETGGTAYNQKF

KGKAILTADKSSTTAYMELRSLTSEDSAVYYCISYAMDYWGQGTSVTVSS

SEQ ID NO. 145 - 3E10 heavy chain variable region
HEVQLQQSGPELVKPGASVKISCKASGDTFTDYYMNWVKQSHGKSLEWIGDINPNYGGITYNQKF

KGKATLTVDTSSSTAYMELRGLTSEDSAVYYCQAYYRNSDYWGQGTTLTVSS

SEQ ID NO. 146 - 3D1 heavy chain variable region
HEVQLQESGPDLVKPSQSLSLTCTVTGFSITSGYGWHWIRQFPGDKLEWMGYISFNGDYNYNPSL

KSRISITRDTSKNQFFLQLSSVTTEDTATYYCASSYDGLFAYWGQGTLVTVSA

SEQ ID NO. 147 - 3C2 heavy chain variable region
HDVQLQESGPDLVKPSQSLSLTCTVTGFSITSGYGWHWIRQFPGNKLEWMGYISFNGDSNYNPSL

KSRISITRDTSKNQFFLQLNSVTSEDTATYYCASSYDGLFAYWGQGPLVTVSA

A

SEQ ID NO.: 148
KSSQSLLHSDGKTYLN

-continued

SEQ ID NO.: 149
LVSKLDS

SEQ ID NO.: 150
WQGTHFPRT

SEQ ID NO.: 151
GYTFTDYNMH

SEQ ID NO.: 152
YINPYNDVTE

SEQ ID NO.: 153
AWFGLRQ

SEQ ID NO.: 154
RSSKSLLHSNGNTYLY

SEQ ID NO.: 155
RMSNLAS

SEQ ID NO.: 156
MQHLEYPYT

SEQ ID NO.: 157
GDTFTDYYMN

SEQ ID NO.: 158
DINPNYGGIT

SEQ ID NO.: 159
QAYYRNSDY

SEQ ID NO.: 160
KASQDVGTAVA

SEQ ID NO.: 161
WTSTRHT

SEQ ID NO.: 162
QQHYSIPLT

SEQ ID NO.: 163
GYIFTDYEIH

SEQ ID NO.: 164
VIDPETGNTA

SEQ ID NO.: 165
MGYSDY

SEQ ID NO.: 166
MVLQTQVFISLLLWISGAYGDIVMTQSPDSLAVSLGERATINCKSSQSLLNSNFQKNFLAWYQQK
PGQPPKLLIYFASTRESSVPDRFSGSGSGTDFTLTISSLQAEDVAVYYCQQHYSTPLTFGQGTKL
EIKRTVAAPSVFIFPPSDEQLKSGTASVVCLLNNFYPREAKVQWKVDNALQSGNSQESVTEQDSK
DSTYSLSSTLTLSKADYEKHKVYACEVTHQGLSSPVTKSFNRGEC

SEQ ID NO.: 167
MDWTWRILFLVAAATGTHAEVQLVQSGAEVKKPGASVKVSCKASGYIFTDYEIHWVRQAPGQGLE
WMGVIDPETGNTAFNQKFKGRVTITADTSTSTAYMELSSLTSEDTAVYYCMGYSDYWGQGTLVTV
SSASTKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKKVEPKSCDKTHTCPPCPAPELLGGPSVFLFPP
KPKDTLMISRTPEVTCVVVDVSHEDPEVKFNWYVDGVEVHNAKTKPREEQYNSTYRVVSVLTVLH
QDWLNGKEYKCKVSNKALPAPIEKTISKAKGQPREPQVYTLPPSRDELTKNQVSLTCLVKGFYPS
DIAVEWESNGQPENNYKTTPPVLDSDGSFFLYSKLTVDKSRWQQGNVFSCSVMHEALHNHYTQKS
LSLSPGK

SEQ ID NO: 168
DIVMTQSPDSLAVSLGERATINCKSSQSLLNSNFQKNFLAWYQQKPGQPPKLLIYFASTRESSVP
DRFSGSGSGTDFTLTISSLQAEDVAVYYCQQHYSTPLTFGQGTKLEIK

-continued

SEQ ID NO.: 169
EVQLVQSGAEVKKPGASVKVSCKASGYIFTDYEIHWVRQAPGQGLEWMGVIDPETGNTAFNQKFK

GRVTITADTSTSTAYMELSSLTSEDTAVYYCMGYSDYWGQGTLVTVSS

SEQ ID NO.: 170
MVLQTQVFISLLLWISGAYGDIVMTQSPSSLSASVGDRVTITCKASQDIHNFLNWFQQKPGKAPK

TLIFRANRLVDGVPSRFSGSGSGTDYTLTISSLQPEDFATYSCLQYDEIPLTFGQGTKLEIKRTV

AAPSVFIFPPSDEQLKSGTASVVCLLNNFYPREAKVQWKVDNALQSGNSQESVTEQDSKDSTYSL

SSTLTLSKADYEKHKVYACEVTHQGLSSPVTKSFNRGEC

SEQ ID NO.: 171
MDWTWRILFLVAAATGTHAEVQLQESGPGLVKPSQTLSLTCTVSGFSITSGYGWHWIRQHPGKGL

EWIGYINYDGHNDYNPSLKSRVTISQDTSKNQFSLKLSSVTAADTAVYYCASSYDGLFAYWGQGT

LVTVSSASTKGPSVFPLAPSSKSTSGGTAALGCLVKDYFPEPVTVSWNSGALTSGVHTFPAVLQS

SGLYSLSSVVTVPSSSLGTQTYICNVNHKPSNTKVDKKVEPKSCDKTHTCPPCPAPELLGGPSVF

LFPPKPKDTLMISRTPEVTCVVVDVSHEDPEVKFNWYVDGVEVHNAKTKPREEQYNSTYRVVSVL

TVLHQDWLNGKEYKCKVSNKALPAPIEKTISKAKGQPREPQVYTLPPSRDELTKNQVSLTCLVKG

FYPSDIAVEWESNGQPENNYKTTPPVLDSDGSFFLYSKLTVDKSRWQQGNVFSCSVMHEALHNHY

TQKSLSLSPGK

SEQ ID NO.: 172
DIVMTQSPSSLSASVGDRVTITCKASQDIHNFLNWFQQKPGKAPKTLIFRANRLVDGVPSRFSGS

GSGTDYTLTISSLQPEDFATYSCLQYDEIPLTFGQGTKLEIK

SEQ ID NO.: 173
EVQLQESGPGLVKPSQTLSLTCTVSGFSITSGYGWHWIRQHPGKGLEWIGYINYDGHNDYNPSLK

SRVTISQDTSKNQFSLKLSSVTAADTAVYYCASSYDGLFAYWGQGTLVTVS

SEQ ID NO.: 186 (3A4 variant light chain variable region consensus 1)
DXVMTQTPLSLXVXXGXXASISCRSSQSLLHSNGNTYLEVVYLQKPGQSPXLLIHTVSNRFSGVP

DRFSGSGSGTDFTLKISRVEAEDXGVYYCFQGSHVPLTFGXGTXLEXK wherein at least one of the amino acids identified by X is an amino acid substitution (conservative or non-conservative) in comparison with a corresponding amino acid in the polypeptide set forth in SEQ ID NO.:48 The amino acid substitution may be, for example conservative.

(3A4 variant light chain variable region consensus 2)
SEQ ID NO.: 187
DX$_{a1}$VMTQTPLSLX$_{a2}$VX$_{a3}$X$_{a4}$GX$_{a5}$X$_{a6}$ASISCRSSQSLLHSNGNTYL EWYLQKPGQSPX$_{a7}$LLIHTVSNRFSGVPDRFSGSGSGTDFTLKISRVEAE DX$_{a8}$GVYYCFQGSHVPLTFGX$_{a9}$GTX$_{a10}$LEX$_{a11}$K Wherein X$_{a1}$ may be a hydrophobic amino acid;
Wherein X$_{a2}$ may be A or P;
Wherein X$_{a3}$ may be neutral hydrophilic amino acid;
Wherein X$_{a4}$ may be L or P;
Wherein X$_{a5}$ may be an acidic amino acid:
Wherein X$_{a6}$ may be Q or P;
Wherein X$_{a7}$ may be a basic amino acid;
Wherein X$_{a8}$ may be a hydrophobic amino acid;
Wherein X$_{a9}$ may be A or Q;
Wherein X$_{a10}$ may be a basic amino acid; or
Wherein X$_{a11}$ may be a hydrophobic amino acid,
wherein at least one of the amino acid identified by X is an amino acid substitution (conservative or non-conservative) in comparison with a corresponding amino acid in the polypeptide set forth in SEQ ID NO.:48.

(3A4 variant light chain variable region consensus 3)
SEQ ID NO.: 188
DX$_{41}$VMTQTPLSLX$_{42}$VX$_{43}$X$_{44}$GX$_{45}$X$_{46}$ASISCRSSQSLLHSNGNTYL

EWYLQKPGQSPX$_{47}$LLIHTVSNRFSGVPDRFSGSGSGTDFTLKISRVEAE

DX$_{48}$GVYYCFQGSHVPLTFGX$_{49}$GTX$_{410}$LEX$_{411}$K

Wherein X$_{41}$ may be V or I
Wherein X$_{42}$ may be A or P
Wherein X$_{43}$ may be S or T
Wherein X$_{44}$ may be L or P
Wherein X$_{45}$ may be D or E
Wherein X$_{46}$ may be Q or P
Wherein X$_{47}$ may be K or Q
Wherein X$_{48}$ may be L or V
Wherein X$_{49}$ may be A or Q
Wherein X$_{410}$ may be R or K or
Wherein X$_{411}$ may be L or I,
wherein at least one of the amino acid identified by X is an amino acid substitution (conservative or non-conservative) in comparison with a corresponding amino acid in the polypeptide set forth in SEQ ID NO.:48.

(3A4 variant 1 light chain variable region: Lvh1)
SEQ ID NO.: 189
DIVMTQTPLSLPVTPGEPASISCRSSQSLLHSNGNTYLEWYLQKPGQSPQ

LLIYTVSNRFSGVPDRFSGSGSGTDFTLKISRVEAEDVGVYYCFQGSHVP

LTFGQGTKLEIK (3A4 variant 2 light chain variable region: Lvh2)
SEQ ID NO.: 190
DVVMTQTPLSLPVTPGEPASISCRSSQSLLHSNGNTYLEWYLQKPGQSPK

LLIYTVSNRFSGVPDRFSGSGSGTDFTLKISRVEAEDVGVYYCFQGSHVP

LTFGQGTKLEIK (3A4 variant heavy chain variable region consensus 1)
SEQ ID NO.: 191
QXQLVQSGXEXXKPGASVKXSCKASGYTFTDDYMSWVXQXXGXXLEWXGD

INPYNGDTNYNQKFKGXXXXTXDXSXSTAYMXLXSLXSEDXAVYYCARDP

GAMDYWGQGTXVTVSS wherein at least one of the amino acid identified by X is an amino acid substitution (conservative or non-conservative) in comparison with a corresponding amino acid in the polypeptide set forth in SEQ ID NO.:46. The amino acid substitution may be, for example conservative.

(3A4 variant heavy chain variable region consensus 2)
SEQ ID NO.: 192
QX$_{b1}$QLVQSGX$_{b2}$EX$_{b3}$X$_{b4}$KPGASVKX$_{b5}$SCKASGYTFTDDYMSWV X$_{b6}$QX$_{b7}$X$_{b8}$GX$_{b9}$X$_{b10}$LEWX$_{b11}$GDINPYNGDTNYNQKFKGX$_{b12}$ X$_{b13}$X$_{b14}$X$_{b15}$TX$_{b16}$DX$_{b17}$SX$_{b18}$STAYMX$_{b19}$LX$_{b20}$SLX$_{b21}$SED X$_{b22}$AVYYCARDPGAMDYWGQGTX$_{b23}$VTVSS Wherein X$_{b1}$ may be a hydrophobic amino acid;
Wherein X$_{b2}$ may be P or A;
Wherein X$_{b3}$ may be a hydrophobic amino acid;
Wherein X$_{b4}$ may be V or K,
Wherein X$_{b5}$ may be a hydrophobic amino acid;
Wherein X$_{b6}$ may be a basic amino acid;
Wherein X$_{b7}$ may be S or A;
Wherein X$_{b8}$ may be H or P;
Wherein X$_{b9}$ may be a basic amino acid;
Wherein X$_{b10}$ may be S or G;
Wherein X$_{b11}$ may be a hydrophobic amino acid;
Wherein X$_{b12}$ may be a basic amino acid;
Wherein X$_{b13}$ may be a hydrophobic amino acid;
Wherein X$_{b14}$ may be I or T;
Wherein X$_{b15}$ may be a hydrophobic amino acid;
Wherein X$_{b16}$ may be a hydrophobic amino acid;
Wherein X$_{b17}$ may be K or T;
Wherein X$_{b18}$ may be a neutral hydrophilic amino acid;
Wherein X$_{b19}$ may be Q or E;
Wherein X$_{b20}$ may be N or S;
Wherein X$_{b21}$ may be T or R;
Wherein X$_{b22}$ may be a neutral hydrophilic amino acid; or
Wherein X$_{b23}$ may be S or L,
wherein at least one of the amino acid identified by X is an amino acid substitution (conservative or non-conservative) in comparison with a corresponding amino acid in the polypeptide set forth in SEQ ID NO.:46.

(3A4 variant heavy chain variable region consensus 3)
SEQ ID NO.: 193
QX$_{B1}$QLVQSGX$_{B2}$EX$_{B3}$X$_{B4}$KPGASVKX$_{B5}$SCKASGYTFTDDYMSWV X$_{B6}$QX$_{B7}$X$_{B8}$GX$_{B9}$X$_{B10}$LEWX$_{B11}$GDINPYNGDTNYNQKFKGX$_{B12}$ X$_{B13}$X$_{B14}$X$_{B15}$TX$_{B16}$DX$_{B17}$SX$_{B18}$STAYMX$_{B19}$LX$_{B20}$S

LX$_{B21}$SEDX$_{B22}$AVYYCARDPGAMDYWGQGTX$_{B23}$VTVSS

Wherein X$_{B1}$ may be I or V;
Wherein X$_{B2}$ may be P or A;
Wherein X$_{B3}$ may be M or V;
Wherein X$_{B4}$ may be V or K;
Wherein X$_{B5}$ may be M or V;
Wherein X$_{B6}$ may be K or R;
Wherein X$_{B7}$ may be S or A;
Wherein X$_{B8}$ may be H or P;
Wherein X$_{B9}$ may be K or Q;
Wherein X$_{B10}$ may be S or G;
Wherein X$_{B11}$ may be I or M;
Wherein X$_{B12}$ may be K or R;
Wherein X$_{B13}$ may be A or V;
Wherein X$_{B14}$ may be i or T;
Wherein X$_{B15}$ may be L or I;
Wherein X$_{B16}$ may be V or A;
Wherein X$_{B17}$ may be K or T;
Wherein X$_{B18}$ may be S or T;
Wherein X$_{B19}$ may be Q or E;
Wherein X$_{B20}$ may be N or S;
Wherein X$_{B21}$ may be T or R;
Wherein X$_{B22}$ may be S or T; or
Wherein X$_{B23}$ may be S or L,
wherein at least one of the amino acid identified by X is an amino acid substitution (conservative or non-conservative) in comparison with a corresponding amino acid in the polypeptide set forth in SEQ ID NO.:46.

(3A4 variant 1 heavy chain variable region: Hvh1)
SEQ ID NO.: 194
QVQLVQSGAEVKKPGASVKVSCKASGYTFTDDYMSWVRQAPGQGLEWMGD

INPYNGDTNYNQKFKGRVTITADTSTSTAYMELSSLRSEDTAVYYCARDP

GAMDYWGQGTLVTVSS (3A4 variant 2 heavy chain variable region: Hvh2)
SEQ ID NO.: 195
QIQLVQSGAEVKKPGASVKVSCKASGYTFTDDYMSWVRQAPGQGLEWMGD

INPYNGDTNYNQKFKGRVTITADKSTSTAYMELSSLRSEDTAVYYCARDP

GAMDYWGQGTLVTVSS (3A4 variant 3 heavy chain variable region: Hvh3)
SEQ ID NO.: 196
QIQLVQSGAEVKKPGASVKVSCKASGYTFTDDYMSWVRQAPGQGLEWIGD

INPYNGDTNYNQKFKGRATLTVDKSTSTAYMELSSLRSEDTAVYYCARDP

GAMDYWGQGTLVTVSS (3A4 variant 4 heavy chain variable region: Hvh4)
SEQ ID NO.: 197
QIQLVQSGAEVKKPGASVKVSCKASGYTFTDDYMSWVKQAPGQGLEWIGD

INPYNGDTNYNQKFKGKATLTVDKSTSTAYMELSSLRSEDTAVYYCARDP

GAMDYWGQGTLVTVSS

3A4 murine light (kappa) chain

SEQ ID NO: 198

DVVMTQTPLSLAVSLGDQASISCRSSQSLLHSNGNTYLEWYLQKPGQSPK
LLIHTVSNRFSGVPDRFSGSGSGTDFTLKISRVEAEDLGVYYCFQGSHVP
LTFGAGTRLELKRTVAAPSVFIFPPSDEQLKSGTASVVCLLNNFYPREAK
VQWKVDNALQSGNSQESVTEQDSKDSTYSLSSTLTLSKADYEKHKVYACE
VTHQGLSSPVTKSFNRGEC

3A4 humanized light (kappa) chain variant 1; Lh1

SEQ ID NO: 199

DIVMTQTPLSLPVTPGEPASISCRSSQSLLHSNGNTYLEVVYLQKPGQSP
QLLIYTVSNRFSGVPDRFSGSGSGTDFTLKISRVEAEDVGVYYCFQGSHV
PLTFGQGTKLEIKRTVAAPSVFIFPPSDEQLKSGTASVVCLLNNFYPREA
KVQWKVDNALQSGNSQESVTEQDSKDSTYSLSSTLTLSKADYEKHKVYAC
EVTHQGLSSPVTKSFNRGEC

3A4 humanized light (kappa) chain variant 2; Lh2

SEQ ID NO: 200

DVVMTQTPLSLPVTPGEPASISCRSSQSLLHSNGNTYLEWYLQKPGQSPK
LLIYTVSNRFSGVPDRFSGSGSGTDFTLKISRVEAEDVGVYYCFQGSHVP
LTFGQGTKLEIKRTVAAPSVFIFPPSDEQLKSGTASVVCLLNNFYPREAK
VQWKVDNALQSGNSQESVTEQDSKDSTYSLSSTLTLSKADYEKHKVYACE
VTHQGLSSPVTKSFNRGEC

3A4 murine heavy (Igg1) chain

SEQ ID NO: 201

QIQLVQSGPEMVKPGASVKMSCKASGYTFTDDYMSWVKQSHGKSLEWIGD
INPYNGDTNYNQKFKGKAILTVDKSSSTAYMQLNSLTSEDSAVYYCARDP
GAMDYWGQGTSVTVSSASTKGPSVFPLAPSSKSTSGGTAALGCLVKDYFP
EPVTVSWNSGALTSGVHTFPAVLQSSGLYSLSSVVTVPSSSLGTQTYICN
VNHKPSNTKVDKKVEPKSCDKTHTCPPCPAPELLGGPSVFLFPPKPKDTL
MISRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTL
PPSRDELTKNQVSLTCLVKGFYPSDIAVEWESNGQPENNYKTTPPVLDSD
GSFFLYSKLTVDKSRWQQGNVFSCSVMHEALHNHYTQKSLSLSPGK

3A4 humanized heavy (Igg1) chain variant 1; Hh1

SEQ ID NO: 202

QVQLVQSGAEVKKPGASVKVSCKASGYTFTDDYMSWVRQAPGQGLEWMGD
INPYNGDTNYNQKFKGRVTITADTSTSTAYMELSSLRSEDTAVYYCARDP
GAMDYWGQGTLVTVSSASTKGPSVFPLAPSSKSTSGGTAALGCLVKDYFP
EPVTVSWNSGALTSGVHTFPAVLQSSGLYSLSSVVTVPSSSLGTQTYICN
VNHKPSNTKVDKKVEPKSCDKTHTCPPCPAPELLGGPSVFLFPPKPKDTL
MISRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTL
PPSRDELTKNQVSLTCLVKGFYPSDIAVEWESNGQPENNYKTTPPVLDSD
GSFFLYSKLTVDKSRWQQGNVFSCSVMHEALHNHYTQKSLSLSPGK

3A4 humanized heavy (Igg1) chain variant 2; Hh2

SEQ ID NO: 203

QIQLVQSGAEVKKPGASVKVSCKASGYTFTDDYMSWVRQAPGQGLEWMGD
INPYNGDTNYNQKFKGRVTITADKSTSTAYMELSSLRSEDTAVYYCARDP
GAMDYWGQGTLVTVSSASTKGPSVFPLAPSSKSTSGGTAALGCLVKDYFP
EPVTVSWNSGALTSGVHTFPAVLQSSGLYSLSSVVTVPSSSLGTQTYICN
VNHKPSNTKVDKKVEPKSCDKTHTCPPCPAPELLGGPSVFLFPPKPKDTL
MISRTPEVTCVVVDVSHEDPEVKFNWYVDGVEVHNAKTKPREEQYNSTYR
WSVLTVLHQDWLNGKEYKCKVSNKALPAPIEKTISKAKGQPREPQVYTLP
PSRDELTKNQVSLTCLVKGFYPSDIAVEWESNGQPENNYKTTPPVLDSDG
SFFLYSKLTVDKSRWQQGNVFSCSVMHEALHNHYTQKSLSLSPGK

3A4 humanized heavy (Igg1) chain variant 3; Hh3

SEQ ID NO: 204

QIQLVQSGAEVKKPGASVKVSCKASGYTFTDDYMSWVRQAPGQGLEWIGD
INPYNGDTNYNQKFKGRATLTVDKSTSTAYMELSSLRSEDTAVYYCARDP
GAMDYWGQGTLVTVSSASTKGPSVFPLAPSSKSTSGGTAALGCLVKDYFP
EPVTVSWNSGALTSGVHTFPAVLQSSGLYSLSSVVTVPSSSLGTQTYICN
VNHKPSNTKVDKKVEPKSCDKTHTCPPCPAPELLGGPSVFLFPPKPKDTL
MISRTPEVTCVVVDVSHEDPEVKFNVYVDGVEVHNAKTKPREEQYNSTY
RVVSVLTVLHQDWLNGKEYKCKVSNKALPAPIEKTISKAKGQPREPQVYT
LPPSRDELTKNQVSLTCLVKGFYPSDIAVEWESNGQPENNYKTTPPVLDS
DGSFFLYSKLTVDKSRWQQGNVFSCSVMHEALHNHYTQKSLSLSPGK

3A4 humanized heavy (Igg1) chain variant 4: Hh4

SEQ ID NO: 205

QIQLVQSGAEVKKPGASVKVSCKASGYTFTDDYMSWVKQAPGQGLEWIGD
INPYNGDTNYNQKFKGKATLTVDKSTSTAYMELSSLRSEDTAVYYCARDP
GAMDYWGQGTLVTVSSASTKGPSVFPLAPSSKSTSGGTAALGCLVKDYFP
EPVTVSWNSGALTSGVHTFPAVLQSSGLYSLSSVVTVPSSSLGTQTYICN
VNHKPSNTKVDKKVEPKSCDKTHTCPPCPAPELLGGPSVFLFPPKPKDTL
MISRTPEVTCVVVDVSHEDPEVKFNWYVDGVEVHNAKTKPREEQYNSTYR
WSVLTVLHQDWLNGKEYKCKVSNKALPAPIEKTISKAKGQPREPQVYTLP
PSRDELTKNQVSLTCLVKGFYPSDIAVEWESNGQPENNYKTTPPVLDSDG
SFFLYSKLTVDKSRWQQGNVFSCSVMHEALHNHYTQKSLSLSPGK

SEQ ID NO: 206

ATACCCAAGCTTGCCACCATGGAGACAGACACAC

SEQ ID NO: 207

ATACCCAAGCTTCATTTCCCGGGAGACAGGGAG

SEQ ID NO: 208

ATACCCAAGCTTGGGCCACCATGAACTTTCTGCTGTCTTGG

SEQ ID NO: 209

ATACCCAAGCTTCTAACACTCTCCCCTGTTGAAG pK-CR5

SEQ ID NO: 210

CTAAATTGTAAGCGTTAATATTTTGTTAAAATTCGCGTTAAATTTTGTT
AAATCAGCTCATTTTTTAACCAATAGGCCGAAATCGGCAAAATCCCTTAT
AAATCAAAAGAATAGACCGAGATAGGGTTGAGTGTTGTTCCAGTTTGGAA
CAAGAGTCCACTATTAAAGAACGTGGACTCCAACGTCAAAGGGCGAAAAA
CCGTCTATCAGGGCGATGGCCCACTACGTGAACCATCACCCTAATCAAGT
TTTTTGGGGTCGAGGTGCCGTAAAGCACTAAATCGGAACCCTAAAGGGAG

-continued

CCCCCGATTTAGAGCTTGACGGGAAAGCCGGCGAACGTGGCGAGAAAGG
AAGGGAAGAAAGCGAAAGGAGCGGGCGCTAGGGCGCTGGCAAGTGTAGCG
GTCACGCTGCGCGTAACCACCACACCCGCCGCGCTTAATGCGCCGCTACA
GGGCGCGTCCCATTCGCCATTCAGGCTGCGCAACTGTTGGGAAGGGCGAT
CGGTGCGGGCCTCTTCGCTATTACGCCAGCTGGCGAAAGGGGATGTGCT
GCAAGGCGATTAAGTTGGGTAACGCCAGGGTTTTCCCAGTCACGACGTTG
TAAAACGACGGCCAGTGAGCGCGCGTAATACGACTCACTATAGGGCGAAT
TGGAGCTCCACCGCGGTGGCGGCCGCTCTAGAACTAGTGGATCCACATCG
GCGCGCCAAATGATTTGCCCTCCCATATGTCCTTCCGAGTGAGAGACACA
AAAAATTCCAACACACTATTGCAATGAAAATAAATTTCCTTTATTAGCCA
GAGGTCGAGATTTAAATAAGCTTGCTAGCAGATCTTTGGACCTGGGAGTG
GACACCTGTGGAGAGAAAGGCAAAGTGGATGTCATTGTCACTCAAGTGTA
TGGCCAGATCGGGCCAGGTGAATATCAAATCCTCCTCGTTTTTGGAAACT
GACAATCTTAGCGCAGAAGTAATGCCCGCTTTTGAGAGGGAGTACTACC
CCAACAGCTGGATCTCAAGCCTGCCACACCTCACCTCGACCATCCGCCGT
CTCAAGACCGCCTACTTTAATTACATCATCAGCAGCACCTCCGCCAGAAA
CAACCCCGACCGCCACCCGCTGCCGCCCGCCACGGTGCTCAGCCTACCTT
GCGACTGTGACTGGTTAGACGCCTTTCTCGAGAGGTTTTCCGATCCGGTC
GATGCGGACTCGCTCAGGTCCCTCGGTGGCGGAGTACCGTTCGGAGGCCG
ACGGGTTTCCGATCCAAGAGTACTGGAAAGACCGCGAAGAGTTTGTCCTC
AACCGCGAGCCCAACAGCTGGCCCTCGCAGACAGCGATGCGGAAGAGAGT
GACCGCGGAGGCTGGATCGGTCCCGGTGTCTTCTATGGAGGTTCAAAACA
GCGTGGATGGCGTCTCCAGGCGATCTGACGGTTCACTAAACGAGCTCTGC
TTATATAGGCCTCCCACCGTACACGCCTACCTCGACCCGGGTACCAATCT
TATAATACAAACAGACCAGATTGTCTGTTTGTTATAATACAAACAGACCA
GATTGTCTGTTTGTTATAATACAAACAGACCAGATTGTCTGTTTGTTATA
ATACAAACAGACCAGATTGTCTGTTTGTTATAATACAAACAGACCAGATT
GTCTGTTTGTTATAATACAAACAGACCAGATTGTCTGTTTGTTAAGGTTG
TCGAGTGAAGACGAAAGGGTTCATTAAGGCGCGCCGTCGACCTCGAGGGG
GGGCCCGGTACCCAGCTTTTGTTCCCTTTAGTGAGGGTTAATTGCGCGCT
TGGCGTAATCATGGTCATAGCTGTTTCCTGTGTGAAATTGTTATCCGCTC
ACAATTCCACACAACATACGAGCCGGAAGCATAAAGTGTAAAGCCTGGGG
TGCCTAATGAGTGAGCTAACTCACATTAATTGCGTTGCGCTCACTGCCCG
CTTTCCAGTCGGGAAACCTGTCGTGCCAGCTGCATTAATGAATCGGCCAA
CGCGCGGGGAGAGGCGGTTTGCGTATTGGGCGCTCTTCCGCTTCCTCGCT
CACTGACTCGCTGCGCTCGGTCGTTCGGCTGCGGCGAGCGGTATCAGCTC
ACTCAAAGGCGGTAATACGGTTATCCACAGAATCAGGGGATAACGCAGGA
AAGAACATGTGAGCAAAAGGCCAGCAAAAGGCCAGGAACCGTAAAAAGGC
CGCGTTGCTGGCGTTTTTCCATAGGCTCCGCCCCCCTGACGAGCATCACA
AAAATCGACGCTCAAGTCAGAGGTGGCGAAACCCGACAGGACTATAAAGA
TACCAGGCGTTTCCCCCTGGAAGCTCCCTCGTGCGCTCTCCTGTTCCGAC

-continued

CCTGCCGCTTACCGGATACCTGTCCGCCTTTCTCCCTTCGGGAAGCGTGG
CGCTTTCTCATAGCTCACGCTGTAGGTATCTCAGTTCGGTGTAGGTCGTT
CGCTCCAAGCTGGGCTGTGTGCACGAACCCCCCGTTCAGCCCGACCGCTG
CGCCTTATCCGGTAACTATCGTCTTGAGTCCAACCCGGTAAGACACGACT
TATCGCCACTGGCAGCAGCCACTGGTAACAGGATTAGCAGAGCGAGGTAT
GTAGGCGGTGCTACAGAGTTCTTGAAGTGGTGGCCTAACTACGGCTACAC
TAGAAGGACAGTATTTGGTATCTGCGCTCTGCTGAAGCCAGTTACCTTCG
GAAAAAGAGTTGGTAGCTCTTGATCCGGCAAACAAACCACCGCTGGTAGC
GGTGGTTTTTTTGTTTGCAAGCAGCAGATTACGCGCAGAAAAAAAGGATC
TCAAGAAGATCCTTTGATCTTTTCTACGGGGTCTGACGCTCAGTGGAACG
AAAACTCACGTTAAGGGATTTTGGTCATGAGATTATCAAAAAGGATCTTC
ACCTAGATCCTTTTAAATTAAAAATGAAGTTTTAAATCAATCTAAAGTAT
ATATGAGTAAACTTGGTCTGACAGTTACCAATGCTTAATCAGTGAGGCAC
CTATCTCAGCGATCTGTCTATTTCGTTCATCCATAGTTGCCTGACTCCCC
GTCGTGTAGATAACTACGATACGGGAGGGCTTACCATCTGGCCCCAGTGC
TGCAATGATACCGCGAGACCCACGCTCACCGGCTCCAGATTTATCAGCAA
TAAACCAGCCAGCCGGAAGGGCCGAGCGCAGAAGTGGTCCTGCAACTTTA
TCCGCCTCCATCCAGTCTATTAATTGTTGCCGGGAAGCTAGAGTAAGTAG
TTCGCCAGTTAATAGTTTGCGCAACGTTGTTGCCATTGCTACAGGCATCG
TGGTGTCACGCTCGTCGTTTGGTATGGCTTCATTCAGCTCCGGTTCCCAA
CGATCAAGGCGAGTTACATGATCCCCCATGTTGTGCAAAAAAGCGGTTAG
CTCCTTCGGTCCTCCGATCGTTGTCAGAAGTAAGTTGGCCGCAGTGTTAT
CACTCATGGTTATGGCAGCACTGCATAATTCTCTTACTGTCATGCCATCC
GTAAGATGCTTTTCTGTGACTGGTGAGTACTCAACCAAGTCATTCTGAGA
ATAGTGTATGCGGCGACCGAGTTGCTCTTGCCCGGCGTCAATACGGGATA
ATACCGCGCCACATAGCAGAACTTTAAAAGTGCTCATCATTGGAAAACGT
TCTTCGGGGCGAAAACTCTCAAGGATCTTACCGCTGTTGAGATCCAGTTC
GATGTAACCCACTCGTGCACCCAACTGATCTTCAGCATCTTTTACTTTCA
CCAGCGTTTCTGGGTGAGCAAAAACAGGAAGGCAAAATGCCGCAAAAAAG
GGAATAAGGGCGACACGGAAATGTTGAATACTCATACTCTTCCTTTTTCA
ATATTATTGAAGCATTTATCAGGGTTATTGTCTCATGAGCGGATACATAT
TTGAATGTATTTAGAAAAATAAACAAATAGGGGTTCCGCGCACATTTCCC
CGAAAAGTGCCAC pMPG-CR5

SEQ ID NO: 211

GTCGACGATACCGTGCACTTAATTAAGCGCGCTCGACCAAATGATTTGCC
CTCCCATATGTCCTTCCGAGTGAGAGACACAAAAAATTCCAACACACTAT
TGCAATGAAAATAAATTTCCTTTATTAGCCAGAGGTCGAGGTCGGGGGAT
CCGTTTAAACTTGGACCTGGGAGTGGACACCTGTGGAGAGAAAGGCAAAG
TGGATGTCATTGTCACTCAAGTGTATGGCCAGATCGGGCCAGGTGAATAT
CAAATCCTCCTCGTTTTTGGAAACTGACAATCTTAGCGCAGAAGTAATGC

```
CCGCTTTTGAGAGGGAGTACTCACCCCAACAGCTGGATCTCAAGCCTGCC
ACACCTCACCTCGACCATCCGCCGTCTCAAGACCGCCTACTTTAATTACA
TCATCAGCAGCACCTCCGCCAGAAACAACCCCGACCGCCACCCGCTGCCG
CCCGCCACGGTGCTCAGCCTACCTTGCGACTGTGACTGGTTAGACGCCTT
TCTCGAGAGGTTTTCCGATCCGGTCGATGCGGACTCGCTCAGGTCCCTCG
GTGGCGGAGTACCGTTCGGAGGCCGACGGGTTTCCGATCCAAGAGTACTG
GAAAGACCGCGAAGAGTTTGTCCTCAACCGCGAGCCCAACAGCTGGCCCT
CGCAGACAGCGATGCGGAAGAGAGTGACCGCGGAGGCTGGATCGGTCCCG
GTGTCTTCTATGGAGGTCAAAACAGCGTGGATGGCGTCTCCAGGCGATCT
GACGGTTCACTAAACGAGCTCTGCTTATATAGGCCTCCCACCGTACACGC
CTACCTCGACCCGGGTACCAATCTTATAATACAAACAGACCAGATTGTCT
GTTTGTTATAATACAAACAGACCAGATTGTCTGTTTGTTATAATACAAAC
AGACCAGATTGTCTGTTTGTTATAATACAAACAGACCAGATTGTCTGTTT
GTTATAATACAAACAGACCAGATTGTCTGTTTGTTATAATACAAACAGAC
CAGATTGTCTGTTTGTTAAGGTTGTCGAGTGAAGACGAAAGGGTTAATTA
AGGCGCGCCGTCGACTAGCTTGGCACGCCAGAAATCCGCGCGGTGGTTTT
TGGGGGTCGGGGGTGTTTGGCAGCCACAGACGCCCGGTGTTCGTGTCGCG
CCAGTACATGCGGTCCATGCCCAGGCCATCCAAAAACCATGGGTCTGTCT
GCTCAGTCCAGTCGTGGACCAGACCCCACGCAACGCCCAAAATAATAACC
CCCACGAACCATAAACCATTCCCCATGGGGGACCCCGTCCCTAACCCACG
GGGCCAGTGGCTATGGCAGGGCCTGCCGCCCCGACGTTGGCTGCGAGCCC
TGGGCCTTCACCCGAACTTGGGGGGTGGGTGGGAAAAGGAAGAAACGC
GGGCGTATTGGCCCCAATGGGGTCTCGGTGGGGTATCGACAGAGTGCCAG
CCCTGGGACCGAACCCCGCGTTTATGAACAAACGACCCAACACCCGTGCG
TTTTATTCTGTCTTTTTATTGCCGTCATAGCGCGGGTTCCTTCCGGTATT
GTCTCCTTCCGTGTTTCAGTTAGCCTCCCCCATCTCCCCTATTCCTTTGC
CCTCGGACGAGTGCTGGGGCGTCGGTTTCCACTATCGGCGAGTACTTCTA
CACAGCCATCGGTCCAGACGGCCGCGCTTCTGCGGGCGATTTGTGTACGC
CCGACAGTCCCGGCTCCGGATCGGACGATTGCGTCGCATCGACCCTGCGC
CCAAGCTGCATCATCGAAATTGCCGTCAACCAAGCTCTGATAGAGTTGGT
CAAGACCAATGCGGAGCATATACGCCCGGAGCCGCGGCGATCCTGCAAGC
TCCGGATGCCTCCGCTCGAAGTAGCGCGTCTGCTGCTCCATACAAGCCAA
CCACGGCCTCCAGAAGAAGATGTTGGCGACCTCGTATTGGGAATCCCCGA
ACATCGCCTCGCTCCAGTCAATGACCGCTGTTATGCGGCCATTGTCCGTC
AGGACATTGTTGGAGCCGAAATCCGCGTGCACGAGGTGCCGGACTTCGGG
GCAGTCCTCGGCCCAAAGCATCAGCTCATCGAGAGCCTGCGCGACGGACG
CACTGACGGTGTCGTCCATCACAGTTTGCCAGTGATACACATGGGGATCA
GCAATCGCGCATATGAAATCACGCCATGTAGTGTATTGACCGATTCCTTG
CGGTCCGAATGGGCCGAACCCGCTCGTCTGGCTAAGATCGGCGCAGCGA
TCGCATCCATGGCCTCCGCGACCGGCTGCAGAACAGCGGGCAGTTCGGTT
TCAGGCAGGTCTTGCAACGTGACACCCTGTGCACGGCGGGAGATGCAATA
```

```
GGTCAGGCTCTCGCTGAATTCCCCAATGTCAAGCACTTCCGGAATCGGGA
GCGCGGCCGATGCAAAGTGCCGATAAACATAACGATCTTTGTAGAAACCA
TCGGCGCAGCTATTTACCCGCAGGACATATCCACGCCCTCCTACATCGAA
GCTGAAAGCACGAGATTCTTCGCCCTCCGAGAGCTGCATCAGGTCGGAGA
CGCTGTCGAACTTTTCGATCAGAAACTTCTCGACAGACGTCGCGGTGAGT
TCAGGCTTTTTCATATCTCATTGCCCGGGATCTGCGGCACGCTGTTGACG
CTGTTAAGCGGGTCGCTGCAGGGTCGCTCGGTGTTCGAGGCCACACGCGT
CACCTTAATATGCGAAGTGGACCTGGGACCGCGCCGCCCCGACTGCATCT
GCGTGTTCGAATTCGCCAATGACAAGACGCTGGGCGGGGTTTGTGTCATC
ATAGAACTAAAGACATGCAAATATATTTCTTCCGGGGACACCGCCAGCAA
ACGCGAGCAACGGGCCACGGGGATGAAGCAGGGCATGGCGGCCGACGCGC
TGGGCTACGTCTTGCTGGCGTTCGCGACGCGAGGCTGGATGGCCTTCCCC
ATTATGATTCTTCTCGCTTCCGGCGGCATCGGGATGCCCGCGTTGCAGGC
CATGCTGTCCAGGCAGGTAGATGACGACCATCAGGGACAGCTTCAAGGAT
CGCTCGCGGCTCTTACCAGCCTAACTTCGATCACTGGACCGCTGATCGTC
ACGGCGATTTATGCCGCCTCGGCGAGCACATGGAACGGGTTGGCATGGAT
TGTAGGCGCCGCCCTATACCTTGTCTGCCTCCCCGCGTTGCGTCGCGGTG
CATGGAGCCGGGCCACCTCGACCTGAATGGAAGCCGGCGGCACCTCGCTA
ACGGATTCACCACTCCAAGAATTGGAGCCAATCAATTCTTGCGGAGAACT
GTGAATGCGCAAACCAACCCTTGGCAGAACATATCCATCGCGTCCGCCAT
CTCCAGCAGCCGCACGCGGCGCAGCAAAAGGCCAGGAACCGTAAAAAGGC
CGCGTTGCTGGCGTTTTTCCATAGGCTCCGCCCCCCTGACGAGCATCACA
AAAATCGACGCTCAAGTCAGAGGTGGCGAAACCCGACAGGACTATAAAGA
TACCAGGCGTTTCCCCCTGGAAGCTCCCTCGTGCGCTCTCCTGTTCCGAC
CCTGCCGCTTACCGGATACCTGTCCGCCTTTCTCCCTTCGGGAAGCGTGG
CGCTTTCTCATAGCTCACGCTGTAGGTATCTCAGTTCGGTGTAGGTCGTT
CGCTCCAAGCTGGGCTGTGTGCACGAACCCCCCGTTCAGCCCGACCGCTG
CGCCTTATCCGGTAACTATCGTCTTGAGTCCAACCCGGTAAGACACGACT
TATCGCCACTGGCAGCAGCCACTGGTAACAGGATTAGCAGAGCGAGGTAT
GTAGGCGGTGCTACAGAGTTCTTGAAGTGGTGGCCTAACTACGGCTACAC
TAGAAGGACAGTATTTGGTATCTGCGCTCTGCTGAAGCCAGTTACCTTCG
GAAAAAGAGTTGGTAGCTCTTGATCCGGCAAACAAACCACCGCTGGTAGC
GGTGGTTTTTTGTTTGCAAGCAGCAGATTACGCGCAGAAAAAAAGGATC
TCAAGAAGATCCTTTGATCTTTTCTACGGGGTCTGACGCTCAGTGGAACG
AAAACTCACGTTAAGGGATTTTGGTCATGAGATTATCAAAAAGGATCTTC
ACCTAGATCCTTTTAAATTAAAAATGAAGTTTTAAATCAATCTAAAGTAT
ATATGAGTAAACTTGGTCTGACAGTTACCAATGCTTAATCAGTGAGGCAC
CTATCTCAGCGATCTGTCTATTTCGTTCATCCATAGTTGCCTGACTCCCC
GTCGTGTAGATAACTACGATACGGGAGGGCTTACCATCTGGCCCCAGTGC
TGCAATGATACCGCGAGACCCACGCTCACCGGCTCCAGATTTATCAGCAA
```

-continued
TAAACCAGCCAGCCGGAAGGGCCGAGCGCAGAAGTGGTCCTGCAACTTTA

TCCGCCTCCATCCAGTCTATTAATTGTTGCCGGGAAGCTAGAGTAAGTAG

TTCGCCAGTTAATAGTTTGCGCAACGTTGTTGCCATTGCTGCAGGCATCG

TGGTGTCACGCTCGTCGTTTGGTATGGCTTCATTCAGCTCCGGTTCCCAA

CGATCAAGGCGAGTTACATGATCCCCCATGTTGTGCAAAAAAGCGGTTAG

CTCCTTCGGTCCTCCGATCGTTGTGAGAAGTAAGTTGGCCGCAGTGTTAT

CACTCATGGTTATGGCAGCACTGCATAATTCTCTTACTGTCATGCCATCC

GTAAGATGCTTTTCTGTGACTGGTGAGTACTCAACCAAGTCATTCTGAGA

ATAGTGTATGCGGCGACCGAGTTGCTCTTGCCCGGCGTCAACACGGGATA

ATACCGCGCCACATAGCAGAACTTTAAAAGTGCTCATCATTGGAAAACGT

TCTTCGGGGCGAAAACTCTCAAGGATCTTACCGCTGTTGAGATCCAGTTC

GATGTAACCCACTCGTGCACCCAACTGATCTTCAGCATCTTTTACTTTCA

CCAGCGTTTCTGGGTGAGCAAAAACAGGAAGGCAAAATGCCGCAAAAAG

GGAATAAGGGCGACACGGAAATGTTGAATACTCATACTCTTCCTTTTTCA

ATATTATTGAAGCATTTATCAGGGTTATTGTCTCATGAGCGGATACATAT

TTGAATGTATTTAGAAAAATAAACAAATAGGGGTTCCGCGCACATTTCCC

CGAAAAGTGCCACCTGACGTCTAAGAAACCATTATTATCATGACATTAAC

CTATAAAAATAGGCGTATCACGAGGCCCTTTCGTCTTCAAGAATTCTCAT

GTTTGACAGCTTATCTCTAGCAGATCCGGAATTCCCCTCCCCAATTTAAA

TGAGGACCTAACCTGTGGAAATCTACTGATGTGGGAGGCTGTAACTGTAC

AAACAGAGGTTATTGGAATAACTAGCATGCTTAACCTTCATGCAGGGTCA

CAAAAAGTGCATGACGATGGTGGAGGAAAACCTATTCAAGGCAGTAATTT

CCACTTCTTTGCTGTTGGTGGAGACCCCTTGGAAATGCAGGGAGTGCTAA

TGAATTACAGGACAAAGTACCCAGATGGTACTATAACCCCTAAAAACCCA

ACAGCCCAGTCCCAGGTAATGAATACTGACCATAAGGCCTATTTGGACAA

AAACAATGCTTATCCAGTTGAGTGCTGGGTTCCTGATCCTAGTAGAAATG

AAAATACTAGGTATTTTGGGACTTTCACAGGAGGGGAAAATGTTCCCCCA

GTACTTCATGTGACCAACACAGCTACCACAGTGTTGCTAGATGAACAGGG

TGTGGGGCCTCTTTGTAAAGCTGATAGCCTGTATGTTTCAGCTGCTGATA

TTTGTGGCCTGTTTACTAACAGCTCTGGAACACAACAGTGGAGAGGCCTT

GCAAGATATTTTAAGATCCGCCTGAGAAAAGATCTGTAAAGAATCCTTA

CCTAATTTCCTTTTTGCTAAGTGACCTTATAAACAGGAGAACCCAGAGAG

TGGATGGGCAGCCTATGTATGTATGGAATCCCAGGTAGAAGAGGTTAGG

GTGTTTGATGGCACAGAAAGACTTCCAGGGGACCCAGATATGATAAGATA

TATTGACAAACAGGGACAATTGCAAACCAAAATGCTTTAAACAGGTGCTT

TTATTGTACATATACATTTAATAAATGCTGCTTTTGTATAAGCCACTTTT

AAGCTTGTGTTATTTTGGGGGTGGTGTTTTAGGCCTTTTAAAACACTGAA

AGCCTTTACACAAATGCAACTCTTGACTATGGGGTCTGACCTTTGGGAA

TGTTCAGCAGGGGCTGAAGTATCTGAGACTTGGGAAGAGCATTGTGATTG

GGATTCAGTGCTTGATCCATGTCCAGAGTCTTCAGTTTCTGAATCCTCTT

CTCTTGTAATATCAAGAATACATTTCCCCATGCATATATTATATTTCATC

-continued
CTTGAAAAAGTATACATACTTATCTCAGAATCCAGCCTTTCCTTCCATTC

AACAATTCTAGAAGTTAAAACTGGGGTAGATGCTATTACAGAGGTAGAAT

GCTTCCTAAACCCAGAAATGGGGGATCTGC

3A4 humanized heavy chain CDR2 polypeptide sequence
SEQ ID NO.: 212
DINPYNGDTN

OGS18500
SEQ ID NO.: 213
ATGCCAAGTGGTCCCAGGCTGATGTTGTGATGACCCAAACTCC

OGS2084
SEQ ID NO:. 214
GGGAAGATGAAGACAGATGGTGCAGCCACAGTCCG

OGS1879
SEQ ID NO.: 215
GGGTTCCAGGTTCCACTGGCCAGATCCAGTTGGTGCAATCTGG

OGS1810
SEQ ID NO.: 216
GGGGCCAGGGGAAAGACAGATGGGCCCTTCGTTGAGGC

REFERENCES

Santana-Davila R. and Perez E. A. (2010) "Treatment options for patients with triple-negative breast cancer" *J Hematol Oncol.* 27:42.

de Ruijter T. C., Veeck J., et al. (2011) "Characteristics of triple-negative breast cancer." *J Cancer Res Clin Oncol.* 137:183.

Ismail-Khan R. and Bui M. M. (2010) "A review of Triple-negative breast cancer" *Cancer Control* 17:173.

Carey L. A., Perou C. M. et al. (2006) "Race, breast cancer subtypes, and survival in the Carolina Breast Cancer Study." *JAMA* 295:2492.

Krieg M., Seynaeve C. et al. (2009) "Sensitivity to first-line chemotherapy for metastatic breast cancer in BRCA1 and BRCA2 mutation carriers." *J Clin Oncol* 27:3764.

Rouzier R., Perou C. M. et al. (2005) "Breast cancer molecular subtypes respond differently to preoperative chemotherapy" *Clin Cancer Res* 11:5678.

Fong P. C., Boss D. S. et al. (2009) "Inhibition of poly(ADP-ribose) polymerase in tumors from BRCA mutation carriers." *N Engl J Med* 361:123.

Dent R., Trudeau M et al. (2007) "Triple-Negative Breast Cancer: Clinical Feature and Patterns of Recurrence" *Clin. Cancer Res.* 13: 4429.

Bernstein L and J. V. Lacey Jr. (2011) "Receptors, Associations, and Risk Factor Differences by Breast Cancer Subtypes: Positive or Negative?" *J Natl Cancer Inst* 103(6): 451-453 (Advanced publication Feb. 23, 2011).

Nofech-Mozes S. et al., (2009) "Patterns of recurrence in the basal and non-basal subtypes of triple-negative breast cancers" *Cancer Res. Treat.* 118: 131-137.

The invention claimed is:

1. A method of treating a subject having triple negative breast cancer or basal-like breast cancer, the method comprising administering an antibody or an antigen binding fragment thereof capable of specific binding to Kidney associated antigen 1 (KAAG1) and conjugated to a therapeutic moiety to the subject, wherein the antibody or antigen binding fragment thereof comprises a CDRH1 as set forth in SEQ ID NO:49, a CDRH2 as set forth in SEQ ID NO:50 or in SEQ ID NO:212, a CDRH3 as set forth in SEQ ID NO:51, a CDRL1 as set forth in SEQ ID NO: 52, a CDRL2 as set forth in SEQ ID NO:53 and a CDRL3 as set forth in SEQ ID NO: 54.

2. The method of claim 1, wherein the triple negative breast cancer or basal-like breast cancer is characterized as being negative for estrogen receptor (ER) expression, progesterone receptor (PgR) expression and/or for Her2 overexpression.

3. The method of claim 1, further comprising administering an anti-cancer agent.

4. The method of claim 1, wherein the therapeutic moiety comprises a cytotoxic agent or an anti-mitotic compound.

5. The method of claim 1, wherein the antibody or antigen binding fragment thereof comprises:
   a) a light chain variable region as set forth in SEQ ID NO:48 and a heavy chain variable region as set forth in SEQ ID NO:46;
   b) a light chain variable region as set forth in SEQ ID NO:186 wherein at least one of the amino acid identified by X is an amino acid substitution in comparison with a corresponding amino acid in the polypeptide set forth in SEQ ID NO:48 and a heavy chain variable region as set forth in SEQ ID NO:191 wherein at least one of the amino acid identified by X is an amino acid substitution in comparison with a corresponding amino acid in the polypeptide set forth in SEQ ID NO:46;
   c) a light chain variable region as set forth in SEQ ID NO:187 and a heavy chain variable region as set forth in SEQ ID NO:192;
   d) a light chain variable region as set forth in SEQ ID NO:188 and a heavy chain variable region as set forth in SEQ ID NO:193;
   e) a light chain variable region as set forth in SEQ ID NO: 189 or SEQ ID NO:190 and a heavy chain variable region as set forth in SEQ ID NO:194, SEQ ID NO:195, SEQ ID NO:196 or SEQ ID NO:197;
   f) a light chain variable region as set forth in SEQ ID NO:189 and a heavy chain variable region as set forth in SEQ ID NO:194;
   g) a light chain variable region as set forth in SEQ ID NO:189 and a heavy chain variable region as set forth in SEQ ID NO:195;
   h) a light chain variable region as set forth in SEQ ID NO:189 and a heavy chain variable region as set forth in SEQ ID NO:196;
   i) a light chain variable region as set forth in SEQ ID NO:189 and a heavy chain variable region as set forth in SEQ ID NO:197;
   j) a light chain variable region as set forth in SEQ ID NO:190 and a heavy chain variable region as set forth in SEQ ID NO:194;
   k) a light chain variable region as set forth in SEQ ID NO:190 and a heavy chain variable region as set forth in SEQ ID NO:195;
   l) a light chain as set forth in SEQ ID NO:199 or SEQ ID NO:200 and a heavy chain as set forth in SEQ ID NO:202, SEQ ID NO:203, SEQ ID NO:204 or SEQ ID NO:205;
   m) a light chain as set forth in SEQ ID NO:199 and a heavy chain as set forth in SEQ ID NO:202;
   n) a light chain as set forth in SEQ ID NO:199 and a heavy chain as set forth in SEQ ID NO:203;
   o) light chain as set forth in SEQ ID NO:199 and a heavy chain as set forth in SEQ ID NO:204;
   p) a light chain as set forth in SEQ ID NO:199 and a heavy chain as set forth in SEQ ID NO:205;
   q) a light chain as set forth in SEQ ID NO:200 and a heavy chain as set forth in SEQ ID NO:202;
   r) a light chain as set forth in SEQ ID NO:200 and a heavy chain as set forth in SEQ ID NO:203;
   s) a light chain as set forth in SEQ ID NO:200 and a heavy chain as set forth in SEQ ID NO:204 or;
   t) a light chain as set forth in SEQ ID NO:200 and a heavy chain as set forth in SEQ ID NO:205.

6. The method of claim 5, wherein the therapeutic moiety comprises a cytotoxic agent or an anti-mitotic compound.

7. A method of treating triple negative breast cancer, the method comprising administering an antibody or an antigen binding fragment thereof capable of specific binding to Kidney associated antigen 1 (KAAG1) to a subject in need thereof, wherein the antibody or antigen binding fragment thereof comprises a CDRH1 as set forth in SEQ ID NO:49, a CDRH2 as set forth in SEQ ID NO:50 or in SEQ ID NO:212, a CDRH3 as set forth in SEQ ID NO:51, a CDRL1 as set forth in SEQ ID NO: 52, a CDRL2 as set forth in SEQ ID NO:53 and a CDRL3 as set forth in SEQ ID NO: 54.

8. The method of claim 7, wherein the antibody or antigen binding fragment thereof is conjugated with a therapeutic moiety.

9. The method of claim 8, wherein the antibody or antigen binding fragment thereof and the therapeutic moiety are conjugated with a linker cleavable after internalization of the antibody or antigen binding fragment thereof in a cell.

10. The method of claim 7, wherein the antibody or antigen binding fragment thereof is a monoclonal antibody, a chimeric antibody, or a humanized antibody or an antigen binding fragment thereof.

11. The method of claim 7, wherein the antibody or antigen binding fragment thereof is administered in combination with an anti-cancer agent.

12. The method of claim 7, wherein the antibody or antigen binding fragment thereof comprises:
- a) a light chain variable region as set forth in SEQ ID NO:48 and a heavy chain variable region as set forth in SEQ ID NO:46;
- b) a light chain variable region as set forth in SEQ ID NO:186 wherein at least one of the amino acid identified by X is an amino acid substitution in comparison with a corresponding amino acid in the polypeptide set forth in SEQ ID NO:48 and a heavy chain variable region as set forth in SEQ ID NO:191 wherein at least one of the amino acid identified by X is an amino acid substitution in comparison with a corresponding amino acid in the polypeptide set forth in SEQ ID NO:46;
- c) a light chain variable region as set forth in SEQ ID NO:187 and a heavy chain variable region as set forth in SEQ ID NO:192;
- d) a light chain variable region as set forth in SEQ ID NO:188 and a heavy chain variable region as set forth in SEQ ID NO:193;
- e) a light chain variable region as set forth in SEQ ID NO: 189 or SEQ ID NO:190 and a heavy chain variable region as set forth in SEQ ID NO:194, SEQ ID NO:195, SEQ ID NO:196 or SEQ ID NO:197;
- f) a light chain variable region as set forth in SEQ ID NO:189 and a heavy chain variable region as set forth in SEQ ID NO:194;
- g) a light chain variable region as set forth in SEQ ID NO:189 and a heavy chain variable region as set forth in SEQ ID NO:195;
- h) a light chain variable region as set forth in SEQ ID NO:189 and a heavy chain variable region as set forth in SEQ ID NO:196;
- i) a light chain variable region as set forth in SEQ ID NO:189 and a heavy chain variable region as set forth in SEQ ID NO:197;
- j) a light chain variable region as set forth in SEQ ID NO:190 and a heavy chain variable region as set forth in SEQ ID NO:194;
- k) a light chain variable region as set forth in SEQ ID NO:190 and a heavy chain variable region as set forth in SEQ ID NO:195;
- l) a light chain as set forth in SEQ ID NO: 199 or SEQ ID NO:200 and a heavy chain as set forth in SEQ ID NO:202, SEQ ID NO:203, SEQ ID NO:204 or SEQ ID NO:205;
- m) a light chain as set forth in SEQ ID NO:199 and a heavy chain as set forth in SEQ ID NO:202;
- n) a light chain as set forth in SEQ ID NO:199 and a heavy chain as set forth in SEQ ID NO:203;
- o) a light chain as set forth in SEQ ID NO:199 and a heavy chain as set forth in SEQ ID NO:204;
- p) a light chain as set forth in SEQ ID NO:199 and a heavy chain as set forth in SEQ ID NO:205;
- q) a light chain as set forth in SEQ ID NO:200 and a heavy chain as set forth in SEQ ID NO:202;
- r) a light chain as set forth in SEQ ID NO:200 and a heavy chain as set forth in SEQ ID NO:203;
- s) a light chain as set forth in SEQ ID NO:200 and a heavy chain as set forth in SEQ ID NO:204 or;
- t) a light chain as set forth in SEQ ID NO:200 and a heavy chain as set forth in SEQ ID NO:205.

13. The method of claim 12, wherein the antibody or antigen binding fragment thereof is conjugated with a therapeutic moiety.

14. The method of claim 13, wherein the therapeutic moiety comprises a cytotoxic agent or an anti-mitotic compound.

15. The method of claim 13, wherein the antibody or antigen binding fragment thereof and the therapeutic moiety are conjugated with a linker cleavable after internalization of the antibody or antigen binding fragment thereof in a cell.

16. A method of treating basal-like breast cancer, the method comprising administering to a subject in need an antibody or an antigen binding fragment thereof capable of specific binding to Kidney associated antigen 1 (KAAG1), wherein the antibody or antigen binding fragment thereof comprises a CDRH1 as set forth in SEQ ID NO:49, a CDRH2 as set forth in SEQ ID NO:50 or in SEQ ID NO:212, a CDRH3 as set forth in SEQ ID NO:51, a CDRL1 as set forth in SEQ ID NO:52, a CDRL2 as set forth in SEQ ID NO:53 and a CDRL3 as set forth in SEQ ID NO:54.

17. The method of claim 16, wherein the antibody or antigen binding fragment thereof is conjugated with a therapeutic moiety.

18. The method of claim 17, wherein the therapeutic moiety comprises a cytotoxic agent or an anti-mitotic compound.

19. The method of claim 17, wherein the antibody or antigen binding fragment thereof and the therapeutic moiety are conjugated with a linker cleavable after internalization of the antibody or antigen binding fragment thereof in a cell.

20. The method of claim 16, wherein the antibody or antigen binding fragment thereof comprises:
- a. a light chain variable region as set forth in SEQ ID NO:48 and a heavy chain variable region as set forth in SEQ ID NO:46;
- b. a light chain variable region as set forth in SEQ ID NO:186 wherein at least one of the amino acid identified by X is an amino acid substitution in comparison with a corresponding amino acid in the polypeptide set forth in SEQ ID NO:48 and a heavy chain variable region as set forth in SEQ ID NO:191 wherein at least one of the amino acid identified by X is an amino acid substitution in comparison with a corresponding amino acid in the polypeptide set forth in SEQ ID NO:46;
- c. a light chain variable region as set forth in SEQ ID NO:187 and a heavy chain variable region as set forth in SEQ ID NO:192;
- d. a light chain variable region as set forth in SEQ ID NO:188 and a heavy chain variable region as set forth in SEQ ID NO:193;
- e. a light chain variable region as set forth in SEQ ID NO: 189 or SEQ ID NO:190 and a heavy chain variable region as set forth in SEQ ID NO:194, SEQ ID NO:195, SEQ ID NO:196 or SEQ ID NO:197;
- f. a light chain variable region as set forth in SEQ ID NO:189 and a heavy chain variable region as set forth in SEQ ID NO:194;
- g. a light chain variable region as set forth in SEQ ID NO:189 and a heavy chain variable region as set forth in SEQ ID NO:195;
- h. a light chain variable region as set forth in SEQ ID NO:189 and a heavy chain variable region as set forth in SEQ ID NO:196;
- i. a light chain variable region as set forth in SEQ ID NO:189 and a heavy chain variable region as set forth in SEQ ID NO:197;
- j. a light chain variable region as set forth in SEQ ID NO:190 and a heavy chain variable region as set forth in SEQ ID NO:194;

k. a light chain variable region as set forth in SEQ ID NO:190 and a heavy chain variable region as set forth in SEQ ID NO:195;
l. a light chain as set forth in SEQ ID NO: 199 or SEQ ID NO:200 and a heavy chain as set forth in SEQ ID NO:202, SEQ ID NO:203, SEQ ID NO:204 or SEQ ID NO:205;
m. a light chain as set forth in SEQ ID NO:199 and a heavy chain as set forth in SEQ ID NO:202;
n. a light chain as set forth in SEQ ID NO:199 and a heavy chain as set forth in SEQ ID NO:203;
o. a light chain as set forth in SEQ ID NO:199 and a heavy chain as set forth in SEQ ID NO:204;
p. a light chain as set forth in SEQ ID NO:199 and a heavy chain as set forth in SEQ ID NO:205;
q. a light chain as set forth in SEQ ID NO:200 and a heavy chain as set forth in SEQ ID NO:202;
r. a light chain as set forth in SEQ ID NO:200 and a heavy chain as set forth in SEQ ID NO:203;
s. a light chain as set forth in SEQ ID NO:200 and a heavy chain as set forth in SEQ ID NO:204 or;
t. a light chain as set forth in SEQ ID NO:200 and a heavy chain as set forth in SEQ ID NO:205.

21. The method of claim 20, wherein the antibody or antigen binding fragment thereof is conjugated with a therapeutic moiety.

22. The method of claim 21, wherein the therapeutic moiety comprises a cytotoxic agent or an anti-mitotic compound.

23. The method of claim 21, wherein the antibody or antigen binding fragment thereof and the therapeutic moiety are conjugated with a linker cleavable after internalization of the antibody or antigen binding fragment thereof in a cell.

* * * * *

SEQUENCE LISTING

<160> NUMBER OF SEQ ID NOS: 217

<210> SEQ ID NO 1
<211> LENGTH: 885
<212> TYPE: DNA
<213> ORGANISM: Homo sapiens
<300> PUBLICATION INFORMATION:
<308> DATABASE ACCESSION NUMBER: UniProtKB/Q9UBP8
<309> DATABASE ENTRY DATE: 1999-12-20
<313> RELEVANT RESIDUES IN SEQ ID NO: (1)..(885)

<400> SEQUENCE: 1

```
gagggcatc aatcacaccg agaagtcaca gcccctcaac cactgaggtg tggggggta      60 gggatctgca tttcttcata tcaaccccac actatagggc acctaaatgg gtgggcggtg   120
ggggagaccg actcacttga gtttcttgaa ggcttcctgg cctccagcca cgtaattgcc   180
cccgctctgg atctggtcta gcttccggat tcggtggcca gtccgcgggg tgtagatgtt   240
cctgacggcc ccaaagggtg cctgaacgcc gccggtcacc tccttcagga agacttcgaa   300
gctggacacc ttcttctcat ggatgacgac gcggcgcccc cgtagaagg ggtccccgtt    360 gcggtacaca agcacgctct tcacgacggg ctgagacagg tggctggacc tggcgctgct   420
gccgctcatc ttccccgctg gccgccgcct cagctcgctg cttcgcgtcg ggaggcacct   480
ccgctgtccc agcggcctca ccgcacccag ggcgcgggat cgcctcctga acgaacgag    540 aaactgacga atccacaggt gaaagagaag taacggccgt gcgcctaggc gtccacccag   600
aggagacact aggagcttgc aggactcgga gtagacgctc aagttttca ccgtggcgtg    660 cacagccaat caggacccgc agtgcgcgca ccacaccagg ttcacctgct acgggcagaa   720
tcaaggtgga cagcttctga gcaggagccg gaaacgcgcg gggccttcaa acaggcacgc   780
ctagtgaggg caggagagag gaggacgcac acacacacac acacaaat atggtgaaac     840 ccaatttctt acatcatatc tgtgctaccc tttccaaaca gccta                   885
```

<210> SEQ ID NO 2
<211> LENGTH: 84
<212> TYPE: PRT
<213> ORGANISM: Homo sapiens
<300> PUBLICATION INFORMATION:
<308> DATABASE ACCESSION NUMBER: UniProtKB/Q9UBP8
<309> DATABASE ENTRY DATE: 1999-12-20
<313> RELEVANT RESIDUES IN SEQ ID NO: (1)..(84)

<400> SEQUENCE: 2

Met Asp Asp Asp Ala Ala Pro Arg Val Glu Gly Val Pro Val Ala Val
1               5                   10                  15

His Lys His Ala Leu His Asp Gly Leu Arg Gln Val Ala Gly Pro Gly
            20                  25                  30

Ala Ala Ala Ala His Leu Pro Arg Trp Pro Pro Gln Leu Ala Ala
        35                  40                  45

Ser Arg Arg Glu Ala Pro Pro Leu Ser Gln Arg Pro His Arg Thr Gln
    50                  55                  60

Gly Ala Gly Ser Pro Pro Glu Thr Asn Glu Lys Leu Thr Asn Pro Gln
65                  70                  75                  80

Val Lys Glu Lys

<210> SEQ ID NO 3
<211> LENGTH: 657
<212> TYPE: DNA
<213> ORGANISM: Artificial Sequence
<220> FEATURE:

<223> OTHER INFORMATION: 3D3 light chain

<400> SEQUENCE: 3

| | | | | | |
|---|---|---|---|---|---|
| gacattgtga | tgacccagtc | tccatcctcc | ctggctgtgt | caataggaca | gaaggtcact | 60 |
| atgaactgca | agtccagtca | gagccttta | aatagtaact | tcaaaagaa | cttttggcc | 120 |
| tggtaccagc | agaaaccagg | ccagtctcct | aaacttctga | tatactttgc | atccactcgg | 180 |
| gaatctagta | tccctgatcg | cttcataggc | agtggatctg | ggacagattt | cactcttacc | 240 |
| atcagcagtg | tgcaggctga | agacctggca | gattacttct | gtcagcaaca | ttatagcact | 300 |
| ccgctcacgt | tcggtgctgg | gaccaagctg | gagctgaaag | ctgtggctgc | accatctgtc | 360 |
| ttcatcttcc | cgccatctga | tgagcagttg | aaatctggaa | ctgcctctgt | tgtgtgcctg | 420 |
| ctgaataact | tctatcccag | agaggccaaa | gtacagtgga | aggtggataa | cgccctccaa | 480 |
| tcgggtaact | cccaggagag | tgtcacagag | caggacagca | aggacagcac | ctacagcctc | 540 |
| agcagcaccc | tgacgctgag | caaagcagac | tacgagaaac | acaaagtcta | cgcctgcgaa | 600 |
| gtcacccatc | agggcctgag | ctcgcccgtc | acaaagagct | tcaacagggg | agagtgt | 657 |

<210> SEQ ID NO 4
<211> LENGTH: 219
<212> TYPE: PRT
<213> ORGANISM: Artificial Sequence
<220> FEATURE:
<223> OTHER INFORMATION: 3D3 light chain

<400> SEQUENCE: 4

Asp Ile Val Met Thr Gln Ser Pro Ser Ser Leu Ala Val Ser Ile Gly
1               5                   10                  15

Gln Lys Val Thr Met Asn Cys Lys Ser Ser Gln Ser Leu Leu Asn Ser
            20                  25                  30

Asn Phe Gln Lys Asn Phe Leu Ala Trp Tyr Gln Gln Lys Pro Gly Gln
        35                  40                  45

Ser Pro Lys Leu Leu Ile Tyr Phe Ala Ser Thr Arg Glu Ser Ser Ile
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Ser Thr Pro Leu Thr Phe Gly Ala Gly Thr Lys Leu Glu Leu
            100                 105                 110

Lys Ala Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 5
<211> LENGTH: 1329
<212> TYPE: DNA
<213> ORGANISM: Artificial Sequence
<220> FEATURE:
<223> OTHER INFORMATION: 3D3 heavy chain

<400> SEQUENCE: 5

```
gaggttcagc tgcagcagtc tgtagctgag ctggtgaggc ctggggcttc agtgacgctg      60
tcctgcaagg cttcgggcta catatttact gactatgaga tacactgggt gaagcagact     120
cctgtgcatg gcctggaatg gattggggtt attgatcctg aaactggtaa tactgccttc     180
aatcagaagt tcaagggcaa ggccacactg actgcagaca tatcctccag cacagcctac     240
atggaactca gcagtttgac atctgaggac tctgccgtct attactgtat gggttattct     300
gattattggg gccaaggcac cactctcaca gtctcctcag cctcaacgaa gggcccatct     360
gtctttcccc tggccccctc ctccaagagc acctctgggg gcacagcggc cctgggctgc     420
ctggtcaagg actacttccc cgaaccggtg acggtgtcgt ggaactcagg cgccctgacc     480
agcggcgtgc acaccttccc ggctgtccta cagtcctcag gactctactc cctcagcagc     540
gtggtgaccg tgccctccag cagcttgggc acccagacct acatctgcaa cgtgaatcac     600
aagcccagca acaccaaggt ggacaagaaa gttgagccca atcttgtga attcactcac     660
acatgcccac cgtgcccagc acctgaactc ctggggggac cgtcagtctt cctcttcccc     720
ccaaaaccca aggacaccct catgatctcc cggacccctg aggtcacatg cgtggtggtg     780
gacgtgagcc acgaagaccc tgaggtcaag ttcaactggt acgtggacgg cgtggaggtg     840
cataatgcca agacaaagcc gcgggaggag cagtacaaca gcacgtaccg tgtggtcagc     900
gtcctcaccg tcctgcacca ggactggctg aatggcaagg agtacaagtg caaggtctcc     960
aacaaagccc tcccagcccc catcgagaaa accatctcca aagccaaagg gcagccccga    1020
gaaccacagg tgtacaccct gcccccatcc cgggatgagc tgaccaagaa ccaggtcagc    1080
ctgacctgcc tggtcaaagg cttctatccc agcgacatcg ccgtggagtg ggagagcaat    1140
gggcagccgg agaacaacta caagaccacg cctcccgtgc tggactccga cggctccttc    1200
ttcctctaca gcaagctcac cgtggacaag agcaggtggc agcaggggaa cgtcttctca    1260
tgctccgtga tgcatgaggc tctgcacaac cactacacgc agaagagcct ctccctgtct    1320
cccgggaaa                                                            1329
```

<210> SEQ ID NO 6
<211> LENGTH: 443
<212> TYPE: PRT
<213> ORGANISM: Artificial Sequence
<220> FEATURE:
<223> OTHER INFORMATION: 3D3 heavy chain

<400> SEQUENCE: 6

Glu Val Gln Leu Gln Gln Ser Val Ala Glu Leu Val Arg Pro Gly Ala
1               5                   10                  15

Ser Val Thr Leu Ser Cys Lys Ala Ser Gly Tyr Ile Phe Thr Asp Tyr
            20                  25                  30

Glu Ile His Trp Val Lys Gln Thr Pro Val His Gly Leu Glu Trp Ile
        35                  40                  45

Gly Val Ile Asp Pro Glu Thr Gly Asn Thr Ala Phe Asn Gln Lys Phe
    50                  55                  60

Lys Gly Lys Ala Thr Leu Thr Ala Asp Ile Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Met Gly Tyr Ser Asp Tyr Trp Gly Gln Gly Thr Thr Leu Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Lys Val Glu Pro Lys Ser Cys Glu Phe Thr His Thr Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Asp
            340                 345                 350

Glu Leu Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 7
<211> LENGTH: 654
<212> TYPE: DNA
<213> ORGANISM: Artificial Sequence
<220> FEATURE:
<223> OTHER INFORMATION: 3G10 light chain

<400> SEQUENCE: 7

```
gatgttttga tgacccaaac tccacgctcc ctgtctgtca gtcttggaga tcaagcctcc      60
atctcttgta gatcgagtca gagccttta  catagtaatg aaacaccta  tttagaatgg     120
tatttgcaga aaccaggcca gcctccaaag gtcctgatct acaaagtttc caaccgattt    180
tctggggtcc cagacaggtt cagtggcagt ggatcaggga cagatttcac actcaagatc    240
agcggagtgg aggctgagga tctgggagtt tattactgct ttcaaggttc acatgttcct    300
ctcacgttcg gtgctgggac caagctggag ctgaaagctg tggctgcacc atctgtcttc    360
atcttcccgc catctgatga gcagttgaaa tctggaactg cctctgttgt gtgcctgctg    420
aataacttct atcccagaga ggccaaagta cagtggaagg tggataacgc cctccaatcg    480
ggtaactccc aggagagtgt cacagagcag gacagcaagg acagcaccta cagcctcagc    540
agcaccctga cgctgagcaa agcagactac gagaaacaca agtctacgc  ctgcgaagtc    600
acccatcagg gcctgagctc gcccgtcaca aagagcttca caggggaga  gtgt           654
```

```
<210> SEQ ID NO 8
<211> LENGTH: 218
<212> TYPE: PRT
<213> ORGANISM: Artificial Sequence
<220> FEATURE:
<223> OTHER INFORMATION: 3G10 light chain

<400> SEQUENCE: 8

Asp Val Leu Met Thr Gln Thr Pro Arg Ser Leu Ser Val Ser Leu Gly
1               5                   10                  15

Asp Gln Ala Ser Ile Ser Cys Arg Ser Ser Gln Ser Leu Leu His Ser
            20                  25                  30

Asn Gly Asn Thr Tyr Leu Glu Trp Tyr Leu Gln Lys Pro Gly Gln Pro
        35                  40                  45

Pro Lys Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Gly Val Glu Ala Glu Asp Leu Gly Val Tyr Tyr Cys Phe Gln Gly
                85                  90                  95

Ser His Val Pro Leu Thr Phe Gly Ala Gly Thr Lys Leu Glu Leu Lys
            100                 105                 110

Ala Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 9
<211> LENGTH: 1335
<212> TYPE: DNA
```

<213> ORGANISM: Artificial Sequence
<220> FEATURE:
<223> OTHER INFORMATION: 3G10 heavy chain

<400> SEQUENCE: 9

```
gagatccagc tgcagcagtc tggacctgag ttggtgaagc ctggggcttc agtgaagata     60
tcctgtaagg cttctggata ccttcact gacaactaca tgaactgggt gaagcagagc     120
catggaaaga gccttgagtg gattggagat attaatcctt actatggtac tactacctac    180
aaccagaagt tcaagggcaa ggccacattg actgtagaca agtcctcccg cacagcctac    240
atggagctcc gcggcctgac atctgaggac tctgcagtct attactgtgc aagagatgac    300
tggtttgatt attggggcca agggactctg gtcactgtct ctgcagcctc aacgaagggc    360
ccatctgtct ttcccctggc ccctcctcc aagagcacct ctgggggcac agcggccctg    420
ggctgcctgg tcaaggacta cttccccgaa ccggtgacgg tgtcgtggaa ctcaggcgcc    480
ctgaccagcg gcgtgcacac cttcccggct gtcctacagt cctcaggact ctactccctc    540
agcagcgtgg tgaccgtgcc ctccagcagc ttgggcaccc agacctacat ctgcaacgtg    600
aatcacaagc ccagcaacac caaggtggac aagaaagttg agcccaaatc ttgtgaattc    660
actcacacat gcccaccgtg cccagcacct gaactcctgg ggggaccgtc agtcttcctc    720
ttccccccaa aacccaagga caccctcatg atctcccgga cccctgaggt cacatgcgtg    780
gtggtggacg tgagccacga agaccctgag gtcaagttca actggtacgt ggacggcgtg    840
gaggtgcata atgccaagac aaagccgcgg gaggagcagt acaacagcac gtaccgtgtg    900
gtcagcgtcc tcaccgtcct gcaccaggac tggctgaatg gcaaggagta caagtgcaag    960
gtctccaaca aagccctccc agcccccatc gagaaaacca tctccaaagc caaagggcag   1020
ccccgagaac acaggtgta caccctgccc ccatcccggg atgagctgac caagaaccag   1080
gtcagcctga cctgcctggt caaaggcttc tatcccagcg acatcgccgt ggagtgggag   1140
agcaatgggc agccggagaa caactacaag accacgcctc ccgtgctgga ctccgacggc   1200
tccttcttcc tctacagcaa gctcaccgtg gacaagagca ggtggcagca ggggaacgtc   1260
ttctcatgct ccgtgatgca tgaggctctg cacaaccact acacgcagaa gagcctctcc   1320
ctgtctcccg ggaaa                                                    1335
```

<210> SEQ ID NO 10
<211> LENGTH: 445
<212> TYPE: PRT
<213> ORGANISM: Artificial Sequence
<220> FEATURE:
<223> OTHER INFORMATION: 3G10 heavy chain

<400> SEQUENCE: 10

```
Glu Ile Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Asn
            20                  25                  30

Tyr Met Asn Trp Val Lys Gln Ser His Gly Lys Ser Leu Glu Trp Ile
        35                  40                  45

Gly Asp Ile Asn Pro Tyr Tyr Gly Thr Thr Thr Tyr Asn Gln Lys Phe
    50                  55                  60

Lys Gly Lys Ala Thr Leu Thr Val Asp Lys Ser Ser Arg Thr Ala Tyr
65                  70                  75                  80

Met Glu Leu Arg Gly Leu Thr Ser Glu Asp Ser Ala Val Tyr Tyr Cys
                85                  90                  95
```

Ala Arg Asp Asp Trp Phe Asp Tyr Trp Gly Gln Gly Thr Leu Val Thr
            100                 105                 110

Val Ser Ala Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
            195                 200                 205

Val Asp Lys Lys Val Glu Pro Lys Ser Cys Glu Phe Thr His Thr Cys
            210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
            405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 11
<211> LENGTH: 639
<212> TYPE: DNA
<213> ORGANISM: Artificial Sequence
<220> FEATURE:
<223> OTHER INFORMATION: 3C4 light chain

<400> SEQUENCE: 11
gacatcgtta tgtctcagtc tccatcttcc atgtatgcat ctctaggaga gagagtcact    60

-continued

| | | | | |
|---|---|---|---|---|
| atcacttgca | aggcgagtca | ggacattcat | aactttttaa | actggttcca gcagaaacca | 120 |
| ggaaaatctc | caaagaccct | gatctttcgt | gcaaacagat | tggtagatgg ggtcccatca | 180 |
| aggttcagtg | gcagtggatc | tgggcaagat | tattctctca | ccatcagcag cctggagttt | 240 |
| gaagatttgg | gaatttattc | ttgtctacag | tatgatgaga | ttccgctcac gttcggtgct | 300 |
| gggaccaagc | tggagctgag | agctgtggct | gcaccatctg | tcttcatctt cccgccatct | 360 |
| gatgagcagt | tgaaatctgg | aactgcctct | gttgtgtgcc | tgctgaataa cttctatccc | 420 |
| agagaggcca | aagtacagtg | gaaggtggat | aacgccctcc | aatcgggtaa ctcccaggag | 480 |
| agtgtcacag | agcaggacag | caaggacagc | acctacagcc | tcagcagcac cctgacgctg | 540 |
| agcaaagcag | actacgagaa | acacaaagtc | tacgcctgcg | aagtcaccca tcagggcctg | 600 |
| agctcgcccg | tcacaaagag | cttcaacagg | ggagagtgt | | 639 |

```
<210> SEQ ID NO 12
<211> LENGTH: 213
<212> TYPE: PRT
<213> ORGANISM: Artificial Sequence
<220> FEATURE:
<223> OTHER INFORMATION: 3C4 light chain

<400> SEQUENCE: 12
```

Asp Ile Val Met Ser Gln Ser Pro Ser Ser Met Tyr Ala Ser Leu Gly
1               5                   10                  15

Glu Arg Val Thr Ile Thr Cys Lys Ala Ser Gln Asp Ile His Asn Phe
            20                  25                  30

Leu Asn Trp Phe Gln Gln Lys Pro Gly Lys Ser Pro Lys Thr Leu Ile
        35                  40                  45

Phe Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Phe
65                  70                  75                  80

Glu Asp Leu Gly Ile Tyr Ser Cys Leu Gln Tyr Asp Glu Ile Pro Leu
                85                  90                  95

Thr Phe Gly Ala Gly Thr Lys Leu Glu Leu Arg Ala Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

```
<210> SEQ ID NO 13
<211> LENGTH: 1341
<212> TYPE: DNA
<213> ORGANISM: Artificial Sequence
<220> FEATURE:
<223> OTHER INFORMATION: 3C4 heavy chain
```

<400> SEQUENCE: 13

```
gaggtgcagc ttcaggagtc aggacctgac ctggtgaaac cttctcagtc actttcactc    60
acctgcactg tcactggctt ctccatcacc agtggttatg ctggcactg gatccggcag    120
tttccaggaa acaaactgga gtggatgggc tacataaact acgatggtca caatgactac    180
aacccatctc tcaaaagtcg aatctctatc actcaagaca catccaagaa ccagttcttc    240
ctgcagttga attctgtgac tactgaggac acagccacat attactgtgc aagcagttac    300
gacggcttat ttgcttactg gggccaaggg actctggtca ctgtctctgc agcctcaacg    360
aagggcccat ctgtctttcc cctggccccc tcctccaaga gcacctctgg gggcacagcg    420
gccctgggct gcctggtcaa ggactacttc cccgaaccgg tgacggtgtc gtggaactca    480
ggcgccctga ccagcggcgt gcacaccttc ccggctgtcc tacagtcctc aggactctac    540
tccctcagca gcgtggtgac cgtgccctcc agcagcttgg gcacccagac ctacatctgc    600
aacgtgaatc acaagcccag caacaccaag gtggacaaga agttgagcc caaatcttgt    660
gaattcactc acacatgccc accgtgccca gcacctgaac tcctgggggg accgtcagtc    720
ttcctcttcc cccaaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcccagcc cccatcgaga aaaccatctc caaagccaaa    1020
gggcagcccc gagaaccaca ggtgtacacc ctgcccccat cccgggatga gctgaccaag    1080
aaccaggtca gcctgacctg cctggtcaaa ggcttctatc ccagcgacat cgccgtggag    1140
tgggagagca atgggcagcc ggagaacaac tacaagacca cgcctcccgt gctggactcc    1200
gacggctcct tcttcctcta cagcaagctc accgtggaca agagcaggtg gcagcagggg    1260
aacgtcttct catgctccgt gatgcatgag gctctgcaca accactacac gcagaagagc    1320
ctctccctgt ctcccgggaa a    1341
```

<210> SEQ ID NO 14
<211> LENGTH: 447
<212> TYPE: PRT
<213> ORGANISM: Artificial Sequence
<220> FEATURE:
<223> OTHER INFORMATION: 3C4 heavy chain

<400> SEQUENCE: 14

```
Glu Val Gln Leu Gln Glu Ser Gly Pro Asp Leu Val Lys Pro Ser Gln
1               5                   10                  15

Ser Leu Ser Leu Thr Cys Thr Val Thr Gly Phe Ser Ile Thr Ser Gly
            20                  25                  30

Tyr Gly Trp His Trp Ile Arg Gln Phe Pro Gly Asn Lys Leu Glu Trp
        35                  40                  45

Met Gly Tyr Ile Asn Tyr Asp Gly His Asn Asp Tyr Asn Pro Ser Leu
    50                  55                  60

Lys Ser Arg Ile Ser Ile Thr Gln Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Ser Ser Tyr Asp Gly Leu Phe Ala Tyr Trp Gly Gln Gly Thr Leu
            100                 105                 110
```

| | | | | | | | | | | |
|---|---|---|---|---|---|---|---|---|---|---|
|Val|Thr|Val|Ser|Ala|Ala|Ser|Thr|Lys|Gly|Pro|Ser|Val|Phe|Pro|Leu|
| |115| | | |120| | | |125| | | | | | |

Val Thr Val Ser Ala Ala Ser Thr Lys Gly Pro Ser Val Phe Pro Leu
    115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Glu Phe Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 15
<211> LENGTH: 339
<212> TYPE: DNA
<213> ORGANISM: Artificial Sequence
<220> FEATURE:
<223> OTHER INFORMATION: 3D3 light chain variable region

<400> SEQUENCE: 15
gacattgtga tgacccagtc tccatcctcc ctggctgtgt caataggaca gaaggtcact    60
atgaactgca gtccagtca gagccttta aatagtaact ttcaaaagaa cttttttggcc   120 tggtaccagc agaaaccagg ccagtctcct aaacttctga tatactttgc atccactcgg   180

```
gaatctagta tccctgatcg cttcataggc agtggatctg ggacagattt cactcttacc    240
atcagcagtg tgcaggctga agacctggca gattacttct gtcagcaaca ttatagcact    300
ccgctcacgt tcggtgctgg gaccaagctg gagctgaaa                            339
```

<210> SEQ ID NO 16
<211> LENGTH: 113
<212> TYPE: PRT
<213> ORGANISM: Artificial Sequence
<220> FEATURE:
<223> OTHER INFORMATION: 3D3 light chain variable region

<400> SEQUENCE: 16

```
Asp Ile Val Met Thr Gln Ser Pro Ser Ser Leu Ala Val Ser Ile Gly
1               5                   10                  15

Gln Lys Val Thr Met Asn Cys Lys Ser Ser Gln Ser Leu Leu Asn Ser
            20                  25                  30

Asn Phe Gln Lys Asn Phe Leu Ala Trp Tyr Gln Gln Lys Pro Gly Gln
        35                  40                  45

Ser Pro Lys Leu Leu Ile Tyr Phe Ala Ser Thr Arg Glu Ser Ser Ile
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Ser Thr Pro Leu Thr Phe Gly Ala Gly Thr Lys Leu Glu Leu
            100                 105                 110

Lys
```

<210> SEQ ID NO 17
<211> LENGTH: 339
<212> TYPE: DNA
<213> ORGANISM: Artificial Sequence
<220> FEATURE:
<223> OTHER INFORMATION: 3D3 heavy chain variable region

<400> SEQUENCE: 17

```
gaggttcagc tgcagcagtc tgtagctgag ctggtgaggc ctggggcttc agtgacgctg    60
tcctgcaagg cttcgggcta catatttact gactatgaga tacactgggt gaagcagact    120
cctgtgcatg gcctggaatg gattggggtt attgatcctg aaactggtaa tactgccttc    180
aatcagaagt tcaagggcaa ggccacactg actgcagaca tatcctccag cacagcctac    240
atggaactca gcagtttgac atctgaggac tctgccgtct attactgtat gggttattct    300
gattattggg gccaaggcac cactctcaca gtctcctca                            339
```

<210> SEQ ID NO 18
<211> LENGTH: 113
<212> TYPE: PRT
<213> ORGANISM: Artificial Sequence
<220> FEATURE:
<223> OTHER INFORMATION: 3D3 heavy chain variable region

<400> SEQUENCE: 18

```
Glu Val Gln Leu Gln Gln Ser Val Ala Glu Leu Val Arg Pro Gly Ala
1               5                   10                  15

Ser Val Thr Leu Ser Cys Lys Ala Ser Gly Tyr Ile Phe Thr Asp Tyr
            20                  25                  30

Glu Ile His Trp Val Lys Gln Thr Pro Val His Gly Leu Glu Trp Ile
```

```
                35                  40                  45
Gly Val Ile Asp Pro Glu Thr Gly Asn Thr Ala Phe Asn Gln Lys Phe
        50                  55                  60
Lys Gly Lys Ala Thr Leu Thr Ala Asp Ile Ser Ser Thr Ala Tyr
 65                  70                  75                  80
Met Glu Leu Ser Ser Leu Thr Ser Glu Asp Ser Ala Val Tyr Tyr Cys
                85                  90                  95
Met Gly Tyr Ser Asp Tyr Trp Gly Gln Gly Thr Thr Leu Thr Val Ser
            100                 105                 110
Ser

<210> SEQ ID NO 19
<211> LENGTH: 336
<212> TYPE: DNA
<213> ORGANISM: Artificial Sequence
<220> FEATURE:
<223> OTHER INFORMATION: 3G10 light chain variable region

<400> SEQUENCE: 19
gatgttttga tgacccaaac tccacgctcc ctgtctgtca gtcttggaga tcaagcctcc      60
atctcttgta gatcgagtca gagccttttta catagtaatg aaacaccta tttagaatgg     120 tatttgcaga aaccaggcca gcctccaaag gtcctgatct acaaagtttc caaccgattt     180
tctggggtcc cagacaggtt cagtggcagt ggatcaggga cagatttcac actcaagatc     240
agcggagtgg aggctgagga tctgggagtt tattactgct ttcaaggttc acatgttcct     300
ctcacgttcg gtgctgggac caagctggag ctgaaa                                336

<210> SEQ ID NO 20
<211> LENGTH: 112
<212> TYPE: PRT
<213> ORGANISM: Artificial Sequence
<220> FEATURE:
<223> OTHER INFORMATION: 3G10 light chain variable region

<400> SEQUENCE: 20

Asp Val Leu Met Thr Gln Thr Pro Arg Ser Leu Ser Val Ser Leu Gly
  1               5                  10                  15
Asp Gln Ala Ser Ile Ser Cys Arg Ser Ser Gln Ser Leu Leu His Ser
                20                  25                  30
Asn Gly Asn Thr Tyr Leu Glu Trp Tyr Leu Gln Lys Pro Gly Gln Pro
            35                  40                  45
Pro Lys Val Leu Ile Tyr Lys Val Ser Asn Arg Phe Ser Gly Val Pro
        50                  55                  60
Asp Arg Phe Ser Gly Ser Gly Ser Gly Thr Asp Phe Thr Leu Lys Ile
 65                  70                  75                  80
Ser Gly Val Glu Ala Glu Asp Leu Gly Val Tyr Tyr Cys Phe Gln Gly
                85                  90                  95
Ser His Val Pro Leu Thr Phe Gly Ala Gly Thr Lys Leu Glu Leu Lys
            100                 105                 110

<210> SEQ ID NO 21
<211> LENGTH: 345
<212> TYPE: DNA
<213> ORGANISM: Artificial Sequence
<220> FEATURE:
<223> OTHER INFORMATION: 3G10 heavy chain variable region

<400> SEQUENCE: 21
```

```
gagatccagc tgcagcagtc tggacctgag ttggtgaagc tggggcttc agtgaagata      60 tcctgtaagg cttctggata caccttcact gacaactaca tgaactgggt gaagcagagc    120
catggaaaga gccttgagtg gattggagat attaatcctt actatggtac tactacctac    180
aaccagaagt tcaagggcaa ggccacattg actgtagaca gtcctcccg cacagcctac    240 atggagctcc gcggcctgac atctgaggac tctgcagtct attactgtgc aagagatgac    300
tggtttgatt attggggcca agggactctg gtcactgtct ctgca                    345
```

```
<210> SEQ ID NO 22
<211> LENGTH: 115
<212> TYPE: PRT
<213> ORGANISM: Artificial Sequence
<220> FEATURE:
<223> OTHER INFORMATION: 3G10 heavy chain variable region

<400> SEQUENCE: 22
```

Glu Ile Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Asn
            20                  25                  30

Tyr Met Asn Trp Val Lys Gln Ser His Gly Lys Ser Leu Glu Trp Ile
        35                  40                  45

Gly Asp Ile Asn Pro Tyr Tyr Gly Thr Thr Thr Tyr Asn Gln Lys Phe
    50                  55                  60

Lys Gly Lys Ala Thr Leu Thr Val Asp Lys Ser Ser Arg Thr Ala Tyr
65                  70                  75                  80

Met Glu Leu Arg Gly Leu Thr Ser Glu Asp Ser Ala Val Tyr Tyr Cys
                85                  90                  95

Ala Arg Asp Asp Trp Phe Asp Tyr Trp Gly Gln Gly Thr Leu Val Thr
            100                 105                 110

Val Ser Ala
        115

```
<210> SEQ ID NO 23
<211> LENGTH: 321
<212> TYPE: DNA
<213> ORGANISM: Artificial Sequence
<220> FEATURE:
<223> OTHER INFORMATION: 3C4 light chain variable region

<400> SEQUENCE: 23
```

```
gacatcgtta tgtctcagtc tccatcttcc atgtatgcat ctctaggaga gagagtcact     60
atcacttgca aggcgagtca ggacattcat aacttttta actggttcca gcagaaacca    120
ggaaaatctc caaagaccct gatctttcgt gcaaacagat tggtagatgg gtcccatca    180 aggttcagtg gcagtggatc tgggcaagat tattctctca ccatcagcag cctggagttt    240
gaagatttgg gaatttattc ttgtctacag tatgatgaga ttccgctcac gttcggtgct    300
gggaccaagc tggagctgag a                                              321
```

```
<210> SEQ ID NO 24
<211> LENGTH: 107
<212> TYPE: PRT
<213> ORGANISM: Artificial Sequence
<220> FEATURE:
<223> OTHER INFORMATION: 3C4 light chain variable region

<400> SEQUENCE: 24
```

Asp Ile Val Met Ser Gln Ser Pro Ser Ser Met Tyr Ala Ser Leu Gly

```
              1               5                  10                 15
            Glu Arg Val Thr Ile Thr Cys Lys Ala Ser Gln Asp Ile His Asn Phe
                            20                 25                 30

Leu Asn Trp Phe Gln Gln Lys Pro Gly Lys Ser Pro Lys Thr Leu Ile
                            35                 40                 45

Phe Arg Ala Asn Arg Leu Val Asp Gly Val Pro Ser Arg Phe Ser Gly
                            50                 55                 60

Ser Gly Ser Gly Gln Asp Tyr Ser Leu Thr Ile Ser Ser Leu Glu Phe
            65                  70                 75                 80

Glu Asp Leu Gly Ile Tyr Ser Cys Leu Gln Tyr Asp Glu Ile Pro Leu
                            85                 90                 95

Thr Phe Gly Ala Gly Thr Lys Leu Glu Leu Arg
                            100                105

<210> SEQ ID NO 25
<211> LENGTH: 351
<212> TYPE: DNA
<213> ORGANISM: Artificial Sequence
<220> FEATURE:
<223> OTHER INFORMATION: 3C4 heavy chain variable region

<400> SEQUENCE: 25
gaggtgcagc ttcaggagtc aggacctgac ctggtgaaac cttctcagtc actttcactc      60
acctgcactg tcactggctt ctccatcacc agtggttatg ctggcactg gatccggcag      120 tttccaggaa acaaactgga gtggatgggc tacataaact acgatggtca caatgactac     180
aacccatctc tcaaaagtcg aatctctatc actcaagaca catccaagaa ccagttcttc     240
ctgcagttga attctgtgac tactgaggac acagccacat attactgtgc aagcagttac     300
gacggcttat ttgcttactg gggccaaggg actctggtca ctgtctctgc a             351

<210> SEQ ID NO 26
<211> LENGTH: 117
<212> TYPE: PRT
<213> ORGANISM: Artificial Sequence
<220> FEATURE:
<223> OTHER INFORMATION: 3C4 heavy chain variable region

<400> SEQUENCE: 26

Glu Val Gln Leu Gln Glu Ser Gly Pro Asp Leu Val Lys Pro Ser Gln
            1               5                  10                 15

Ser Leu Ser Leu Thr Cys Thr Val Thr Gly Phe Ser Ile Thr Ser Gly
                            20                 25                 30

Tyr Gly Trp His Trp Ile Arg Gln Phe Pro Gly Asn Lys Leu Glu Trp
                            35                 40                 45

Met Gly Tyr Ile Asn Tyr Asp Gly His Asn Asp Tyr Asn Pro Ser Leu
                            50                 55                 60

Lys Ser Arg Ile Ser Ile Thr Gln Asp Thr Ser Lys Asn Gln Phe Phe
            65                  70                 75                 80

Leu Gln Leu Asn Ser Val Thr Thr Glu Asp Thr Ala Thr Tyr Tyr Cys
                            85                 90                 95

Ala Ser Ser Tyr Asp Gly Leu Phe Ala Tyr Trp Gly Gln Gly Thr Leu
                            100                105                110

Val Thr Val Ser Ala
                            115

<210> SEQ ID NO 27
<211> LENGTH: 17
```

```
<212> TYPE: PRT
<213> ORGANISM: Artificial Sequence
<220> FEATURE:
<223> OTHER INFORMATION: 3D3 light chain CDR1

<400> SEQUENCE: 27

Lys Ser Ser Gln Ser Leu Leu Asn Ser Asn Phe Gln Lys Asn Phe Leu
1               5                   10                  15

Ala

<210> SEQ ID NO 28
<211> LENGTH: 7
<212> TYPE: PRT
<213> ORGANISM: Artificial Sequence
<220> FEATURE:
<223> OTHER INFORMATION: 3D3 light chain CDR2

<400> SEQUENCE: 28

Phe Ala Ser Thr Arg Glu Ser
1               5

<210> SEQ ID NO 29
<211> LENGTH: 9
<212> TYPE: PRT
<213> ORGANISM: Artificial Sequence
<220> FEATURE:
<223> OTHER INFORMATION: 3D3 light chain CDR3

<400> SEQUENCE: 29

Gln Gln His Tyr Ser Thr Pro Leu Thr
1               5

<210> SEQ ID NO 30
<211> LENGTH: 10
<212> TYPE: PRT
<213> ORGANISM: Artificial Sequence
<220> FEATURE:
<223> OTHER INFORMATION: 3D3 heavy chain CDR1

<400> SEQUENCE: 30

Gly Tyr Ile Phe Thr Asp Tyr Glu Ile His
1               5                   10

<210> SEQ ID NO 31
<211> LENGTH: 10
<212> TYPE: PRT
<213> ORGANISM: Artificial Sequence
<220> FEATURE:
<223> OTHER INFORMATION: 3D3 heavy chain CDR2

<400> SEQUENCE: 31

Val Ile Asp Pro Glu Thr Gly Asn Thr Ala
1               5                   10

<210> SEQ ID NO 32
<211> LENGTH: 6
<212> TYPE: PRT
<213> ORGANISM: Artificial Sequence
<220> FEATURE:
<223> OTHER INFORMATION: 3D3 heavy chain CDR3

<400> SEQUENCE: 32

Met Gly Tyr Ser Asp Tyr
1               5

<210> SEQ ID NO 33
```

<211> LENGTH: 16
<212> TYPE: PRT
<213> ORGANISM: Artificial Sequence
<220> FEATURE:
<223> OTHER INFORMATION: 3G10 light chain CDR1

<400> SEQUENCE: 33

Arg Ser Ser Gln Ser Leu Leu His Ser Asn Gly Asn Thr Tyr Leu Glu
1               5                   10                  15

<210> SEQ ID NO 34
<211> LENGTH: 7
<212> TYPE: PRT
<213> ORGANISM: Artificial Sequence
<220> FEATURE:
<223> OTHER INFORMATION: 3G10 light chain CDR2

<400> SEQUENCE: 34

Lys Val Ser Asn Arg Phe Ser
1               5

<210> SEQ ID NO 35
<211> LENGTH: 9
<212> TYPE: PRT
<213> ORGANISM: Artificial Sequence
<220> FEATURE:
<223> OTHER INFORMATION: 3G10 light chain CDR3

<400> SEQUENCE: 35

Phe Gln Gly Ser His Val Pro Leu Thr
1               5

<210> SEQ ID NO 36
<211> LENGTH: 10
<212> TYPE: PRT
<213> ORGANISM: Artificial Sequence
<220> FEATURE:
<223> OTHER INFORMATION: 3G10 heavy chain CDR1

<400> SEQUENCE: 36

Gly Tyr Thr Phe Thr Asp Asn Tyr Met Asn
1               5                   10

<210> SEQ ID NO 37
<211> LENGTH: 10
<212> TYPE: PRT
<213> ORGANISM: Artificial Sequence
<220> FEATURE:
<223> OTHER INFORMATION: 3G10 heavy chain CDR2

<400> SEQUENCE: 37

Asp Ile Asn Pro Tyr Tyr Gly Thr Thr Thr
1               5                   10

<210> SEQ ID NO 38
<211> LENGTH: 8
<212> TYPE: PRT
<213> ORGANISM: Artificial Sequence
<220> FEATURE:
<223> OTHER INFORMATION: 3G10 heavy chain CDR3

<400> SEQUENCE: 38

Ala Arg Asp Asp Trp Phe Asp Tyr
1               5

<210> SEQ ID NO 39
<211> LENGTH: 11

```
<212> TYPE: PRT
<213> ORGANISM: Artificial Sequence
<220> FEATURE:
<223> OTHER INFORMATION: 3C4 light chain CDR1

<400> SEQUENCE: 39

Lys Ala Ser Gln Asp Ile His Asn Phe Leu Asn
1               5                   10

<210> SEQ ID NO 40
<211> LENGTH: 7
<212> TYPE: PRT
<213> ORGANISM: Artificial Sequence
<220> FEATURE:
<223> OTHER INFORMATION: 3C4 light chain CDR2

<400> SEQUENCE: 40

Arg Ala Asn Arg Leu Val Asp
1               5

<210> SEQ ID NO 41
<211> LENGTH: 9
<212> TYPE: PRT
<213> ORGANISM: Artificial Sequence
<220> FEATURE:
<223> OTHER INFORMATION: 3C4 light chain CDR3

<400> SEQUENCE: 41

Leu Gln Tyr Asp Glu Ile Pro Leu Thr
1               5

<210> SEQ ID NO 42
<211> LENGTH: 11
<212> TYPE: PRT
<213> ORGANISM: Artificial Sequence
<220> FEATURE:
<223> OTHER INFORMATION: 3C4 heavy chain CDR1

<400> SEQUENCE: 42

Gly Phe Ser Ile Thr Ser Gly Tyr Gly Trp His
1               5                   10

<210> SEQ ID NO 43
<211> LENGTH: 9
<212> TYPE: PRT
<213> ORGANISM: Artificial Sequence
<220> FEATURE:
<223> OTHER INFORMATION: 3C4 heavy chain CDR2

<400> SEQUENCE: 43

Tyr Ile Asn Tyr Asp Gly His Asn Asp
1               5

<210> SEQ ID NO 44
<211> LENGTH: 10
<212> TYPE: PRT
<213> ORGANISM: Artificial Sequence
<220> FEATURE:
<223> OTHER INFORMATION: 3C4 heavy chain CDR3

<400> SEQUENCE: 44

Ala Ser Ser Tyr Asp Gly Leu Phe Ala Tyr
1               5                   10

<210> SEQ ID NO 45
<211> LENGTH: 348
<212> TYPE: DNA
```

<213> ORGANISM: Artificial Sequence
<220> FEATURE:
<223> OTHER INFORMATION: 3A4 heavy chain variable region

<400> SEQUENCE: 45

```
cagatccagt tggtgcaatc tggacctgag atggtgaagc ctggggcttc agtgaagatg    60
tcctgtaagg cttctggata cacattcact gacgactaca tgagctgggt gaaacagagc   120
catggaaaga gccttgagtg gattggagat attaatcctt acaacggtga tactaactac   180
aaccagaagt tcaagggcaa ggccatattg actgtagaca atcctccag cacagcctac    240
atgcagctca acagcctgac atcggaagac tcagcagtct attactgtgc aagagacccg   300
ggggctatgg actactgggg tcaaggaacc tcagtcaccg tctcctca                348
```

<210> SEQ ID NO 46
<211> LENGTH: 116
<212> TYPE: PRT
<213> ORGANISM: Artificial Sequence
<220> FEATURE:
<223> OTHER INFORMATION: 3A4 heavy chain variable region

<400> SEQUENCE: 46

```
Gln Ile Gln Leu Val Gln Ser Gly Pro Glu Met Val Lys Pro Gly Ala
 1               5                  10                  15
Ser Val Lys Met Ser Cys Lys Ala Ser Gly Tyr Thr Phe Thr Asp Asp
            20                  25                  30
Tyr Met Ser Trp Val Lys Gln Ser His Gly Lys Ser Leu Glu Trp Ile
        35                  40                  45
Gly Asp Ile Asn Pro Tyr Asn Gly Asp Thr Asn Tyr Asn Gln Lys Phe
    50                  55                  60
Lys Gly Lys Ala Ile Leu Thr Val Asp Lys Ser Ser Thr Ala Tyr
65                  70                  75                  80
Met Gln Leu Asn Ser Leu Thr Ser Glu Asp Ser Ala Val Tyr Tyr Cys
                85                  90                  95
Ala Arg Asp Pro Gly Ala Met Asp Tyr Trp Gly Gln Gly Thr Ser Val
            100                 105                 110
Thr Val Ser Ser
        115
```

<210> SEQ ID NO 47
<211> LENGTH: 336
<212> TYPE: DNA
<213> ORGANISM: Artificial Sequence
<220> FEATURE:
<223> OTHER INFORMATION: 3A4 light chain variable region

<400> SEQUENCE: 47

```
gatgttgtga tgacccaaac tccactctcc ctggctgtca gtcttggaga tcaagcctcc    60
atctcttgca gatctagtca gagccttcta catagtaatg aaacaccta tttagaatgg   120
taccttcaga aaccaggcca gtctccaaag ctcctgatcc acacagtttc caaccgattt   180
tctggggtcc cagacagatt cagtggcagt ggatcaggga cagatttcac actcaagatc   240
agcagagtgg aggctgagga tctgggagtt tattactgct ttcaaggttc acatgttccg   300
ctcacgttcg gtgctgggac caggctggag ctgaaa                            336
```

<210> SEQ ID NO 48
<211> LENGTH: 112
<212> TYPE: PRT
<213> ORGANISM: Artificial Sequence

```
<220> FEATURE:
<223> OTHER INFORMATION: 3A4 light chain variable region

<400> SEQUENCE: 48

Asp Val Val Met Thr Gln Thr Pro Leu Ser Leu Ala Val Ser Leu Gly
1               5                   10                  15

Asp Gln Ala Ser Ile Ser Cys Arg Ser Ser Gln Ser Leu Leu His Ser
            20                  25                  30

Asn Gly Asn Thr Tyr Leu Glu Trp Tyr Leu Gln Lys Pro Gly Gln Ser
        35                  40                  45

Pro Lys Leu Leu Ile His Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Arg Leu Glu Leu Lys
            100                 105                 110

<210> SEQ ID NO 49
<211> LENGTH: 10
<212> TYPE: PRT
<213> ORGANISM: Artificial Sequence
<220> FEATURE:
<223> OTHER INFORMATION: 3A4 heavy chain CDR1

<400> SEQUENCE: 49

Gly Tyr Thr Phe Thr Asp Asp Tyr Met Ser
1               5                   10

<210> SEQ ID NO 50
<211> LENGTH: 17
<212> TYPE: PRT
<213> ORGANISM: Artificial Sequence
<220> FEATURE:
<223> OTHER INFORMATION: 3A4 heavy chain CDR2

<400> SEQUENCE: 50

Asp Ile Asn Pro Tyr Asn Gly Asp Thr Asn Tyr Asn Gln Lys Phe Lys
1               5                   10                  15

Gly

<210> SEQ ID NO 51
<211> LENGTH: 7
<212> TYPE: PRT
<213> ORGANISM: Artificial Sequence
<220> FEATURE:
<223> OTHER INFORMATION: 3A4 heavy chain CDR3

<400> SEQUENCE: 51

Asp Pro Gly Ala Met Asp Tyr
1               5

<210> SEQ ID NO 52
<211> LENGTH: 16
<212> TYPE: PRT
<213> ORGANISM: Artificial Sequence
<220> FEATURE:
<223> OTHER INFORMATION: 3A4 light chain CDR1

<400> SEQUENCE: 52

Arg Ser Ser Gln Ser Leu Leu His Ser Asn Gly Asn Thr Tyr Leu Glu
1               5                   10                  15
```

<210> SEQ ID NO 53
<211> LENGTH: 7
<212> TYPE: PRT
<213> ORGANISM: Artificial Sequence
<220> FEATURE:
<223> OTHER INFORMATION: 3A4 light chain CDR2

<400> SEQUENCE: 53

Thr Val Ser Asn Arg Phe Ser
1               5

<210> SEQ ID NO 54
<211> LENGTH: 9
<212> TYPE: PRT
<213> ORGANISM: Artificial Sequence
<220> FEATURE:
<223> OTHER INFORMATION: 3A4 light chain CDR3

<400> SEQUENCE: 54

Phe Gln Gly Ser His Val Pro Leu Thr
1               5

<210> SEQ ID NO 55
<211> LENGTH: 33
<212> TYPE: DNA
<213> ORGANISM: Artificial Sequence
<220> FEATURE:
<223> OTHER INFORMATION: Primer OSG 1773

<400> SEQUENCE: 55
gtaagcagcg ctgtggctgc accatctgtc ttc                           33

<210> SEQ ID NO 56
<211> LENGTH: 35
<212> TYPE: DNA
<213> ORGANISM: Artificial Sequence
<220> FEATURE:
<223> OTHER INFORMATION: Primer OSG 1774

<400> SEQUENCE: 56
gtaagcgcta gcctaacact ctcccctgtt gaagc                         35

<210> SEQ ID NO 57
<211> LENGTH: 321
<212> TYPE: DNA
<213> ORGANISM: Artificial Sequence
<220> FEATURE:
<223> OTHER INFORMATION: Human kappa constant region

<400> SEQUENCE: 57
gctgtggctg caccatctgt cttcatcttc ccgccatctg atgagcagtt gaaatctgga      60
actgcctctg ttgtgtgcct gctgaataac ttctatccca gagaggccaa agtacagtgg     120
aaggtggata cgcccctcca atcgggtaac tcccaggaga gtgtcacaga gcaggacagc     180
aaggacagca cctacagcct cagcagcacc ctgacgctga gcaaagcaga ctacgagaaa     240
cacaaagtct acgcctgcga agtcacccat cagggcctga gctcgcccgt cacaaagagc     300
ttcaacaggg gagagtgtta g                                              321

<210> SEQ ID NO 58
<211> LENGTH: 106
<212> TYPE: PRT
<213> ORGANISM: Artificial Sequence
<220> FEATURE:

<223> OTHER INFORMATION: Human kappa constant region

<400> SEQUENCE: 58

```
Ala Val Ala Ala Pro Ser Val Phe Ile Phe Pro Pro Ser Asp Glu Gln
1               5                   10                  15
Leu Lys Ser Gly Thr Ala Ser Val Val Cys Leu Leu Asn Asn Phe Tyr
            20                  25                  30
Pro Arg Glu Ala Lys Val Gln Trp Lys Val Asp Asn Ala Leu Gln Ser
        35                  40                  45
Gly Asn Ser Gln Glu Ser Val Thr Glu Gln Asp Ser Lys Asp Ser Thr
    50                  55                  60
Tyr Ser Leu Ser Ser Thr Leu Thr Leu Ser Lys Ala Asp Tyr Glu Lys
65                  70                  75                  80
His Lys Val Tyr Ala Cys Glu Val Thr His Gln Gly Leu Ser Ser Pro
                85                  90                  95
Val Thr Lys Ser Phe Asn Arg Gly Glu Cys
            100                 105
```

<210> SEQ ID NO 59
<211> LENGTH: 6385
<212> TYPE: DNA
<213> ORGANISM: Artificial Sequence
<220> FEATURE:
<223> OTHER INFORMATION: Plasmid pTTVK1

<400> SEQUENCE: 59

```
cttgagccgg cggatggtcg aggtgaggtg tggcaggctt gagatccagc tgttggggtg      60
agtactccct ctcaaaagcg ggcattactt ctgcgctaag attgtcagtt ccaaaaacg      120
aggaggattt gatattcacc tggcccgatc tggccataca cttgagtgac aatgacatcc     180
actttgcctt tctctccaca ggtgtccact cccaggtcca agtttaaacg gatctctagc     240
gaattcatga actttctgct gtcttgggtg cattggagcc ttgccttgct gctctacctc     300
caccatgcca agtggtccca ggcttgagac ggagcttaca gcgctgtggc tgcaccatct     360
gtcttcatct ccgcgccatc tgatgagcag ttgaaatctg gaactgcctc tgttgtgtgc     420
ctgctgaata acttctatcc cagagaggcc aaagtacagt ggaaggtgga taacgccctc     480
caatcgggta actcccagga gagtgtcaca gagcaggaca gcaaggacag cacctacagc     540
ctcagcagca ccctgacgct gagcaaagca gactacgaga acacaaaagt ctacgcctgc     600
gaagtcaccc atcagggcct gagctcgccc gtcacaaaga gcttcaacag gggagagtgt     660
tagggtaccg cggccgcttc gaatgagatc ccccgacctc gacctctggc taataaagga     720
aatttatttt cattgcaata gtgtgttgga attttttgtg tctctcactc ggaaggacat     780
atgggagggc aaatcatttg gtcgagatcc tcggagatc tctagctaga gccccgccgc     840
cggacgaact aaacctgact acggcatctc tgcccttct cgcggggca gtgcatgtaa      900
tcccttcagt tggttggtac aacttgccaa ctgggcctg ttccacatgt gacacggggg      960
gggaccaaac acaaagggt tctctgactg tagttgacat ccttataaat ggatgtgcac     1020
atttgccaac actgagtggc tttcatcctg gagcagactt tgcagtctgt ggactgcaac    1080
acaacattgc ctttatgtgt aactcttggc tgaagctctt acaccaatgc tgggggacat    1140
gtacctccca ggggcccagg aagactacgg gaggctacac caacgtcaat cagaggggcc    1200
tgtgtagcta ccgataagcg gacccctcaag agggcattag caatagtgtt tataaggccc    1260
ccttgttaac cctaaacggg tagcatatgc ttcccgggta gtagtatata ctatccagac    1320
```

```
taaccctaat tcaatagcat atgttaccca acgggaagca tatgctatcg aattagggtt    1380
agtaaaaggg tcctaaggaa cagcgatatc tcccacccca tgagctgtca cggttttatt    1440 tacatgggt  caggattcca cgagggtagt gaaccatttt agtcacaagg cagtggctg     1500 aagatcaagg agcgggcagt gaactctcct gaatcttcgc ctgcttcttc attctccttc    1560
gtttagctaa tagaataact gctgagttgt gaacagtaag gtgtatgtga ggtgctcgaa    1620
aacaaggttt caggtgacgc ccccagaata aaatttggac gggggggttca gtggtggcat    1680 tgtgctatga caccaatata accctcacaa acccccttggg caataaatac tagtgtagga   1740
atgaaacatt ctgaatatct ttaacaatag aaatccatgg ggtggggaca agccgtaaag    1800
actggatgtc catctcacac gaatttatgg ctatgggcaa cacataatcc tagtgcaata    1860
tgatactggg gttattaaga tgtgtcccag gcagggacca agacaggtga accatgttgt    1920
tacactctat ttgtaacaag gggaaagaga gtggacgccg acagcagcgg actccactgg    1980
ttgtctctaa caccccgaa aattaaacgg ggctccacgc caatgggcc cataaacaaa      2040 gacaagtggc cactcttttt tttgaaattg tggagtgggg gcacgcgtca gccccacac    2100 gccgccctgc ggttttggac tgtaaaataa gggtgtaata acttggctga ttgtaacccc    2160
gctaaccact gcggtcaaac cacttgccca caaaaccact aatggcaccc cggggaatac    2220
ctgcataagt aggtgggcgg gccaagatag gggcgcgatt gctgcgatct ggaggacaaa    2280
ttacacacac ttgcgcctga cgccaagca cagggttgtt ggtcctcata ttcacgaggt     2340
cgctgagagc acgtgggct aatgttgcca tgggtagcat atactaccca aatatctgga    2400
tagcatatgc tatcctaatc tatatctggg tagcataggc tatcctaatc tatatctggg    2460
tagcatatgc tatcctaatc tatatctggg tagtatatgc tatcctaatt tatatctggg    2520
tagcataggc tatcctaatc tatatctggg tagcatatgc tatcctaatc tatatctggg    2580
tagtatatgc tatcctaatc tgtatccggg tagcatatgc tatcctaata gagattaggg    2640
tagtatatgc tatcctaatt tatatctggg tagcatatac tacccaaata tctggatagc    2700
atatgctatc ctaatctata tctgggtagc atatgctatc ctaatctata tctgggtagc    2760
ataggctatc ctaatctata tctgggtagc atatgctatc ctaatctata tctgggtagt    2820
atatgctatc ctaatttata tctgggtagc ataggctatc ctaatctata tctgggtagc    2880
atatgctatc ctaatctata tctgggtagt atatgctatc ctaatctgta tccgggtagc    2940
atatgctatc ctcacgatga taagctgtca acatgagaa ttaattcttg aagacgaaag     3000
ggcctcgtga tacgcctatt tttataggtt aatgtcatga taataatggt tcttagacg     3060 tcaggtggca cttttcgggg aaatgtgcgc ggaacccta tttgtttatt tttctaaata     3120
cattcaaata tgtatccgct catgagacaa taaccctgat aaatgcttca ataatattga    3180
aaaaggaaga gtatgagtat caacatttc cgtgtcgccc ttattccctt ttttgcggca     3240
ttttgccttc ctgtttttgc tcacccagaa acgctggtga agtaaaaga tgctgaagat     3300 cagttgggtg cacgagtggg ttacatcgaa ctggatctca acagcggtaa gatccttgag    3360
agttttcgcc ccgaagaacg ttttccaatg atgagcactt taaagttct gctatgtggc     3420 gcggtattat cccgtgttga cgccgggcaa gagcaactcg gtcgccgcat acactattct    3480
cagaatgact tggttgagta ctcaccagtc acagaaaagc atcttacgga tggcatgaca    3540
gtaagagaat tatgcagtgc tgccataacc atgagtgata acactgcggc caacttactt    3600
ctgacaacga tcggaggacc gaaggagcta accgcttttt tgcacaacat ggggatcat     3660 gtaactcgcc ttgatcgttg ggaaccggag ctgaatgaag ccataccaaa cgacgagcgt    3720
```

```
gacaccacga tgcctgcagc aatggcaaca acgttgcgca aactattaac tggcgaacta    3780
cttactctag cttcccggca acaattaata gactggatgg aggcggataa agttgcagga    3840
ccacttctgc gctcggccct tccggctggc tggtttattg ctgataaatc tggagccggt    3900
gagcgtgggt ctcgcggtat cattgcagca ctggggccag atggtaagcc ctcccgtatc    3960
gtagttatct acacgacggg gagtcaggca actatggatg aacgaaatag acagatcgct    4020
gagataggtg cctcactgat taagcattgg taactgtcag accaagttta ctcatatata    4080
ctttagattg atttaaaact tcattttaa tttaaaagga tctaggtgaa gatccttttt    4140
gataatctca tgaccaaaat cccttaacgt gagttttcgt tccactgagc gtcagacccc    4200
gtagaaaaga tcaaaggatc ttcttgagat cctttttttc tgcgcgtaat ctgctgcttg    4260
caaacaaaaa aaccaccgct accagcggtg gtttgtttgc cggatcaaga gctaccaact    4320 cttttttccga aggtaactgg cttcagcaga gcgcagatac caaatactgt ccttctagtg    4380
tagccgtagt taggccacca cttcaagaac tctgtagcac cgcctacata cctcgctctg    4440
ctaatcctgt taccagtggc tgctgccagt ggcgataagt cgtgtcttac cgggttggac    4500
tcaagacgat agttaccgga taaggcgcag cggtcgggct gaacggggggt tcgtgcaca    4560 cagcccagct tggagcgaac gacctacacc gaactgagat acctacagcg tgagcattga    4620
gaaagcgcca cgcttcccga agggagaaag gcggacaggt atccggtaag cggcagggtc    4680
ggaacaggag agcgcacgag ggagcttcca gggggaaacg cctggtatct ttatagtcct    4740
gtcgggtttc gccaccctg acttgagcgt cgatttttgt gatgctcgtc aggggggcgg    4800
agcctatgga aaaacgccag caacgcggcc ttttttacggt tcctggcctt ttgctggcct    4860
tttgctcaca tgttctttcc tgcgttatcc cctgattctg tggataaccg tattaccgcc    4920
tttgagtgag ctgataccgc tcgccgcagc cgaacgaccg agcgcagcga gtcagtgagc    4980
gaggaagcgg aagagcgccc aatacgcaaa ccgcctctcc ccgcgcgttg gccgattcat    5040
taatgcagct ggcacgacag gtttcccgac tggaaagcgg gcagtgagcg caacgcaatt    5100
aatgtgagtt agctcactca ttaggcaccc caggctttac actttatgct tccggctcgt    5160
atgttgtgtg gaattgtgag cggataacaa tttcacacag gaaacagcta tgaccatgat    5220
tacgccaagc tctagctaga ggtcgaccaa ttctcatgtt tgacagctta tcatcgcaga    5280
tccgggcaac gttgttgcat tgctgcaggc gcagaactgg taggtatggc agatctatac    5340
attgaatcaa tattggcaat tagccatatt agtcattggt tatatagcat aaatcaatat    5400
tggctattgg ccattgcata cgttgtatct atatcataat atgtacattt atattggctc    5460
atgtccaata tgaccgccat gttgacattg attattgact agttattaat agtaatcaat    5520
tacggggtca ttagttcata gcccatatat ggagttccgc gttacataac ttacggtaaa    5580
tggcccgcct ggctgaccgc ccaacgaccc ccgcccattg acgtcaataa tgacgtatgt    5640
tcccatagta acgccaatag ggactttcca ttgacgtcaa tgggtggagt atttacggta    5700
aactgcccac ttggcagtac atcaagtgta tcatatgcca agtccgcccc ctattgacgt    5760
caatgacggt aaatggcccg cctggcatta tgcccagtac atgaccttac gggactttcc    5820
tacttggcag tacatctacg tattagtcat cgctattacc atggtgatgc ggttttggca    5880
gtacaccaat gggcgtggat agcggtttga ctcacgggga tttccaagtc tccaccccat    5940
tgacgtcaat gggagtttgt tttggcacca aaatcaacgg gactttccaa aatgtcgtaa    6000
taaccccgcc ccgttgacgc aaatgggcgg taggcgtgta cggtgggagg tctatataag    6060
```

```
cagagctcgt ttagtgaacc gtcagatcct cactctcttc cgcatcgctg tctgcgaggg    6120
ccagctgttg ggctcgcggt tgaggacaaa ctcttcgcgg tctttccagt actcttggat    6180
cggaaacccg tcggcctccg aacggtactc cgccaccgag ggacctgagc gagtccgcat    6240
cgaccggatc ggaaaacctc tcgagaaagg cgtctaacca gtcacagtcg caaggtaggc    6300
tgagcaccgt ggcgggcggc agcgggtggc ggtcgggggtt gtttctggcg gaggtgctgc    6360
tgatgatgta attaaagtag gcggt                                          6385
```

```
<210> SEQ ID NO 60
<211> LENGTH: 43
<212> TYPE: DNA
<213> ORGANISM: Artificial Sequence
<220> FEATURE:
<223> OTHER INFORMATION: primer

<400> SEQUENCE: 60
atgccaagtg gtcccaggct gacattgtga tgacccagtc tcc                      43

<210> SEQ ID NO 61
<211> LENGTH: 43
<212> TYPE: DNA
<213> ORGANISM: Artificial Sequence
<220> FEATURE:
<223> OTHER INFORMATION: primer

<400> SEQUENCE: 61
atgccaagtg gtcccaggct gatgttttga tgacccaaac tcc                      43

<210> SEQ ID NO 62
<211> LENGTH: 43
<212> TYPE: DNA
<213> ORGANISM: Artificial Sequence
<220> FEATURE:
<223> OTHER INFORMATION: primer

<400> SEQUENCE: 62
atgccaagtg gtcccaggct gacatcgtta tgtctcagtc tcc                      43

<210> SEQ ID NO 63
<211> LENGTH: 32
<212> TYPE: DNA
<213> ORGANISM: Artificial Sequence
<220> FEATURE:
<223> OTHER INFORMATION: primer

<400> SEQUENCE: 63
gggaagatga agacagatgg tgcagccaca gc                                  32

<210> SEQ ID NO 64
<211> LENGTH: 50
<212> TYPE: DNA
<213> ORGANISM: Artificial Sequence
<220> FEATURE:
<223> OTHER INFORMATION: primer

<400> SEQUENCE: 64
gtaagcgcta gcgcctcaac gaagggccca tctgtctttc ccctggcccc                50

<210> SEQ ID NO 65
<211> LENGTH: 37
<212> TYPE: DNA
<213> ORGANISM: Artificial Sequence
<220> FEATURE:
<223> OTHER INFORMATION: primer
```

-continued

<400> SEQUENCE: 65
gtaagcgaat tcacaagatt tgggctcaac tttcttg    37

<210> SEQ ID NO 66
<211> LENGTH: 309
<212> TYPE: DNA
<213> ORGANISM: Artificial Sequence
<220> FEATURE:
<223> OTHER INFORMATION: Human IgG1 CH1 region

<400> SEQUENCE: 66
gcctccacca agggcccatc ggtcttcccc ctggcaccct cctccaagag cacctctggg    60
ggcacagcag ccctgggctg cctggtcaag gactacttcc ccgaaccggt gacggtgtcg    120
tggaactcag cgccctgac cagcggcgtg cacaccttcc cggctgtcct acagtcctca    180
ggactctact ccctcagcag cgtggtgacc gtgccctcca gcagcttggg cacccagacc    240
tacatctgca acgtgaatca caagcccagc aacaccaagg tggacaagaa agttgagccc    300
aaatcttgt    309

<210> SEQ ID NO 67
<211> LENGTH: 103
<212> TYPE: PRT
<213> ORGANISM: Artificial Sequence
<220> FEATURE:
<223> OTHER INFORMATION: Human IgG1 CH1 region

<400> SEQUENCE: 67

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys
            100

<210> SEQ ID NO 68
<211> LENGTH: 5379
<212> TYPE: DNA
<213> ORGANISM: Artificial Sequence
<220> FEATURE:
<223> OTHER INFORMATION: Plasmid pYD15

<400> SEQUENCE: 68
cttgagccgg cggatggtcg aggtgaggtg tggcaggctt gagatccagc tgttggggtg    60
agtactccct ctcaaaagcg ggcattactt ctgcgctaag attgtcagtt tccaaaaacg    120
aggaggattt gatattcacc tggcccgatc tggccataca cttgagtgac aatgacatcc    180
actttgcctt tctctccaca ggtgtccact cccaggtcca gtttgccgc caccatggag    240 acagacacac tcctgctatg gtactgctg ctctgggttc caggttccac tggcggagac    300
ggagcttacg ggcccatctg tctttcccct ggccccctcc tccaagagca cctctggggg    360

```
cacagcggcc ctgggctgcc tggtcaagga ctacttcccc gaaccggtga cggtgtcgtg    420
gaactcaggc gccctgacca gcggcgtgca caccttcccg gctgtcctac agtcctcagg    480
actctactcc ctcagcagcg tggtgaccgt gccctccagc agcttgggca cccagaccta    540
catctgcaac gtgaatcaca agcccagcaa caccaaggtg gacaagaaag ttgagcccaa    600
atcttgtgaa ttcactcaca catgcccacc gtgcccagca cctgaactcc tggggggacc    660
gtcagtcttc ctcttccccc caaaacccaa ggacaccctc atgatctccc ggacccctga    720
ggtcacatgc gtggtggtgg acgtgagcca cgaagaccct gaggtcaagt tcaactggta    780
cgtggacggc gtggaggtgc ataatgccaa gacaaagccg cgggaggagc agtacaacag    840
cacgtaccgt gtggtcagcg tcctcaccgt cctgcaccag gactggctga atggcaagga    900
gtacaagtgc aaggtctcca acaaagccct cccagccccc atcgagaaaa ccatctccaa    960
agccaaaggg cagccccgag aaccacaggt gtacaccctg cccccatccc gggatgagct   1020
gaccaagaac caggtcagcc tgacctgcct ggtcaaaggc ttctatccca gcgacatcgc   1080
cgtggagtgg gagagcaatg ggcagccgga gaacaactac aagaccacgc ctcccgtgct   1140
ggactccgac ggctccttct tcctctacag caagctcacc gtggacaaga gcaggtggca   1200 gcagggggaac gtcttctcat gctccgtgat gcatgaggct ctgcacaacc actacacgca   1260
gaagagcctc tccctgtctc cgggaaaatg atccccgac ctcgacctct ggctaataaa   1320
ggaaatttat tttcattgca atagtgtgtt ggaattttt gtgtctctca ctcggaagga   1380
catatgggag ggcaaatcat ttggtcgaga tccctcggag atctctagct agagcccgc   1440 cgccggacga actaaacctg actacggcat ctctgcccct tcttcgcggg gcagtgcatg   1500
taatcccttc agttggttgg tacaacttgc caactgaacc ctaaacgggt agcatatgct   1560
tcccgggtag tagtatatac tatccagact aaccctaatt caatagcata tgttacccaa   1620
cgggaagcat atgctatcga attagggtta gtaaaagggt cctaaggaac agcgatgtag   1680
gtgggcgggc caagataggg gcgcgattgc tgcgatctgg aggacaaatt acacacactt   1740
gcgcctgagc gccaagcaca gggttgttgg tcctcatatt cacgaggtcg ctgagagcac   1800
ggtgggctaa tgttgccatg ggtagcatat actacccaaa tatctggata gcatatgcta   1860
tcctaatcta tatctgggta gcataggcta tcctaatcta tatctgggta gcatatgcta   1920
tcctaatcta tatctgggta gtatatgcta tcctaattta tatctgggta gcataggcta   1980
tcctaatcta tatctgggta gcatatgcta tcctaatcta tatctgggta gtatatgcta   2040
tcctaatctg tatccgggta gcatatgcta tcctaataga gattagggta gtatatgcta   2100
tcctaattta tatctgggta gcatatacta cccaaatatc tggatagcat atgctatcct   2160
aatctatatc tgggtagcat atgctatcct aatctatatc tgggtagcat aggctatcct   2220
aatctatatc tgggtagcat atgctatcct aatctatatc tgggtagtat atgctatcct   2280
aatttatatc tgggtagcat aggctatcct aatctatatc tgggtagcat atgctatcct   2340
aatctatatc tgggtagtat atgctatcct aatctgtatc cgggtagcat atgctatcct   2400
cacgatgata agctgtcaaa catgagaatt aattcttgaa gacgaaaggg cctcgtgata   2460
cgcctatttt tataggttaa tgtcatgata ataatggttt cttagacgtc aggtggcact   2520
tttcggggaa atgtgcgcgg aacccctatt tgtttatttt tctaaataca ttcaaatatg   2580
tatccgctca tgagacaata accctgataa atgcttcaat aatattgaaa aggaagagt   2640 atgagtattc aacatttccg tgtcgccctt attcccttt ttgcggcatt ttgccttcct   2700
```

```
gtttttgctc acccagaaac gctggtgaaa gtaaagatg ctgaagatca gttgggtgca      2760
cgagtgggtt acatcgaact ggatctcaac agcggtaaga tccttgagag ttttcgcccc      2820
gaagaacgtt ttccaatgat gagcactttt aaagttctgc tatgtggcgc ggtattatcc      2880
cgtgttgacg ccgggcaaga gcaactcggt cgccgcatac actattctca gaatgacttg      2940
gttgagtact caccagtcac agaaaagcat cttacggatg gcatgacagt aagagaatta      3000
tgcagtgctg ccataaccat gagtgataac actgcggcca acttacttct gacaacgatc      3060
ggaggaccga aggagctaac cgcttttttg cacaacatgg gggatcatgt aactcgcctt      3120
gatcgttggg aaccggagct gaatgaagcc ataccaaacg acgagcgtga caccacgatg      3180
cctgcagcaa tggcaacaac gttgcgcaaa ctattaactg gcgaactact tactctagct      3240
tcccggcaac aattaataga ctggatggag gcggataaag ttgcaggacc acttctgcgc      3300
tcggcccttc cggctggctg gtttattgct gataaatctg gagccggtga gcgtgggtct      3360
cgcggtatca ttgcagcact ggggccagat ggtaagccct cccgtatcgt agttatctac      3420
acgacgggga gtcaggcaac tatggatgaa cgaaatagac agatcgctga taggtgcc      3480 tcactgatta agcattggta actgtcagac caagtttact catatatact ttagattgat      3540
ttaaaacttc attttaatt taaaaggatc taggtgaaga tccttttga taatctcatg      3600 accaaaatcc cttaacgtga gttttcgttc cactgagcgt cagacccgt agaaaagatc      3660 aaaggatctt cttgagatcc ttttttctg cgcgtaatct gctgcttgca acaaaaaaa      3720 ccaccgctac cagcggtggt ttgtttgccg gatcaagagc taccaactct ttttccgaag      3780
gtaactggct tcagcagagc gcagatacca atactgtcc ttctagtgta gccgtagtta      3840
ggccaccact tcaagaactc tgtagcaccg cctacatacc tcgctctgct aatcctgtta      3900
ccagtggctg ctgccagtgg cgataagtcg tgtcttaccg ggttggactc aagacgatag      3960
ttaccggata aggcgcagcg tcgggctga acggggggtt cgtgcacaca gcccagcttg      4020
gagcgaacga cctacaccga actgagatac ctacagcgtg agcattgaga aagcgccacg      4080
cttcccgaag ggagaaaggc ggacaggtat ccggtaagcg gcagggtcgg aacaggagag      4140
cgcacgaggg agcttccagg gggaaacgcc tggtatcttt atagtcctgt cgggtttcgc      4200
cacctctgac ttgagcgtcg atttttgtga tgctcgtcag ggggcggag cctatggaaa      4260 aacgccagca acgcggcctt tttacggttc ctggcctttt gctggccttt tgctcacatg      4320 ttcttttcctg cgttatcccc tgattctgtg ataaccgta ttaccgcctt tgagtgagct      4380
gataccgctc gccgcagccg aacgaccgag cgcagcgagt cagtgagcga ggaagcgtac      4440
atttatattg gctcatgtcc aatatgaccg ccatgttgac attgattatt gactagttat      4500
taatagtaat caattacggg gtcattagtt catagcccat atatggagtt ccgcgttaca      4560
taacttacgg taaatggccc gcctggctga ccgcccaacg acccccgccc attgacgtca      4620
ataatgacgt atgttcccat agtaacgcca tagggactt tccattgacg tcaatgggtg      4680
gagtatttac ggtaaactgc ccacttggca gtacatcaag tgtatcatat gccaagtccg      4740 cccctattg acgtcaatga cggtaaatgg cccgcctggc attatgccca gtacatgacc      4800
ttacgggact ttcctacttg gcagtacatc tacgtattag tcatcgctat taccatggtg      4860
atgcggtttt ggcagtacac caatgggcgt ggatagcggt ttgactcacg ggatttcca      4920 agtctccacc ccattgacgt caatgggagt ttgttttggc accaaaatca acgggacttt      4980
ccaaaatgtc gtaataaccc cgccccgttg acgcaaatgg gcggtaggcg tgtacggtgg      5040
gaggtctata taagcagagc tcgtttagtg aaccgtcaga tcctcactct cttccgcatc      5100
```

```
gctgtctgcg agggccagct gttgggctcg cggttgagga caaactcttc gcggtctttc    5160
cagtactctt ggatcggaaa cccgtcggcc tccgaacggt actccgccac cgagggacct    5220
gagcgagtcc gcatcgaccg gatcggaaaa cctctcgaga aaggcgtcta accagtcaca    5280
gtcgcaaggt aggctgagca ccgtggcggg cggcagcggg tggcggtcgg ggttgtttct    5340
ggcggaggtg ctgctgatga tgtaattaaa gtaggcggt                            5379
```

<210> SEQ ID NO 69
<211> LENGTH: 43
<212> TYPE: DNA
<213> ORGANISM: Artificial Sequence
<220> FEATURE:
<223> OTHER INFORMATION: primer

<400> SEQUENCE: 69
gggttccagg ttccactggc gaggttcagc tgcagcagtc tgt                       43

<210> SEQ ID NO 70
<211> LENGTH: 43
<212> TYPE: DNA
<213> ORGANISM: Artificial Sequence
<220> FEATURE:
<223> OTHER INFORMATION: primer

<400> SEQUENCE: 70
gggttccagg ttccactggc gaggtgcagc ttcaggagtc agg                       43

<210> SEQ ID NO 71
<211> LENGTH: 38
<212> TYPE: DNA
<213> ORGANISM: Artificial Sequence
<220> FEATURE:
<223> OTHER INFORMATION: primer

<400> SEQUENCE: 71
ggggccaggg gaaagacaga tgggcccttc gttgaggc                             38

<210> SEQ ID NO 72
<211> LENGTH: 17
<212> TYPE: PRT
<213> ORGANISM: Artificial Sequence
<220> FEATURE:
<223> OTHER INFORMATION: light chain CDR1 consensus
<220> FEATURE:
<221> NAME/KEY: MISC_FEATURE
<222> LOCATION: (1)..(1)
<223> OTHER INFORMATION: Xaa may be a basic amino acid
<220> FEATURE:
<221> NAME/KEY: MISC_FEATURE
<222> LOCATION: (4)..(4)
<223> OTHER INFORMATION: Xaa may be a basic amino acid
<220> FEATURE:
<221> NAME/KEY: MISC_FEATURE
<222> LOCATION: (8)..(8)
<223> OTHER INFORMATION: Xaa may be H, Y or N
<220> FEATURE:
<221> NAME/KEY: MISC_FEATURE
<222> LOCATION: (9)..(9)
<223> OTHER INFORMATION: Xaa may be S, T, N or R
<220> FEATURE:
<221> NAME/KEY: MISC_FEATURE
<222> LOCATION: (10)..(10)
<223> OTHER INFORMATION: Xaa may be absent, S or N
<220> FEATURE:
<221> NAME/KEY: MISC_FEATURE
<222> LOCATION: (11)..(11)
<223> OTHER INFORMATION: Xaa may be D, F or N
<220> FEATURE:

```
<221> NAME/KEY: MISC_FEATURE
<222> LOCATION: (12)..(12)
<223> OTHER INFORMATION: Xaa may be G or Q
<220> FEATURE:
<221> NAME/KEY: MISC_FEATURE
<222> LOCATION: (13)..(13)
<223> OTHER INFORMATION: Xaa may be K, L or N
<220> FEATURE:
<221> NAME/KEY: MISC_FEATURE
<222> LOCATION: (14)..(14)
<223> OTHER INFORMATION: Xaa may be T or N
<220> FEATURE:
<221> NAME/KEY: MISC_FEATURE
<222> LOCATION: (15)..(15)
<223> OTHER INFORMATION: Xaa may be an aromatic amino acid
<220> FEATURE:
<221> NAME/KEY: MISC_FEATURE
<222> LOCATION: (17)..(17)
<223> OTHER INFORMATION: Xaa may be A, N, E or Y

<400> SEQUENCE: 72

Xaa Ser Ser Xaa Ser Leu Leu Xaa Xaa Xaa Xaa Xaa Xaa Xaa Xaa Leu
1               5                   10                  15

Xaa

<210> SEQ ID NO 73
<211> LENGTH: 11
<212> TYPE: PRT
<213> ORGANISM: Artificial Sequence
<220> FEATURE:
<223> OTHER INFORMATION: light chain CDR1 consensus
<220> FEATURE:
<221> NAME/KEY: MISC_FEATURE
<222> LOCATION: (6)..(6)
<223> OTHER INFORMATION: Xaa may be an hydrophobic amino acid
<220> FEATURE:
<221> NAME/KEY: MISC_FEATURE
<222> LOCATION: (7)..(7)
<223> OTHER INFORMATION: Xaa may be G or H
<220> FEATURE:
<221> NAME/KEY: MISC_FEATURE
<222> LOCATION: (8)..(8)
<223> OTHER INFORMATION: Xaa may be T, N or R
<220> FEATURE:
<221> NAME/KEY: MISC_FEATURE
<222> LOCATION: (9)..(9)
<223> OTHER INFORMATION: Xaa may be F, Y or A
<220> FEATURE:
<221> NAME/KEY: MISC_FEATURE
<222> LOCATION: (10)..(10)
<223> OTHER INFORMATION: Xaa may be an hydrophobic amino acid
<220> FEATURE:
<221> NAME/KEY: MISC_FEATURE
<222> LOCATION: (11)..(11)
<223> OTHER INFORMATION: Xaa may be N or A

<400> SEQUENCE: 73

Lys Ala Ser Gln Asp Xaa Xaa Xaa Xaa Xaa Xaa
1               5                   10

<210> SEQ ID NO 74
<211> LENGTH: 7
<212> TYPE: PRT
<213> ORGANISM: Artificial Sequence
<220> FEATURE:
<223> OTHER INFORMATION: light chain CDR2 consensus
<220> FEATURE:
<221> NAME/KEY: MISC_FEATURE
<222> LOCATION: (2)..(2)
<223> OTHER INFORMATION: Xaa may be A or G
<220> FEATURE:
<221> NAME/KEY: MISC_FEATURE
<222> LOCATION: (5)..(5)
<223> OTHER INFORMATION: Xaa may be R or T
```

```
<220> FEATURE:
<221> NAME/KEY: MISC_FEATURE
<222> LOCATION: (6)..(6)
<223> OTHER INFORMATION: Xaa may be E, K or A

<400> SEQUENCE: 74

Phe Xaa Ser Thr Xaa Xaa Ser
1               5

<210> SEQ ID NO 75
<211> LENGTH: 7
<212> TYPE: PRT
<213> ORGANISM: Artificial Sequence
<220> FEATURE:
<223> OTHER INFORMATION: light chain CDR2 consensus
<220> FEATURE:
<221> NAME/KEY: MISC_FEATURE
<222> LOCATION: (1)..(1)
<223> OTHER INFORMATION: Xaa may be L or K
<220> FEATURE:
<221> NAME/KEY: MISC_FEATURE
<222> LOCATION: (4)..(4)
<223> OTHER INFORMATION: Xaa may be a basic amino acid
<220> FEATURE:
<221> NAME/KEY: MISC_FEATURE
<222> LOCATION: (5)..(5)
<223> OTHER INFORMATION: Xaa may be L or R
<220> FEATURE:
<221> NAME/KEY: MISC_FEATURE
<222> LOCATION: (6)..(6)
<223> OTHER INFORMATION: Xaa may be D or F

<400> SEQUENCE: 75

Xaa Val Ser Xaa Xaa Xaa Ser
1               5

<210> SEQ ID NO 76
<211> LENGTH: 7
<212> TYPE: PRT
<213> ORGANISM: Artificial Sequence
<220> FEATURE:
<223> OTHER INFORMATION: light chain CDR2 consensus
<220> FEATURE:
<221> NAME/KEY: MISC_FEATURE
<222> LOCATION: (1)..(1)
<223> OTHER INFORMATION: Xaa may be a basic amino acid
<220> FEATURE:
<221> NAME/KEY: MISC_FEATURE
<222> LOCATION: (7)..(7)
<223> OTHER INFORMATION: Xaa may be D or A

<400> SEQUENCE: 76

Xaa Ala Asn Arg Leu Val Xaa
1               5

<210> SEQ ID NO 77
<211> LENGTH: 9
<212> TYPE: PRT
<213> ORGANISM: Artificial Sequence
<220> FEATURE:
<223> OTHER INFORMATION: light chain CDR3 consensus
<220> FEATURE:
<221> NAME/KEY: MISC_FEATURE
<222> LOCATION: (1)..(1)
<223> OTHER INFORMATION: Xaa may be Q or L
<220> FEATURE:
<221> NAME/KEY: MISC_FEATURE
<222> LOCATION: (3)..(3)
<223> OTHER INFORMATION: Xaa may be an aromatic amino acid
<220> FEATURE:
<221> NAME/KEY: MISC_FEATURE
<222> LOCATION: (4)..(4)
<223> OTHER INFORMATION: Xaa may be D, F or Y
```

```
<220> FEATURE:
<221> NAME/KEY: MISC_FEATURE
<222> LOCATION: (5)..(5)
<223> OTHER INFORMATION: Xaa may be E, A, N or S
<220> FEATURE:
<221> NAME/KEY: MISC_FEATURE
<222> LOCATION: (6)..(6)
<223> OTHER INFORMATION: Xaa may be I, F or T

<400> SEQUENCE: 77

Xaa Gln Xaa Xaa Xaa Xaa Pro Leu Thr
1               5

<210> SEQ ID NO 78
<211> LENGTH: 9
<212> TYPE: PRT
<213> ORGANISM: Artificial Sequence
<220> FEATURE:
<223> OTHER INFORMATION: light chain CDR3 consensus
<220> FEATURE:
<221> NAME/KEY: MISC_FEATURE
<222> LOCATION: (4)..(4)
<223> OTHER INFORMATION: Xaa may be an aromatic amino acid
<220> FEATURE:
<221> NAME/KEY: MISC_FEATURE
<222> LOCATION: (5)..(5)
<223> OTHER INFORMATION: Xaa may be N or S
<220> FEATURE:
<221> NAME/KEY: MISC_FEATURE
<222> LOCATION: (6)..(6)
<223> OTHER INFORMATION: Xaa may be I or T

<400> SEQUENCE: 78

Gln Gln His Xaa Xaa Xaa Pro Leu Thr
1               5

<210> SEQ ID NO 79
<211> LENGTH: 9
<212> TYPE: PRT
<213> ORGANISM: Artificial Sequence
<220> FEATURE:
<223> OTHER INFORMATION: light chain CDR3 consensus
<220> FEATURE:
<221> NAME/KEY: MISC_FEATURE
<222> LOCATION: (1)..(1)
<223> OTHER INFORMATION: Xaa may be an aromatic amino acid
<220> FEATURE:
<221> NAME/KEY: MISC_FEATURE
<222> LOCATION: (4)..(4)
<223> OTHER INFORMATION: Xaa may be a neutral hydrophilic amino acid
<220> FEATURE:
<221> NAME/KEY: MISC_FEATURE
<222> LOCATION: (6)..(6)
<223> OTHER INFORMATION: Xaa may be F or V
<220> FEATURE:
<221> NAME/KEY: MISC_FEATURE
<222> LOCATION: (8)..(8)
<223> OTHER INFORMATION: Xaa may be R or L

<400> SEQUENCE: 79

Xaa Gln Gly Xaa His Xaa Pro Xaa Thr
1               5

<210> SEQ ID NO 80
<211> LENGTH: 10
<212> TYPE: PRT
<213> ORGANISM: Artificial Sequence
<220> FEATURE:
<223> OTHER INFORMATION: heavy chain CDR1 consensus
<220> FEATURE:
<221> NAME/KEY: MISC_FEATURE
<222> LOCATION: (3)..(3)
<223> OTHER INFORMATION: Xaa may be T, I or K
```

```
<220> FEATURE:
<221> NAME/KEY: MISC_FEATURE
<222> LOCATION: (5)..(5)
<223> OTHER INFORMATION: Xaa may be a neutral hydrophilic amino acid
<220> FEATURE:
<221> NAME/KEY: MISC_FEATURE
<222> LOCATION: (6)..(6)
<223> OTHER INFORMATION: Xaa may be an acidic amino acid
<220> FEATURE:
<221> NAME/KEY: MISC_FEATURE
<222> LOCATION: (8)..(8)
<223> OTHER INFORMATION: Xaa may be E, N or D
<220> FEATURE:
<221> NAME/KEY: MISC_FEATURE
<222> LOCATION: (9)..(9)
<223> OTHER INFORMATION: Xaa may be an hydrophobic amino acid

<400> SEQUENCE: 80

Gly Tyr Xaa Phe Xaa Xaa Tyr Xaa Xaa His
1               5                   10

<210> SEQ ID NO 81
<211> LENGTH: 10
<212> TYPE: PRT
<213> ORGANISM: Artificial Sequence
<220> FEATURE:
<223> OTHER INFORMATION: heavy chain CDR2 consensus
<220> FEATURE:
<221> NAME/KEY: MISC_FEATURE
<222> LOCATION: (1)..(1)
<223> OTHER INFORMATION: Xaa may be V or G
<220> FEATURE:
<221> NAME/KEY: MISC_FEATURE
<222> LOCATION: (2)..(2)
<223> OTHER INFORMATION: Xaa may be an hydrophobic amino acid
<220> FEATURE:
<221> NAME/KEY: MISC_FEATURE
<222> LOCATION: (5)..(5)
<223> OTHER INFORMATION: Xaa may be A, G or E
<220> FEATURE:
<221> NAME/KEY: MISC_FEATURE
<222> LOCATION: (8)..(8)
<223> OTHER INFORMATION: Xaa may be R, G, D, A, S, N or V
<220> FEATURE:
<221> NAME/KEY: MISC_FEATURE
<222> LOCATION: (10)..(10)
<223> OTHER INFORMATION: Xaa may be an hydrophobic amino acid

<400> SEQUENCE: 81

Xaa Xaa Asp Pro Xaa Thr Gly Xaa Thr Xaa
1               5                   10

<210> SEQ ID NO 82
<211> LENGTH: 10
<212> TYPE: PRT
<213> ORGANISM: Artificial Sequence
<220> FEATURE:
<223> OTHER INFORMATION: heavy chain CDR2 consensus
<220> FEATURE:
<221> NAME/KEY: MISC_FEATURE
<222> LOCATION: (2)..(2)
<223> OTHER INFORMATION: Xaa may be an hydrophobic amino acid
<220> FEATURE:
<221> NAME/KEY: MISC_FEATURE
<222> LOCATION: (5)..(5)
<223> OTHER INFORMATION: Xaa may be A, E or G
<220> FEATURE:
<221> NAME/KEY: MISC_FEATURE
<222> LOCATION: (8)..(8)
<223> OTHER INFORMATION: Xaa may be R, G, A, S, N, V or D

<400> SEQUENCE: 82

Val Xaa Asp Pro Xaa Thr Gly Xaa Thr Ala
1               5                   10
```

```
<210> SEQ ID NO 83
<211> LENGTH: 9
<212> TYPE: PRT
<213> ORGANISM: Artificial Sequence
<220> FEATURE:
<223> OTHER INFORMATION: heavy chain CDR2 consensus
<220> FEATURE:
<221> NAME/KEY: MISC_FEATURE
<222> LOCATION: (3)..(3)
<223> OTHER INFORMATION: Xaa may be S or N
<220> FEATURE:
<221> NAME/KEY: MISC_FEATURE
<222> LOCATION: (4)..(4)
<223> OTHER INFORMATION: Xaa may be an aromatic amino acid
<220> FEATURE:
<221> NAME/KEY: MISC_FEATURE
<222> LOCATION: (5)..(5)
<223> OTHER INFORMATION: Xaa may be D, E or N
<220> FEATURE:
<221> NAME/KEY: MISC_FEATURE
<222> LOCATION: (7)..(7)
<223> OTHER INFORMATION: Xaa may be D or H
<220> FEATURE:
<221> NAME/KEY: MISC_FEATURE
<222> LOCATION: (8)..(8)
<223> OTHER INFORMATION: Xaa may be Y, S or N
<220> FEATURE:
<221> NAME/KEY: MISC_FEATURE
<222> LOCATION: (9)..(9)
<223> OTHER INFORMATION: Xaa may be D, E or N

<400> SEQUENCE: 83

Tyr Ile Xaa Xaa Xaa Gly Xaa Xaa Xaa
1               5

<210> SEQ ID NO 84
<211> LENGTH: 10
<212> TYPE: PRT
<213> ORGANISM: Artificial Sequence
<220> FEATURE:
<223> OTHER INFORMATION: heavy chain CDR2 consensus
<220> FEATURE:
<221> NAME/KEY: MISC_FEATURE
<222> LOCATION: (1)..(1)
<223> OTHER INFORMATION: Xaa may be N or Y
<220> FEATURE:
<221> NAME/KEY: MISC_FEATURE
<222> LOCATION: (7)..(7)
<223> OTHER INFORMATION: Xaa may be E, D or N

<400> SEQUENCE: 84

Xaa Ile Asn Pro Tyr Asn Xaa Val Thr Glu
1               5                   10

<210> SEQ ID NO 85
<211> LENGTH: 10
<212> TYPE: PRT
<213> ORGANISM: Artificial Sequence
<220> FEATURE:
<223> OTHER INFORMATION: heavy chain CDR2 consensus
<220> FEATURE:
<221> NAME/KEY: MISC_FEATURE
<222> LOCATION: (5)..(5)
<223> OTHER INFORMATION: Xaa may be N or Y
<220> FEATURE:
<221> NAME/KEY: MISC_FEATURE
<222> LOCATION: (8)..(8)
<223> OTHER INFORMATION: Xaa may be G or T
<220> FEATURE:
<221> NAME/KEY: MISC_FEATURE
<222> LOCATION: (9)..(9)
<223> OTHER INFORMATION: Xaa may be I or T
```

```
<400> SEQUENCE: 85

Asp Ile Asn Pro Xaa Tyr Gly Xaa Xaa Thr
1               5                   10

<210> SEQ ID NO 86
<211> LENGTH: 6
<212> TYPE: PRT
<213> ORGANISM: Artificial Sequence
<220> FEATURE:
<223> OTHER INFORMATION: heavy chain CDR3 consensus
<220> FEATURE:
<221> NAME/KEY: MISC_FEATURE
<222> LOCATION: (2)..(2)
<223> OTHER INFORMATION: Xaa may be G or S
<220> FEATURE:
<221> NAME/KEY: MISC_FEATURE
<222> LOCATION: (3)..(3)
<223> OTHER INFORMATION: Xaa may be Y or H
<220> FEATURE:
<221> NAME/KEY: MISC_FEATURE
<222> LOCATION: (4)..(4)
<223> OTHER INFORMATION: Xaa may be A or S

<400> SEQUENCE: 86

Met Xaa Xaa Xaa Asp Tyr
1               5

<210> SEQ ID NO 87
<211> LENGTH: 7
<212> TYPE: PRT
<213> ORGANISM: Artificial Sequence
<220> FEATURE:
<223> OTHER INFORMATION: heavy chain CDR3 consensus
<220> FEATURE:
<221> NAME/KEY: MISC_FEATURE
<222> LOCATION: (2)..(2)
<223> OTHER INFORMATION: Xaa may be G or S
<220> FEATURE:
<221> NAME/KEY: MISC_FEATURE
<222> LOCATION: (5)..(5)
<223> OTHER INFORMATION: Xaa may be absent or M

<400> SEQUENCE: 87

Ile Xaa Tyr Ala Xaa Asp Tyr
1               5

<210> SEQ ID NO 88
<211> LENGTH: 7
<212> TYPE: PRT
<213> ORGANISM: Artificial Sequence
<220> FEATURE:
<223> OTHER INFORMATION: heavy chain CDR3 consensus
<220> FEATURE:
<221> NAME/KEY: MISC_FEATURE
<222> LOCATION: (2)..(2)
<223> OTHER INFORMATION: Xaa may be R or W
<220> FEATURE:
<221> NAME/KEY: MISC_FEATURE
<222> LOCATION: (3)..(3)
<223> OTHER INFORMATION: Xaa may be an aromatic amino acid
<220> FEATURE:
<221> NAME/KEY: MISC_FEATURE
<222> LOCATION: (7)..(7)
<223> OTHER INFORMATION: Xaa may be a basic amino acid

<400> SEQUENCE: 88

Ala Xaa Xaa Gly Leu Arg Xaa
1               5

<210> SEQ ID NO 89
<211> LENGTH: 17
```

```
<212> TYPE: PRT
<213> ORGANISM: Artificial Sequence
<220> FEATURE:
<223> OTHER INFORMATION: CDRL1 consensus
<220> FEATURE:
<221> NAME/KEY: MISC_FEATURE
<222> LOCATION: (8)..(8)
<223> OTHER INFORMATION: Xaa may be N or H
<220> FEATURE:
<221> NAME/KEY: MISC_FEATURE
<222> LOCATION: (9)..(9)
<223> OTHER INFORMATION: Xaa may be S or T
<220> FEATURE:
<221> NAME/KEY: MISC_FEATURE
<222> LOCATION: (10)..(10)
<223> OTHER INFORMATION: Xaa may be S, N or D
<220> FEATURE:
<221> NAME/KEY: MISC_FEATURE
<222> LOCATION: (11)..(11)
<223> OTHER INFORMATION: Xaa may be N or G
<220> FEATURE:
<221> NAME/KEY: MISC_FEATURE
<222> LOCATION: (12)..(12)
<223> OTHER INFORMATION: Xaa may be Q, N or K
<220> FEATURE:
<221> NAME/KEY: MISC_FEATURE
<222> LOCATION: (13)..(13)
<223> OTHER INFORMATION: Xaa may be K or L

<400> SEQUENCE: 89

Lys Ser Ser Gln Ser Leu Leu Xaa Xaa Xaa Xaa Xaa Xaa Asn Tyr Leu
1               5                   10                  15

Ala

<210> SEQ ID NO 90
<211> LENGTH: 11
<212> TYPE: PRT
<213> ORGANISM: Artificial Sequence
<220> FEATURE:
<223> OTHER INFORMATION: CDRL1 consensus
<220> FEATURE:
<221> NAME/KEY: MISC_FEATURE
<222> LOCATION: (8)..(8)
<223> OTHER INFORMATION: Xaa may be N or T
<220> FEATURE:
<221> NAME/KEY: MISC_FEATURE
<222> LOCATION: (9)..(9)
<223> OTHER INFORMATION: Xaa may be Y or F

<400> SEQUENCE: 90

Lys Ala Ser Gln Asp Ile His Xaa Xaa Leu Asn
1               5                   10

<210> SEQ ID NO 91
<211> LENGTH: 7
<212> TYPE: PRT
<213> ORGANISM: Artificial Sequence
<220> FEATURE:
<223> OTHER INFORMATION: CDRL2 consensus

<400> SEQUENCE: 91

Phe Ala Ser Thr Arg Glu Ser
1               5

<210> SEQ ID NO 92
<211> LENGTH: 7
<212> TYPE: PRT
<213> ORGANISM: Artificial Sequence
<220> FEATURE:
<223> OTHER INFORMATION: CDRL2 consensus

<400> SEQUENCE: 92
```

```
Leu Val Ser Lys Leu Asp Ser
1               5

<210> SEQ ID NO 93
<211> LENGTH: 7
<212> TYPE: PRT
<213> ORGANISM: Artificial Sequence
<220> FEATURE:
<223> OTHER INFORMATION: CDRL2 consensus

<400> SEQUENCE: 93

Arg Ala Asn Arg Leu Val Asp
1               5

<210> SEQ ID NO 94
<211> LENGTH: 9
<212> TYPE: PRT
<213> ORGANISM: Artificial Sequence
<220> FEATURE:
<223> OTHER INFORMATION: CDRL3 consensus

<400> SEQUENCE: 94

Gln Gln His Tyr Ser Thr Pro Leu Thr
1               5

<210> SEQ ID NO 95
<211> LENGTH: 9
<212> TYPE: PRT
<213> ORGANISM: Artificial Sequence
<220> FEATURE:
<223> OTHER INFORMATION: CDRL3 consensus
<220> FEATURE:
<221> NAME/KEY: MISC_FEATURE
<222> LOCATION: (1)..(1)
<223> OTHER INFORMATION: Xaa may be W or L
<220> FEATURE:
<221> NAME/KEY: MISC_FEATURE
<222> LOCATION: (3)..(3)
<223> OTHER INFORMATION: Xaa may be Y or G
<220> FEATURE:
<221> NAME/KEY: MISC_FEATURE
<222> LOCATION: (4)..(4)
<223> OTHER INFORMATION: Xaa may be D or T
<220> FEATURE:
<221> NAME/KEY: MISC_FEATURE
<222> LOCATION: (5)..(5)
<223> OTHER INFORMATION: Xaa may be A, E or H

<400> SEQUENCE: 95

Xaa Gln Xaa Xaa Xaa Phe Pro Arg Thr
1               5

<210> SEQ ID NO 96
<211> LENGTH: 10
<212> TYPE: PRT
<213> ORGANISM: Artificial Sequence
<220> FEATURE:
<223> OTHER INFORMATION: CDRH1 consensus
<220> FEATURE:
<221> NAME/KEY: MISC_FEATURE
<222> LOCATION: (3)..(3)
<223> OTHER INFORMATION: Xaa may be T or I
<220> FEATURE:
<221> NAME/KEY: MISC_FEATURE
<222> LOCATION: (6)..(6)
<223> OTHER INFORMATION: Xaa may be D or E
<220> FEATURE:
<221> NAME/KEY: MISC_FEATURE
<222> LOCATION: (8)..(8)
<223> OTHER INFORMATION: Xaa may be E or N
<220> FEATURE:
```

```
<221> NAME/KEY: MISC_FEATURE
<222> LOCATION: (9)..(9)
<223> OTHER INFORMATION: Xaa may be M, I or V

<400> SEQUENCE: 96

Gly Tyr Xaa Phe Thr Xaa Tyr Xaa Xaa His
1               5                   10

<210> SEQ ID NO 97
<211> LENGTH: 11
<212> TYPE: PRT
<213> ORGANISM: Artificial Sequence
<220> FEATURE:
<223> OTHER INFORMATION: CDRH1 consensus
<220> FEATURE:
<221> NAME/KEY: MISC_FEATURE
<222> LOCATION: (3)..(3)
<223> OTHER INFORMATION: Xaa may be T or S

<400> SEQUENCE: 97

Gly Phe Xaa Ile Thr Ser Gly Tyr Gly Trp His
1               5                   10

<210> SEQ ID NO 98
<211> LENGTH: 10
<212> TYPE: PRT
<213> ORGANISM: Artificial Sequence
<220> FEATURE:
<223> OTHER INFORMATION: CDRH2 consensus
<220> FEATURE:
<221> NAME/KEY: MISC_FEATURE
<222> LOCATION: (1)..(1)
<223> OTHER INFORMATION: Xaa may be V, N or G
<220> FEATURE:
<221> NAME/KEY: MISC_FEATURE
<222> LOCATION: (2)..(2)
<223> OTHER INFORMATION: Xaa may be I or L
<220> FEATURE:
<221> NAME/KEY: MISC_FEATURE
<222> LOCATION: (5)..(5)
<223> OTHER INFORMATION: Xaa may be E, A or G
<220> FEATURE:
<221> NAME/KEY: MISC_FEATURE
<222> LOCATION: (6)..(6)
<223> OTHER INFORMATION: Xaa may be T or Y
<220> FEATURE:
<221> NAME/KEY: MISC_FEATURE
<222> LOCATION: (8)..(8)
<223> OTHER INFORMATION: Xaa can be any naturally occurring amino acid

<400> SEQUENCE: 98

Xaa Xaa Asp Pro Xaa Xaa Gly Xaa Thr Ala
1               5                   10

<210> SEQ ID NO 99
<211> LENGTH: 6
<212> TYPE: PRT
<213> ORGANISM: Artificial Sequence
<220> FEATURE:
<223> OTHER INFORMATION: CDRH2 consensus
<220> FEATURE:
<221> NAME/KEY: MISC_FEATURE
<222> LOCATION: (3)..(3)
<223> OTHER INFORMATION: Xaa may be N or S
<220> FEATURE:
<221> NAME/KEY: MISC_FEATURE
<222> LOCATION: (4)..(4)
<223> OTHER INFORMATION: Xaa may be F or Y
<220> FEATURE:
<221> NAME/KEY: MISC_FEATURE
<222> LOCATION: (5)..(5)
<223> OTHER INFORMATION: Xaa may be N or D
```

```
<400> SEQUENCE: 99

Tyr Ile Xaa Xaa Xaa Gly
1               5

<210> SEQ ID NO 100
<211> LENGTH: 6
<212> TYPE: PRT
<213> ORGANISM: Artificial Sequence
<220> FEATURE:
<223> OTHER INFORMATION: CDRH3 consensus
<220> FEATURE:
<221> NAME/KEY: MISC_FEATURE
<222> LOCATION: (4)..(4)
<223> OTHER INFORMATION: Xaa may be S or A

<400> SEQUENCE: 100

Met Gly Tyr Xaa Asp Tyr
1               5

<210> SEQ ID NO 101
<211> LENGTH: 10
<212> TYPE: PRT
<213> ORGANISM: Artificial Sequence
<220> FEATURE:
<223> OTHER INFORMATION: CDRH3 consensus

<400> SEQUENCE: 101

Ala Ser Ser Tyr Asp Gly Phe Leu Ala Tyr
1               5                   10

<210> SEQ ID NO 102
<211> LENGTH: 7
<212> TYPE: PRT
<213> ORGANISM: Artificial Sequence
<220> FEATURE:
<223> OTHER INFORMATION: CDRH3 consensus
<220> FEATURE:
<221> NAME/KEY: MISC_FEATURE
<222> LOCATION: (2)..(2)
<223> OTHER INFORMATION: Xaa may be R or W
<220> FEATURE:
<221> NAME/KEY: MISC_FEATURE
<222> LOCATION: (3)..(3)
<223> OTHER INFORMATION: Xaa may be W or F
<220> FEATURE:
<221> NAME/KEY: MISC_FEATURE
<222> LOCATION: (7)..(7)
<223> OTHER INFORMATION: Xaa may be Q or N

<400> SEQUENCE: 102

Ala Xaa Xaa Gly Leu Arg Xaa
1               5

<210> SEQ ID NO 103
<211> LENGTH: 112
<212> TYPE: PRT
<213> ORGANISM: Artificial Sequence
<220> FEATURE:
<223> OTHER INFORMATION: 3A2 light chain variable region

<400> SEQUENCE: 103

Asp Ala Val Met Thr Gln Ile Pro Leu Thr Leu Ser Val Thr Ile Gly
1               5                   10                  15

Gln Pro Ala Ser Leu Ser Cys Lys Ser Ser Gln Ser Leu Leu His Ser
            20                  25                  30

Asp Gly Lys Thr Tyr Leu Asn Trp Leu Leu Gln Arg Pro Gly Gln Ser
        35                  40                  45
```

```
Pro Lys Arg Leu Ile Ser Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Leu Tyr Tyr Cys Trp Gln Gly
                85                  90                  95

Thr His Phe Pro Arg Thr Phe Ala Gly Gly Thr Asn Leu Glu Ile Lys
                100                 105                 110
```

<210> SEQ ID NO 104
<211> LENGTH: 112
<212> TYPE: PRT
<213> ORGANISM: Artificial Sequence
<220> FEATURE:
<223> OTHER INFORMATION: 3F6 light chain variable region

<400> SEQUENCE: 104

```
Ser Ile Val Met Thr Gln Thr Pro Leu Thr Leu Ser Val Thr Ile Gly
1               5                   10                  15

Gln Pro Ala Ser Ile Thr Cys Lys Ser Ser Gln Ser Leu Leu Tyr Ser
                20                  25                  30

Asp Gly Lys Thr Tyr Leu Asn Trp Leu Leu Gln Arg Pro Gly Gln Ser
            35                  40                  45

Pro Lys Arg Leu Ile Ser Leu Val Ser Lys Leu Asp Ser Gly Val Pro
    50                  55                  60

Asp Gly Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Arg Thr Phe Gly Gly Gly Thr Lys Leu Glu Ile Lys
                100                 105                 110
```

<210> SEQ ID NO 105
<211> LENGTH: 112
<212> TYPE: PRT
<213> ORGANISM: Artificial Sequence
<220> FEATURE:
<223> OTHER INFORMATION: 3E8 light chain variable region

<400> SEQUENCE: 105

```
Asp Ala Val Met Thr Gln Ile Pro Leu Thr Leu Ser Val Thr Ile Gly
1               5                   10                  15

Gln Pro Ala Ser Ile Ser Cys Lys Ser Ser Gln Ser Leu Leu His Ser
                20                  25                  30

Asp Gly Lys Thr Tyr Leu Asn Trp Leu Leu Gln Arg Pro Gly Gln Ser
            35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Arg Thr Phe Gly Gly Gly Thr Lys Leu Glu Ile Lys
                100                 105                 110
```

<210> SEQ ID NO 106
<211> LENGTH: 112
<212> TYPE: PRT
<213> ORGANISM: Artificial Sequence
<220> FEATURE:
<223> OTHER INFORMATION: 3E10 light chain variable region

<400> SEQUENCE: 106

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Tyr Thr Phe Gly Gly Gly Thr Lys Leu Glu Ile Lys
            100                 105                 110

<210> SEQ ID NO 107
<211> LENGTH: 113
<212> TYPE: PRT
<213> ORGANISM: Artificial Sequence
<220> FEATURE:
<223> OTHER INFORMATION: 3A9 light chain variable region

<400> SEQUENCE: 107

Asp Ile Val Met Thr Gln Ser Pro Ser Ser Leu Ala Met Ser Leu Gly
1               5                   10                  15

Gln Lys Val Thr Met Ser Cys Lys Ser Ser Gln Ser Leu Leu Asn Ser
            20                  25                  30

Asn Asn Gln Leu Asn Tyr Leu Ala Trp Tyr Gln Gln Lys Pro Gly Gln
        35                  40                  45

Ser Pro Lys Leu Leu Val Tyr Phe Ala Ser Thr Arg Lys Ser Gly Val
    50                  55                  60

Pro Asp Arg Phe Ile Gly Ser Gly Ser Gly Thr Asp Phe Thr Leu Thr
65                  70                  75                  80

Ile Thr Ser Val Gln Ala Glu Asp Leu Ala Asp Tyr Phe Cys Gln Gln
                85                  90                  95

His Phe Asn Thr Pro Leu Thr Phe Gly Ala Gly Thr Lys Leu Glu Leu
            100                 105                 110

Lys

<210> SEQ ID NO 108
<211> LENGTH: 113
<212> TYPE: PRT
<213> ORGANISM: Artificial Sequence
<220> FEATURE:
<223> OTHER INFORMATION: 3B1 light chain variable region

<400> SEQUENCE: 108

Asp Ile Val Met Thr Gln Ser Pro Ser Ser Leu Ala Ile Ser Val Gly
1               5                   10                  15

Gln Lys Val Thr Met Ser Cys Lys Ser Ser Gln Ser Leu Leu Asn Ser
            20                  25                  30

Ser Asn Gln Lys Asn Tyr Leu Ala Trp Tyr Gln Gln Lys Pro Gly Gln
        35                  40                  45

Ser Pro Lys Leu Leu Val Phe Phe Ala Ser Thr Arg Glu Ser Gly Val

```
                    50                  55                  60
Pro Asp Arg Phe Ile Gly Ser Gly Ser Gly Thr Asp Phe Thr Leu Thr
 65                  70                  75                  80

Ile Ser Ser Val Gln Ala Glu Asp Leu Ala Asp Tyr Phe Cys Gln Gln
                     85                  90                  95

His Tyr Ser Ile Pro Leu Thr Phe Gly Ala Gly Thr Lys Leu Glu Leu
                100                 105                 110

Lys

<210> SEQ ID NO 109
<211> LENGTH: 113
<212> TYPE: PRT
<213> ORGANISM: Artificial Sequence
<220> FEATURE:
<223> OTHER INFORMATION: 3G5 light chain variable region

<400> SEQUENCE: 109

Asp Ile Val Met Thr Gln Ser Pro Ser Ser Leu Ala Met Ser Val Gly
 1               5                  10                  15

Gln Lys Val Thr Met Ser Cys Lys Ser Ser Gln Ser Leu Leu Asn Ser
                20                  25                  30

Ser Asn Gln Lys Asn Tyr Leu Ala Trp Tyr Gln Gln Lys Pro Gly Gln
             35                  40                  45

Ser Pro Lys Leu Leu Val Phe Phe Ala Ser Thr Arg Glu Ser Gly Val
         50                  55                  60

Pro Asp Arg Phe Ile Gly Ser Gly Ser Gly Thr Asp Phe Thr Leu Thr
 65                  70                  75                  80

Ile Thr Ser Val Gln Ala Glu Asp Leu Ala Asp Tyr Phe Cys Gln Gln
                     85                  90                  95

His Tyr Ser Ile Pro Leu Thr Phe Gly Ser Gly Thr Lys Leu Glu Leu
                100                 105                 110

Lys

<210> SEQ ID NO 110
<211> LENGTH: 113
<212> TYPE: PRT
<213> ORGANISM: Artificial Sequence
<220> FEATURE:
<223> OTHER INFORMATION: 3B2 light chain variable region

<400> SEQUENCE: 110

Asp Ile Val Met Thr Gln Ser Pro Ser Ser Leu Ala Met Ser Val Gly
 1               5                  10                  15

Gln Lys Val Thr Met Ser Cys Lys Ser Ser Gln Ser Leu Leu Asn Ser
                20                  25                  30

Ser Asn Gln Lys Asn Tyr Leu Ala Trp Tyr Gln Gln Lys Pro Gly Gln
             35                  40                  45

Ser Pro Lys Leu Leu Val Tyr Phe Ala Ser Thr Arg Glu Ser Gly Val
         50                  55                  60

Pro Asp Arg Phe Ile Gly Ser Gly Ser Gly Thr Asp Phe Thr Leu Thr
 65                  70                  75                  80

Ile Ser Ser Val Gln Ala Glu Asp Leu Ala Asp Tyr Phe Cys Gln Gln
                     85                  90                  95

His Tyr Ser Ile Pro Leu Thr Phe Gly Ala Gly Thr Lys Leu Glu Leu
                100                 105                 110

Lys
```

<210> SEQ ID NO 111
<211> LENGTH: 113
<212> TYPE: PRT
<213> ORGANISM: Artificial Sequence
<220> FEATURE:
<223> OTHER INFORMATION: 3B8 light chain variable region

<400> SEQUENCE: 111

```
Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
            20                  25                  30

Ser Asn Gln Lys Asn Tyr Leu Ala Trp Tyr Gln Gln Lys Pro Gly Gln
        35                  40                  45

Ser Pro Lys Leu Leu Val Tyr Phe Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Ser Thr Pro Leu Thr Phe Gly Ala Gly Thr Lys Leu Glu Leu
            100                 105                 110

Lys
```

<210> SEQ ID NO 112
<211> LENGTH: 113
<212> TYPE: PRT
<213> ORGANISM: Artificial Sequence
<220> FEATURE:
<223> OTHER INFORMATION: 3G8 light chain variable region

<400> SEQUENCE: 112

```
Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
            20                  25                  30

Ser Asn Gln Lys Asn Tyr Leu Ala Trp Tyr Gln Gln Lys Pro Gly Gln
        35                  40                  45

Ser Pro Lys Leu Leu Val Tyr Phe Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Ser Thr Pro Leu Thr Phe Gly Ala Gly Thr Lys Leu Glu Leu
            100                 105                 110

Lys
```

<210> SEQ ID NO 113
<211> LENGTH: 113
<212> TYPE: PRT
<213> ORGANISM: Artificial Sequence
<220> FEATURE:
<223> OTHER INFORMATION: 3F7 light chain variable region

<400> SEQUENCE: 113

```
Asp Ile Val Met Thr Gln Ser Pro Ser Ser Leu Ala Met Ser Val Gly
1               5                   10                  15
```

Gln Lys Val Thr Met Ser Cys Lys Ser Ser Gln Ser Leu Leu Asn Ser
                20                  25                  30

Ser Asn Gln Lys Asn Tyr Leu Ala Trp Tyr Gln Lys Pro Gly Gln
        35                  40                  45

Ser Pro Lys Leu Leu Ile Tyr Phe Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Ser Thr Pro Leu Thr Phe Gly Ala Gly Thr Lys Leu Glu Leu
                100                 105                 110

Lys

<210> SEQ ID NO 114
<211> LENGTH: 113
<212> TYPE: PRT
<213> ORGANISM: Artificial Sequence
<220> FEATURE:
<223> OTHER INFORMATION: 3E9 light chain variable region

<400> SEQUENCE: 114

Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
                20                  25                  30

Ser Asn Gln Lys Asn Tyr Leu Ala Trp Tyr Gln Gln Lys Pro Gly Gln
        35                  40                  45

Ser Pro Lys Leu Leu Val Tyr Phe Ala Ser Thr Arg Glu Ser Gly Val
    50                  55                  60

Pro Asp Arg Phe Ile Gly Ser Gly Ser Gly Thr Glu Phe Thr Leu Thr
65                  70                  75                  80

Ile Thr Ser Val Gln Ala Glu Asp Leu Ala Asp Tyr Phe Cys Gln Gln
                85                  90                  95

His Tyr Ser Thr Pro Leu Thr Phe Gly Ala Gly Thr Lys Leu Glu Leu
                100                 105                 110

Lys

<210> SEQ ID NO 115
<211> LENGTH: 113
<212> TYPE: PRT
<213> ORGANISM: Artificial Sequence
<220> FEATURE:
<223> OTHER INFORMATION: 3C3 light chain variable region

<400> SEQUENCE: 115

Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
                20                  25                  30

Ser Asn Gln Lys Asn Tyr Leu Ala Trp Tyr Gln Gln Lys Pro Gly Gln
        35                  40                  45

Ser Pro Lys Leu Leu Val Tyr Phe Gly Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Gly Val Gln Ala Glu Asp Leu Ala Asp Tyr Phe Cys Gln Gln

His Tyr Ser Thr Pro Leu Thr Phe Gly Ala Gly Thr Lys Leu Glu Leu
                100                 105                 110
Lys

<210> SEQ ID NO 116
<211> LENGTH: 113
<212> TYPE: PRT
<213> ORGANISM: Artificial Sequence
<220> FEATURE:
<223> OTHER INFORMATION: 3E12 light chain variable region

<400> SEQUENCE: 116

Asp Ile Val Met Thr Gln Ser Pro Ser Ser Leu Ala Met Ser Val Gly
1               5                   10                  15

Gln Lys Val Thr Met Asn Cys Lys Ser Ser Gln Ser Leu Leu Asn Arg
            20                  25                  30

Ser Asn Gln Lys Asn Tyr Leu Ala Trp Tyr Gln Gln Lys Pro Gly Gln
        35                  40                  45

Ser Pro Lys Leu Leu Val Tyr Phe Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Ser Ile Pro Leu Thr Phe Gly Ala Gly Thr Lys Leu Glu Leu
                100                 105                 110
Lys

<210> SEQ ID NO 117
<211> LENGTH: 113
<212> TYPE: PRT
<213> ORGANISM: Artificial Sequence
<220> FEATURE:
<223> OTHER INFORMATION: 4A2 light chain variable region

<400> SEQUENCE: 117

Asp Ile Val Met Thr Gln Ser Pro Ser Ser Leu Ala Met Ser Val Gly
1               5                   10                  15

Gln Lys Val Thr Met Asn Cys Lys Ser Ser Gln Ser Leu Leu Asn Asn
            20                  25                  30

Ser Asn Gln Lys Asn Tyr Leu Ala Trp Tyr Gln Gln Lys Pro Gly Gln
        35                  40                  45

Ser Pro Lys Leu Leu Leu Tyr Phe Ala Ser Thr Arg Glu Ser Gly Val
    50                  55                  60

Pro Asp Arg Phe Ile Gly Ser Gly Ser Gly Thr Tyr Phe Thr Leu Thr
65                  70                  75                  80

Ile Ser Ser Val Gln Ala Glu Asp Leu Ala Asp Tyr Phe Cys Gln Gln
                85                  90                  95

His Tyr Ser Thr Pro Leu Thr Phe Gly Ala Gly Thr Lys Leu Asp Leu
                100                 105                 110
Lys

<210> SEQ ID NO 118
<211> LENGTH: 113
<212> TYPE: PRT
<213> ORGANISM: Artificial Sequence
<220> FEATURE:

<223> OTHER INFORMATION: 3F10 light chain variable region

<400> SEQUENCE: 118

Asp Ile Val Met Thr Gln Ser Pro Ser Ser Leu Thr Met Ser Val Gly
1               5                   10                  15

Gln Lys Val Thr Met Ser Cys Lys Ser Ser Gln Ser Leu Leu Asn Thr
            20                  25                  30

Ser Asn Gln Leu Asn Tyr Leu Ala Trp Tyr Gln Gln Lys Pro Gly Gln
        35                  40                  45

Ser Pro Lys Leu Leu Val Tyr Phe Ala Ser Thr Thr Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Ser Thr Pro Leu Thr Phe Gly Ala Gly Thr Lys Leu Glu Leu
            100                 105                 110

Lys

<210> SEQ ID NO 119
<211> LENGTH: 113
<212> TYPE: PRT
<213> ORGANISM: Artificial Sequence
<220> FEATURE:
<223> OTHER INFORMATION: 3F4 light chain variable region

<400> SEQUENCE: 119

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Thr
            20                  25                  30

Ser Asn Gln Lys Asn Tyr Leu Ala Trp Tyr Gln Gln Lys Pro Gly Gln
        35                  40                  45

Ser Pro Lys Leu Leu Val Tyr Phe Ala Ser Thr Arg Ala Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Ser Thr Pro Leu Thr Phe Gly Ala Gly Thr Lys Leu Glu Leu
            100                 105                 110

Lys

<210> SEQ ID NO 120
<211> LENGTH: 113
<212> TYPE: PRT
<213> ORGANISM: Artificial Sequence
<220> FEATURE:
<223> OTHER INFORMATION: 3B11 light chain variable region

<400> SEQUENCE: 120

Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
            20                  25                  30

Ser Asn Gln Lys Asn Tyr Leu Ala Trp Tyr Gln Gln Lys Pro Gly Gln
        35                  40                  45

```
Ser Pro Lys Leu Leu Val Tyr Phe Ala Ser Thr Arg Glu Ser Gly Val
    50                  55                  60
Pro Asp Arg Phe Ile Gly Ser Gly Ser Gly Thr Asp Phe Thr Leu Thr
65                  70                  75                  80
Ile Ser Ser Val Gln Ala Glu Asp Leu Ala Asp Tyr Phe Cys Gln Gln
                85                  90                  95
His Tyr Ser Thr Pro Leu Thr Phe Gly Ala Gly Thr Lys Leu Glu Leu
                100                 105                 110
Lys
```

```
<210> SEQ ID NO 121
<211> LENGTH: 107
<212> TYPE: PRT
<213> ORGANISM: Artificial Sequence
<220> FEATURE:
<223> OTHER INFORMATION: 3G12 light chain variable region

<400> SEQUENCE: 121

Asp Ile Val Met Thr Gln Ser Pro Lys Phe Met Ser Thr Ser Val Gly
1               5                   10                  15
Asp Arg Val Ser Ile Thr Cys Lys Ala Ser Gln Asp Val Gly Thr Ala
                20                  25                  30
Val Ala Trp Tyr Gln Gln Lys Pro Gly Gln Ser Pro Glu Leu Leu Ile
            35                  40                  45
Tyr Trp Thr Ser Thr Arg His Thr Gly Val Pro Asp Arg Phe Ser Gly
    50                  55                  60
Ser Gly Ser Gly Thr Asp Phe Thr Leu Thr Ile Ser Ser Val Gln Ala
65                  70                  75                  80
Glu Asp Leu Ala Asp Tyr Phe Cys Gln Gln His Tyr Ser Ile Pro Leu
                85                  90                  95
Thr Phe Gly Ala Gly Thr Lys Leu Glu Leu Arg
                100                 105
```

```
<210> SEQ ID NO 122
<211> LENGTH: 107
<212> TYPE: PRT
<213> ORGANISM: Artificial Sequence
<220> FEATURE:
<223> OTHER INFORMATION: 3D1 light chain variable region

<400> SEQUENCE: 122

Asp Ile Lys Met Thr Gln Ser Pro Ser Ser Met Tyr Ala Ser Leu Gly
1               5                   10                  15
Glu Arg Val Thr Ile Thr Cys Lys Ala Ser Gln Asp Ile His Thr Tyr
                20                  25                  30
Leu Asn Trp Phe Gln Gln Lys Pro Gly Lys Ser Pro Glu Thr Leu Ile
            35                  40                  45
Tyr Arg Ala Asn Arg Leu Val Asp Gly Val Pro Ser Arg Phe Ser Gly
    50                  55                  60
Ser Gly Ser Gly Gln Asp Tyr Ser Leu Thr Ile Ser Ser Leu Glu Tyr
65                  70                  75                  80
Glu Asp Met Gly Ile Tyr Tyr Cys Leu Gln Tyr Asp Glu Phe Pro Leu
                85                  90                  95
Thr Phe Gly Ala Gly Thr Lys Leu Glu Leu Lys
                100                 105
```

```
<210> SEQ ID NO 123
<211> LENGTH: 107
```

```
<212> TYPE: PRT
<213> ORGANISM: Artificial Sequence
<220> FEATURE:
<223> OTHER INFORMATION: 3C2 light chain variable region

<400> SEQUENCE: 123

Asp Ile Gln Met Thr Gln Ser Pro Ser Ser Met Tyr Ala Ser Leu Gly
1               5                   10                  15

Glu Arg Val Thr Leu Thr Cys Lys Ala Ser Gln Asp Ile His Asn Tyr
            20                  25                  30

Leu Asn Trp Phe Gln Gln Lys Pro Gly Lys Ser Pro Lys Thr Leu Ile
        35                  40                  45

His Arg Ala Asn Arg Leu Val Ala Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Leu Gly Ile Tyr Tyr Cys Leu Gln Tyr Asp Ala Phe Pro Leu
                85                  90                  95

Thr Phe Gly Ala Gly Thr Lys Leu Glu Leu Lys
            100                 105

<210> SEQ ID NO 124
<211> LENGTH: 107
<212> TYPE: PRT
<213> ORGANISM: Artificial Sequence
<220> FEATURE:
<223> OTHER INFORMATION: 3E6 light chain variable region

<400> SEQUENCE: 124

Asp Ile Gln Met Thr Gln Ser Pro Ser Ser Met Tyr Ala Ser Leu Gly
1               5                   10                  15

Glu Arg Val Thr Leu Thr Cys Lys Ala Ser Gln Asp Ile His Asn Tyr
            20                  25                  30

Leu Asn Trp Phe Gln Gln Lys Pro Gly Lys Ser Pro Lys Thr Leu Ile
        35                  40                  45

His Arg Ala Asn Arg Leu Val Ala Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Leu Gly Ile Tyr Tyr Cys Leu Gln Tyr Asp Ala Phe Pro Leu
                85                  90                  95

Thr Phe Gly Ala Gly Thr Lys Leu Glu Leu Lys
            100                 105

<210> SEQ ID NO 125
<211> LENGTH: 107
<212> TYPE: PRT
<213> ORGANISM: Artificial Sequence
<220> FEATURE:
<223> OTHER INFORMATION: 3H3 light chain variable region

<400> SEQUENCE: 125

Asp Ile Val Met Ser Gln Ser Pro Ser Ser Met Tyr Ala Ser Leu Gly
1               5                   10                  15

Glu Arg Val Thr Ile Thr Cys Lys Ala Ser Gln Asp Ile His Arg Phe
            20                  25                  30

Leu Asn Trp Phe Gln Gln Lys Pro Gly Lys Ser Pro Lys Thr Leu Ile
        35                  40                  45

Phe His Ala Asn Arg Leu Val Asp Gly Val Pro Ser Arg Phe Ser Gly
```

```
                50                  55                  60
Ser Gly Ser Gly Leu Asp Tyr Ser Leu Thr Ile Ser Ser Leu Glu Tyr
 65                  70                  75                  80

Glu Asp Met Gly Ile Tyr Phe Cys Leu Gln Tyr Asp Ala Phe Pro Leu
                 85                  90                  95

Thr Phe Gly Ala Gly Thr Lys Leu Glu Leu Lys
            100                 105
```

<210> SEQ ID NO 126
<211> LENGTH: 115
<212> TYPE: PRT
<213> ORGANISM: Artificial Sequence
<220> FEATURE:
<223> OTHER INFORMATION: 3A2 heavy chain variable region

<400> SEQUENCE: 126

```
His Glu Ile Gln Leu Gln Gln Ser Gly Pro Glu Leu Val Lys Pro Gly
 1               5                  10                  15

Ala Ser Val Lys Met Ser Cys Lys Thr Ser Gly Tyr Thr Phe Thr Asp
                20                  25                  30

Tyr Asn Met His Trp Val Lys Gln Lys Pro Gly Gln Gly Leu Glu Trp
             35                  40                  45

Ile Gly Tyr Ile Asn Pro Tyr Asn Asp Val Thr Glu Tyr Asn Glu Lys
 50                  55                  60

Phe Lys Gly Arg Ala Thr Leu Thr Ser Asp Lys Ser Ser Ser Thr Ala
 65                  70                  75                  80

Tyr Met Asp Leu Ser Ser Leu Thr Ser Asp Asp Ser Ala Val Tyr Phe
                 85                  90                  95

Cys Ala Trp Phe Gly Leu Arg Gln Trp Gly Gln Gly Thr Leu Val Thr
            100                 105                 110

Val Ser Thr
        115
```

<210> SEQ ID NO 127
<211> LENGTH: 115
<212> TYPE: PRT
<213> ORGANISM: Artificial Sequence
<220> FEATURE:
<223> OTHER INFORMATION: 3F6 heavy chain variable region

<400> SEQUENCE: 127

```
His Glu Val Gln Leu Gln Gln Ser Gly Pro Glu Leu Val Lys Pro Gly
 1               5                  10                  15

Ala Ser Val Lys Met Ser Cys Lys Ala Ser Gly Tyr Ile Phe Thr Glu
                20                  25                  30

Tyr Asn Ile His Trp Val Lys Gln Lys Pro Gly Gln Gly Pro Glu Trp
             35                  40                  45

Ile Gly Asn Ile Asn Pro Tyr Asn Asp Val Thr Glu Tyr Asn Glu Lys
 50                  55                  60

Phe Lys Gly Lys Ala Thr Leu Thr Ser Asp Lys Ala Ser Ser Thr Ala
 65                  70                  75                  80

Tyr Met Asp Leu Ser Ser Leu Thr Ser Glu Asp Ser Ala Val Tyr Tyr
                 85                  90                  95

Cys Ala Arg Trp Gly Leu Arg Asn Trp Gly Gln Gly Thr Leu Val Thr
            100                 105                 110

Val Ser Ala
        115
```

<210> SEQ ID NO 128
<211> LENGTH: 115
<212> TYPE: PRT
<213> ORGANISM: Artificial Sequence
<220> FEATURE:
<223> OTHER INFORMATION: 3E8 heavy chain variable region

<400> SEQUENCE: 128

```
His Glu Val Gln Leu Gln Gln Ser Val Pro Glu Leu Val Lys Pro Gly
1               5                   10                  15
Ala Ser Val Lys Met Ser Cys Lys Thr Ser Gly Tyr Thr Phe Thr Glu
            20                  25                  30
Tyr Asn Met His Trp Val Lys Gln Lys Pro Gly Gln Gly Pro Glu Trp
        35                  40                  45
Ile Gly Asn Ile Asn Pro Tyr Asn Asn Val Thr Glu Tyr Asn Glu Lys
    50                  55                  60
Phe Lys Gly Lys Ala Thr Leu Thr Ser Asp Lys Ser Ser Ser Thr Ala
65                  70                  75                  80
Tyr Leu Asp Leu Ser Ser Leu Thr Ser Glu Asp Ser Ala Val Tyr Tyr
                85                  90                  95
Cys Ala Arg Trp Gly Leu Arg Asn Trp Gly Gln Gly Thr Leu Val Thr
            100                 105                 110
Val Ser Ala
        115
```

<210> SEQ ID NO 129
<211> LENGTH: 114
<212> TYPE: PRT
<213> ORGANISM: Artificial Sequence
<220> FEATURE:
<223> OTHER INFORMATION: 3A9 heavy chain variable region

<400> SEQUENCE: 129

```
His Gln Val Gln Val Gln Gln Pro Gly Ala Glu Leu Val Arg Pro Gly
1               5                   10                  15
Ala Ser Val Thr Leu Ser Cys Lys Ala Ser Gly Tyr Ile Phe Thr Asp
            20                  25                  30
Tyr Glu Val His Trp Val Arg Gln Arg Pro Val His Gly Leu Glu Trp
        35                  40                  45
Ile Gly Val Ile Asp Pro Glu Thr Gly Asp Thr Ala Tyr Asn Gln Lys
    50                  55                  60
Phe Lys Gly Lys Ala Thr Leu Thr Ala Asp Lys Ser Ser Ser Thr Ala
65                  70                  75                  80
Tyr Met Glu Leu Ser Ser Leu Thr Ala Glu Asp Ser Ala Val Tyr Tyr
                85                  90                  95
Cys Ile Gly Tyr Ala Asp Tyr Trp Gly Gln Gly Thr Thr Leu Thr Val
            100                 105                 110
Ser Ser
```

<210> SEQ ID NO 130
<211> LENGTH: 114
<212> TYPE: PRT
<213> ORGANISM: Artificial Sequence
<220> FEATURE:
<223> OTHER INFORMATION: 3B1 heavy chain variable region

<400> SEQUENCE: 130

```
His Gln Val Gln Leu Gln Gln Pro Gly Ala Glu Leu Val Arg Pro Gly
1               5                   10                  15
```

Ala Ser Val Thr Leu Ser Cys Lys Ala Ser Gly Tyr Thr Phe Thr Asp
            20                  25                  30

Tyr Glu Ile His Trp Val Lys Gln Thr Pro Val His Gly Leu Glu Trp
        35                  40                  45

Ile Gly Val Ile Asp Pro Glu Thr Gly Thr Ala Tyr Asn Gln Lys
    50                  55                  60

Phe Lys Gly Lys Ala Thr Leu Thr Thr Asp Lys Ser Ser Ser Thr Ala
65                  70                  75                  80

Tyr Met Glu Leu Arg Ser Leu Thr Ser Glu Asp Ser Ala Val Tyr Tyr
                85                  90                  95

Cys Met Gly Tyr Ser Asp Tyr Trp Gly Gln Gly Thr Thr Leu Thr Val
            100                 105                 110

Ser Ser

<210> SEQ ID NO 131
<211> LENGTH: 114
<212> TYPE: PRT
<213> ORGANISM: Artificial Sequence
<220> FEATURE:
<223> OTHER INFORMATION: 3B2 heavy chain variable region

<400> SEQUENCE: 131

His Glu Val Gln Leu Gln Gln Ser Gly Ala Glu Leu Val Arg Pro Gly
1               5                   10                  15

Ala Ser Val Thr Leu Ser Cys Lys Ala Ser Gly Tyr Thr Phe Thr Asp
            20                  25                  30

Tyr Glu Ile His Trp Val Lys Gln Thr Pro Val His Gly Leu Glu Trp
        35                  40                  45

Ile Gly Val Ile Asp Pro Glu Thr Gly Ala Thr Ala Tyr Asn Gln Lys
    50                  55                  60

Phe Lys Gly Lys Ala Thr Leu Thr Ala Asp Lys Ser Ser Ser Thr Ala
65                  70                  75                  80

Tyr Met Glu Leu Ser Ser Leu Thr Ser Glu Asp Ser Ala Val Tyr Tyr
                85                  90                  95

Cys Met Gly Tyr Ser Asp Tyr Trp Gly Gln Gly Thr Thr Leu Thr Val
            100                 105                 110

Ser Ser

<210> SEQ ID NO 132
<211> LENGTH: 114
<212> TYPE: PRT
<213> ORGANISM: Artificial Sequence
<220> FEATURE:
<223> OTHER INFORMATION: 3F4 heavy chain variable region

<400> SEQUENCE: 132

His Glu Val Gln Leu Gln Gln Ser Gly Ala Glu Leu Val Arg Pro Gly
1               5                   10                  15

Ala Ser Val Thr Leu Ser Cys Lys Ala Ser Gly Tyr Thr Phe Thr Asp
            20                  25                  30

Tyr Glu Ile His Trp Val Lys Gln Thr Pro Val His Gly Leu Glu Trp
        35                  40                  45

Ile Gly Val Ile Asp Pro Glu Thr Gly Ser Thr Ala Tyr Asn Gln Lys
    50                  55                  60

Phe Lys Gly Lys Ala Thr Leu Thr Ala Asp Lys Ala Ser Ser Thr Ala
65                  70                  75                  80

```
Tyr Met Glu Leu Ser Ser Leu Thr Ser Glu Asp Ser Ala Val Tyr Tyr
                85                  90                  95

Cys Met Gly Tyr Ser Asp Tyr Trp Gly Gln Gly Thr Thr Leu Thr Val
            100                 105                 110

Ser Ser

<210> SEQ ID NO 133
<211> LENGTH: 114
<212> TYPE: PRT
<213> ORGANISM: Artificial Sequence
<220> FEATURE:
<223> OTHER INFORMATION: 3E9 heavy chain variable region

<400> SEQUENCE: 133

His Glu Val Gln Leu Gln Gln Ser Gly Ala Glu Leu Val Arg Pro Gly
1               5                   10                  15

Ala Ser Ala Thr Leu Ser Cys Lys Ala Ser Gly Tyr Thr Phe Thr Asp
                20                  25                  30

Tyr Glu Met His Trp Val Lys Gln Thr Pro Val His Gly Leu Glu Trp
            35                  40                  45

Ile Gly Val Ile Asp Pro Glu Thr Gly Ser Thr Ala Tyr Asn Gln Lys
50                  55                  60

Phe Lys Gly Lys Ala Thr Leu Thr Ala Asp Lys Ser Ser Ser Thr Ala
65                  70                  75                  80

Tyr Met Glu Leu Ser Ser Leu Thr Ser Glu Asp Ser Ala Val Tyr Tyr
                85                  90                  95

Cys Met Gly Tyr Ala Asp Tyr Trp Gly Gln Gly Thr Thr Leu Thr Val
            100                 105                 110

Ser Ser

<210> SEQ ID NO 134
<211> LENGTH: 114
<212> TYPE: PRT
<213> ORGANISM: Artificial Sequence
<220> FEATURE:
<223> OTHER INFORMATION: 3B8 heavy chain variable region

<400> SEQUENCE: 134

His Glu Val Gln Leu Gln Gln Ser Gly Ala Glu Leu Val Arg Pro Gly
1               5                   10                  15

Ala Ser Val Thr Leu Ser Cys Lys Ala Ser Gly Tyr Thr Phe Thr Asp
                20                  25                  30

Tyr Glu Ile His Trp Val Lys Gln Thr Pro Val His Gly Leu Glu Trp
            35                  40                  45

Ile Gly Val Ile Asp Pro Glu Thr Gly Asp Thr Ala Tyr Asn Gln Asn
50                  55                  60

Phe Thr Gly Lys Ala Thr Leu Thr Ala Asp Lys Ser Ser Ser Thr Ala
65                  70                  75                  80

Tyr Met Glu Leu Ser Ser Leu Thr Ser Glu Asp Ser Ala Val Tyr Tyr
                85                  90                  95

Cys Met Gly Tyr Ala Asp Tyr Trp Gly Gln Gly Thr Thr Leu Thr Val
            100                 105                 110

Ser Ser

<210> SEQ ID NO 135
<211> LENGTH: 114
<212> TYPE: PRT
<213> ORGANISM: Artificial Sequence
```

```
<220> FEATURE:
<223> OTHER INFORMATION: 3G8 heavy chain variable region

<400> SEQUENCE: 135

His Gln Val Gln Leu Lys Gln Ser Gly Ala Glu Leu Val Arg Pro Gly
 1               5                  10                  15

Ala Ser Val Thr Leu Ser Cys Lys Ala Ser Gly Tyr Thr Phe Thr Asp
            20                  25                  30

Tyr Glu Val His Trp Val Lys Gln Thr Pro Val His Gly Leu Glu Trp
        35                  40                  45

Ile Gly Val Ile Asp Pro Ala Thr Gly Asp Thr Ala Tyr Asn Gln Lys
    50                  55                  60

Phe Lys Gly Lys Ala Thr Leu Thr Ala Asp Lys Ser Ser Ser Thr Ala
 65                 70                  75                  80

Tyr Met Glu Val Ser Ser Leu Thr Ser Glu Asp Ser Ala Val Tyr Tyr
                85                  90                  95

Cys Met Gly Tyr Ser Asp Tyr Trp Gly Gln Gly Thr Thr Leu Thr Val
            100                 105                 110

Ser Ser

<210> SEQ ID NO 136
<211> LENGTH: 114
<212> TYPE: PRT
<213> ORGANISM: Artificial Sequence
<220> FEATURE:
<223> OTHER INFORMATION: 3F7 heavy chain variable region

<400> SEQUENCE: 136

His Gln Ala Tyr Leu Gln Gln Ser Gly Ala Glu Leu Val Arg Pro Gly
 1               5                  10                  15

Ala Ser Val Thr Leu Ser Cys Lys Ala Ser Gly Tyr Thr Phe Thr Asp
            20                  25                  30

Tyr Glu Ile His Trp Val Lys Gln Thr Pro Val His Gly Leu Glu Trp
        35                  40                  45

Ile Gly Val Ile Asp Pro Glu Thr Gly Asp Thr Ala Tyr Asn Gln Lys
    50                  55                  60

Phe Lys Asp Lys Ala Thr Leu Thr Ala Asp Lys Ala Ser Ser Thr Ala
 65                 70                  75                  80

Tyr Met Glu Leu Ser Ser Leu Thr Ser Glu Asp Ser Ala Val Tyr Tyr
                85                  90                  95

Cys Met Gly Tyr Ser Asp Tyr Trp Gly Gln Gly Thr Thr Leu Thr Val
            100                 105                 110

Ser Ser

<210> SEQ ID NO 137
<211> LENGTH: 114
<212> TYPE: PRT
<213> ORGANISM: Artificial Sequence
<220> FEATURE:
<223> OTHER INFORMATION: 3E12 heavy chain variable region

<400> SEQUENCE: 137

His Gln Val Gln Leu Gln Gln Ser Glu Ala Glu Leu Val Lys Pro Gly
 1               5                  10                  15

Ala Ser Val Lys Leu Ser Cys Lys Ala Ser Gly Tyr Thr Phe Thr Asp
            20                  25                  30

Tyr Glu Ile His Trp Val Lys Gln Thr Pro Val His Gly Leu Glu Trp
        35                  40                  45
```

```
Ile Gly Val Ile Asp Pro Glu Thr Gly Asp Thr Ala Tyr Asn Gln Lys
 50                  55                  60

Phe Lys Gly Lys Ala Thr Leu Thr Ala Asp Lys Ser Ser Ser Thr Ala
 65                  70                  75                  80

Tyr Met Glu Leu Ser Arg Leu Thr Ser Glu Asp Ser Ala Val Tyr Tyr
                 85                  90                  95

Cys Met Gly His Ser Asp Tyr Trp Gly Gln Gly Thr Thr Leu Thr Val
                100                 105                 110

Ser Ser

<210> SEQ ID NO 138
<211> LENGTH: 114
<212> TYPE: PRT
<213> ORGANISM: Artificial Sequence
<220> FEATURE:
<223> OTHER INFORMATION: 3G12 heavy chain variable region

<400> SEQUENCE: 138

His Glu Val Gln Leu Gln Gln Ser Val Ala Glu Leu Val Arg Pro Gly
 1               5                  10                  15

Ala Ser Val Thr Val Ser Cys Lys Ala Ser Gly Tyr Ile Phe Thr Asp
                 20                  25                  30

Tyr Glu Ile His Trp Val Lys Gln Thr Pro Ala His Gly Leu Glu Trp
             35                  40                  45

Ile Gly Val Ile Asp Pro Glu Thr Gly Asn Thr Ala Phe Asn Gln Lys
 50                  55                  60

Phe Lys Gly Lys Ala Thr Leu Thr Ala Asp Ile Ser Ser Ser Thr Ala
 65                  70                  75                  80

Tyr Met Glu Leu Ser Ser Leu Thr Ser Glu Asp Ser Ala Val Tyr Tyr
                 85                  90                  95

Cys Met Gly Tyr Ser Asp Tyr Trp Gly Gln Gly Thr Thr Leu Thr Val
                100                 105                 110

Ser Ser

<210> SEQ ID NO 139
<211> LENGTH: 114
<212> TYPE: PRT
<213> ORGANISM: Artificial Sequence
<220> FEATURE:
<223> OTHER INFORMATION: 3F10 heavy chain variable region

<400> SEQUENCE: 139

His Glu Val Gln Leu Gln Gln Ser Val Ala Glu Leu Val Arg Pro Gly
 1               5                  10                  15

Ala Pro Val Thr Leu Ser Cys Lys Ala Ser Gly Tyr Thr Phe Thr Asp
                 20                  25                  30

Tyr Glu Val His Trp Val Lys Gln Thr Pro Val His Gly Leu Glu Trp
             35                  40                  45

Ile Gly Val Ile Asp Pro Glu Thr Gly Ala Thr Ala Tyr Asn Gln Lys
 50                  55                  60

Phe Lys Gly Lys Ala Thr Leu Thr Ala Asp Lys Ser Ser Ser Ala Ala
 65                  70                  75                  80

Tyr Met Glu Leu Ser Arg Leu Thr Ser Glu Asp Ser Ala Val Tyr Tyr
                 85                  90                  95

Cys Met Ser Tyr Ser Asp Tyr Trp Gly Gln Gly Thr Thr Leu Thr Val
                100                 105                 110
```

Ser Ser

<210> SEQ ID NO 140
<211> LENGTH: 114
<212> TYPE: PRT
<213> ORGANISM: Artificial Sequence
<220> FEATURE:
<223> OTHER INFORMATION: 3C3 heavy chain variable region

<400> SEQUENCE: 140

His Glu Val Gln Leu Gln Gln Ser Val Ala Glu Val Val Arg Pro Gly
1               5                   10                  15

Ala Ser Val Thr Leu Ser Cys Lys Ala Ser Gly Tyr Thr Phe Thr Asp
            20                  25                  30

Tyr Glu Ile His Trp Val Lys Gln Thr Pro Val His Gly Leu Glu Trp
        35                  40                  45

Ile Gly Val Ile Asp Pro Glu Thr Gly Val Thr Ala Tyr Asn Gln Arg
    50                  55                  60

Phe Arg Asp Lys Ala Thr Leu Thr Thr Asp Lys Ser Ser Ser Thr Ala
65                  70                  75                  80

Tyr Met Glu Leu Ser Ser Leu Thr Ser Glu Asp Ser Ala Val Tyr Phe
                85                  90                  95

Cys Met Gly Tyr Ser Asp Tyr Trp Gly Gln Gly Thr Thr Leu Thr Val
            100                 105                 110

Ser Ser

<210> SEQ ID NO 141
<211> LENGTH: 114
<212> TYPE: PRT
<213> ORGANISM: Artificial Sequence
<220> FEATURE:
<223> OTHER INFORMATION: 3G5 heavy chain variable region

<400> SEQUENCE: 141

His Gln Val Gln Leu Gln Gln Pro Gly Ala Glu Leu Val Arg Pro Gly
1               5                   10                  15

Ala Ser Val Thr Leu Ser Cys Lys Ala Ser Gly Tyr Thr Phe Thr Asp
            20                  25                  30

Tyr Glu Ile His Trp Val Lys Gln Thr Pro Val His Gly Leu Glu Trp
        35                  40                  45

Ile Gly Val Leu Asp Pro Gly Thr Gly Arg Thr Ala Tyr Asn Gln Lys
    50                  55                  60

Phe Lys Asp Lys Ala Thr Leu Ser Ala Asp Lys Ser Ser Ser Thr Ala
65                  70                  75                  80

Tyr Met Glu Leu Ser Ser Leu Thr Ser Glu Asp Ser Ala Val Tyr Tyr
                85                  90                  95

Cys Met Ser Tyr Ser Asp Tyr Trp Gly Pro Gly Thr Thr Leu Thr Val
            100                 105                 110

Ser Ser

<210> SEQ ID NO 142
<211> LENGTH: 114
<212> TYPE: PRT
<213> ORGANISM: Artificial Sequence
<220> FEATURE:
<223> OTHER INFORMATION: 3B11 heavy chain variable region

<400> SEQUENCE: 142

His Glu Val Gln Leu Gln Gln Ser Val Ala Glu Leu Val Arg Pro Gly

```
            1               5                  10                 15
          Ala Ser Val Thr Leu Ser Cys Lys Ala Ser Gly Tyr Thr Phe Thr Asp
                          20                 25                 30

Tyr Glu Met His Trp Val Lys Gln Thr Pro Val Arg Gly Leu Glu Trp
                      35                 40                 45

Ile Gly Val Ile Asp Pro Ala Thr Gly Asp Thr Ala Tyr Asn Gln Lys
                  50                 55                 60

Phe Lys Gly Lys Ala Thr Leu Thr Ala Asp Lys Ser Ser Ser Ala Ala
           65                 70                 75                 80

Phe Met Glu Leu Ser Ser Leu Thr Ser Glu Asp Ser Ala Val Tyr Tyr
                          85                 90                 95

Cys Met Gly Tyr Ser Asp Tyr Trp Gly Gln Gly Thr Thr Leu Thr Val
                          100                105                110

Ser Ser

<210> SEQ ID NO 143
<211> LENGTH: 115
<212> TYPE: PRT
<213> ORGANISM: Artificial Sequence
<220> FEATURE:
<223> OTHER INFORMATION: 3E6 heavy chain variable region

<400> SEQUENCE: 143

His Gln Val Gln Leu Gln Gln Ser Gly Ala Glu Leu Val Arg Pro Gly
           1               5                  10                 15

Ala Ser Val Thr Leu Ser Cys Lys Ala Ser Gly Tyr Thr Phe Ser Asp
                          20                 25                 30

Tyr Glu Met His Trp Val Lys Gln Thr Pro Val His Gly Leu Glu Trp
                      35                 40                 45

Ile Gly Gly Ile Asp Pro Glu Thr Gly Asp Thr Val Tyr Asn Gln Lys
                  50                 55                 60

Phe Lys Gly Lys Ala Thr Leu Thr Ala Asp Lys Ser Ser Ser Thr Ala
           65                 70                 75                 80

Tyr Met Glu Leu Ser Ser Leu Thr Ser Glu Asp Ser Ala Val Tyr Tyr
                          85                 90                 95

Cys Ile Ser Tyr Ala Met Asp Tyr Trp Gly Gln Gly Thr Ser Val Thr
                          100                105                110

Val Ser Ser
                  115

<210> SEQ ID NO 144
<211> LENGTH: 115
<212> TYPE: PRT
<213> ORGANISM: Artificial Sequence
<220> FEATURE:
<223> OTHER INFORMATION: 4A2 heavy chain variable region

<400> SEQUENCE: 144

His Gln Val Lys Leu Gln Gln Ser Gly Thr Glu Leu Val Arg Pro Gly
           1               5                  10                 15

Ala Ser Val Thr Leu Ser Cys Lys Ala Ser Gly Tyr Lys Phe Thr Asp
                          20                 25                 30

Tyr Glu Met His Trp Val Lys Gln Thr Pro Val His Gly Leu Glu Trp
                      35                 40                 45

Ile Gly Gly Ile Asp Pro Glu Thr Gly Thr Ala Tyr Asn Gln Lys
                  50                 55                 60

Phe Lys Gly Lys Ala Ile Leu Thr Ala Asp Lys Ser Ser Thr Thr Ala
```

```
                65                  70                  75                  80
Tyr Met Glu Leu Arg Ser Leu Thr Ser Glu Asp Ser Ala Val Tyr Tyr
                    85                  90                  95

Cys Ile Ser Tyr Ala Met Asp Tyr Trp Gly Gln Gly Thr Ser Val Thr
                    100                 105                 110

Val Ser Ser
        115

<210> SEQ ID NO 145
<211> LENGTH: 117
<212> TYPE: PRT
<213> ORGANISM: Artificial Sequence
<220> FEATURE:
<223> OTHER INFORMATION: 3E10 heavy chain variable region

<400> SEQUENCE: 145

His Glu Val Gln Leu Gln Gln Ser Gly Pro Glu Leu Val Lys Pro Gly
1               5                   10                  15

Ala Ser Val Lys Ile Ser Cys Lys Ala Ser Gly Asp Thr Phe Thr Asp
                20                  25                  30

Tyr Tyr Met Asn Trp Val Lys Gln Ser His Gly Lys Ser Leu Glu Trp
            35                  40                  45

Ile Gly Asp Ile Asn Pro Asn Tyr Gly Gly Ile Thr Tyr Asn Gln Lys
        50                  55                  60

Phe Lys Gly Lys Ala Thr Leu Thr Val Asp Thr Ser Ser Ser Thr Ala
65                  70                  75                  80

Tyr Met Glu Leu Arg Gly Leu Thr Ser Glu Asp Ser Ala Val Tyr Tyr
                    85                  90                  95

Cys Gln Ala Tyr Tyr Arg Asn Ser Asp Tyr Trp Gly Gln Gly Thr Thr
                    100                 105                 110

Leu Thr Val Ser Ser
        115

<210> SEQ ID NO 146
<211> LENGTH: 118
<212> TYPE: PRT
<213> ORGANISM: Artificial Sequence
<220> FEATURE:
<223> OTHER INFORMATION: 3D1 heavy chain variable region

<400> SEQUENCE: 146

His Glu Val Gln Leu Gln Glu Ser Gly Pro Asp Leu Val Lys Pro Ser
1               5                   10                  15

Gln Ser Leu Ser Leu Thr Cys Thr Val Thr Gly Phe Ser Ile Thr Ser
                20                  25                  30

Gly Tyr Gly Trp His Trp Ile Arg Gln Phe Pro Gly Asp Lys Leu Glu
            35                  40                  45

Trp Met Gly Tyr Ile Ser Phe Asn Gly Asp Tyr Asn Tyr Asn Pro Ser
        50                  55                  60

Leu Lys Ser Arg Ile Ser Ile Thr Arg Asp Thr Ser Lys Asn Gln Phe
65                  70                  75                  80

Phe Leu Gln Leu Ser Ser Val Thr Thr Glu Asp Thr Ala Thr Tyr Tyr
                    85                  90                  95

Cys Ala Ser Ser Tyr Asp Gly Leu Phe Ala Tyr Trp Gly Gln Gly Thr
                    100                 105                 110

Leu Val Thr Val Ser Ala
        115
```

<210> SEQ ID NO 147
<211> LENGTH: 118
<212> TYPE: PRT
<213> ORGANISM: Artificial Sequence
<220> FEATURE:
<223> OTHER INFORMATION: 3C2 heavy chain variable region

<400> SEQUENCE: 147

```
His Asp Val Gln Leu Gln Glu Ser Gly Pro Asp Leu Val Lys Pro Ser
 1               5                  10                  15

Gln Ser Leu Ser Leu Thr Cys Thr Val Thr Gly Phe Ser Ile Thr Ser
             20                  25                  30

Gly Tyr Gly Trp His Trp Ile Arg Gln Phe Pro Gly Asn Lys Leu Glu
         35                  40                  45

Trp Met Gly Tyr Ile Ser Phe Asn Gly Asp Ser Asn Tyr Asn Pro Ser
     50                  55                  60

Leu Lys Ser Arg Ile Ser Ile Thr Arg Asp Thr Ser Lys Asn Gln Phe
 65                  70                  75                  80

Phe Leu Gln Leu Asn Ser Val Thr Ser Glu Asp Thr Ala Thr Tyr Tyr
                 85                  90                  95

Cys Ala Ser Ser Tyr Asp Gly Leu Phe Ala Tyr Trp Gly Gln Gly Pro
            100                 105                 110

Leu Val Thr Val Ser Ala
        115
```

<210> SEQ ID NO 148
<211> LENGTH: 16
<212> TYPE: PRT
<213> ORGANISM: Artificial Sequence
<220> FEATURE:
<223> OTHER INFORMATION: 3A2 light chain CDR1

<400> SEQUENCE: 148

```
Lys Ser Ser Gln Ser Leu Leu His Ser Asp Gly Lys Thr Tyr Leu Asn
 1               5                  10                  15
```

<210> SEQ ID NO 149
<211> LENGTH: 7
<212> TYPE: PRT
<213> ORGANISM: Artificial Sequence
<220> FEATURE:
<223> OTHER INFORMATION: 3A2 light chain CDR2

<400> SEQUENCE: 149

```
Leu Val Ser Lys Leu Asp Ser
 1               5
```

<210> SEQ ID NO 150
<211> LENGTH: 9
<212> TYPE: PRT
<213> ORGANISM: Artificial Sequence
<220> FEATURE:
<223> OTHER INFORMATION: 3A2 light chain CDR3

<400> SEQUENCE: 150

```
Trp Gln Gly Thr His Phe Pro Arg Thr
 1               5
```

<210> SEQ ID NO 151
<211> LENGTH: 10
<212> TYPE: PRT
<213> ORGANISM: Artificial Sequence
<220> FEATURE:

```
<223> OTHER INFORMATION: 3A2 heavy chain CDR1

<400> SEQUENCE: 151

Gly Tyr Thr Phe Thr Asp Tyr Asn Met His
1               5                   10

<210> SEQ ID NO 152
<211> LENGTH: 10
<212> TYPE: PRT
<213> ORGANISM: Artificial Sequence
<220> FEATURE:
<223> OTHER INFORMATION: 3A2 heavy chain CDR2

<400> SEQUENCE: 152

Tyr Ile Asn Pro Tyr Asn Asp Val Thr Glu
1               5                   10

<210> SEQ ID NO 153
<211> LENGTH: 7
<212> TYPE: PRT
<213> ORGANISM: Artificial Sequence
<220> FEATURE:
<223> OTHER INFORMATION: 3A2 heavy chain CDR3

<400> SEQUENCE: 153

Ala Trp Phe Gly Leu Arg Gln
1               5

<210> SEQ ID NO 154
<211> LENGTH: 16
<212> TYPE: PRT
<213> ORGANISM: Artificial Sequence
<220> FEATURE:
<223> OTHER INFORMATION: 3E10 light chain CDR1

<400> SEQUENCE: 154

Arg Ser Ser Lys Ser Leu Leu His Ser Asn Gly Asn Thr Tyr Leu Tyr
1               5                   10                  15

<210> SEQ ID NO 155
<211> LENGTH: 7
<212> TYPE: PRT
<213> ORGANISM: Artificial Sequence
<220> FEATURE:
<223> OTHER INFORMATION: 3E10 light chain CDR2

<400> SEQUENCE: 155

Arg Met Ser Asn Leu Ala Ser
1               5

<210> SEQ ID NO 156
<211> LENGTH: 9
<212> TYPE: PRT
<213> ORGANISM: Artificial Sequence
<220> FEATURE:
<223> OTHER INFORMATION: 3E10 light chain CDR3

<400> SEQUENCE: 156

Met Gln His Leu Glu Tyr Pro Tyr Thr
1               5

<210> SEQ ID NO 157
<211> LENGTH: 10
<212> TYPE: PRT
<213> ORGANISM: Artificial Sequence
<220> FEATURE:
<223> OTHER INFORMATION: 3E10 heavy chain CDR1
```

<400> SEQUENCE: 157

Gly Asp Thr Phe Thr Asp Tyr Tyr Met Asn
1               5                   10

<210> SEQ ID NO 158
<211> LENGTH: 10
<212> TYPE: PRT
<213> ORGANISM: Artificial Sequence
<220> FEATURE:
<223> OTHER INFORMATION: 3E10 heavy chain CDR2

<400> SEQUENCE: 158

Asp Ile Asn Pro Asn Tyr Gly Gly Ile Thr
1               5                   10

<210> SEQ ID NO 159
<211> LENGTH: 9
<212> TYPE: PRT
<213> ORGANISM: Artificial Sequence
<220> FEATURE:
<223> OTHER INFORMATION: 3E10 heavy chain CDR3

<400> SEQUENCE: 159

Gln Ala Tyr Tyr Arg Asn Ser Asp Tyr
1               5

<210> SEQ ID NO 160
<211> LENGTH: 11
<212> TYPE: PRT
<213> ORGANISM: Artificial Sequence
<220> FEATURE:
<223> OTHER INFORMATION: 3G12 light chain CDR1

<400> SEQUENCE: 160

Lys Ala Ser Gln Asp Val Gly Thr Ala Val Ala
1               5                   10

<210> SEQ ID NO 161
<211> LENGTH: 7
<212> TYPE: PRT
<213> ORGANISM: Artificial Sequence
<220> FEATURE:
<223> OTHER INFORMATION: 3G12 light chain CDR2

<400> SEQUENCE: 161

Trp Thr Ser Thr Arg His Thr
1               5

<210> SEQ ID NO 162
<211> LENGTH: 9
<212> TYPE: PRT
<213> ORGANISM: Artificial Sequence
<220> FEATURE:
<223> OTHER INFORMATION: 3G12 light chain CDR3

<400> SEQUENCE: 162

Gln Gln His Tyr Ser Ile Pro Leu Thr
1               5

<210> SEQ ID NO 163
<211> LENGTH: 10
<212> TYPE: PRT
<213> ORGANISM: Artificial Sequence
<220> FEATURE:
<223> OTHER INFORMATION: 3G12 heavy chain CDR1

-continued

<400> SEQUENCE: 163

Gly Tyr Ile Phe Thr Asp Tyr Glu Ile His
1               5                   10

<210> SEQ ID NO 164
<211> LENGTH: 10
<212> TYPE: PRT
<213> ORGANISM: Artificial Sequence
<220> FEATURE:
<223> OTHER INFORMATION: 3G12 heavy chain CDR2

<400> SEQUENCE: 164

Val Ile Asp Pro Glu Thr Gly Asn Thr Ala
1               5                   10

<210> SEQ ID NO 165
<211> LENGTH: 6
<212> TYPE: PRT
<213> ORGANISM: Artificial Sequence
<220> FEATURE:
<223> OTHER INFORMATION: 3G12 heavy chain CDR3

<400> SEQUENCE: 165

Met Gly Tyr Ser Asp Tyr
1               5

<210> SEQ ID NO 166
<211> LENGTH: 240
<212> TYPE: PRT
<213> ORGANISM: Artificial Sequence
<220> FEATURE:
<223> OTHER INFORMATION: humanized 3D3 light chain

<400> SEQUENCE: 166

Met Val Leu Gln Thr Gln Val Phe Ile Ser Leu Leu Leu Trp Ile Ser
1               5                   10                  15

Gly Ala Tyr Gly Asp Ile Val Met Thr Gln Ser Pro Asp Ser Leu Ala
                20                  25                  30

Val Ser Leu Gly Glu Arg Ala Thr Ile Asn Cys Lys Ser Gln Ser
            35                  40                  45

Leu Leu Asn Ser Asn Phe Gln Lys Asn Phe Leu Ala Trp Tyr Gln Gln
        50                  55                  60

Lys Pro Gly Gln Pro Pro Lys Leu Leu Ile Tyr Phe Ala Ser Thr Arg
65                  70                  75                  80

Glu Ser Ser Val Pro Asp Arg Phe Ser Gly Ser Gly Ser Gly Thr Asp
                85                  90                  95

Phe Thr Leu Thr Ile Ser Ser Leu Gln Ala Glu Asp Val Ala Val Tyr
            100                 105                 110

Tyr Cys Gln Gln His Tyr Ser Thr Pro Leu Thr Phe Gly Gln Gly Thr
        115                 120                 125

Lys Leu Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

```
Lys Ala Asp Tyr Glu Lys His Lys Val Tyr Ala Cys Glu Val Thr His
    210                 215                 220
Gln Gly Leu Ser Ser Pro Val Thr Lys Ser Phe Asn Arg Gly Glu Cys
225                 230                 235                 240
```

<210> SEQ ID NO 167
<211> LENGTH: 462
<212> TYPE: PRT
<213> ORGANISM: Artificial Sequence
<220> FEATURE:
<223> OTHER INFORMATION: humanized 3D3 heavy chain

<400> SEQUENCE: 167

```
Met Asp Trp Thr Trp Arg Ile Leu Phe Leu Val Ala Ala Thr Gly
1               5                   10                  15
Thr His Ala Glu Val Gln Leu Val Gln Ser Gly Ala Glu Val Lys Lys
                20                  25                  30
Pro Gly Ala Ser Val Lys Val Ser Cys Lys Ala Ser Gly Tyr Ile Phe
            35                  40                  45
Thr Asp Tyr Glu Ile His Trp Val Arg Gln Ala Pro Gly Gln Gly Leu
    50                  55                  60
Glu Trp Met Gly Val Ile Asp Pro Glu Thr Gly Asn Thr Ala Phe Asn
65                  70                  75                  80
Gln Lys Phe Lys Gly Arg Val Thr Ile Thr Ala Asp Thr Ser Thr Ser
                85                  90                  95
Thr Ala Tyr Met Glu Leu Ser Ser Leu Thr Ser Glu Asp Thr Ala Val
            100                 105                 110
Tyr Tyr Cys Met Gly Tyr Ser Asp Tyr Trp Gly Gln Gly Thr Leu Val
        115                 120                 125
Thr Val Ser Ser Ala Ser Thr Lys Gly Pro Ser Val Phe Pro Leu Ala
    130                 135                 140
Pro Ser Ser Lys Ser Thr Ser Gly Gly Thr Ala Ala Leu Gly Cys Leu
145                 150                 155                 160
Val Lys Asp Tyr Phe Pro Glu Pro Val Thr Val Ser Trp Asn Ser Gly
                165                 170                 175
Ala Leu Thr Ser Gly Val His Thr Phe Pro Ala Val Leu Gln Ser Ser
            180                 185                 190
Gly Leu Tyr Ser Leu Ser Ser Val Val Thr Val Pro Ser Ser Ser Leu
        195                 200                 205
Gly Thr Gln Thr Tyr Ile Cys Asn Val Asn His Lys Pro Ser Asn Thr
    210                 215                 220
Lys Val Asp Lys Lys Val Glu Pro Lys Ser Cys Asp Lys Thr His Thr
225                 230                 235                 240
Cys Pro Pro Cys Pro Ala Pro Glu Leu Leu Gly Gly Pro Ser Val Phe
                245                 250                 255
Leu Phe Pro Pro Lys Pro Lys Asp Thr Leu Met Ile Ser Arg Thr Pro
            260                 265                 270
Glu Val Thr Cys Val Val Val Asp Val Ser His Glu Asp Pro Glu Val
        275                 280                 285
Lys Phe Asn Trp Tyr Val Asp Gly Val Glu Val His Asn Ala Lys Thr
    290                 295                 300
Lys Pro Arg Glu Glu Gln Tyr Asn Ser Thr Tyr Arg Val Val Ser Val
305                 310                 315                 320
Leu Thr Val Leu His Gln Asp Trp Leu Asn Gly Lys Glu Tyr Lys Cys
                325                 330                 335
```

```
Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
            355                 360                 365

Ser Arg Asp Glu Leu Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
            435                 440                 445

Asn His Tyr Thr Gln Lys Ser Leu Ser Leu Ser Pro Gly Lys
            450                 455                 460

<210> SEQ ID NO 168
<211> LENGTH: 113
<212> TYPE: PRT
<213> ORGANISM: Artificial Sequence
<220> FEATURE:
<223> OTHER INFORMATION: humanized 3D3 light chain variable region

<400> SEQUENCE: 168

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Asn Phe Gln Lys Asn Phe Leu Ala Trp Tyr Gln Lys Pro Gly Gln
            35                  40                  45

Pro Pro Lys Leu Leu Ile Tyr Phe Ala Ser Thr Arg Glu Ser Ser Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Ser Thr Pro Leu Thr Phe Gly Gln Gly Thr Lys Leu Glu Ile
            100                 105                 110

Lys

<210> SEQ ID NO 169
<211> LENGTH: 113
<212> TYPE: PRT
<213> ORGANISM: Artificial Sequence
<220> FEATURE:
<223> OTHER INFORMATION: humanized 3D3 heavy chain variable region

<400> SEQUENCE: 169

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asp Tyr
            20                  25                  30

Glu Ile His Trp Val Arg Gln Ala Pro Gly Gln Gly Leu Glu Trp Met
            35                  40                  45

Gly Val Ile Asp Pro Glu Thr Gly Asn Thr Ala Phe Asn Gln Lys Phe
        50                  55                  60
```

```
Lys Gly Arg Val Thr Ile Thr Ala Asp Thr Ser Ser Thr Ala Tyr
 65                  70                  75                  80

Met Glu Leu Ser Ser Leu Thr Ser Glu Asp Thr Ala Val Tyr Tyr Cys
                 85                  90                  95

Met Gly Tyr Ser Asp Tyr Trp Gly Gln Gly Thr Leu Val Thr Val Ser
            100                 105                 110

Ser

<210> SEQ ID NO 170
<211> LENGTH: 234
<212> TYPE: PRT
<213> ORGANISM: Artificial Sequence
<220> FEATURE:
<223> OTHER INFORMATION: humanized 3C4 light chain

<400> SEQUENCE: 170

Met Val Leu Gln Thr Gln Val Phe Ile Ser Leu Leu Leu Trp Ile Ser
 1               5                  10                  15

Gly Ala Tyr Gly Asp Ile Val Met Thr Gln Ser Pro Ser Ser Leu Ser
                20                  25                  30

Ala Ser Val Gly Asp Arg Val Thr Ile Thr Cys Lys Ala Ser Gln Asp
            35                  40                  45

Ile His Asn Phe Leu Asn Trp Phe Gln Gln Lys Pro Gly Lys Ala Pro
        50                  55                  60

Lys Thr Leu Ile Phe Arg Ala Asn Arg Leu Val Asp Gly Val Pro Ser
 65                  70                  75                  80

Arg Phe Ser Gly Ser Gly Ser Gly Thr Asp Tyr Thr Leu Thr Ile Ser
                 85                  90                  95

Ser Leu Gln Pro Glu Asp Phe Ala Thr Tyr Ser Cys Leu Gln Tyr Asp
            100                 105                 110

Glu Ile Pro Leu Thr Phe Gly Gln Gly Thr Lys Leu Glu Ile Lys Arg
        115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 171
<211> LENGTH: 466
<212> TYPE: PRT
<213> ORGANISM: Artificial Sequence
<220> FEATURE:
<223> OTHER INFORMATION: humanized 3C4 heavy chain

<400> SEQUENCE: 171

Met Asp Trp Thr Trp Arg Ile Leu Phe Leu Val Ala Ala Ala Thr Gly
 1               5                  10                  15
```

```
Thr His Ala Glu Val Gln Leu Gln Glu Ser Gly Pro Gly Leu Val Lys
            20                  25                  30

Pro Ser Gln Thr Leu Ser Leu Thr Cys Thr Val Ser Gly Phe Ser Ile
        35                  40                  45

Thr Ser Gly Tyr Gly Trp His Trp Ile Arg Gln His Pro Gly Lys Gly
50                  55                  60

Leu Glu Trp Ile Gly Tyr Ile Asn Tyr Asp Gly His Asn Asp Tyr Asn
65                  70                  75                  80

Pro Ser Leu Lys Ser Arg Val Thr Ile Ser Gln Asp Thr Ser Lys Asn
                85                  90                  95

Gln Phe Ser Leu Lys Leu Ser Ser Val Thr Ala Ala Asp Thr Ala Val
            100                 105                 110

Tyr Tyr Cys Ala Ser Ser Tyr Asp Gly Leu Phe Ala Tyr Trp Gly Gln
        115                 120                 125

Gly Thr Leu Val Thr Val Ser Ser Ala Ser Thr Lys Gly Pro Ser Val
130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Asp Glu Leu Thr Lys Asn Gln Val Ser Leu
370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430
```

```
Lys Ser Arg Trp Gln Gln Gly Asn Val Phe Ser Cys Ser Val Met His
            435                 440                 445

Glu Ala Leu His Asn His Tyr Thr Gln Lys Ser Leu Ser Leu Ser Pro
    450                 455                 460

Gly Lys
465

<210> SEQ ID NO 172
<211> LENGTH: 107
<212> TYPE: PRT
<213> ORGANISM: Artificial Sequence
<220> FEATURE:
<223> OTHER INFORMATION: humanized 3C4 light chain variable region

<400> SEQUENCE: 172

Asp Ile Val Met Thr Gln Ser Pro Ser Ser Leu Ser Ala Ser Val Gly
1               5                   10                  15

Asp Arg Val Thr Ile Thr Cys Lys Ala Ser Gln Asp Ile His Asn Phe
            20                  25                  30

Leu Asn Trp Phe Gln Gln Lys Pro Gly Lys Ala Pro Lys Thr Leu Ile
        35                  40                  45

Phe Arg Ala Asn Arg Leu Val Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Ser Cys Leu Gln Tyr Asp Glu Ile Pro Leu
                85                  90                  95

Thr Phe Gly Gln Gly Thr Lys Leu Glu Ile Lys
            100                 105

<210> SEQ ID NO 173
<211> LENGTH: 116
<212> TYPE: PRT
<213> ORGANISM: Artificial Sequence
<220> FEATURE:
<223> OTHER INFORMATION: humanized 3C4 heavy chain variable region

<400> SEQUENCE: 173

Glu Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Ile Thr Ser Gly
            20                  25                  30

Tyr Gly Trp His Trp Ile Arg Gln His Pro Gly Lys Gly Leu Glu Trp
        35                  40                  45

Ile Gly Tyr Ile Asn Tyr Asp Gly His Asn Asp Tyr Asn Pro Ser Leu
    50                  55                  60

Lys Ser Arg Val Thr Ile Ser Gln Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Ser Ser Tyr Asp Gly Leu Phe Ala Tyr Trp Gly Gln Gly Thr Leu
            100                 105                 110

Val Thr Val Ser
        115

<210> SEQ ID NO 174
<211> LENGTH: 113
<212> TYPE: PRT
<213> ORGANISM: Artificial Sequence
```

```
<220> FEATURE:
<223> OTHER INFORMATION: Humanized 3D3 light chain variable region
      consensus 1
<220> FEATURE:
<221> NAME/KEY: MISC_FEATURE
<222> LOCATION: (9)..(9)
<223> OTHER INFORMATION: Xaa is an amino acid substitution in comparison
      with SEQ ID NO.:16
<220> FEATURE:
<221> NAME/KEY: MISC_FEATURE
<222> LOCATION: (15)..(15)
<223> OTHER INFORMATION: Xaa is an amino acid substitution in comparison
      with SEQ ID NO.:16
<220> FEATURE:
<221> NAME/KEY: MISC_FEATURE
<222> LOCATION: (17)..(17)
<223> OTHER INFORMATION: Xaa is an amino acid substitution in comparison
      with SEQ ID NO.:16
<220> FEATURE:
<221> NAME/KEY: MISC_FEATURE
<222> LOCATION: (18)..(18)
<223> OTHER INFORMATION: Xaa is an amino acid substitution in comparison
      with SEQ ID NO.:16
<220> FEATURE:
<221> NAME/KEY: MISC_FEATURE
<222> LOCATION: (19)..(19)
<223> OTHER INFORMATION: Xaa is an amino acid substitution in comparison
      with SEQ ID NO.:16
<220> FEATURE:
<221> NAME/KEY: MISC_FEATURE
<222> LOCATION: (21)..(21)
<223> OTHER INFORMATION: Xaa is an amino acid substitution in comparison
      with SEQ ID NO.:16
<220> FEATURE:
<221> NAME/KEY: MISC_FEATURE
<222> LOCATION: (49)..(49)
<223> OTHER INFORMATION: Xaa is an amino acid substitution in comparison
      with SEQ ID NO.:16
<220> FEATURE:
<221> NAME/KEY: MISC_FEATURE
<222> LOCATION: (64)..(64)
<223> OTHER INFORMATION: Xaa is an amino acid substitution in comparison
      with SEQ ID NO.:16
<220> FEATURE:
<221> NAME/KEY: MISC_FEATURE
<222> LOCATION: (69)..(69)
<223> OTHER INFORMATION: Xaa is an amino acid substitution in comparison
      with SEQ ID NO.:16
<220> FEATURE:
<221> NAME/KEY: MISC_FEATURE
<222> LOCATION: (84)..(84)
<223> OTHER INFORMATION: Xaa is an amino acid substitution in comparison
      with SEQ ID NO.:16
<220> FEATURE:
<221> NAME/KEY: MISC_FEATURE
<222> LOCATION: (89)..(89)
<223> OTHER INFORMATION: Xaa is an amino acid substitution in comparison
      with SEQ ID NO.:16
<220> FEATURE:
<221> NAME/KEY: MISC_FEATURE
<222> LOCATION: (91)..(91)
<223> OTHER INFORMATION: Xaa is an amino acid substitution in comparison
      with SEQ ID NO.:16
<220> FEATURE:
<221> NAME/KEY: MISC_FEATURE
<222> LOCATION: (93)..(93)
<223> OTHER INFORMATION: Xaa is an amino acid substitution in comparison
      with SEQ ID NO.:16
<220> FEATURE:
<221> NAME/KEY: MISC_FEATURE
<222> LOCATION: (106)..(106)
<223> OTHER INFORMATION: Xaa is an amino acid substitution in comparison
      with SEQ ID NO.:16
<220> FEATURE:
<221> NAME/KEY: MISC_FEATURE
<222> LOCATION: (112)..(112)
<223> OTHER INFORMATION: Xaa is an amino acid substitution in comparison
      with SEQ ID NO.:16
```

-continued

```
<400> SEQUENCE: 174

Asp Ile Val Met Thr Gln Ser Pro Xaa Ser Leu Ala Val Ser Xaa Gly
1               5                   10                  15

Xaa Xaa Xaa Thr Xaa Asn Cys Lys Ser Ser Gln Ser Leu Leu Asn Ser
            20                  25                  30

Asn Phe Gln Lys Asn Phe Leu Ala Trp Tyr Gln Gln Lys Pro Gly Gln
        35                  40                  45

Xaa Pro Lys Leu Leu Ile Tyr Phe Ala Ser Thr Arg Glu Ser Ser Xaa
50                  55                  60

Pro Asp Arg Phe Xaa Gly Ser Gly Ser Gly Thr Asp Phe Thr Leu Thr
65                  70                  75                  80

Ile Ser Ser Xaa Gln Ala Glu Asp Xaa Ala Xaa Tyr Xaa Cys Gln Gln
                85                  90                  95

His Tyr Ser Thr Pro Leu Thr Phe Gly Xaa Gly Thr Lys Leu Glu Xaa
            100                 105                 110

Lys

<210> SEQ ID NO 175
<211> LENGTH: 113
<212> TYPE: PRT
<213> ORGANISM: Artificial Sequence
<220> FEATURE:
<223> OTHER INFORMATION: Humanized 3D3 light chain variable region
      consensus 2
<220> FEATURE:
<221> NAME/KEY: MISC_FEATURE
<222> LOCATION: (9)..(9)
<223> OTHER INFORMATION: Xaa may be D or S
<220> FEATURE:
<221> NAME/KEY: MISC_FEATURE
<222> LOCATION: (15)..(15)
<223> OTHER INFORMATION: Xaa may be an hydrophobic amino acid
<220> FEATURE:
<221> NAME/KEY: MISC_FEATURE
<222> LOCATION: (17)..(17)
<223> OTHER INFORMATION: Xaa may be E or Q
<220> FEATURE:
<221> NAME/KEY: MISC_FEATURE
<222> LOCATION: (18)..(18)
<223> OTHER INFORMATION: Xaa may be a basic amino acid
<220> FEATURE:
<221> NAME/KEY: MISC_FEATURE
<222> LOCATION: (19)..(19)
<223> OTHER INFORMATION: Xaa may be an hydrophobic amino acid
<220> FEATURE:
<221> NAME/KEY: MISC_FEATURE
<222> LOCATION: (21)..(21)
<223> OTHER INFORMATION: Xaa may be an hydrophobic amino acid
<220> FEATURE:
<221> NAME/KEY: MISC_FEATURE
<222> LOCATION: (49)..(49)
<223> OTHER INFORMATION: Xaa may be P or S
<220> FEATURE:
<221> NAME/KEY: MISC_FEATURE
<222> LOCATION: (64)..(64)
<223> OTHER INFORMATION: Xaa may be an hydrophobic amino acid
<220> FEATURE:
<221> NAME/KEY: MISC_FEATURE
<222> LOCATION: (69)..(69)
<223> OTHER INFORMATION: Xaa may be S or I
<220> FEATURE:
<221> NAME/KEY: MISC_FEATURE
<222> LOCATION: (84)..(84)
<223> OTHER INFORMATION: Xaa may be an hydrophobic amino acid
<220> FEATURE:
<221> NAME/KEY: MISC_FEATURE
<222> LOCATION: (89)..(89)
<223> OTHER INFORMATION: Xaa may be an hydrophobic amino acid
<220> FEATURE:
<221> NAME/KEY: MISC_FEATURE
```

```
<222> LOCATION: (91)..(91)
<223> OTHER INFORMATION: Xaa may be V or D
<220> FEATURE:
<221> NAME/KEY: MISC_FEATURE
<222> LOCATION: (93)..(93)
<223> OTHER INFORMATION: Xaa may be an aromatic amino acid
<220> FEATURE:
<221> NAME/KEY: MISC_FEATURE
<222> LOCATION: (106)..(106)
<223> OTHER INFORMATION: Xaa may be Q or A
<220> FEATURE:
<221> NAME/KEY: MISC_FEATURE
<222> LOCATION: (112)..(112)
<223> OTHER INFORMATION: Xaa may be an hydrophobic amino acid

<400> SEQUENCE: 175

Asp Ile Val Met Thr Gln Ser Pro Xaa Ser Leu Ala Val Ser Xaa Gly
 1               5                  10                  15

Xaa Xaa Xaa Thr Xaa Asn Cys Lys Ser Ser Gln Ser Leu Leu Asn Ser
            20                  25                  30

Asn Phe Gln Lys Asn Phe Leu Ala Trp Tyr Gln Gln Lys Pro Gly Gln
        35                  40                  45

Xaa Pro Lys Leu Leu Ile Tyr Phe Ala Ser Thr Arg Glu Ser Ser Xaa
 50                  55                  60

Pro Asp Arg Phe Xaa Gly Ser Gly Ser Gly Thr Asp Phe Thr Leu Thr
 65                  70                  75                  80

Ile Ser Ser Xaa Gln Ala Glu Asp Xaa Ala Xaa Tyr Xaa Cys Gln Gln
                85                  90                  95

His Tyr Ser Thr Pro Leu Thr Phe Gly Xaa Gly Thr Lys Leu Glu Xaa
            100                 105                 110

Lys

<210> SEQ ID NO 176
<211> LENGTH: 113
<212> TYPE: PRT
<213> ORGANISM: Artificial Sequence
<220> FEATURE:
<223> OTHER INFORMATION: Humanized 3D3 light chain variable region
      consensus 3
<220> FEATURE:
<221> NAME/KEY: MISC_FEATURE
<222> LOCATION: (9)..(9)
<223> OTHER INFORMATION: Xaa may be D or S
<220> FEATURE:
<221> NAME/KEY: MISC_FEATURE
<222> LOCATION: (15)..(15)
<223> OTHER INFORMATION: Xaa may be L or I
<220> FEATURE:
<221> NAME/KEY: MISC_FEATURE
<222> LOCATION: (17)..(17)
<223> OTHER INFORMATION: Xaa may be E or Q
<220> FEATURE:
<221> NAME/KEY: MISC_FEATURE
<222> LOCATION: (18)..(18)
<223> OTHER INFORMATION: Xaa may be R or K
<220> FEATURE:
<221> NAME/KEY: MISC_FEATURE
<222> LOCATION: (19)..(19)
<223> OTHER INFORMATION: Xaa may be A or V
<220> FEATURE:
<221> NAME/KEY: MISC_FEATURE
<222> LOCATION: (21)..(21)
<223> OTHER INFORMATION: Xaa may be I or M
<220> FEATURE:
<221> NAME/KEY: MISC_FEATURE
<222> LOCATION: (49)..(49)
<223> OTHER INFORMATION: Xaa may be P or S
<220> FEATURE:
<221> NAME/KEY: MISC_FEATURE
<222> LOCATION: (64)..(64)
```

```
<223> OTHER INFORMATION: Xaa may be V or I
<220> FEATURE:
<221> NAME/KEY: MISC_FEATURE
<222> LOCATION: (69)..(69)
<223> OTHER INFORMATION: Xaa may be S or I
<220> FEATURE:
<221> NAME/KEY: MISC_FEATURE
<222> LOCATION: (84)..(84)
<223> OTHER INFORMATION: Xaa may be L or V
<220> FEATURE:
<221> NAME/KEY: MISC_FEATURE
<222> LOCATION: (89)..(89)
<223> OTHER INFORMATION: Xaa may be v or L
<220> FEATURE:
<221> NAME/KEY: MISC_FEATURE
<222> LOCATION: (91)..(91)
<223> OTHER INFORMATION: Xaa may be V or D
<220> FEATURE:
<221> NAME/KEY: MISC_FEATURE
<222> LOCATION: (93)..(93)
<223> OTHER INFORMATION: Xaa may be Y or F
<220> FEATURE:
<221> NAME/KEY: MISC_FEATURE
<222> LOCATION: (106)..(106)
<223> OTHER INFORMATION: Xaa may be Q or A
<220> FEATURE:
<221> NAME/KEY: MISC_FEATURE
<222> LOCATION: (112)..(112)
<223> OTHER INFORMATION: Xaa may be I or L

<400> SEQUENCE: 176

Asp Ile Val Met Thr Gln Ser Pro Xaa Ser Leu Ala Val Ser Xaa Gly
1               5                   10                  15

Xaa Xaa Xaa Thr Xaa Asn Cys Lys Ser Ser Gln Ser Leu Leu Asn Ser
            20                  25                  30

Asn Phe Gln Lys Asn Phe Leu Ala Trp Tyr Gln Gln Lys Pro Gly Gln
        35                  40                  45

Xaa Pro Lys Leu Leu Ile Tyr Phe Ala Ser Thr Arg Glu Ser Ser Xaa
50                  55                  60

Pro Asp Arg Phe Xaa Gly Ser Gly Ser Gly Thr Asp Phe Thr Leu Thr
65                  70                  75                  80

Ile Ser Ser Xaa Gln Ala Glu Asp Xaa Ala Xaa Tyr Xaa Cys Gln Gln
                85                  90                  95

His Tyr Ser Thr Pro Leu Thr Phe Gly Xaa Gly Thr Lys Leu Glu Xaa
            100                 105                 110

Lys

<210> SEQ ID NO 177
<211> LENGTH: 113
<212> TYPE: PRT
<213> ORGANISM: Artificial Sequence
<220> FEATURE:
<223> OTHER INFORMATION: Humanized 3D3 heavy chain variable region
      consensus 1
<220> FEATURE:
<221> NAME/KEY: MISC_FEATURE
<222> LOCATION: (5)..(5)
<223> OTHER INFORMATION: Xaa is an amino acid substitution in comparison
      with SEQ ID NO.:18
<220> FEATURE:
<221> NAME/KEY: MISC_FEATURE
<222> LOCATION: (8)..(8)
<223> OTHER INFORMATION: Xaa is an amino acid substitution in comparison
      with SEQ ID NO.:18
<220> FEATURE:
<221> NAME/KEY: MISC_FEATURE
<222> LOCATION: (11)..(11)
<223> OTHER INFORMATION: Xaa is an amino acid substitution in comparison
      with SEQ ID NO.:18
<220> FEATURE:
```

```
<221> NAME/KEY: MISC_FEATURE
<222> LOCATION: (12)..(12)
<223> OTHER INFORMATION: Xaa is an amino acid substitution in comparison
      with SEQ ID NO.:18
<220> FEATURE:
<221> NAME/KEY: MISC_FEATURE
<222> LOCATION: (13)..(13)
<223> OTHER INFORMATION: Xaa is an amino acid substitution in comparison
      with SEQ ID NO.:18
<220> FEATURE:
<221> NAME/KEY: MISC_FEATURE
<222> LOCATION: (19)..(19)
<223> OTHER INFORMATION: Xaa is an amino acid substitution in comparison
      with SEQ ID NO.:18
<220> FEATURE:
<221> NAME/KEY: MISC_FEATURE
<222> LOCATION: (20)..(20)
<223> OTHER INFORMATION: Xaa is an amino acid substitution in comparison
      with SEQ ID NO.:18
<220> FEATURE:
<221> NAME/KEY: MISC_FEATURE
<222> LOCATION: (38)..(38)
<223> OTHER INFORMATION: Xaa is an amino acid substitution in comparison
      with SEQ ID NO.:18
<220> FEATURE:
<221> NAME/KEY: MISC_FEATURE
<222> LOCATION: (40)..(40)
<223> OTHER INFORMATION: Xaa is an amino acid substitution in comparison
      with SEQ ID NO.:18
<220> FEATURE:
<221> NAME/KEY: MISC_FEATURE
<222> LOCATION: (42)..(42)
<223> OTHER INFORMATION: Xaa is an amino acid substitution in comparison
      with SEQ ID NO.:18
<220> FEATURE:
<221> NAME/KEY: MISC_FEATURE
<222> LOCATION: (43)..(43)
<223> OTHER INFORMATION: Xaa is an amino acid substitution in comparison
      with SEQ ID NO.:18
<220> FEATURE:
<221> NAME/KEY: MISC_FEATURE
<222> LOCATION: (48)..(48)
<223> OTHER INFORMATION: Xaa is an amino acid substitution in comparison
      with SEQ ID NO.:18
<220> FEATURE:
<221> NAME/KEY: MISC_FEATURE
<222> LOCATION: (67)..(67)
<223> OTHER INFORMATION: Xaa is an amino acid substitution in comparison
      with SEQ ID NO.:18
<220> FEATURE:
<221> NAME/KEY: MISC_FEATURE
<222> LOCATION: (68)..(68)
<223> OTHER INFORMATION: Xaa is an amino acid substitution in comparison
      with SEQ ID NO.:18
<220> FEATURE:
<221> NAME/KEY: MISC_FEATURE
<222> LOCATION: (70)..(70)
<223> OTHER INFORMATION: Xaa is an amino acid substitution in comparison
      with SEQ ID NO.:18
<220> FEATURE:
<221> NAME/KEY: MISC_FEATURE
<222> LOCATION: (74)..(74)
<223> OTHER INFORMATION: Xaa is an amino acid substitution in comparison
      with SEQ ID NO.:18
<220> FEATURE:
<221> NAME/KEY: MISC_FEATURE
<222> LOCATION: (76)..(76)
<223> OTHER INFORMATION: Xaa is an amino acid substitution in comparison
      with SEQ ID NO.:18
<220> FEATURE:
<221> NAME/KEY: MISC_FEATURE
<222> LOCATION: (91)..(91)
<223> OTHER INFORMATION: Xaa is an amino acid substitution in comparison
      with SEQ ID NO.:18
<220> FEATURE:
<221> NAME/KEY: MISC_FEATURE
<222> LOCATION: (108)..(108)
<223> OTHER INFORMATION: Xaa is an amino acid substitution in comparison
      with SEQ ID NO.:18
```

-continued

```
<220> FEATURE:
<221> NAME/KEY: MISC_FEATURE
<222> LOCATION: (109)..(109)
<223> OTHER INFORMATION: Xaa is an amino acid substitution in comparison
      with SEQ ID NO.:18

<400> SEQUENCE: 177

Glu Val Gln Leu Xaa Gln Ser Xaa Ala Glu Xaa Xaa Xaa Pro Gly Ala
1               5                   10                  15

Ser Val Xaa Xaa Ser Cys Lys Ala Ser Gly Tyr Ile Phe Thr Asp Tyr
            20                  25                  30

Glu Ile His Trp Val Xaa Gln Xaa Pro Xaa Xaa Gly Leu Glu Trp Xaa
        35                  40                  45

Gly Val Ile Asp Pro Glu Thr Gly Asn Thr Ala Phe Asn Gln Lys Phe
    50                  55                  60

Lys Gly Xaa Xaa Thr Xaa Thr Ala Asp Xaa Ser Xaa Ser Thr Ala Tyr
65                  70                  75                  80

Met Glu Leu Ser Ser Leu Thr Ser Glu Asp Xaa Ala Val Tyr Tyr Cys
                85                  90                  95

Met Gly Tyr Ser Asp Tyr Trp Gly Gln Gly Thr Xaa Xaa Thr Val Ser
            100                 105                 110

Ser

<210> SEQ ID NO 178
<211> LENGTH: 113
<212> TYPE: PRT
<213> ORGANISM: Artificial Sequence
<220> FEATURE:
<223> OTHER INFORMATION: Humanized 3D3 heavy chain variable region
      consensus 2
<220> FEATURE:
<221> NAME/KEY: MISC_FEATURE
<222> LOCATION: (5)..(5)
<223> OTHER INFORMATION: Xaa may be V or Q
<220> FEATURE:
<221> NAME/KEY: MISC_FEATURE
<222> LOCATION: (8)..(8)
<223> OTHER INFORMATION: Xaa may be G or V
<220> FEATURE:
<221> NAME/KEY: MISC_FEATURE
<222> LOCATION: (11)..(11)
<223> OTHER INFORMATION: Xaa may be an hydrophobic amino acid
<220> FEATURE:
<221> NAME/KEY: MISC_FEATURE
<222> LOCATION: (12)..(12)
<223> OTHER INFORMATION: Xaa may be K or V
<220> FEATURE:
<221> NAME/KEY: MISC_FEATURE
<222> LOCATION: (13)..(13)
<223> OTHER INFORMATION: Xaa may be a basic amino acid
<220> FEATURE:
<221> NAME/KEY: MISC_FEATURE
<222> LOCATION: (19)..(19)
<223> OTHER INFORMATION: Xaa may be K or T
<220> FEATURE:
<221> NAME/KEY: MISC_FEATURE
<222> LOCATION: (20)..(20)
<223> OTHER INFORMATION: Xaa may be an hydrophobic amino acid
<220> FEATURE:
<221> NAME/KEY: MISC_FEATURE
<222> LOCATION: (38)..(38)
<223> OTHER INFORMATION: Xaa may be a basic amino acid
<220> FEATURE:
<221> NAME/KEY: MISC_FEATURE
<222> LOCATION: (40)..(40)
<223> OTHER INFORMATION: Xaa may be A or T
<220> FEATURE:
<221> NAME/KEY: MISC_FEATURE
<222> LOCATION: (42)..(42)
<223> OTHER INFORMATION: Xaa may be G or V
```

```
<220> FEATURE:
<221> NAME/KEY: MISC_FEATURE
<222> LOCATION: (43)..(43)
<223> OTHER INFORMATION: Xaa may be Q or H
<220> FEATURE:
<221> NAME/KEY: MISC_FEATURE
<222> LOCATION: (48)..(48)
<223> OTHER INFORMATION: Xaa may be an hydrophobic amino acid
<220> FEATURE:
<221> NAME/KEY: MISC_FEATURE
<222> LOCATION: (67)..(67)
<223> OTHER INFORMATION: Xaa may be a basic amino acid
<220> FEATURE:
<221> NAME/KEY: MISC_FEATURE
<222> LOCATION: (68)..(68)
<223> OTHER INFORMATION: Xaa may be an hydrophobic amino acid
<220> FEATURE:
<221> NAME/KEY: MISC_FEATURE
<222> LOCATION: (70)..(70)
<223> OTHER INFORMATION: Xaa may be an hydrophobic amino acid
<220> FEATURE:
<221> NAME/KEY: MISC_FEATURE
<222> LOCATION: (74)..(74)
<223> OTHER INFORMATION: Xaa may be T or I
<220> FEATURE:
<221> NAME/KEY: MISC_FEATURE
<222> LOCATION: (76)..(76)
<223> OTHER INFORMATION: Xaa may be a neutral hydrophilic amino acid
<220> FEATURE:
<221> NAME/KEY: MISC_FEATURE
<222> LOCATION: (91)..(91)
<223> OTHER INFORMATION: Xaa may be a neutral hydrophilic amino acid
<220> FEATURE:
<221> NAME/KEY: MISC_FEATURE
<222> LOCATION: (108)..(108)
<223> OTHER INFORMATION: Xaa may be L or T
<220> FEATURE:
<221> NAME/KEY: MISC_FEATURE
<222> LOCATION: (109)..(109)
<223> OTHER INFORMATION: Xaa may be an hydrophobic amino acid

<400> SEQUENCE: 178

Glu Val Gln Leu Xaa Gln Ser Xaa Ala Glu Xaa Xaa Xaa Pro Gly Ala
1               5                   10                  15

Ser Val Xaa Xaa Ser Cys Lys Ala Ser Gly Tyr Ile Phe Thr Asp Tyr
            20                  25                  30

Glu Ile His Trp Val Xaa Gln Xaa Pro Xaa Xaa Gly Leu Glu Trp Xaa
        35                  40                  45

Gly Val Ile Asp Pro Glu Thr Gly Asn Thr Ala Phe Asn Gln Lys Phe
    50                  55                  60

Lys Gly Xaa Xaa Thr Xaa Thr Ala Asp Xaa Ser Xaa Ser Thr Ala Tyr
65                  70                  75                  80

Met Glu Leu Ser Ser Leu Thr Ser Glu Asp Xaa Ala Val Tyr Tyr Cys
                85                  90                  95

Met Gly Tyr Ser Asp Tyr Trp Gly Gln Gly Thr Xaa Xaa Thr Val Ser
            100                 105                 110

Ser

<210> SEQ ID NO 179
<211> LENGTH: 113
<212> TYPE: PRT
<213> ORGANISM: Artificial Sequence
<220> FEATURE:
<223> OTHER INFORMATION: Humanized 3D3 heavy chain variable region
      consensus 3
<220> FEATURE:
<221> NAME/KEY: MISC_FEATURE
<222> LOCATION: (5)..(5)
<223> OTHER INFORMATION: Xaa may be V or Q
<220> FEATURE:
```

```
<221> NAME/KEY: MISC_FEATURE
<222> LOCATION: (8)..(8)
<223> OTHER INFORMATION: Xaa may be G or V
<220> FEATURE:
<221> NAME/KEY: MISC_FEATURE
<222> LOCATION: (11)..(11)
<223> OTHER INFORMATION: Xaa may be V or L
<220> FEATURE:
<221> NAME/KEY: MISC_FEATURE
<222> LOCATION: (12)..(12)
<223> OTHER INFORMATION: Xaa may be K or V
<220> FEATURE:
<221> NAME/KEY: MISC_FEATURE
<222> LOCATION: (13)..(13)
<223> OTHER INFORMATION: Xaa may be K or R
<220> FEATURE:
<221> NAME/KEY: MISC_FEATURE
<222> LOCATION: (19)..(19)
<223> OTHER INFORMATION: Xaa may be K or T
<220> FEATURE:
<221> NAME/KEY: MISC_FEATURE
<222> LOCATION: (20)..(20)
<223> OTHER INFORMATION: Xaa may be V or L
<220> FEATURE:
<221> NAME/KEY: MISC_FEATURE
<222> LOCATION: (38)..(38)
<223> OTHER INFORMATION: Xaa may be R or K
<220> FEATURE:
<221> NAME/KEY: MISC_FEATURE
<222> LOCATION: (40)..(40)
<223> OTHER INFORMATION: Xaa may be A or T
<220> FEATURE:
<221> NAME/KEY: MISC_FEATURE
<222> LOCATION: (42)..(42)
<223> OTHER INFORMATION: Xaa may be G or V
<220> FEATURE:
<221> NAME/KEY: MISC_FEATURE
<222> LOCATION: (43)..(43)
<223> OTHER INFORMATION: Xaa may be Q or H
<220> FEATURE:
<221> NAME/KEY: MISC_FEATURE
<222> LOCATION: (48)..(48)
<223> OTHER INFORMATION: Xaa may be M or I
<220> FEATURE:
<221> NAME/KEY: MISC_FEATURE
<222> LOCATION: (67)..(67)
<223> OTHER INFORMATION: Xaa may be R or K
<220> FEATURE:
<221> NAME/KEY: MISC_FEATURE
<222> LOCATION: (68)..(68)
<223> OTHER INFORMATION: Xaa may be V or A
<220> FEATURE:
<221> NAME/KEY: MISC_FEATURE
<222> LOCATION: (70)..(70)
<223> OTHER INFORMATION: Xaa may be I or L
<220> FEATURE:
<221> NAME/KEY: MISC_FEATURE
<222> LOCATION: (74)..(74)
<223> OTHER INFORMATION: Xaa may be T or I
<220> FEATURE:
<221> NAME/KEY: MISC_FEATURE
<222> LOCATION: (76)..(76)
<223> OTHER INFORMATION: Xaa may be T or S
<220> FEATURE:
<221> NAME/KEY: MISC_FEATURE
<222> LOCATION: (91)..(91)
<223> OTHER INFORMATION: Xaa may be T or S
<220> FEATURE:
<221> NAME/KEY: MISC_FEATURE
<222> LOCATION: (108)..(108)
<223> OTHER INFORMATION: Xaa may be L or T
<220> FEATURE:
<221> NAME/KEY: MISC_FEATURE
<222> LOCATION: (109)..(109)
<223> OTHER INFORMATION: Xaa may be V or L

<400> SEQUENCE: 179

Glu Val Gln Leu Xaa Gln Ser Xaa Ala Glu Xaa Xaa Xaa Pro Gly Ala
```

```
                1               5                      10                      15
            Ser Val Xaa Xaa Ser Cys Lys Ala Ser Gly Tyr Ile Phe Thr Asp Tyr
                        20                  25                  30
            Glu Ile His Trp Val Xaa Gln Xaa Pro Xaa Xaa Gly Leu Glu Trp Xaa
                        35                  40                  45
            Gly Val Ile Asp Pro Glu Thr Gly Asn Thr Ala Phe Asn Gln Lys Phe
                        50                  55                  60
            Lys Gly Xaa Xaa Thr Xaa Thr Ala Asp Xaa Ser Xaa Ser Thr Ala Tyr
             65                  70                  75                  80
            Met Glu Leu Ser Ser Leu Thr Ser Glu Asp Xaa Ala Val Tyr Tyr Cys
                        85                  90                  95
            Met Gly Tyr Ser Asp Tyr Trp Gly Gln Gly Thr Xaa Xaa Thr Val Ser
                        100                 105                 110
            Ser
```

<210> SEQ ID NO 180
<211> LENGTH: 107
<212> TYPE: PRT
<213> ORGANISM: Artificial Sequence
<220> FEATURE:
<223> OTHER INFORMATION: Humanized 3C4 light chain variable region
      consensus 1
<220> FEATURE:
<221> NAME/KEY: MISC_FEATURE
<222> LOCATION: (5)..(5)
<223> OTHER INFORMATION: Xaa is an amino acid substitution in comparison
      with SEQ ID NO.:24
<220> FEATURE:
<221> NAME/KEY: MISC_FEATURE
<222> LOCATION: (11)..(11)
<223> OTHER INFORMATION: Xaa is an amino acid substitution in comparison
      with SEQ ID NO.:24
<220> FEATURE:
<221> NAME/KEY: MISC_FEATURE
<222> LOCATION: (12)..(12)
<223> OTHER INFORMATION: Xaa is an amino acid substitution in comparison
      with SEQ ID NO.:24
<220> FEATURE:
<221> NAME/KEY: MISC_FEATURE
<222> LOCATION: (15)..(15)
<223> OTHER INFORMATION: Xaa is an amino acid substitution in comparison
      with SEQ ID NO.:24
<220> FEATURE:
<221> NAME/KEY: MISC_FEATURE
<222> LOCATION: (17)..(17)
<223> OTHER INFORMATION: Xaa is an amino acid substitution in comparison
      with SEQ ID NO.:24
<220> FEATURE:
<221> NAME/KEY: MISC_FEATURE
<222> LOCATION: (43)..(43)
<223> OTHER INFORMATION: Xaa is an amino acid substitution in comparison
      with SEQ ID NO.:24
<220> FEATURE:
<221> NAME/KEY: MISC_FEATURE
<222> LOCATION: (69)..(69)
<223> OTHER INFORMATION: Xaa is an amino acid substitution in comparison
      with SEQ ID NO.:24
<220> FEATURE:
<221> NAME/KEY: MISC_FEATURE
<222> LOCATION: (72)..(72)
<223> OTHER INFORMATION: Xaa is an amino acid substitution in comparison
      with SEQ ID NO.:24
<220> FEATURE:
<221> NAME/KEY: MISC_FEATURE
<222> LOCATION: (79)..(79)
<223> OTHER INFORMATION: Xaa is an amino acid substitution in comparison
      with SEQ ID NO.:24
<220> FEATURE:
<221> NAME/KEY: MISC_FEATURE
<222> LOCATION: (80)..(80)
<223> OTHER INFORMATION: Xaa is an amino acid substitution in comparison

```
      with SEQ ID NO.:24
<220> FEATURE:
<221> NAME/KEY: MISC_FEATURE
<222> LOCATION: (83)..(83)
<223> OTHER INFORMATION: Xaa is an amino acid substitution in comparison
      with SEQ ID NO.:24
<220> FEATURE:
<221> NAME/KEY: MISC_FEATURE
<222> LOCATION: (84)..(84)
<223> OTHER INFORMATION: Xaa is an amino acid substitution in comparison
      with SEQ ID NO.:24
<220> FEATURE:
<221> NAME/KEY: MISC_FEATURE
<222> LOCATION: (85)..(85)
<223> OTHER INFORMATION: Xaa is an amino acid substitution in comparison
      with SEQ ID NO.:24
<220> FEATURE:
<221> NAME/KEY: MISC_FEATURE
<222> LOCATION: (100)..(100)
<223> OTHER INFORMATION: Xaa is an amino acid substitution in comparison
      with SEQ ID NO.:24
<220> FEATURE:
<221> NAME/KEY: MISC_FEATURE
<222> LOCATION: (106)..(106)
<223> OTHER INFORMATION: Xaa is an amino acid substitution in comparison
      with SEQ ID NO.:24
<220> FEATURE:
<221> NAME/KEY: MISC_FEATURE
<222> LOCATION: (107)..(107)
<223> OTHER INFORMATION: Xaa can be any naturally occurring amino acid

<400> SEQUENCE: 180

Asp Ile Val Met Xaa Gln Ser Pro Ser Ser Xaa Xaa Ala Ser Xaa Gly
1               5                   10                  15

Xaa Arg Val Thr Ile Thr Cys Lys Ala Ser Gln Asp Ile His Asn Phe
            20                  25                  30

Leu Asn Trp Phe Gln Gln Lys Pro Gly Lys Xaa Pro Lys Thr Leu Ile
        35                  40                  45

Phe Arg Ala Asn Arg Leu Val Asp Gly Val Pro Ser Arg Phe Ser Gly
    50                  55                  60

Ser Gly Ser Gly Xaa Asp Tyr Xaa Leu Thr Ile Ser Ser Leu Xaa Xaa
65                  70                  75                  80

Glu Asp Xaa Xaa Xaa Tyr Ser Cys Leu Gln Tyr Asp Glu Ile Pro Leu
                85                  90                  95

Thr Phe Gly Xaa Gly Thr Lys Leu Glu Xaa Xaa
            100                 105

<210> SEQ ID NO 181
<211> LENGTH: 107
<212> TYPE: PRT
<213> ORGANISM: Artificial Sequence
<220> FEATURE:
<223> OTHER INFORMATION: Humanized 3C4 light chain variable region
      consensus 2
<220> FEATURE:
<221> NAME/KEY: MISC_FEATURE
<222> LOCATION: (5)..(5)
<223> OTHER INFORMATION: Xaa may be a neutral hydrophilic amino acid
<220> FEATURE:
<221> NAME/KEY: MISC_FEATURE
<222> LOCATION: (11)..(11)
<223> OTHER INFORMATION: Xaa may be an hydrophobic amino acid
<220> FEATURE:
<221> NAME/KEY: MISC_FEATURE
<222> LOCATION: (12)..(12)
<223> OTHER INFORMATION: Xaa may be S or Y
<220> FEATURE:
<221> NAME/KEY: MISC_FEATURE
<222> LOCATION: (15)..(15)
<223> OTHER INFORMATION: Xaa may be an hydrophobic amino acid
<220> FEATURE:
```

```
<221> NAME/KEY: MISC_FEATURE
<222> LOCATION: (17)..(17)
<223> OTHER INFORMATION: Xaa may be an acidic amino acid
<220> FEATURE:
<221> NAME/KEY: MISC_FEATURE
<222> LOCATION: (43)..(43)
<223> OTHER INFORMATION: Xaa may be A or S
<220> FEATURE:
<221> NAME/KEY: MISC_FEATURE
<222> LOCATION: (69)..(69)
<223> OTHER INFORMATION: Xaa may be T or Q
<220> FEATURE:
<221> NAME/KEY: MISC_FEATURE
<222> LOCATION: (72)..(72)
<223> OTHER INFORMATION: Xaa may be a neutral hydrophilic amino acid
<220> FEATURE:
<221> NAME/KEY: MISC_FEATURE
<222> LOCATION: (79)..(79)
<223> OTHER INFORMATION: Xaa may be Q or E
<220> FEATURE:
<221> NAME/KEY: MISC_FEATURE
<222> LOCATION: (80)..(80)
<223> OTHER INFORMATION: Xaa may be P or F
<220> FEATURE:
<221> NAME/KEY: MISC_FEATURE
<222> LOCATION: (83)..(83)
<223> OTHER INFORMATION: Xaa may be F or L
<220> FEATURE:
<221> NAME/KEY: MISC_FEATURE
<222> LOCATION: (84)..(84)
<223> OTHER INFORMATION: Xaa may be A or G
<220> FEATURE:
<221> NAME/KEY: MISC_FEATURE
<222> LOCATION: (85)..(85)
<223> OTHER INFORMATION: Xaa may be T or I
<220> FEATURE:
<221> NAME/KEY: MISC_FEATURE
<222> LOCATION: (100)..(100)
<223> OTHER INFORMATION: Xaa may be Q or A
<220> FEATURE:
<221> NAME/KEY: MISC_FEATURE
<222> LOCATION: (106)..(106)
<223> OTHER INFORMATION: Xaa may be an hydrophobic amino acid
<220> FEATURE:
<221> NAME/KEY: MISC_FEATURE
<222> LOCATION: (107)..(107)
<223> OTHER INFORMATION: Xaa may be a basic amino acid

<400> SEQUENCE: 181

Asp Ile Val Met Xaa Gln Ser Pro Ser Ser Xaa Xaa Ala Ser Xaa Gly
1               5                  10                  15

Xaa Arg Val Thr Ile Thr Cys Lys Ala Ser Gln Asp Ile His Asn Phe
            20                  25                  30

Leu Asn Trp Phe Gln Gln Lys Pro Gly Lys Xaa Pro Lys Thr Leu Ile
        35                  40                  45

Phe Arg Ala Asn Arg Leu Val Asp Gly Val Pro Ser Arg Phe Ser Gly
    50                  55                  60

Ser Gly Ser Gly Xaa Asp Tyr Xaa Leu Thr Ile Ser Ser Leu Xaa Xaa
65                  70                  75                  80

Glu Asp Xaa Xaa Xaa Tyr Ser Cys Leu Gln Tyr Asp Glu Ile Pro Leu
                85                  90                  95

Thr Phe Gly Xaa Gly Thr Lys Leu Glu Xaa Xaa
            100                 105

<210> SEQ ID NO 182
<211> LENGTH: 107
<212> TYPE: PRT
<213> ORGANISM: Artificial Sequence
<220> FEATURE:
<223> OTHER INFORMATION: Humanized 3C4 light chain variable region
      consensus 3
```

```
<220> FEATURE:
<221> NAME/KEY: MISC_FEATURE
<222> LOCATION: (5)..(5)
<223> OTHER INFORMATION: Xaa may be T or S
<220> FEATURE:
<221> NAME/KEY: MISC_FEATURE
<222> LOCATION: (11)..(11)
<223> OTHER INFORMATION: Xaa may be L or M
<220> FEATURE:
<221> NAME/KEY: MISC_FEATURE
<222> LOCATION: (12)..(12)
<223> OTHER INFORMATION: Xaa may be S or Y
<220> FEATURE:
<221> NAME/KEY: MISC_FEATURE
<222> LOCATION: (15)..(15)
<223> OTHER INFORMATION: Xaa may be V or L
<220> FEATURE:
<221> NAME/KEY: MISC_FEATURE
<222> LOCATION: (17)..(17)
<223> OTHER INFORMATION: Xaa may be D or E
<220> FEATURE:
<221> NAME/KEY: MISC_FEATURE
<222> LOCATION: (43)..(43)
<223> OTHER INFORMATION: Xaa may be A or S
<220> FEATURE:
<221> NAME/KEY: MISC_FEATURE
<222> LOCATION: (69)..(69)
<223> OTHER INFORMATION: Xaa may be T or Q
<220> FEATURE:
<221> NAME/KEY: MISC_FEATURE
<222> LOCATION: (72)..(72)
<223> OTHER INFORMATION: Xaa may be T or S
<220> FEATURE:
<221> NAME/KEY: MISC_FEATURE
<222> LOCATION: (79)..(79)
<223> OTHER INFORMATION: Xaa may be Q or E
<220> FEATURE:
<221> NAME/KEY: MISC_FEATURE
<222> LOCATION: (80)..(80)
<223> OTHER INFORMATION: Xaa may be P or F
<220> FEATURE:
<221> NAME/KEY: MISC_FEATURE
<222> LOCATION: (83)..(83)
<223> OTHER INFORMATION: Xaa may be F or L
<220> FEATURE:
<221> NAME/KEY: MISC_FEATURE
<222> LOCATION: (84)..(84)
<223> OTHER INFORMATION: Xaa may be A or G
<220> FEATURE:
<221> NAME/KEY: MISC_FEATURE
<222> LOCATION: (85)..(85)
<223> OTHER INFORMATION: Xaa may be T or I
<220> FEATURE:
<221> NAME/KEY: MISC_FEATURE
<222> LOCATION: (100)..(100)
<223> OTHER INFORMATION: Xaa may be Q or A
<220> FEATURE:
<221> NAME/KEY: MISC_FEATURE
<222> LOCATION: (106)..(106)
<223> OTHER INFORMATION: Xaa may be I or L
<220> FEATURE:
<221> NAME/KEY: MISC_FEATURE
<222> LOCATION: (107)..(107)
<223> OTHER INFORMATION: Xaa may be K or R

<400> SEQUENCE: 182

Asp Ile Val Met Xaa Gln Ser Pro Ser Ser Xaa Xaa Ala Ser Xaa Gly
1               5                   10                  15

Xaa Arg Val Thr Ile Thr Cys Lys Ala Ser Gln Asp Ile His Asn Phe
            20                  25                  30

Leu Asn Trp Phe Gln Gln Lys Pro Gly Lys Xaa Pro Lys Thr Leu Ile
        35                  40                  45

Phe Arg Ala Asn Arg Leu Val Asp Gly Val Pro Ser Arg Phe Ser Gly
    50                  55                  60
```

-continued

Ser Gly Ser Gly Xaa Asp Tyr Xaa Leu Thr Ile Ser Ser Leu Xaa Xaa
65                  70                  75                  80

Glu Asp Xaa Xaa Xaa Tyr Ser Cys Leu Gln Tyr Asp Glu Ile Pro Leu
                85                  90                  95

Thr Phe Gly Xaa Gly Thr Lys Leu Glu Xaa Xaa
            100                 105

<210> SEQ ID NO 183
<211> LENGTH: 117
<212> TYPE: PRT
<213> ORGANISM: Artificial Sequence
<220> FEATURE:
<223> OTHER INFORMATION: Humanized 3C4 heavy chain variable region
      consensus 1
<220> FEATURE:
<221> NAME/KEY: MISC_FEATURE
<222> LOCATION: (10)..(10)
<223> OTHER INFORMATION: Xaa is an amino acid substitution in comparison
      with SEQ ID NO.:26
<220> FEATURE:
<221> NAME/KEY: MISC_FEATURE
<222> LOCATION: (17)..(17)
<223> OTHER INFORMATION: Xaa is an amino acid substitution in comparison
      with SEQ ID NO.:26
<220> FEATURE:
<221> NAME/KEY: MISC_FEATURE
<222> LOCATION: (25)..(25)
<223> OTHER INFORMATION: Xaa is an amino acid substitution in comparison
      with SEQ ID NO.:26
<220> FEATURE:
<221> NAME/KEY: MISC_FEATURE
<222> LOCATION: (41)..(41)
<223> OTHER INFORMATION: Xaa is an amino acid substitution in comparison
      with SEQ ID NO.:26
<220> FEATURE:
<221> NAME/KEY: MISC_FEATURE
<222> LOCATION: (44)..(44)
<223> OTHER INFORMATION: Xaa is an amino acid substitution in comparison
      with SEQ ID NO.:26
<220> FEATURE:
<221> NAME/KEY: MISC_FEATURE
<222> LOCATION: (45)..(45)
<223> OTHER INFORMATION: Xaa is an amino acid substitution in comparison
      with SEQ ID NO.:26
<220> FEATURE:
<221> NAME/KEY: MISC_FEATURE
<222> LOCATION: (49)..(49)
<223> OTHER INFORMATION: Xaa is an amino acid substitution in comparison
      with SEQ ID NO.:26
<220> FEATURE:
<221> NAME/KEY: MISC_FEATURE
<222> LOCATION: (68)..(68)
<223> OTHER INFORMATION: Xaa is an amino acid substitution in comparison
      with SEQ ID NO.:26
<220> FEATURE:
<221> NAME/KEY: MISC_FEATURE
<222> LOCATION: (69)..(69)
<223> OTHER INFORMATION: Xaa is an amino acid substitution in comparison
      with SEQ ID NO.:26
<220> FEATURE:
<221> NAME/KEY: MISC_FEATURE
<222> LOCATION: (71)..(71)
<223> OTHER INFORMATION: Xaa is an amino acid substitution in comparison
      with SEQ ID NO.:26
<220> FEATURE:
<221> NAME/KEY: MISC_FEATURE
<222> LOCATION: (80)..(80)
<223> OTHER INFORMATION: Xaa is an amino acid substitution in comparison
      with SEQ ID NO.:26
<220> FEATURE:
<221> NAME/KEY: MISC_FEATURE
<222> LOCATION: (82)..(82)
<223> OTHER INFORMATION: Xaa is an amino acid substitution in comparison
      with SEQ ID NO.:26
<220> FEATURE:
<221> NAME/KEY: MISC_FEATURE

```
<222> LOCATION: (84)..(84)
<223> OTHER INFORMATION: Xaa is an amino acid substitution in comparison
      with SEQ ID NO.:26
<220> FEATURE:
<221> NAME/KEY: MISC_FEATURE
<222> LOCATION: (88)..(88)
<223> OTHER INFORMATION: Xaa is an amino acid substitution in comparison
      with SEQ ID NO.:26
<220> FEATURE:
<221> NAME/KEY: MISC_FEATURE
<222> LOCATION: (89)..(89)
<223> OTHER INFORMATION: Xaa is an amino acid substitution in comparison
      with SEQ ID NO.:26
<220> FEATURE:
<221> NAME/KEY: MISC_FEATURE
<222> LOCATION: (93)..(93)
<223> OTHER INFORMATION: Xaa is an amino acid substitution in comparison
      with SEQ ID NO.:26
<220> FEATURE:
<221> NAME/KEY: MISC_FEATURE
<222> LOCATION: (117)..(117)
<223> OTHER INFORMATION: Xaa is an amino acid substitution in comparison
      with SEQ ID NO.:26

<400> SEQUENCE: 183

Glu Val Gln Leu Gln Glu Ser Gly Pro Xaa Leu Val Lys Pro Ser Gln
1               5                   10                  15

Xaa Leu Ser Leu Thr Cys Thr Val Xaa Gly Phe Ser Ile Thr Ser Gly
            20                  25                  30

Tyr Gly Trp His Trp Ile Arg Gln Xaa Pro Gly Xaa Xaa Leu Glu Trp
        35                  40                  45

Xaa Gly Tyr Ile Asn Tyr Asp Gly His Asn Asp Tyr Asn Pro Ser Leu
    50                  55                  60

Lys Ser Arg Xaa Xaa Ile Xaa Gln Asp Thr Ser Lys Asn Gln Phe Xaa
65                  70                  75                  80

Leu Xaa Leu Xaa Ser Val Thr Xaa Xaa Asp Thr Ala Xaa Tyr Tyr Cys
            85                  90                  95

Ala Ser Ser Tyr Asp Gly Leu Phe Ala Tyr Trp Gly Gln Gly Thr Leu
            100                 105                 110

Val Thr Val Ser Xaa
        115

<210> SEQ ID NO 184
<211> LENGTH: 117
<212> TYPE: PRT
<213> ORGANISM: Artificial Sequence
<220> FEATURE:
<223> OTHER INFORMATION: Humanized 3C4 heavy chain variable region
      consensus 2
<220> FEATURE:
<221> NAME/KEY: MISC_FEATURE
<222> LOCATION: (10)..(10)
<223> OTHER INFORMATION: xaa may be G or D
<220> FEATURE:
<221> NAME/KEY: MISC_FEATURE
<222> LOCATION: (17)..(17)
<223> OTHER INFORMATION: Xaa may be a neutral hydrophilic amino acid
<220> FEATURE:
<221> NAME/KEY: MISC_FEATURE
<222> LOCATION: (25)..(25)
<223> OTHER INFORMATION: Xaa may be a neutral hydrophilic amino acid
<220> FEATURE:
<221> NAME/KEY: MISC_FEATURE
<222> LOCATION: (41)..(41)
<223> OTHER INFORMATION: Xaa may be H or F
<220> FEATURE:
<221> NAME/KEY: MISC_FEATURE
<222> LOCATION: (44)..(44)
<223> OTHER INFORMATION: Xaa may be K or N
<220> FEATURE:
```

```
<221> NAME/KEY: MISC_FEATURE
<222> LOCATION: (45)..(45)
<223> OTHER INFORMATION: Xaa may be G or K
<220> FEATURE:
<221> NAME/KEY: MISC_FEATURE
<222> LOCATION: (49)..(49)
<223> OTHER INFORMATION: Xaa may be an hydrophobic amino acid
<220> FEATURE:
<221> NAME/KEY: MISC_FEATURE
<222> LOCATION: (68)..(68)
<223> OTHER INFORMATION: Xaa may be an hydrophobic amino acid
<220> FEATURE:
<221> NAME/KEY: MISC_FEATURE
<222> LOCATION: (69)..(69)
<223> OTHER INFORMATION: Xaa may be a neutral hydrophilic amino acid
<220> FEATURE:
<221> NAME/KEY: MISC_FEATURE
<222> LOCATION: (71)..(71)
<223> OTHER INFORMATION: Xaa may be a neutral hydrophilic amino acid
<220> FEATURE:
<221> NAME/KEY: MISC_FEATURE
<222> LOCATION: (80)..(80)
<223> OTHER INFORMATION: Xaa may be a neutral hydrophilic amino acid
<220> FEATURE:
<221> NAME/KEY: MISC_FEATURE
<222> LOCATION: (82)..(82)
<223> OTHER INFORMATION: Xaa may be a basic amino acid
<220> FEATURE:
<221> NAME/KEY: MISC_FEATURE
<222> LOCATION: (84)..(84)
<223> OTHER INFORMATION: Xaa may be S or N
<220> FEATURE:
<221> NAME/KEY: MISC_FEATURE
<222> LOCATION: (88)..(88)
<223> OTHER INFORMATION: Xaa may be A or T
<220> FEATURE:
<221> NAME/KEY: MISC_FEATURE
<222> LOCATION: (89)..(89)
<223> OTHER INFORMATION: Xaa may be A or E
<220> FEATURE:
<221> NAME/KEY: MISC_FEATURE
<222> LOCATION: (93)..(93)
<223> OTHER INFORMATION: Xaa may be V or T
<220> FEATURE:
<221> NAME/KEY: MISC_FEATURE
<222> LOCATION: (117)..(117)
<223> OTHER INFORMATION: Xaa may be any amino acid, A or absent

<400> SEQUENCE: 184

Glu Val Gln Leu Gln Glu Ser Gly Pro Xaa Leu Val Lys Pro Ser Gln
1               5                   10                  15

Xaa Leu Ser Leu Thr Cys Thr Val Xaa Gly Phe Ser Ile Thr Ser Gly
            20                  25                  30

Tyr Gly Trp His Trp Ile Arg Gln Xaa Pro Gly Xaa Xaa Leu Glu Trp
        35                  40                  45

Xaa Gly Tyr Ile Asn Tyr Asp Gly His Asn Asp Tyr Asn Pro Ser Leu
    50                  55                  60

Lys Ser Arg Xaa Xaa Ile Xaa Gln Asp Thr Ser Lys Asn Gln Phe Xaa
65                  70                  75                  80

Leu Xaa Leu Xaa Ser Val Thr Xaa Xaa Asp Thr Ala Xaa Tyr Tyr Cys
            85                  90                  95

Ala Ser Ser Tyr Asp Gly Leu Phe Ala Tyr Trp Gly Gln Gly Thr Leu
            100                 105                 110

Val Thr Val Ser Xaa
        115

<210> SEQ ID NO 185
<211> LENGTH: 117
<212> TYPE: PRT
<213> ORGANISM: Artificial Sequence
```

```
<220> FEATURE:
<223> OTHER INFORMATION: Humanized 3C4 heavy chain variable region
      consensus 3
<220> FEATURE:
<221> NAME/KEY: MISC_FEATURE
<222> LOCATION: (10)..(10)
<223> OTHER INFORMATION: Xaa may be G or D
<220> FEATURE:
<221> NAME/KEY: MISC_FEATURE
<222> LOCATION: (17)..(17)
<223> OTHER INFORMATION: Xaa may be T or S
<220> FEATURE:
<221> NAME/KEY: MISC_FEATURE
<222> LOCATION: (25)..(25)
<223> OTHER INFORMATION: Xaa may be S or T
<220> FEATURE:
<221> NAME/KEY: MISC_FEATURE
<222> LOCATION: (41)..(41)
<223> OTHER INFORMATION: Xaa may be H or F
<220> FEATURE:
<221> NAME/KEY: MISC_FEATURE
<222> LOCATION: (44)..(44)
<223> OTHER INFORMATION: Xaa may be K or N
<220> FEATURE:
<221> NAME/KEY: MISC_FEATURE
<222> LOCATION: (45)..(45)
<223> OTHER INFORMATION: Xaa may be G or K
<220> FEATURE:
<221> NAME/KEY: MISC_FEATURE
<222> LOCATION: (49)..(49)
<223> OTHER INFORMATION: Xaa may be I or M
<220> FEATURE:
<221> NAME/KEY: MISC_FEATURE
<222> LOCATION: (68)..(68)
<223> OTHER INFORMATION: Xaa may be V or I
<220> FEATURE:
<221> NAME/KEY: MISC_FEATURE
<222> LOCATION: (69)..(69)
<223> OTHER INFORMATION: Xaa may be T or S
<220> FEATURE:
<221> NAME/KEY: MISC_FEATURE
<222> LOCATION: (71)..(71)
<223> OTHER INFORMATION: Xaa may be S or T
<220> FEATURE:
<221> NAME/KEY: MISC_FEATURE
<222> LOCATION: (80)..(80)
<223> OTHER INFORMATION: Xaa may be S or F
<220> FEATURE:
<221> NAME/KEY: MISC_FEATURE
<222> LOCATION: (82)..(82)
<223> OTHER INFORMATION: Xaa may be K or Q
<220> FEATURE:
<221> NAME/KEY: MISC_FEATURE
<222> LOCATION: (84)..(84)
<223> OTHER INFORMATION: Xaa may be S or N
<220> FEATURE:
<221> NAME/KEY: MISC_FEATURE
<222> LOCATION: (88)..(88)
<223> OTHER INFORMATION: Xaa may be A or T
<220> FEATURE:
<221> NAME/KEY: MISC_FEATURE
<222> LOCATION: (89)..(89)
<223> OTHER INFORMATION: Xaa may be A or E
<220> FEATURE:
<221> NAME/KEY: MISC_FEATURE
<222> LOCATION: (93)..(93)
<223> OTHER INFORMATION: Xaa may be V or T
<220> FEATURE:
<221> NAME/KEY: MISC_FEATURE
<222> LOCATION: (117)..(117)
<223> OTHER INFORMATION: Xaa may be A or absent

<400> SEQUENCE: 185

Glu Val Gln Leu Gln Glu Ser Gly Pro Xaa Leu Val Lys Pro Ser Gln
1               5                   10                  15

Xaa Leu Ser Leu Thr Cys Thr Val Xaa Gly Phe Ser Ile Thr Ser Gly
            20                  25                  30
```

```
Tyr Gly Trp His Trp Ile Arg Gln Xaa Pro Gly Xaa Xaa Leu Glu Trp
        35                  40                  45

Xaa Gly Tyr Ile Asn Tyr Asp Gly His Asn Asp Tyr Asn Pro Ser Leu
 50                  55                  60

Lys Ser Arg Xaa Xaa Ile Xaa Gln Asp Thr Ser Lys Asn Gln Phe Xaa
 65                  70                  75                  80

Leu Xaa Leu Xaa Ser Val Thr Xaa Xaa Asp Thr Ala Xaa Tyr Tyr Cys
            85                  90                  95

Ala Ser Ser Tyr Asp Gly Leu Phe Ala Tyr Trp Gly Gln Gly Thr Leu
            100                 105                 110

Val Thr Val Ser Xaa
        115

<210> SEQ ID NO 186
<211> LENGTH: 112
<212> TYPE: PRT
<213> ORGANISM: Artificial Sequence
<220> FEATURE:
<223> OTHER INFORMATION: 3A4 variant light chain variable region
      consensus 1
<220> FEATURE:
<221> NAME/KEY: MISC_FEATURE
<222> LOCATION: (2)..(2)
<223> OTHER INFORMATION: Xaa is an amino acid substitution in comparison
      with SEQ ID NO.:48
<220> FEATURE:
<221> NAME/KEY: MISC_FEATURE
<222> LOCATION: (12)..(12)
<223> OTHER INFORMATION: Xaa is an amino acid substitution in comparison
      with SEQ ID NO.:48
<220> FEATURE:
<221> NAME/KEY: MISC_FEATURE
<222> LOCATION: (14)..(14)
<223> OTHER INFORMATION: Xaa is an amino acid substitution in comparison
      with SEQ ID NO.:48
<220> FEATURE:
<221> NAME/KEY: MISC_FEATURE
<222> LOCATION: (15)..(15)
<223> OTHER INFORMATION: Xaa is an amino acid substitution in comparison
      with SEQ ID NO.:48
<220> FEATURE:
<221> NAME/KEY: MISC_FEATURE
<222> LOCATION: (17)..(17)
<223> OTHER INFORMATION: Xaa is an amino acid substitution in comparison
      with SEQ ID NO.:48
<220> FEATURE:
<221> NAME/KEY: MISC_FEATURE
<222> LOCATION: (18)..(18)
<223> OTHER INFORMATION: Xaa is an amino acid substitution in comparison
      with SEQ ID NO.:48
<220> FEATURE:
<221> NAME/KEY: MISC_FEATURE
<222> LOCATION: (50)..(50)
<223> OTHER INFORMATION: Xaa is an amino acid substitution in comparison
      with SEQ ID NO.:48
<220> FEATURE:
<221> NAME/KEY: MISC_FEATURE
<222> LOCATION: (88)..(88)
<223> OTHER INFORMATION: Xaa is an amino acid substitution in comparison
      with SEQ ID NO.:48
<220> FEATURE:
<221> NAME/KEY: MISC_FEATURE
<222> LOCATION: (105)..(105)
<223> OTHER INFORMATION: Xaa is an amino acid substitution in comparison
      with SEQ ID NO.:48
<220> FEATURE:
<221> NAME/KEY: MISC_FEATURE
<222> LOCATION: (108)..(108)
<223> OTHER INFORMATION: Xaa is an amino acid substitution in comparison
      with SEQ ID NO.:48
<220> FEATURE:
<221> NAME/KEY: MISC_FEATURE
```

```
<222> LOCATION: (111)..(111)
<223> OTHER INFORMATION: Xaa is an amino acid substitution in comparison
      with SEQ ID NO.:48

<400> SEQUENCE: 186

Asp Xaa Met Thr Gln Thr Pro Leu Ser Leu Xaa Val Xaa Xaa Gly
1               5                   10                  15

Xaa Xaa Ala Ser Ile Ser Cys Arg Ser Ser Gln Ser Leu Leu His Ser
            20                  25                  30

Asn Gly Asn Thr Tyr Leu Glu Trp Tyr Leu Gln Lys Pro Gly Gln Ser
        35                  40                  45

Pro Xaa Leu Leu Ile His Thr Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Xaa Gly Val Tyr Tyr Cys Phe Gln Gly
                85                  90                  95

Ser His Val Pro Leu Thr Phe Gly Xaa Gly Thr Xaa Leu Glu Xaa Lys
            100                 105                 110

<210> SEQ ID NO 187
<211> LENGTH: 112
<212> TYPE: PRT
<213> ORGANISM: Artificial Sequence
<220> FEATURE:
<223> OTHER INFORMATION: 3A4 variant light chain variable region
      consensus 2
<220> FEATURE:
<221> NAME/KEY: MISC_FEATURE
<222> LOCATION: (2)..(2)
<223> OTHER INFORMATION: Xaa may be an hydrophobic amino acid
<220> FEATURE:
<221> NAME/KEY: MISC_FEATURE
<222> LOCATION: (12)..(12)
<223> OTHER INFORMATION: Xaa may be A or P
<220> FEATURE:
<221> NAME/KEY: MISC_FEATURE
<222> LOCATION: (14)..(14)
<223> OTHER INFORMATION: Xaa may be a neutral hydrophilic amino acid
<220> FEATURE:
<221> NAME/KEY: MISC_FEATURE
<222> LOCATION: (15)..(15)
<223> OTHER INFORMATION: Xaa may be L or P
<220> FEATURE:
<221> NAME/KEY: MISC_FEATURE
<222> LOCATION: (17)..(17)
<223> OTHER INFORMATION: Xaa may be an acidic amino acid
<220> FEATURE:
<221> NAME/KEY: MISC_FEATURE
<222> LOCATION: (18)..(18)
<223> OTHER INFORMATION: Xaa may be Q or P
<220> FEATURE:
<221> NAME/KEY: MISC_FEATURE
<222> LOCATION: (50)..(50)
<223> OTHER INFORMATION: Xaa may be a basic amino acid
<220> FEATURE:
<221> NAME/KEY: MISC_FEATURE
<222> LOCATION: (88)..(88)
<223> OTHER INFORMATION: Xaa may be an hydrophobic amino acid
<220> FEATURE:
<221> NAME/KEY: MISC_FEATURE
<222> LOCATION: (105)..(105)
<223> OTHER INFORMATION: Xaa may be A or Q
<220> FEATURE:
<221> NAME/KEY: MISC_FEATURE
<222> LOCATION: (108)..(108)
<223> OTHER INFORMATION: Xaa may be a basic amino acid
<220> FEATURE:
<221> NAME/KEY: MISC_FEATURE
<222> LOCATION: (111)..(111)
<223> OTHER INFORMATION: Xaa may be an hydrophobic amino acid
```

<400> SEQUENCE: 187

Asp Xaa Val Met Thr Gln Thr Pro Leu Ser Leu Xaa Val Xaa Xaa Gly
1               5                   10                  15

Xaa Xaa Ala Ser Ile Ser Cys Arg Ser Ser Gln Ser Leu Leu His Ser
            20                  25                  30

Asn Gly Asn Thr Tyr Leu Glu Trp Tyr Leu Gln Lys Pro Gly Gln Ser
        35                  40                  45

Pro Xaa Leu Leu Ile His Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Xaa Gly Val Tyr Tyr Cys Phe Gln Gly
                85                  90                  95

Ser His Val Pro Leu Thr Phe Gly Xaa Gly Thr Xaa Leu Glu Xaa Lys
                100                 105                 110

<210> SEQ ID NO 188
<211> LENGTH: 112
<212> TYPE: PRT
<213> ORGANISM: Artificial Sequence
<220> FEATURE:
<223> OTHER INFORMATION: 3A4 variant light chain variable region
      consensus 3
<220> FEATURE:
<221> NAME/KEY: MISC_FEATURE
<222> LOCATION: (2)..(2)
<223> OTHER INFORMATION: Xaa may be V or I
<220> FEATURE:
<221> NAME/KEY: MISC_FEATURE
<222> LOCATION: (12)..(12)
<223> OTHER INFORMATION: Xaa may be A or P
<220> FEATURE:
<221> NAME/KEY: MISC_FEATURE
<222> LOCATION: (14)..(14)
<223> OTHER INFORMATION: Xaa may be S or T
<220> FEATURE:
<221> NAME/KEY: MISC_FEATURE
<222> LOCATION: (15)..(15)
<223> OTHER INFORMATION: Xaa may be L or P
<220> FEATURE:
<221> NAME/KEY: MISC_FEATURE
<222> LOCATION: (17)..(17)
<223> OTHER INFORMATION: Xaa may be D or E
<220> FEATURE:
<221> NAME/KEY: MISC_FEATURE
<222> LOCATION: (18)..(18)
<223> OTHER INFORMATION: Xaa may be Q or P
<220> FEATURE:
<221> NAME/KEY: MISC_FEATURE
<222> LOCATION: (50)..(50)
<223> OTHER INFORMATION: Xaa may be K or Q
<220> FEATURE:
<221> NAME/KEY: MISC_FEATURE
<222> LOCATION: (88)..(88)
<223> OTHER INFORMATION: Xaa may be L or V
<220> FEATURE:
<221> NAME/KEY: MISC_FEATURE
<222> LOCATION: (105)..(105)
<223> OTHER INFORMATION: Xaa may be A or Q
<220> FEATURE:
<221> NAME/KEY: MISC_FEATURE
<222> LOCATION: (108)..(108)
<223> OTHER INFORMATION: Xaa may be R or K
<220> FEATURE:
<221> NAME/KEY: MISC_FEATURE
<222> LOCATION: (111)..(111)
<223> OTHER INFORMATION: Xaa may be L or I

<400> SEQUENCE: 188

Asp Xaa Val Met Thr Gln Thr Pro Leu Ser Leu Xaa Val Xaa Xaa Gly
1               5                   10                  15

Xaa Xaa Ala Ser Ile Ser Cys Arg Ser Ser Gln Ser Leu Leu His Ser
            20                  25                  30

Asn Gly Asn Thr Tyr Leu Glu Trp Tyr Leu Gln Lys Pro Gly Gln Ser
        35                  40                  45

Pro Xaa Leu Leu Ile His Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Xaa Gly Val Tyr Tyr Cys Phe Gln Gly
                85                  90                  95

Ser His Val Pro Leu Thr Phe Gly Xaa Gly Thr Xaa Leu Glu Xaa Lys
            100                 105                 110

<210> SEQ ID NO 189
<211> LENGTH: 112
<212> TYPE: PRT
<213> ORGANISM: Artificial Sequence
<220> FEATURE:
<223> OTHER INFORMATION: 3A4 variant-1 light chain variable region: Lvh1

<400> SEQUENCE: 189

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gln Gly Thr Lys Leu Glu Ile Lys
            100                 105                 110

<210> SEQ ID NO 190
<211> LENGTH: 112
<212> TYPE: PRT
<213> ORGANISM: Artificial Sequence
<220> FEATURE:
<223> OTHER INFORMATION: 3A4 variant-2 light chain variable region: Lvh2

<400> SEQUENCE: 190

Asp Val Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gln Gly Thr Lys Leu Glu Ile Lys
            100                 105                 110

<210> SEQ ID NO 191
<211> LENGTH: 116
<212> TYPE: PRT
<213> ORGANISM: Artificial Sequence
<220> FEATURE:
<223> OTHER INFORMATION: 3A4 variant heavy chain variable region
      consensus 1
<220> FEATURE:
<221> NAME/KEY: MISC_FEATURE
<222> LOCATION: (2)..(2)
<223> OTHER INFORMATION: Xaa is an amino acid substitution in comparison
      with SEQ ID NO.:46
<220> FEATURE:
<221> NAME/KEY: MISC_FEATURE
<222> LOCATION: (9)..(9)
<223> OTHER INFORMATION: Xaa is an amino acid substitution in comparison
      with SEQ ID NO.:46
<220> FEATURE:
<221> NAME/KEY: MISC_FEATURE
<222> LOCATION: (11)..(11)
<223> OTHER INFORMATION: Xaa is an amino acid substitution in comparison
      with SEQ ID NO.:46
<220> FEATURE:
<221> NAME/KEY: MISC_FEATURE
<222> LOCATION: (12)..(12)
<223> OTHER INFORMATION: Xaa is an amino acid substitution in comparison
      with SEQ ID NO.:46
<220> FEATURE:
<221> NAME/KEY: MISC_FEATURE
<222> LOCATION: (20)..(20)
<223> OTHER INFORMATION: Xaa is an amino acid substitution in comparison
      with SEQ ID NO.:46
<220> FEATURE:
<221> NAME/KEY: MISC_FEATURE
<222> LOCATION: (38)..(38)
<223> OTHER INFORMATION: Xaa is an amino acid substitution in comparison
      with SEQ ID NO.:46
<220> FEATURE:
<221> NAME/KEY: MISC_FEATURE
<222> LOCATION: (40)..(40)
<223> OTHER INFORMATION: Xaa is an amino acid substitution in comparison
      with SEQ ID NO.:46
<220> FEATURE:
<221> NAME/KEY: MISC_FEATURE
<222> LOCATION: (41)..(41)
<223> OTHER INFORMATION: Xaa is an amino acid substitution in comparison
      with SEQ ID NO.:46
<220> FEATURE:
<221> NAME/KEY: MISC_FEATURE
<222> LOCATION: (43)..(43)
<223> OTHER INFORMATION: Xaa is an amino acid substitution in comparison
      with SEQ ID NO.:46
<220> FEATURE:
<221> NAME/KEY: MISC_FEATURE
<222> LOCATION: (44)..(44)
<223> OTHER INFORMATION: Xaa is an amino acid substitution in comparison
      with SEQ ID NO.:46
<220> FEATURE:
<221> NAME/KEY: MISC_FEATURE
<222> LOCATION: (48)..(48)
<223> OTHER INFORMATION: Xaa is an amino acid substitution in comparison
      with SEQ ID NO.:46
<220> FEATURE:
<221> NAME/KEY: MISC_FEATURE
<222> LOCATION: (67)..(67)
<223> OTHER INFORMATION: Xaa is an amino acid substitution in comparison
      with SEQ ID NO.:46
<220> FEATURE:
<221> NAME/KEY: MISC_FEATURE
<222> LOCATION: (68)..(68)
<223> OTHER INFORMATION: Xaa is an amino acid substitution in comparison
      with SEQ ID NO.:46
<220> FEATURE:
<221> NAME/KEY: MISC_FEATURE

```
<222> LOCATION: (69)..(69)
<223> OTHER INFORMATION: Xaa is an amino acid substitution in comparison
      with SEQ ID NO.:46
<220> FEATURE:
<221> NAME/KEY: MISC_FEATURE
<222> LOCATION: (70)..(70)
<223> OTHER INFORMATION: Xaa is an amino acid substitution in comparison
      with SEQ ID NO.:46
<220> FEATURE:
<221> NAME/KEY: MISC_FEATURE
<222> LOCATION: (72)..(72)
<223> OTHER INFORMATION: Xaa is an amino acid substitution in comparison
      with SEQ ID NO.:46
<220> FEATURE:
<221> NAME/KEY: MISC_FEATURE
<222> LOCATION: (74)..(74)
<223> OTHER INFORMATION: Xaa is an amino acid substitution in comparison
      with SEQ ID NO.:46
<220> FEATURE:
<221> NAME/KEY: MISC_FEATURE
<222> LOCATION: (76)..(76)
<223> OTHER INFORMATION: Xaa is an amino acid substitution in comparison
      with SEQ ID NO.:46
<220> FEATURE:
<221> NAME/KEY: MISC_FEATURE
<222> LOCATION: (82)..(82)
<223> OTHER INFORMATION: Xaa is an amino acid substitution in comparison
      with SEQ ID NO.:46
<220> FEATURE:
<221> NAME/KEY: MISC_FEATURE
<222> LOCATION: (84)..(84)
<223> OTHER INFORMATION: Xaa is an amino acid substitution in comparison
      with SEQ ID NO.:46
<220> FEATURE:
<221> NAME/KEY: MISC_FEATURE
<222> LOCATION: (87)..(87)
<223> OTHER INFORMATION: Xaa is an amino acid substitution in comparison
      with SEQ ID NO.:46
<220> FEATURE:
<221> NAME/KEY: MISC_FEATURE
<222> LOCATION: (91)..(91)
<223> OTHER INFORMATION: Xaa is an amino acid substitution in comparison
      with SEQ ID NO.:46
<220> FEATURE:
<221> NAME/KEY: MISC_FEATURE
<222> LOCATION: (111)..(111)
<223> OTHER INFORMATION: Xaa is an amino acid substitution in comparison
      with SEQ ID NO.:46

<400> SEQUENCE: 191

Gln Xaa Gln Leu Val Gln Ser Gly Xaa Glu Xaa Xaa Lys Pro Gly Ala
1               5                   10                  15

Ser Val Lys Xaa Ser Cys Lys Ala Ser Gly Tyr Thr Phe Thr Asp Asp
                20                  25                  30

Tyr Met Ser Trp Val Xaa Gln Xaa Xaa Gly Xaa Xaa Leu Glu Trp Xaa
            35                  40                  45

Gly Asp Ile Asn Pro Tyr Asn Gly Asp Thr Asn Tyr Asn Gln Lys Phe
50                  55                  60

Lys Gly Xaa Xaa Xaa Xaa Thr Xaa Asp Xaa Ser Xaa Ser Thr Ala Tyr
65                  70                  75                  80

Met Xaa Leu Xaa Ser Leu Xaa Ser Glu Asp Xaa Ala Val Tyr Tyr Cys
            85                  90                  95

Ala Arg Asp Pro Gly Ala Met Asp Tyr Trp Gly Gln Gly Thr Xaa Val
            100                 105                 110

Thr Val Ser Ser
        115

<210> SEQ ID NO 192
<211> LENGTH: 116
<212> TYPE: PRT
```

```
<213> ORGANISM: Artificial Sequence
<220> FEATURE:
<223> OTHER INFORMATION: 3A4 variant heavy chain variable region
      consensus 2
<220> FEATURE:
<221> NAME/KEY: MISC_FEATURE
<222> LOCATION: (2)..(2)
<223> OTHER INFORMATION: Xaa may be an hydrophobic amino acid
<220> FEATURE:
<221> NAME/KEY: MISC_FEATURE
<222> LOCATION: (9)..(9)
<223> OTHER INFORMATION: Xaa may be P or A
<220> FEATURE:
<221> NAME/KEY: MISC_FEATURE
<222> LOCATION: (11)..(11)
<223> OTHER INFORMATION: Xaa may be an hydrophobic amino acid
<220> FEATURE:
<221> NAME/KEY: MISC_FEATURE
<222> LOCATION: (12)..(12)
<223> OTHER INFORMATION: Xaa may be V or K
<220> FEATURE:
<221> NAME/KEY: MISC_FEATURE
<222> LOCATION: (20)..(20)
<223> OTHER INFORMATION: Xaa may be an hydrophobic amino acid
<220> FEATURE:
<221> NAME/KEY: MISC_FEATURE
<222> LOCATION: (38)..(38)
<223> OTHER INFORMATION: Xaa may be a basic amino acid
<220> FEATURE:
<221> NAME/KEY: MISC_FEATURE
<222> LOCATION: (40)..(40)
<223> OTHER INFORMATION: Xaa may be S or A
<220> FEATURE:
<221> NAME/KEY: MISC_FEATURE
<222> LOCATION: (41)..(41)
<223> OTHER INFORMATION: Xaa may be H or P
<220> FEATURE:
<221> NAME/KEY: MISC_FEATURE
<222> LOCATION: (43)..(43)
<223> OTHER INFORMATION: Xaa may be a basic amino acid
<220> FEATURE:
<221> NAME/KEY: MISC_FEATURE
<222> LOCATION: (44)..(44)
<223> OTHER INFORMATION: Xaa may be S or G
<220> FEATURE:
<221> NAME/KEY: MISC_FEATURE
<222> LOCATION: (48)..(48)
<223> OTHER INFORMATION: Xaa may be an hydrophobic amino acid
<220> FEATURE:
<221> NAME/KEY: MISC_FEATURE
<222> LOCATION: (67)..(67)
<223> OTHER INFORMATION: Xaa may be a basic amino acid
<220> FEATURE:
<221> NAME/KEY: MISC_FEATURE
<222> LOCATION: (68)..(68)
<223> OTHER INFORMATION: Xaa may be an hydrophobic amino acid
<220> FEATURE:
<221> NAME/KEY: MISC_FEATURE
<222> LOCATION: (69)..(69)
<223> OTHER INFORMATION: Xaa may be I or T
<220> FEATURE:
<221> NAME/KEY: MISC_FEATURE
<222> LOCATION: (70)..(70)
<223> OTHER INFORMATION: Xaa may be an hydrophobic amino acid
<220> FEATURE:
<221> NAME/KEY: MISC_FEATURE
<222> LOCATION: (72)..(72)
<223> OTHER INFORMATION: Xaa may be an hydrophobic amino acid
<220> FEATURE:
<221> NAME/KEY: MISC_FEATURE
<222> LOCATION: (74)..(74)
<223> OTHER INFORMATION: Xaa may be K or T
<220> FEATURE:
<221> NAME/KEY: MISC_FEATURE
<222> LOCATION: (76)..(76)
<223> OTHER INFORMATION: Xaa may be a neutral hydrophilic amino acid
<220> FEATURE:
<221> NAME/KEY: MISC_FEATURE
<222> LOCATION: (82)..(82)
```

<223> OTHER INFORMATION: Xaa may be Q or E
<220> FEATURE:
<221> NAME/KEY: MISC_FEATURE
<222> LOCATION: (84)..(84)
<223> OTHER INFORMATION: Xaa may be N or S
<220> FEATURE:
<221> NAME/KEY: MISC_FEATURE
<222> LOCATION: (87)..(87)
<223> OTHER INFORMATION: Xaa may be T or R
<220> FEATURE:
<221> NAME/KEY: MISC_FEATURE
<222> LOCATION: (91)..(91)
<223> OTHER INFORMATION: Xaa may be a neutral hydrophilic amino acid
<220> FEATURE:
<221> NAME/KEY: MISC_FEATURE
<222> LOCATION: (111)..(111)
<223> OTHER INFORMATION: Xaa may be S or L

<400> SEQUENCE: 192

Gln Xaa Gln Leu Val Gln Ser Gly Xaa Glu Xaa Xaa Lys Pro Gly Ala
1               5                   10                  15

Ser Val Lys Xaa Ser Cys Lys Ala Ser Gly Tyr Thr Phe Thr Asp Asp
            20                  25                  30

Tyr Met Ser Trp Val Xaa Gln Xaa Xaa Gly Xaa Gly Xaa Leu Glu Trp Xaa
        35                  40                  45

Gly Asp Ile Asn Pro Tyr Asn Gly Asp Thr Asn Tyr Asn Gln Lys Phe
50                  55                  60

Lys Gly Xaa Xaa Xaa Xaa Thr Xaa Asp Xaa Ser Xaa Ser Thr Ala Tyr
65                  70                  75                  80

Met Xaa Leu Xaa Ser Leu Xaa Ser Glu Asp Xaa Ala Val Tyr Tyr Cys
            85                  90                  95

Ala Arg Asp Pro Gly Ala Met Asp Tyr Trp Gly Gln Gly Thr Xaa Val
                100                 105                 110

Thr Val Ser Ser
        115

<210> SEQ ID NO 193
<211> LENGTH: 116
<212> TYPE: PRT
<213> ORGANISM: Artificial Sequence
<220> FEATURE:
<223> OTHER INFORMATION: 3A4 variant heavy chain variable region
      consensus 3
<220> FEATURE:
<221> NAME/KEY: MISC_FEATURE
<222> LOCATION: (2)..(2)
<223> OTHER INFORMATION: Xaa may be I or V
<220> FEATURE:
<221> NAME/KEY: MISC_FEATURE
<222> LOCATION: (9)..(9)
<223> OTHER INFORMATION: Xaa may be P or A
<220> FEATURE:
<221> NAME/KEY: MISC_FEATURE
<222> LOCATION: (11)..(11)
<223> OTHER INFORMATION: Xaa may be M or V
<220> FEATURE:
<221> NAME/KEY: MISC_FEATURE
<222> LOCATION: (12)..(12)
<223> OTHER INFORMATION: Xaa may be V or K
<220> FEATURE:
<221> NAME/KEY: MISC_FEATURE
<222> LOCATION: (20)..(20)
<223> OTHER INFORMATION: Xaa may be M or V
<220> FEATURE:
<221> NAME/KEY: MISC_FEATURE
<222> LOCATION: (38)..(38)
<223> OTHER INFORMATION: Xaa may be K or R
<220> FEATURE:
<221> NAME/KEY: MISC_FEATURE
<222> LOCATION: (40)..(40)

-continued

```
<223> OTHER INFORMATION: Xaa may be S or A
<220> FEATURE:
<221> NAME/KEY: MISC_FEATURE
<222> LOCATION: (41)..(41)
<223> OTHER INFORMATION: Xaa may be H or P
<220> FEATURE:
<221> NAME/KEY: MISC_FEATURE
<222> LOCATION: (43)..(43)
<223> OTHER INFORMATION: Xaa may be K or Q
<220> FEATURE:
<221> NAME/KEY: MISC_FEATURE
<222> LOCATION: (44)..(44)
<223> OTHER INFORMATION: Xaa may be S or G
<220> FEATURE:
<221> NAME/KEY: MISC_FEATURE
<222> LOCATION: (48)..(48)
<223> OTHER INFORMATION: Xaa may be I or M
<220> FEATURE:
<221> NAME/KEY: MISC_FEATURE
<222> LOCATION: (67)..(67)
<223> OTHER INFORMATION: Xaa may be K or R
<220> FEATURE:
<221> NAME/KEY: MISC_FEATURE
<222> LOCATION: (68)..(68)
<223> OTHER INFORMATION: Xaa may be A or V
<220> FEATURE:
<221> NAME/KEY: MISC_FEATURE
<222> LOCATION: (69)..(69)
<223> OTHER INFORMATION: Xaa may be I or T
<220> FEATURE:
<221> NAME/KEY: MISC_FEATURE
<222> LOCATION: (70)..(70)
<223> OTHER INFORMATION: Xaa may be L or I
<220> FEATURE:
<221> NAME/KEY: MISC_FEATURE
<222> LOCATION: (72)..(72)
<223> OTHER INFORMATION: Xaa may be V or A
<220> FEATURE:
<221> NAME/KEY: MISC_FEATURE
<222> LOCATION: (74)..(74)
<223> OTHER INFORMATION: Xaa may be K or T
<220> FEATURE:
<221> NAME/KEY: MISC_FEATURE
<222> LOCATION: (76)..(76)
<223> OTHER INFORMATION: Xaa may be S or T
<220> FEATURE:
<221> NAME/KEY: MISC_FEATURE
<222> LOCATION: (82)..(82)
<223> OTHER INFORMATION: Xaa may be Q or E
<220> FEATURE:
<221> NAME/KEY: MISC_FEATURE
<222> LOCATION: (84)..(84)
<223> OTHER INFORMATION: Xaa may be N or S
<220> FEATURE:
<221> NAME/KEY: MISC_FEATURE
<222> LOCATION: (87)..(87)
<223> OTHER INFORMATION: Xaa may be T or R
<220> FEATURE:
<221> NAME/KEY: MISC_FEATURE
<222> LOCATION: (91)..(91)
<223> OTHER INFORMATION: Xaa may be S or T
<220> FEATURE:
<221> NAME/KEY: MISC_FEATURE
<222> LOCATION: (111)..(111)
<223> OTHER INFORMATION: Xaa may be S or L

<400> SEQUENCE: 193

Gln Xaa Gln Leu Val Gln Ser Gly Xaa Glu Xaa Xaa Lys Pro Gly Ala
1               5                   10                  15

Ser Val Lys Xaa Ser Cys Lys Ala Ser Gly Tyr Thr Phe Thr Asp Asp
            20                  25                  30

Tyr Met Ser Trp Val Xaa Gln Xaa Gly Xaa Xaa Leu Glu Trp Xaa
        35                  40                  45

Gly Asp Ile Asn Pro Tyr Asn Gly Asp Thr Asn Tyr Asn Gln Lys Phe
50                  55                  60
```

```
Lys Gly Xaa Xaa Xaa Xaa Thr Xaa Asp Xaa Ser Xaa Ser Thr Ala Tyr
 65                  70                  75                  80

Met Xaa Leu Xaa Ser Leu Xaa Ser Glu Asp Xaa Ala Val Tyr Tyr Cys
                 85                  90                  95

Ala Arg Asp Pro Gly Ala Met Asp Tyr Trp Gly Gln Gly Thr Xaa Val
                100                 105                 110

Thr Val Ser Ser
        115
```

<210> SEQ ID NO 194
<211> LENGTH: 116
<212> TYPE: PRT
<213> ORGANISM: Artificial Sequence
<220> FEATURE:
<223> OTHER INFORMATION: 3A4 variant-1 heavy chain variable region: Hvh1

<400> SEQUENCE: 194

```
Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Asp Asp
                 20                  25                  30

Tyr Met Ser Trp Val Arg Gln Ala Pro Gly Gln Gly Leu Glu Trp Met
             35                  40                  45

Gly Asp Ile Asn Pro Tyr Asn Gly Asp Thr Asn Tyr Asn Gln Lys Phe
         50                  55                  60

Lys Gly Arg Val Thr Ile Thr Ala Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Pro Gly Ala Met Asp Tyr Trp Gly Gln Gly Thr Leu Val
                100                 105                 110

Thr Val Ser Ser
        115
```

<210> SEQ ID NO 195
<211> LENGTH: 116
<212> TYPE: PRT
<213> ORGANISM: Artificial Sequence
<220> FEATURE:
<223> OTHER INFORMATION: 3A4 variant-2 heavy chain variable region: Hvh2

<400> SEQUENCE: 195

```
Gln Ile Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Asp Asp
                 20                  25                  30

Tyr Met Ser Trp Val Arg Gln Ala Pro Gly Gln Gly Leu Glu Trp Met
             35                  40                  45

Gly Asp Ile Asn Pro Tyr Asn Gly Asp Thr Asn Tyr Asn Gln Lys Phe
         50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Pro Gly Ala Met Asp Tyr Trp Gly Gln Gly Thr Leu Val
                100                 105                 110

Thr Val Ser Ser
```

```
<210> SEQ ID NO 196
<211> LENGTH: 116
<212> TYPE: PRT
<213> ORGANISM: Artificial Sequence
<220> FEATURE:
<223> OTHER INFORMATION: 3A4 variant-3 heavy chain variable region: Hvh3

<400> SEQUENCE: 196

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Asp
            20                  25                  30

Tyr Met Ser Trp Val Arg Gln Ala Pro Gly Gln Gly Leu Glu Trp Ile
        35                  40                  45

Gly Asp Ile Asn Pro Tyr Asn Gly Asp Thr Asn Tyr Asn Gln Lys Phe
    50                  55                  60

Lys Gly Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Gly Ala Met Asp Tyr Trp Gly Gln Gly Thr Leu Val
            100                 105                 110

Thr Val Ser Ser
        115

<210> SEQ ID NO 197
<211> LENGTH: 116
<212> TYPE: PRT
<213> ORGANISM: Artificial Sequence
<220> FEATURE:
<223> OTHER INFORMATION: 3A4 variant-4 heavy chain variable region: Hvh4

<400> SEQUENCE: 197

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Asp
            20                  25                  30

Tyr Met Ser Trp Val Lys Gln Ala Pro Gly Gln Gly Leu Glu Trp Ile
        35                  40                  45

Gly Asp Ile Asn Pro Tyr Asn Gly Asp Thr Asn Tyr Asn Gln Lys Phe
    50                  55                  60

Lys Gly Lys Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Gly Ala Met Asp Tyr Trp Gly Gln Gly Thr Leu Val
            100                 105                 110

Thr Val Ser Ser
        115

<210> SEQ ID NO 198
<211> LENGTH: 219
<212> TYPE: PRT
<213> ORGANISM: Artificial Sequence
<220> FEATURE:
<223> OTHER INFORMATION: 3A4 murine light (kappa) chain

<400> SEQUENCE: 198
```

Asp Val Val Met Thr Gln Thr Pro Leu Ser Leu Ala Val Ser Leu Gly
1               5                   10                  15

Asp Gln Ala Ser Ile Ser Cys Arg Ser Ser Gln Ser Leu Leu His Ser
            20                  25                  30

Asn Gly Asn Thr Tyr Leu Glu Trp Tyr Leu Gln Lys Pro Gly Gln Ser
        35                  40                  45

Pro Lys Leu Leu Ile His Thr Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Leu Gly Val Tyr Tyr Cys Phe Gln Gly
                85                  90                  95

Ser His Val Pro Leu Thr Phe Gly Ala Gly Thr Arg Leu Glu Leu Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
    210                 215

<210> SEQ ID NO 199
<211> LENGTH: 219
<212> TYPE: PRT
<213> ORGANISM: Artificial Sequence
<220> FEATURE:
<223> OTHER INFORMATION: 3A4 humanized ligh (kappa) chain variant 1: Lh1

<400> SEQUENCE: 199

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Phe Gln Gly
                85                  90                  95

Ser His Val Pro Leu Thr Phe Gly Gln Gly Thr Lys Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

```
Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 200
<211> LENGTH: 219
<212> TYPE: PRT
<213> ORGANISM: Artificial Sequence
<220> FEATURE:
<223> OTHER INFORMATION: 3A4 humanized ligh (kappa) chain variant 2: Lh2

<400> SEQUENCE: 200

```
Asp Val Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 201
<211> LENGTH: 446
<212> TYPE: PRT
<213> ORGANISM: Artificial Sequence
<220> FEATURE:
<223> OTHER INFORMATION: 3A4 murine heavy (IgG1) chain

<400> SEQUENCE: 201

Gln Ile Gln Leu Val Gln Ser Gly Pro Glu Met Val Lys Pro Gly Ala

-continued

```
1               5                   10                  15
Ser Val Lys Met Ser Cys Lys Ala Ser Gly Tyr Thr Phe Thr Asp Asp
            20                  25                  30

Tyr Met Ser Trp Val Lys Gln Ser His Gly Lys Ser Leu Glu Trp Ile
            35                  40                  45

Gly Asp Ile Asn Pro Tyr Asn Gly Asp Thr Asn Tyr Asn Gln Lys Phe
            50                  55                  60

Lys Gly Lys Ala Ile Leu Thr Val Asp Lys Ser Ser Ser Thr Ala Tyr
65                  70                  75                  80

Met Gln Leu Asn Ser Leu Thr Ser Glu Asp Ser Ala Val Tyr Tyr Cys
                    85                  90                  95

Ala Arg Asp Pro Gly Ala Met Asp Tyr Trp Gly Gln Gly Thr Ser Val
                    100                 105                 110

Thr Val Ser Ser Ala Ser Thr Lys Gly Pro Ser Val Phe Pro Leu Ala
                    115                 120                 125

Pro Ser Ser Lys Ser Thr Ser Gly Gly Thr Ala Ala Leu Gly Cys Leu
                    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                    165                 170                 175

Gly Leu Tyr Ser Leu Ser Ser Val Val Thr Val Pro Ser Ser Ser Leu
                    180                 185                 190

Gly Thr Gln Thr Tyr Ile Cys Asn Val Asn His Lys Pro Ser Asn Thr
                    195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                    245                 250                 255

Glu Val Thr Cys Val Val Val Asp Val Ser His Glu Asp Pro Glu Val
                    260                 265                 270

Lys Phe Asn Trp Tyr Val Asp Gly Val Glu Val His Asn Ala Lys Thr
                    275                 280                 285

Lys Pro Arg Glu Glu Gln Tyr Asn Ser Thr Tyr Arg Val Val Ser Val
                    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                    325                 330                 335

Lys Ala Lys Gly Gln Pro Arg Glu Pro Gln Val Tyr Thr Leu Pro Pro
                    340                 345                 350

Ser Arg Asp Glu Leu Thr Lys Asn Gln Val Ser Leu Thr Cys Leu Val
                    355                 360                 365

Lys Gly Phe Tyr Pro Ser Asp Ile Ala Val Glu Trp Glu Ser Asn Gly
                    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                    405                 410                 415

Gln Gln Gly Asn Val Phe Ser Cys Ser Val Met His Glu Ala Leu His
                    420                 425                 430
```

Asn His Tyr Thr Gln Lys Ser Leu Ser Leu Ser Pro Gly Lys
         435                 440                 445

<210> SEQ ID NO 202
<211> LENGTH: 446
<212> TYPE: PRT
<213> ORGANISM: Artificial Sequence
<220> FEATURE:
<223> OTHER INFORMATION: 3A4 humanized heavy (Igg1) chain variant 1: Hh1

<400> SEQUENCE: 202

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Asp
            20                  25                  30

Tyr Met Ser Trp Val Arg Gln Ala Pro Gly Gln Gly Leu Glu Trp Met
        35                  40                  45

Gly Asp Ile Asn Pro Tyr Asn Gly Asp Thr Asn Tyr Asn Gln Lys Phe
    50                  55                  60

Lys Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Gly Ala Met Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

```
Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
        370                 375                 380

Gln Pro Glu Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
                435                 440                 445

<210> SEQ ID NO 203
<211> LENGTH: 446
<212> TYPE: PRT
<213> ORGANISM: Artificial Sequence
<220> FEATURE:
<223> OTHER INFORMATION: 3A4 humanized heavy (Igg1) chain variant 2: Hh2

<400> SEQUENCE: 203

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Asp
                20                  25                  30

Tyr Met Ser Trp Val Arg Gln Ala Pro Gly Gln Gly Leu Glu Trp Met
            35                  40                  45

Gly Asp Ile Asn Pro Tyr Asn Gly Asp Thr Asn Tyr Asn Gln Lys Phe
        50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Gly Ala Met Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270
```

```
Lys Phe Asn Trp Tyr Val Asp Gly Val Glu Val His Asn Ala Lys Thr
                275                 280                 285

Lys Pro Arg Glu Glu Gln Tyr Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
                435                 440                 445

<210> SEQ ID NO 204
<211> LENGTH: 446
<212> TYPE: PRT
<213> ORGANISM: Artificial Sequence
<220> FEATURE:
<223> OTHER INFORMATION: 3A4 humanized heavy (Igg1) chain variant 3: Hh3

<400> SEQUENCE: 204

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Asp
            20                  25                  30

Tyr Met Ser Trp Val Arg Gln Ala Pro Gly Gln Gly Leu Glu Trp Ile
        35                  40                  45

Gly Asp Ile Asn Pro Tyr Asn Gly Asp Thr Asn Tyr Asn Gln Lys Phe
    50                  55                  60

Lys Gly Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Gly Ala Met Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190
```

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 205
<211> LENGTH: 446
<212> TYPE: PRT
<213> ORGANISM: Artificial Sequence
<220> FEATURE:
<223> OTHER INFORMATION: 3A4 humanized heavy (Igg1) chain variant 4: Hh4

<400> SEQUENCE: 205

Gln Ile Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Asp
            20                  25                  30

Tyr Met Ser Trp Val Lys Gln Ala Pro Gly Gln Gly Leu Glu Trp Ile
        35                  40                  45

Gly Asp Ile Asn Pro Tyr Asn Gly Asp Thr Asn Tyr Asn Gln Lys Phe
    50                  55                  60

Lys Gly Lys Ala Thr Leu Thr Val Asp Lys Ser Thr Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Gly Ala Met Asp Tyr Trp Gly Gln Gly Thr Leu Val
            100                 105                 110

```
Thr Val Ser Ser Ala Ser Thr Lys Gly Pro Ser Val Phe Pro Leu Ala
            115                 120                 125
Pro Ser Ser Lys Ser Thr Ser Gly Gly Thr Ala Ala Leu Gly Cys Leu
130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
            165                 170                 175
Gly Leu Tyr Ser Leu Ser Ser Val Val Thr Val Pro Ser Ser Ser Leu
            180                 185                 190
Gly Thr Gln Thr Tyr Ile Cys Asn Val Asn His Lys Pro Ser Asn Thr
            195                 200                 205
Lys Val Asp Lys Lys Val Glu Pro Lys Ser Cys Asp Lys Thr His Thr
210                 215                 220
Cys Pro Pro Cys Pro Ala Pro Glu Leu Leu Gly Gly Pro Ser Val Phe
225                 230                 235                 240
Leu Phe Pro Pro Lys Pro Lys Asp Thr Leu Met Ile Ser Arg Thr Pro
            245                 250                 255
Glu Val Thr Cys Val Val Val Asp Val Ser His Glu Asp Pro Glu Val
            260                 265                 270
Lys Phe Asn Trp Tyr Val Asp Gly Val Glu Val His Asn Ala Lys Thr
            275                 280                 285
Lys Pro Arg Glu Glu Gln Tyr Asn Ser Thr Tyr Arg Val Val Ser Val
            290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
            325                 330                 335
Lys Ala Lys Gly Gln Pro Arg Glu Pro Gln Val Tyr Thr Leu Pro Pro
            340                 345                 350
Ser Arg Asp Glu Leu Thr Lys Asn Gln Val Ser Leu Thr Cys Leu Val
            355                 360                 365
Lys Gly Phe Tyr Pro Ser Asp Ile Ala Val Glu Trp Glu Ser Asn Gly
            370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
            405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys
            435                 440                 445

<210> SEQ ID NO 206
<211> LENGTH: 34
<212> TYPE: DNA
<213> ORGANISM: Artificial Sequence
<220> FEATURE:
<223> OTHER INFORMATION: primer

<400> SEQUENCE: 206
atacccaagc ttgccaccat ggagacagac acac                              34

<210> SEQ ID NO 207
<211> LENGTH: 33
```

<210> SEQ ID NO 208
<211> LENGTH: 41
<212> TYPE: DNA
<213> ORGANISM: Artificial Sequence
<220> FEATURE:
<223> OTHER INFORMATION: primer

<400> SEQUENCE: 207
atacccaagc ttcatttccc gggagacagg gag                                   33

<210> SEQ ID NO 208
<211> LENGTH: 41
<212> TYPE: DNA
<213> ORGANISM: Artificial Sequence
<220> FEATURE:
<223> OTHER INFORMATION: primer

<400> SEQUENCE: 208
atacccaagc ttgggccacc atgaactttc tgctgtcttg g                          41

<210> SEQ ID NO 209
<211> LENGTH: 34
<212> TYPE: DNA
<213> ORGANISM: Artificial Sequence
<220> FEATURE:
<223> OTHER INFORMATION: primer

<400> SEQUENCE: 209
atacccaagc ttctaacact ctcccctgtt gaag                                  34

<210> SEQ ID NO 210
<211> LENGTH: 3962
<212> TYPE: DNA
<213> ORGANISM: Artificial Sequence
<220> FEATURE:
<223> OTHER INFORMATION: plasmid pK-CR5

<400> SEQUENCE: 210
ctaaattgta agcgttaata tttttgttaaa attcgcgtta aattttttgtt aaatcagctc     60 atttttttaac caataggccg aaatcggcaa atcccttat aaatcaaaag aatagaccga    120
gatagggttg agtgttgttc cagtttggaa caagagtcca ctattaaaga acgtggactc    180
caacgtcaaa gggcgaaaaa ccgtctatca gggcgatggc ccactacgtg aaccatcacc    240
ctaatcaagt tttttggggt cgaggtgccg taaagcacta atcggaacc ctaaagggag     300 cccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgcgtaata cgactcacta gggcgaat tggagctcca     660 ccgcggtggc ggccgctcta gaactagtgg atccacatcg gcgcgccaaa tgatttgccc    720
tcccatatgt ccttccgagt gagagacaca aaaaattcca acacactatt gcaatgaaaa    780
taaatttcct ttattagcca gaggtcgaga tttaaataag cttgctagca gatctttgga    840
cctgggagtg gacacctgtg gagagaaagg caaagtggat gtcattgtca ctcaagtgta    900
tggccagatc gggccaggtg aatatcaaat cctcctcgtt tttggaaact gacaatctta    960
gcgcagaagt aatgcccgct tttgagaggg agtactcacc ccaacagctg gatctcaagc   1020
ctgccacacc tcacctcgac catccgccgt ctcaagaccg cctactttaa ttacatcatc   1080

```
agcagcacct ccgccagaaa caaccccgac cgccacccgc tgccgcccgc cacggtgctc    1140
agcctacctt gcgactgtga ctggttagac gcctttctcg agaggttttc cgatccggtc    1200
gatgcggact cgctcaggtc cctcggtggc ggagtaccgt tcggaggccg acgggtttcc    1260
gatccaagag tactggaaag accgcgaaga gtttgtcctc aaccgcgagc caacagctg     1320 gccctcgcag acagcgatgc ggaagagagt gaccgcggag gctggatcgg tcccggtgtc    1380
ttctatggag gtcaaaacag cgtggatggc gtctccaggc gatctgacgg ttcactaaac    1440
gagctctgct tatataggcc tcccaccgta cacgcctacc tcgacccggg taccaatctt    1500
ataatacaaa cagaccagat tgtctgtttg ttataataca aacagaccag attgtctgtt    1560
tgttataata caaacagacc agattgtctg tttgttataa tacaaacaga ccagattgtc    1620
tgtttgttat aatacaaaca gaccagattg tctgtttgtt aatacaaa cagaccagat     1680 tgtctgtttg ttaaggttgt cgagtgaaga cgaaagggtt cattaaggcg cgccgtcgac    1740
ctcgaggggg ggcccggtac ccagcttttg ttcccttta tgagggttaa ttgcgcgctt     1800
ggcgtaatca tggtcatagc tgtttcctgt gtgaaattgt tatccgctca caattccaca    1860
caacatacga gccggaagca taaagtgtaa agcctggggt gcctaatgag tgagctaact    1920
cacattaatt gcgttgcgct cactgcccgc tttccagtcg ggaaacctgt cgtgccagct    1980
gcattaatga atcggccaac gcgcggggag aggcggtttg cgtattgggc gctcttccgc    2040
ttcctcgctc actgactcgc tgcgctcggt cgttcggctg cggcgagcgg tatcagctca    2100
ctcaaaggcg gtaatacggt tatccacaga atcaggggat aacgcaggaa agaacatgtg    2160
agcaaaaggc cagcaaaagg ccaggaaccg taaaaaggcc gcgttgctgg cgtttttcca    2220
taggctccgc ccccctgacg agcatcacaa aaatcgacgc tcaagtcaga ggtggcgaaa    2280
cccgacagga ctataaagat accaggcgtt tccccctgga agctccctcg tgcgctctcc    2340
tgttccgacc ctgccgctta ccggatacct gtccgccttt ctcccttcgg aagcgtggc    2400 gctttctcat agctcacgct gtaggtatct cagttcggtg taggtcgttc gctccaagct    2460
gggctgtgtg cacgaacccc ccgttcagcc cgaccgctgc gccttatccg gtaactatcg    2520
tcttgagtcc aacccggtaa gacacgactt atcgccactg gcagcagcca ctggtaacag    2580
gattagcaga gcgaggtatg taggcggtgc tacagagttc ttgaagtggt ggcctaacta    2640
cggctacact agaaggacag tatttggtat ctgcgctctg ctgaagccag ttaccttcgg    2700
aaaaagagtt ggtagctctt gatccggcaa acaaaccacc gctggtagcg gtggtttttt    2760
tgtttgcaag cagcagatta cgcgcagaaa aaaaggatct caagaagatc ctttgatctt    2820
ttctacgggg tctgacgctc agtggaacga aaactcacgt taagggattt tggtcatgag    2880
attatcaaaa aggatcttca cctagatcct tttaaattaa aaatgaagtt ttaaatcaat    2940
ctaaagtata tatgagtaaa cttggtctga cagttaccaa tgcttaatca gtgaggcacc    3000
tatctcagcg atctgtctat ttcgttcatc catagttgcc tgactccccg tcgtgtagat    3060
aactacgata cgggagggct taccatctgg ccccagtgct gcaatgatac cgcgagaccc    3120
acgctcaccg gctccagatt tatcagcaat aaaccagcca gccggaaggg ccgagcgcag    3180
aagtggtcct gcaactttat ccgcctccat ccagtctatt aattgttgcc gggaagctag    3240
agtaagtagt tcgccagtta atagtttgcg caacgttgtt gccattgcta caggcatcgt    3300
ggtgtcacgc tcgtcgtttg gtatggcttc attcagctcc ggttcccaac gatcaaggcg    3360
agttacatga tcccccatgt tgtgcaaaaa agcggttagc tccttcggtc ctccgatcgt    3420
tgtcagaagt aagttggccg cagtgttatc actcatggtt atggcagcac tgcataattc    3480
```

```
tcttactgtc atgccatccg taagatgctt ttctgtgact ggtgagtact caaccaagtc   3540
attctgagaa tagtgtatgc ggcgaccgag ttgctcttgc ccggcgtcaa tacgggataa   3600
taccgcgcca catagcagaa ctttaaaagt gctcatcatt ggaaaacgtt cttcggggcg   3660
aaaactctca aggatcttac cgctgttgag atccagttcg atgtaaccca ctcgtgcacc   3720
caactgatct tcagcatctt ttactttcac cagcgtttct gggtgagcaa aacaggaag    3780 gcaaaatgcc gcaaaaaagg gaataagggc gacacggaaa tgttgaatac tcatactctt   3840
cctttttcaa tattattgaa gcatttatca gggttattgt ctcatgagcg gatacatatt   3900
tgaatgtatt tagaaaaata aacaataggg gttccgcgc acatttcccc gaaaagtgcc    3960
ac                                                                  3962

<210> SEQ ID NO 211
<211> LENGTH: 6530
<212> TYPE: DNA
<213> ORGANISM: Artificial Sequence
<220> FEATURE:
<223> OTHER INFORMATION: plasmid pMPG-CR5

<400> SEQUENCE: 211
gtcgacgata ccgtgcactt aattaagcgc gctcgaccaa atgatttgcc ctcccatatg     60
tccttccgag tgagagacac aaaaaattcc aacacactat gcaatgaaa ataaatttcc    120 tttattagcc agaggtcgag gtcggggat ccgtttaaac ttggacctgg gagtggacac    180
ctgtggagag aaaggcaaag tggatgtcat tgtcactcaa gtgtatggcc agatcgggcc    240
aggtgaatat caaatcctcc tcgttttgg aaactgacaa tcttagcgca gaagtaatgc    300
ccgcttttga gagggagtac tcaccccaac agctggatct caagcctgcc acacctcacc    360
tcgaccatcc gccgtctcaa gaccgcctac tttaattaca tcatcagcag cacctccgcc    420
agaaacaacc ccgaccgcca cccgctgccg cccgccacgg tgctcagcct accttgcgac    480
tgtgactggt tagacgcctt tctcgagagg ttttccgatc cggtcgatgc ggactcgctc    540
aggtccctcg gtggcggagt accgttcgga ggccgacggg tttccgatcc aagagtactg    600
gaaagaccgc gaagagtttg tcctcaaccg cgagcccaac agctggccct cgcagacagc    660
gatgcggaag agagtgaccg cggaggctgg atcggtcccg gtgtcttcta tggaggtcaa    720
aacagcgtga tggcgtctc caggcgatct gacggttcac taaacgagct ctgcttatat    780
aggcctccca ccgtacacgc ctacctcgac ccgggtacca atcttataat acaaacagac    840
cagattgtct gtttgttata atacaaacag accagattgt ctgttgtta taatacaaac    900 agaccagatt gtctgtttgt tataatacaa acagaccaga ttgtctgttt gttataatac    960
aaacagacca gattgtctgt tgttataat acaaacagac cagattgtct gtttgttaag   1020
gttgtcgagt gaagacgaaa gggttaatta aggcgcgccg tcgactagct tggcacgcca   1080
gaaatccgcg cggtggtttt tggggtcgg gggtgtttgg cagccacaga cgcccggtgt   1140
tcgtgtcgcg ccagtacatg cggtccatgc ccaggccatc caaaaaccat gggtctgtct   1200
gctcagtcca gtcgtggacc agaccccacg caacgcccaa ataataaacc cccacgaacc   1260
ataaaccatt cccatgggg gaccccgtcc ctaaccacg gggccagtgg ctatggcagg    1320
gcctgccgcc ccgacgttgg ctgcgagccc tgggccttca cccgaacttg gggggtgggg   1380
tggggaaaag gaagaaacgc gggcgtattg gccccaatgg ggtctcggtg gggtatcgac   1440
agagtgccag ccctgggacc gaaccccgcg tttatgaaca aacgacccaa cacccgtgcg   1500
```

-continued

| | |
|---|---|
| ttttattctg tctttttatt gccgtcatag cgcgggttcc ttccggtatt gtctccttcc | 1560 |
| gtgtttcagt tagcctcccc catctcccct attccttttgc cctcggacga gtgctggggc | 1620 |
| gtcggtttcc actatcggcg agtacttcta cacagccatc ggtccagacg ccgcgcttc | 1680 |
| tgcgggcgat ttgtgtacgc ccgacagtcc cggctccgga tcggacgatt gcgtcgcatc | 1740 |
| gaccctgcgc ccaagctgca tcatcgaaat tgccgtcaac caagctctga tagagttggt | 1800 |
| caagaccaat gcggagcata tacgcccgga gccgcggcga tcctgcaagc tccggatgcc | 1860 |
| tccgctcgaa gtagcgcgtc tgctgctcca tacaagccaa ccacggcctc cagaagaaga | 1920 |
| tgttggcgac ctcgtattgg gaatccccga acatcgcctc gctccagtca atgaccgctg | 1980 |
| ttatgcggcc attgtccgtc aggacattgt tggagccgaa atccgcgtgc acgaggtgcc | 2040 |
| ggacttcggg gcagtcctcg gcccaaagca tcagctcatc gagagcctgc gcgacggacg | 2100 |
| cactgacggt gtcgtccatc acagtttgcc agtgatacac atgggatca gcaatcgcgc | 2160 |
| atatgaaatc acgccatgta gtgtattgac cgattccttg cggtccgaat gggccgaacc | 2220 |
| cgctcgtctg gctaagatcg gccgcagcga tcgcatccat ggcctccgcg accggctgca | 2280 |
| gaacagcggg cagttcggtt tcaggcaggt cttgcaacgt gacaccctgt gcacggcggg | 2340 |
| agatgcaata ggtcaggctc tcgctgaatt ccccaatgtc aagcacttcc ggaatcggga | 2400 |
| gcgcggccga tgcaaagtgc cgataaacat aacgatcttt gtagaaacca tcggcgcagc | 2460 |
| tatttacccg caggacatat ccacgccctc ctacatcgaa gctgaaagca cgagattctt | 2520 |
| cgccctccga gagctgcatc aggtcggaga cgctgtcgaa cttttcgatc agaaacttct | 2580 |
| cgacagacgt cgcggtgagt tcaggctttt tcatatctca ttgcccggga tctgcggcac | 2640 |
| gctgttgacg ctgttaagcg ggtcgctgca gggtcgctcg gtgttcgagg ccacacgcgt | 2700 |
| caccttaata tgcgaagtgg acctgggacc cgcgccgccc gactgcatct gcgtgttcga | 2760 |
| attcgccaat gacaagacgc tgggcgggt tgtgtcatc atagaactaa agacatgcaa | 2820 |
| atatatttct tccggggaca ccgccagcaa acgcgagcaa cgggcacgg ggatgaagca | 2880 |
| gggcatggcg gccgacgcgc tgggctacgt cttgctggcg ttcgcgacgc gaggctggat | 2940 |
| ggccttcccc attatgattc ttctcgcttc cggcggcatc gggatgcccg cgttgcaggc | 3000 |
| catgctgtcc aggcaggtag atgacgacca tcagggacag cttcaaggat cgctcgcggc | 3060 |
| tcttaccagc ctaacttcga tcactggacc gctgatcgtc acggcgattt atgccgcctc | 3120 |
| ggcgagcaca tggaacgggt tggcatggat tgtaggcgcc gccctatacc ttgtctgcct | 3180 |
| ccccgcgttg cgtcgcggtg catggagccg ggccacctcg acctgaatgg aagcggcgg | 3240 |
| cacctcgcta acggattcac cactccaaga attggagcca atcaattctt gcggagaact | 3300 |
| gtgaatgcga aaaccaaccc ttggcagaac atatccatcg cgtccgccat ctccagcagc | 3360 |
| cgcacgcggc gcagcaaaag gccaggaacc gtaaaaaggc cgcgttgctg gcgttttttcc | 3420 |
| ataggctccg cccccctgac gagcatcaca aaaatcgacg ctcaagtcag aggtggcgaa | 3480 |
| acccgacagg actataaaga taccaggcgt ttccccctgg aagctccctc gtgcgctctc | 3540 |
| ctgttccgac cctgccgctt accggatacc tgtccgcctt tctcccttcg ggaagcgtgg | 3600 |
| cgctttctca tagctcacgc tgtaggtatc tcagttcggt gtaggtcgtt cgctccaagc | 3660 |
| tgggctgtgt gcacgaaccc cccgttcagc ccgaccgctg cgccttatcc ggtaactatc | 3720 |
| gtcttgagtc caacccggta agacacgact tatcgccact ggcagcagcc actggtaaca | 3780 |
| ggattagcag agcgaggtat gtaggcggtg ctacagagtt cttgaagtgg tggcctaact | 3840 |
| acggctacac tagaaggaca gtatttggta tctgcgctct gctgaagcca gttaccttcg | 3900 |

```
gaaaaagagt tggtagctct tgatccggca aacaaaccac cgctggtagc ggtggttttt   3960
ttgtttgcaa gcagcagatt acgcgcagaa aaaaaggatc tcaagaagat cctttgatct   4020
tttctacggg gtctgacgct cagtggaacg aaaactcacg ttaagggatt ttggtcatga   4080
gattatcaaa aaggatcttc acctagatcc ttttaaatta aaaatgaagt tttaaatcaa   4140
tctaaagtat atatgagtaa acttggtctg acagttacca atgcttaatc agtgaggcac   4200
ctatctcagc gatctgtcta tttcgttcat ccatagttgc ctgactcccc gtcgtgtaga   4260
taactacgat acgggagggc ttaccatctg gccccagtgc tgcaatgata ccgcgagacc   4320
cacgctcacc ggctccagat ttatcagcaa taaaccagcc agccggaagg gccgagcgca   4380
gaagtggtcc tgcaacttta tccgcctcca tccagtctat taattgttgc cgggaagcta   4440
gagtaagtag ttcgccagtt aatagtttgc gcaacgttgt tgccattgct gcaggcatcg   4500
tggtgtcacg ctcgtcgttt ggtatggctt cattcagctc cggttcccaa cgatcaaggc   4560
gagttacatg atcccccatg ttgtgcaaaa aagcggttag ctccttcggt cctccgatcg   4620
ttgtcagaag taagttggcc gcagtgttat cactcatggt tatggcagca ctgcataatt   4680
ctcttactgt catgccatcc gtaagatgct tttctgtgac tggtgagtac tcaaccaagt   4740
cattctgaga atagtgtatg cggcgaccga gttgctcttg cccggcgtca acacgggata   4800
ataccgcgcc acatagcaga actttaaaag tgctcatcat tggaaaacgt tcttcggggc   4860
gaaaactctc aaggatctta ccgctgttga gatccagttc gatgtaaccc actcgtgcac   4920
ccaactgatc ttcagcatct tttactttca ccagcgtttc tgggtgagca aaaacaggaa   4980
ggcaaaatgc cgcaaaaaag ggaataaggg cgacacggaa atgttgaata ctcatactct   5040
tcctttttca atattattga agcatttatc agggttattg tctcatgagc ggatacatat   5100
ttgaatgtat ttagaaaaat aaacaaatag gggttccgcg cacatttccc cgaaaagtgc   5160
cacctgacgt ctaagaaacc attattatca tgacattaac ctataaaaat aggcgtatca   5220
cgaggccctt tcgtcttcaa gaattctcat gtttgacagc ttatctctag cagatccgga   5280
attcccctcc ccaatttaaa tgaggaccta acctgtggaa atctactgat gtgggaggct   5340
gtaactgtac aaacagaggt tattggaata actagcatgc ttaaccttca tgcagggtca   5400
caaaaagtgc atgacgatgg tggaggaaaa cctattcaag gcagtaattt ccacttcttt   5460
gctgttggtg gagacccctt ggaaatgcag ggagtgctaa tgaattacag acaaagtac    5520 ccagatggta ctataacccc taaaaaccca acagcccagt cccaggtaat gaatactgac   5580
cataaggcct atttggacaa aaacaatgct tatccagttg agtgctgggt tcctgatcct   5640
agtagaaatg aaaatactag gtattttggg actttcacag gagggaaaa tgttccccca    5700 gtacttcatg tgaccaacac agctaccaca gtgttgctag atgaacaggg tgtgggcct    5760 ctttgtaaag ctgatagcct gtatgtttca gctgctgata tttgtggcct gtttactaac   5820
agctctggaa cacaacagtg gagaggcctt gcaagatatt ttaagatccg cctgagaaaa   5880
agatctgtaa agaatcctta cctaatttcc tttttgctaa gtgaccttat aaacaggaga   5940
acccagagag tggatgggca gcctatgtat ggtatggaat cccaggtaga agaggttagg   6000
gtgtttgatg gcacagaaag acttccaggg gacccagata tgataagata tattgacaaa   6060
cagggacaat tgcaaaccaa aatgctttaa acaggtgctt ttattgtaca tatacattta   6120
ataaatgctg cttttgtata agccactttt aagcttgtgt tattttgggg gtggtgtttt   6180
aggcctttta aaacactgaa agcctttaca caaatgcaac tcttgactat ggggggtctga  6240
```

-continued

```
ccttttgggaa tgttcagcag gggctgaagt atctgagact tgggaagagc attgtgattg    6300
ggattcagtg cttgatccat gtccagagtc ttcagtttct gaatcctctt ctcttgtaat    6360
atcaagaata catttcccca tgcatatatt atatttcatc cttgaaaaag tatacatact    6420
tatctcagaa tccagccttt ccttccattc aacaattcta gaagttaaaa ctggggtaga    6480
tgctattaca gaggtagaat gcttcctaaa cccagaaatg ggggatctgc                6530
```

<210> SEQ ID NO 212
<211> LENGTH: 10
<212> TYPE: PRT
<213> ORGANISM: Artificial Sequence
<220> FEATURE:
<223> OTHER INFORMATION: 3A4 heavy chain CDR2

<400> SEQUENCE: 212

Asp Ile Asn Pro Tyr Asn Gly Asp Thr Asn
1               5                   10

<210> SEQ ID NO 213
<211> LENGTH: 43
<212> TYPE: DNA
<213> ORGANISM: Artificial Sequence
<220> FEATURE:
<223> OTHER INFORMATION: primer

<400> SEQUENCE: 213

```
atgccaagtg gtcccaggct gatgttgtga tgacccaaac tcc                         43
```

<210> SEQ ID NO 214
<211> LENGTH: 35
<212> TYPE: DNA
<213> ORGANISM: Artificial Sequence
<220> FEATURE:
<223> OTHER INFORMATION: primer

<400> SEQUENCE: 214

```
gggaagatga agacagatgg tgcagccaca gtccg                                  35
```

<210> SEQ ID NO 215
<211> LENGTH: 43
<212> TYPE: DNA
<213> ORGANISM: Artificial Sequence
<220> FEATURE:
<223> OTHER INFORMATION: primer

<400> SEQUENCE: 215

```
gggttccagg ttccactggc cagatccagt tggtgcaatc tgg                         43
```

<210> SEQ ID NO 216
<211> LENGTH: 38
<212> TYPE: DNA
<213> ORGANISM: Artificial Sequence
<220> FEATURE:
<223> OTHER INFORMATION: primer

<400> SEQUENCE: 216

```
ggggccaggg gaaagacaga tgggcccttc gttgaggc                               38
```

<210> SEQ ID NO 217
<211> LENGTH: 6
<212> TYPE: PRT

```
<213> ORGANISM: Artificial Sequence
<220> FEATURE:
<223> OTHER INFORMATION: Description of Artificial Sequence: Synthetic
      6xHis tag

<400> SEQUENCE: 217

His His His His His His
1               5
```